(12) United States Patent
Codarri-Deak et al.

(10) Patent No.: US 11,130,810 B2
(45) Date of Patent: Sep. 28, 2021

(54) BISPECIFIC ANTIBODIES SPECIFIC FOR PD1 AND TIM3

(71) Applicant: Hoffmann-La Roche Inc., Little Falls, NJ (US)

(72) Inventors: Laura Codarri-Deak, Schlieren (CH); Georg Fertig, Penzberg (DE); Jens Fischer, Penzberg (DE); Christian Klein, Schlieren (CH); Viktor Levitski, Schlieren (CH); Valeria Lifke, Penzberg (DE); Mario Perro, Schlieren (CH); Joerg Thomas Regula, Penzberg (DE); Tilman Schlothauer, Penzberg (DE); Stefan Seeber, Penzberg (DE); Pablo Umana, Schlieren (CH); Ildiko Wuensche, Penzberg (DE); Adrian Zwick, Penzberg (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 16/367,017

(22) Filed: Mar. 27, 2019

(65) Prior Publication Data
US 2019/0322748 A1 Oct. 24, 2019

Related U.S. Application Data

(62) Division of application No. 15/280,372, filed on Sep. 29, 2016, now Pat. No. 10,287,352.

(30) Foreign Application Priority Data

Oct. 2, 2015 (EP) .................................... 15188036
Oct. 2, 2015 (EP) .................................... 15188065

(51) Int. Cl.
*C07K 16/28* (2006.01)
*A61K 39/00* (2006.01)

(52) U.S. Cl.
CPC ...... *C07K 16/2818* (2013.01); *C07K 16/2803* (2013.01); *A61K 2039/505* (2013.01); *C07K 2317/24* (2013.01); *C07K 2317/31* (2013.01); *C07K 2317/41* (2013.01); *C07K 2317/51* (2013.01); *C07K 2317/515* (2013.01); *C07K 2317/52* (2013.01); *C07K 2317/55* (2013.01); *C07K 2317/56* (2013.01); *C07K 2317/66* (2013.01); *C07K 2317/71* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 6,500,422 | B2 | 12/2002 | Biffoni et al. |
| 7,563,869 | B2 | 7/2009 | Honjo et al. |
| 7,595,048 | B2 | 9/2009 | Honjo et al. |
| 8,552,156 | B2 | 10/2013 | Takayanagi et al. |
| 9,067,999 | B1 | 6/2015 | Honjo et al. |
| 9,084,776 | B2 | 7/2015 | Korman et al. |
| 9,163,087 | B2 | 10/2015 | Kuchroo et al. |
| 9,382,323 | B2 | 7/2016 | Brinkmann et al. |
| 9,834,607 | B2 | 12/2017 | Kuchroo et al. |
| 9,880,176 | B2 | 1/2018 | Jaga et al. |
| 9,945,869 | B2 | 4/2018 | Stubenrauch et al. |
| 10,287,352 | B2 | 5/2019 | Codarri-Deak et al. |
| 10,344,089 | B2 | 7/2019 | Thudium et al. |
| 10,392,445 | B2 | 8/2019 | Amann et al. |
| 10,562,903 | B2 | 2/2020 | Bartels et al. |
| 10,596,173 | B2 | 3/2020 | Lu et al. |
| 10,718,762 | B2 | 7/2020 | Seeber et al. |
| 10,761,097 | B2 | 9/2020 | Stubenrauch et al. |
| 10,934,352 | B2 | 3/2021 | Kuchroo et al. |
| 2006/0165685 | A1 | 7/2006 | Kreysch |
| 2007/0036783 | A1 | 2/2007 | Humeau et al. |
| 2007/0122378 | A1 | 5/2007 | Freeman et al. |
| 2009/0217401 | A1 | 8/2009 | Korman et al. |
| 2009/0175867 | A1 | 9/2009 | Thompson et al. |
| 2010/0190266 | A1 | 7/2010 | Sakita et al. |
| 2010/0247521 | A1 | 9/2010 | Jones et al. |
| 2011/0070238 | A1 | 3/2011 | Triebel et al. |
| 2012/0189617 | A1 | 7/2012 | Takayanagi et al. |

(Continued)

FOREIGN PATENT DOCUMENTS

| CN | 101490085 | 7/2007 |
| CN | 103608080 A | 2/2014 |

(Continued)

OTHER PUBLICATIONS

Agata, Y., et al., "Expression of the PD-1 antigen on the surface of stimulated mouse T and B lymphocytes" Int Immunol 8(5):765-772 (Feb. 6, 1996).
Aggarwal, B., et al., "Signalling pathways of the TNF superfamily: a double-edged sword" Nat Rev Immunol 3(9):745-756 (Sep. 1, 2003).
Almagro, J., et al., "Humanization of antibodies" Front Biosci 13:1619-1633 (Jan. 1, 2008).
Araki, K., et al., "Programmed Cell Death 1-Directed Immunotherapy for Enhancing T-Cell Function" Cold Spring Harb Symp Quant Biol 78:239-247 (2013).

(Continued)

*Primary Examiner* — Nelson B Moseley, II
(74) *Attorney, Agent, or Firm* — Genentech, Inc.

(57) ABSTRACT

The invention relates to bispecific antibodies comprising a first antigen-binding site that specifically binds to PD1 and a second antigen-binding site that specifically binds to TIM3, in particular to bispecific antibodies, wherein the bispecific antibody binds to 5 TIM3 with a lower binding affinity when compared to the binding to PD1. The invention further relates to methods of producing these molecules and to methods of using the same.

36 Claims, 22 Drawing Sheets

Specification includes a Sequence Listing.

(56) References Cited

U.S. PATENT DOCUMENTS

| | | |
|---|---|---|
| 2012/0244112 A1 | 9/2012 | Ast et al. |
| 2013/0156774 A1* | 6/2013 | Kuchroo ............... A61P 35/00 424/136.1 |
| 2014/0242076 A1* | 8/2014 | Kadouche ......... C07K 16/2833 424/136.1 |
| 2014/0242611 A1 | 8/2014 | Bazin et al. |
| 2014/0271684 A1 | 9/2014 | Li et al. |
| 2015/0024410 A1 | 1/2015 | Jaga et al. |
| 2015/0044690 A1 | 2/2015 | Nakada et al. |
| 2015/0090936 A1 | 4/2015 | Hu et al. |
| 2015/0203579 A1 | 7/2015 | Papadopoulos et al. |
| 2015/0204847 A1 | 7/2015 | Thomas et al. |
| 2015/0210769 A1 | 7/2015 | Freeman et al. |
| 2015/0259420 A1 | 9/2015 | Triebel et al. |
| 2015/0315296 A1 | 11/2015 | Schaefer et al. |
| 2016/0257749 A1 | 9/2016 | Lifke et al. |
| 2016/0376367 A1 | 12/2016 | Yuan et al. |
| 2017/0114135 A1 | 4/2017 | Codarri-deak et al. |
| 2017/0198037 A1 | 7/2017 | Bonvini et al. |
| 2017/0247454 A1 | 8/2017 | Benz et al. |
| 2018/0072804 A1 | 3/2018 | Lifke et al. |
| 2018/0326010 A1 | 11/2018 | Codarri Deak et al. |
| 2018/0326011 A1 | 11/2018 | Codarri Deak et al. |
| 2018/0326054 A1 | 11/2018 | Codarri Deak et al. |
| 2018/0328920 A1 | 11/2018 | Seeber et al. |
| 2019/0185566 A1 | 6/2019 | Koller et al. |
| 2019/0248877 A1 | 8/2019 | Amann et al. |
| 2019/0382480 A1 | 12/2019 | Lifke et al. |
| 2019/0382489 A1 | 12/2019 | Benz et al. |
| 2019/0382507 A1 | 12/2019 | Amann et al. |
| 2020/0247904 A1 | 8/2020 | Amann et al. |
| 2020/0277372 A1 | 9/2020 | Codarri Deak et al. |
| 2021/0009656 A1 | 1/2021 | Bruenker et al. |

FOREIGN PATENT DOCUMENTS

| | | |
|---|---|---|
| CN | 103858010 | 6/2014 |
| CN | 104428315 B1 | 9/2017 |
| CN | 2012/145493 | 10/2020 |
| EA | 005404 B1 | 2/2005 |
| EA | 201690333 A1 | 6/2016 |
| EP | 3455254 A1 | 3/2019 |
| JP | 2005-526018 A1 | 9/2005 |
| JP | 2007-523602 A | 8/2007 |
| JP | 2012-503984 A | 2/2012 |
| JP | 2012-515766 | 7/2012 |
| JP | 2013-521769 A | 6/2013 |
| JP | 2014-506793 A | 3/2014 |
| JP | 2014-523401 A | 9/2014 |
| JP | 2017-505125 A | 2/2017 |
| RU | 2406760 C2 | 12/2010 |
| RU | 2494107 C2 | 9/2013 |
| TW | 2010019958 A1 | 6/2010 |
| TW | 201406784 A | 2/2014 |
| TW | 201540727 A | 11/2015 |
| WO | 96/27603 A1 | 9/1996 |
| WO | 00/24782 A2 | 5/2000 |
| WO | 02/02773 A3 | 1/2002 |
| WO | 02/02773 A2 | 2/2002 |
| WO | 03/042402 A2 | 5/2003 |
| WO | 03/063792 A2 | 8/2003 |
| WO | 2004/004771 A1 | 1/2004 |
| WO | 2004/056875 A1 | 7/2004 |
| WO | 2004/069876 A1 | 8/2004 |
| WO | 2004/072286 A1 | 8/2004 |
| WO | 2004/078928 A2 | 9/2004 |
| WO | 2004/087196 A2 | 10/2004 |
| WO | 2005/087797 A1 | 9/2005 |
| WO | 2006/121168 A1 | 11/2006 |
| WO | 2006/133396 A2 | 12/2006 |
| WO | 2007/005874 A2 | 1/2007 |
| WO | 2007/062466 A1 | 6/2007 |
| WO | 2008/071447 A2 | 6/2008 |
| WO | 2008/083174 A2 | 7/2008 |
| WO | 2008/138920 | 11/2008 |
| WO | 2008/156712 A1 | 12/2008 |
| WO | 2009/014708 A2 | 1/2009 |
| WO | 2009/024531 A1 | 2/2009 |
| WO | 2009/052623 A1 | 4/2009 |
| WO | 2009/101611 A1 | 8/2009 |
| WO | 2009/114335 A2 | 9/2009 |
| WO | 2009/154335 A2 | 12/2009 |
| WO | 2010/10051 A1 | 1/2010 |
| WO | 2010/019570 A2 | 2/2010 |
| WO | 2010/027423 A2 | 3/2010 |
| WO | 2010/027828 A2 | 3/2010 |
| WO | 2010/029434 A1 | 3/2010 |
| WO | 2010/029435 A1 | 3/2010 |
| WO | 2010/036959 A2 | 4/2010 |
| WO | 2010/063011 A2 | 6/2010 |
| WO | 2010/084999 A1 | 8/2010 |
| WO | 2010/089411 A2 | 8/2010 |
| WO | 2010/112193 A1 | 10/2010 |
| WO | 2010/145792 A1 | 12/2010 |
| WO | 2011/066342 A2 | 6/2011 |
| WO | 2011/109789 A2 | 9/2011 |
| WO | 2011/110604 A1 | 9/2011 |
| WO | 2011/110621 A1 | 9/2011 |
| WO | 2011/155607 A1 | 12/2011 |
| WO | 2011/159877 A2 | 12/2011 |
| WO | 2012/020006 A2 | 2/2012 |
| WO | 2012/107417 A1 | 8/2012 |
| WO | 2012/130831 A1 | 10/2012 |
| WO | 2012/145493 A1 | 10/2012 |
| WO | 2012/006490 A2 | 1/2013 |
| WO | 2013/004970 | 1/2013 |
| WO | 2013/014668 A1 | 1/2013 |
| WO | 2013/113663 A1 | 8/2013 |
| WO | 2013/164694 A1 | 11/2013 |
| WO | 2014/008218 A1 | 1/2014 |
| WO | 2014/009465 A1 | 1/2014 |
| WO | 2014/023679 A1 | 2/2014 |
| WO | 2014/055784 | 4/2014 |
| WO | 2014/179664 A2 | 6/2014 |
| WO | 2014/140180 A1 | 9/2014 |
| WO | 2015/018528 A1 | 2/2015 |
| WO | 2015/048312 A1 | 4/2015 |
| WO | 2015/085847 A1 | 6/2015 |
| WO | 2015/095423 A2 A3 | 6/2015 |
| WO | 2015/107026 A1 | 7/2015 |
| WO | 2015/112800 A1 | 7/2015 |
| WO | 2015/112900 A1 | 7/2015 |
| WO | 2015/116539 A1 | 8/2015 |
| WO | 2015/138920 A1 | 9/2015 |
| WO | 2015/150447 A1 | 10/2015 |
| WO | 2015/164665 A1 | 10/2015 |
| WO | 2015/200119 A1 | 12/2015 |
| WO | 2016/028672 A1 | 2/2016 |
| WO | 2016/075278 A1 | 5/2016 |
| WO | 2016/079050 A1 | 5/2016 |
| WO | 2016041448 A1 | 5/2016 |
| WO | 2016/092419 A1 | 6/2016 |
| WO | 2016/106159 A1 | 6/2016 |
| WO | 2016/126858 A2 | 8/2016 |
| WO | 2016/200782 A1 | 12/2016 |
| WO | 2016/210129 A1 | 12/2016 |
| WO | 2017/015560 A2 | 1/2017 |
| WO | 2017/037203 A1 | 3/2017 |
| WO | 2017/050144 A1 | 4/2017 |
| WO | 2017/055399 A1 | 4/2017 |
| WO | 2017/055404 A1 | 4/2017 |
| WO | 2017/055443 A1 | 4/2017 |
| WO | 2017/096026 A1 | 6/2017 |
| WO | 2017/172517 A1 | 10/2017 |
| WO | 2017/194442 A1 | 11/2017 |
| WO | 2017/194641 A1 | 11/2017 |
| WO | 2018/184964 A1 | 10/2018 |
| WO | 2018/184965 A1 | 10/2018 |

(56) References Cited

FOREIGN PATENT DOCUMENTS

| WO | 2018/185043 A1 | 10/2018 |
| WO | 2018/185046 A1 | 10/2018 |

OTHER PUBLICATIONS

Ascierto, P. et al., "Clinical Experiences With Anti-CD137 and Anti-PD1 Therapeutic Antibodies" Semin Oncol 27(5):508-516 (Oct. 1, 2020).

Ascierto, P., et al., "2015: The Year of Anti-PD-1/PD-L1s Against Melanoma and Beyond" Ebiomedicine 2(2):92-93 (Feb. 1, 2015).

Banner, D., et al., "Crystal Structure of the Soluble Human 55 kd TNF Receptor-Human TNFβ Complex: Implications for TNF Receptor Activation" Cell 73(3):431-445 (May 7, 1993).

Barber, D., et al., "Restoring function in exhausted CD8 T cells during chronic viral infection" Nature 439(7077):682-687 (Feb. 9, 2006).

Baumann, R., et al., "Functional expression of CD134 by neutrophils" Eur J Immunol 34(8):2268-2275 (Aug. 1, 2004).

Bennett, F., et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses" J Immunol 170(2):711-718 (Jan. 15, 2003).

Bernett, M., et al., "Multiple Bispecific Checkpoint Combinations Promote T cell activation" (Investor Relations presentation) Xencor Inc., Monrovia, California—U.S., pgs. 1 (2016) https://investors.xencor.com/static-files/f388d30a-3d0d-4a69-9a43-876a3b38f79f.

Blackburn, S., et al., "Coregulation of CD8+ T cell exhaustion by multiple inhibitory receptors during chronic viral infection" Nat Immunol 10(1):29-37 (Jan. 1, 2009).

Blank, C., et al., "Contribution of the PD-L1/PD-1 pathway to T-cell exhaustion: an update on implications for chronic infections and tumor evasion" Cancer Immunol Immun 56(5):739-745 (May 1, 2007).

Bodmer, J. et al., "The molecular architecture of the TNF superfamily" Trends Biochem Sci 27(1):19-26 (Jan. 1, 2002).

Brahmer, J., et al., "Phase I Study of Single-Agent Anti-Programmed Death-1 (MDX-1106) in Refractory Solid Tumors: Safety, Clinical Activity, Pharmacodynamics, and Immunologic Correlates" J Clin Oncol 28(19):3167-3175 (Jul. 1, 2010).

Brand, F. X., et al., "Prospect for Anti-HER2 Receptor Therapy in Breast Cancer" Anitcancer Res 26(1B):463-470 (Jan. 31, 2006).

Broll, K., et al., "CD137 Expression in Tumor Vessel Walls High Correlation With Malignant Tumors" Am J Clin Pathol 115(4):543-549 (Apr. 1, 2001).

Buechele, C, et al., "4-1BB ligand modulates direct and Rituximab-induced NK-cell reactivity in chronic lymphocytic leukemia" Eur J Immunol 42(3):737-748 (Mar 1, 2012).

Chen, S., et al., "Combination of 4-1BB Agonist and PD-1 Antagonist Promotes Antitumor Effector/Memory CD8 T Cells in a Poorly Immunogenic Tumor Model" Cancer Immunol Res 3(2):149-160 (Feb. 1, 2015).

Chen, Ex., et al., "A novel human IL-2 mutein with minimal systemic toxicity exerts greater antitumor efficacy than wild-type IL-2" Cell Death Dis 9(10 Suppl 989):1-12 (Oct. 1, 2018).

Choi, b., et al., "4-1BB Functions As a Survival Factor in Dendritic Cells" J Immunol 182(7): 4107-4115 (Apr. 1, 2009).

Croft, M. et al., "The significance of OX40 and OX40L to T-cell biology and immune disease" Immunol Rev 229(1):173-191 (May 1, 2009).

Cuadros, C., et al., "Vaccination with dendritic cells pulsed with apoptotic tumors in combination with anti-OX40 and anti-4-1BB monoclonal antibodies induces T cell-mediated protective immunity in Her-2/neu transgenic mice" Int J Cancer 116(6):934-943 (Oct. 10, 2005).

Curran, M., et al., "Combination CTLA-4 blockade and 4-1BB activation enhances tumor rejection by increasing T-cell infiltration, proliferation, and cytokine production" PLOS One 6(4):e19499, 1-11 (Apr. 29, 2011).

Dermer, G., et al., "Another anniversary for the war on cancer" Nat Biotechnol 12:320 (Mar. 1, 1994).

Diehl, L., et al., "In Vivo Triggering Through 4-1BB Enables Th-Independent Priming of CTL in the Presence of an Intact CD28 Costimulatory Pathway" J Immunol 168(8): 3755-3762 (Apr. 15, 2002).

Dubrot, J., et al., "Treatment with anti-CD137 mAbs causes intense accumulations of liver T cells without selective antitumor immunotherapeutic effects in this organ" Cancer Immunol Immun 59(8):1223-1233 (Aug. 1, 2010).

Frankel, A.E., et al., "Characterization of diphtheria fusion proteins targeted to the human interleukin-3 receptor" Protein Eng 13(8):575-581 (Aug. 1, 2000).

Freshney, R.I., et al. Culture of Animal Cells: A Manual of Basic Technique New York: Alan R. Liss, Inc., 1-7 (1983).

Futagawa, T., et al., "Expression and function of 4-1 BB and 4-1BB ligand on murine dendritic cells" Int Immunol 14(3): 275-286 (Mar. 1, 2002).

Gehring, A., et al., "Profile of Tumor Antigen-Specific CD8 T Cells in Patients With Hepatitis B Virus-Related Hepatocelluar Carcinoma" Gastroenterology 137(2): 682-690 (Aug. 1, 2009).

George, J. et al., "Differential Effects on Anti-β2-Glycoprotein I Antibodies on Endothelial Cells and on the Manifestations of Experimental Antiphospholipid Syndrome" Circulation 98(9): 900-906 (Mar. 10, 1998).

Golden-Mason, L., et al., "Negative Immune Regulator Tim-3 Is Overexpresses on T Cells in Hepatitis C Virus Infection and Its Blockade Rescues Dysfunctional CD4 and CD8 T Cells" J Jirol 83(18):9122-9130 (Sep. 1, 2009).

Golden-Mason, L., et al., "Upregualtion of PD-1 Expression on Circulating and Intrahepatic Hepatitis C Virus-Specific CD8 T Cells Associated with Reversible Immune Dysfunction" J Virol 81(17):9249-9258 (Sep. 1, 2007).

Guo, Z., et al., "Combined TIM-3 blockade and CD137 activation affordsd the long-term protection in a murine model of ovarian cancer." J Transl Med 11(215):1-11 (Sep 17, 2013).

Gura, T., "Systems for Identifying New Drugs Are Often Faulty" Science 278(5340):1041-1042 (Nov. 7, 1997).

Hafler, D., et al., "TIMs: central regulators of immune responses" J Exp Med 205(12):2699-2701 (Nov. 24, 2008).

Heinisch, I., et al., "CD137 activation abrogates granulocytemacrophage colony-stimulating factor-mediated anti-apoptosis in neutophils" Eur J Immunol 30(12):3441-3446 (Dec. 1, 2000).

Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).

Hornig, N., et al., "Evaluating combinations of costimulatory antibody-ligand fusion proteins for targeted cancer immunotherapy" Cancer Immunol Immunother 62(8):1369-1380 (May 17, 2013).

Hu, C.Y., et al., "Interleukin-2 reverses CD+ T cell exhaustion in clinical malignant pleural effusion of lung cancer" Clin Exp Immunol 186(1):106-114 (Oct. 1, 2016).

Huard, B., et al., "Characterization of the major histocompatibility complex class II binding site on LAG-3 protein" PNAS USA 94(11):5744-5749 (May 27, 1997).

"International Preliminary Report on Patentability—PCT/EP2015/075820", pp. 1-8 (May 18, 2017).

"International Search Report—PCT/EP2015/075820":pp. 1-8 (Feb. 4, 2016).

"International Search Report—PCT/EP2016/073248":pp. 1-11 (Feb. 15, 2017).

Jain, R. et al., "Barriers to drug delivery in solid tumors" Sci Am:58-65 (Jul. 1994).

Jin, H., et al., "Cooperation of Tim-3 and PD-1 in CD8 T-cell exhaustion during chronic viral !infection" PNAS 107(33):14733-14738 (Aug. 17, 2010).

Jones, R., et al., "Tim-3 expression defines a novel population of dysfunctional T cells with highly elevated frequencies in progressive HIV-1 infection" J Exp Med 205(12):2763-2779 (Nov. 24, 2008).

Ju, S., et al., "Eradication of established renal cell carcinoma by a combination of 5-fluorouracil and anti-4-1BB monoclonal antibody in mice" Int J Cancer 122(12):2784-2790 (Jun. 15, 2008).

(56) References Cited

OTHER PUBLICATIONS

Kienzle, G., et al., "CD137 (ILA/4-1BB), expressed by primary human monocytes, induces monocyte activation and apoptosis of B lymphocytes" Int Immunol 12(1):73-82 (Jan. 1, 2000).
Kikushige, Y., et al., "TIM-3 as a Novel Therapeutic Target for Eradicating Acute Myelogenous Leukemia Stem Cells" Int J Hematol 98(6):627-633 (Dec. 1, 2013).
Kim, D., et al., "4-1BB Engagement Costimulates NKT Cell Activation and Exacerbates NKT Cell Ligand-Induced Airway Hyperresponsiveness and Inflammation" J Immunol 180(4):2062-2068 (Feb. 1, 2008).
Kim, Y. H., et al., "Mechanisms involved in synergistic anticancer effects of anti-4-1BB and cyclophosphamide therapy." Mol Cancer Ther 8(2):469-478 (Feb. 1, 2009).
Klebanoff, C., et al., "IL-15 enhances the in vivo antitumor activity of tumor-reactive CD8+ T Cells" PNAS USA 101(7):1969-1974 (Feb. 17, 2004).
Klooster, R., et al., "Generation of immuno-modulatory receptor binding bispecific antibodies to modulate tumor immunity (B088)" Poster ICIC, New York, NY-US, pgs. 1 (Sep. 26,2016) https://merus.nl/app/uploads/2019/02/Poster-ICIC-New-York-26Sep16.pdf.
Koguchi, K., et al., "Dysregulated T cell expression of TIM3 in multiple sclerosis" J Exp Med 203(6):1413-1418 (Jun. 12, 2006).
Kraman, M. et al., "A LAG-3/PD-L1 bispecific antibody inhibits tumour growth in two syngeneic colon carcinoma models" Cancer Res 77(13) (Jul. 1, 2017).
Kwon, B., et al., "cDNA sequences of two inducible T-cell genes" PNAS USA 86(6):1963-1967 (Mar. 1, 1989).
Lee, H., et al., "Combinatorial therapy for liver metastatic colon cancer: dendritic cell vaccine and low-dose agonistic anti-4-1BB antibody costimulatory signal" J Surg Res 169(1):e43- 50 (Jul. 1, 2011).
Levitsky, V., et al., "The clonal composition of a peptide-specific oligoclonal CTL repertoire selected in response to persistent EBV infection is stable over time." J Immunol 161(2):594-601 (Jun. 30, 1998).
Li, F., et al., "Inhibitory Fcγ Receptor Engagement Drives Adjuvant and Anti-Tumor Activities of Agonistic CD40 Antibodies" Science 333(6045):1030-1034 (Aug. 19, 2011).
Lin, W., et al., "Fc-dependent expression of CD137 on human NK cells: insights into agonistic effects of anti-CD137 monoclonal antibodies" Blood 112(3):699-707 (Aug. 1, 2008).
Lippincott-Schwartz et al., "Antibodies as Cell Biological Tools" Current Protocols in Cell Biology:16.0.1-16.0.2 ( 2002).
Majeti, R., et al., "Dysregulated gene expression networks in human acute myelogenous leukemia stem cells" PNAS 106(9):3396-3401 (Mar. 3, 2009).
Mariuzza, R. et al., "The structural basis of antigen-antibody recognition" Annu Rev. Biophys Chem 16:139-159 (Jun. 1, 1987).
Markwick, L., et al., "Blockade of PD1 and TIM3 Restores Innate and Adaptive Immunity in Patients With Acute Alcoholic Hepatitis" Gastroenterology, 148(3):590-602 (Mar1 1, 2015).
McMahan, R., et al., "Dual TIM-3/PD-1 Expression on Non-Effector CD4+ T Cells and. HCV-Specific CD8+ T Cells is Associated with Development of Persistence in Acute HCV Infection" Hepatology (Abstract #1368), 50( Suppl 4) ( 2009).
Melero, I. et al., "Monoclonal Antibodies Against the 4-1BB T-cell Activation Molecule Eradicate Established Tumors" Nat Med 3(6):682-685 (Jun. 1, 1997).
Melero, I. et al., "NK1.1 Cells Express 4-1BB (CDw137) Costimulatory Molecule and Are Required for Tumor Immunity Elicited by Anti-4-1BB Monoclonal Antibodies" Cell Immunol 190(2 Suppl CI981396):167-172 (Dec. 15, 1998).
Merchant, A., et al., "An efficient route to human bispecific IgG" Nat Biotechnol 116(7):677-681 (Jul. 1, 1998).
Monney, L., et al., "Th1-specific cell surface protein Tim-3 regulates macrophage activation and severity of an autoimmune disease" Nature 415(6871):536-541 (Jan. 31, 2002).
Morales-Kastresana, A., et al., "Combined immunostimulatory monocolonal antibodies extend survival in an aggressive transgenic heptocellular carcinoma mouse model" Clin Cancer Res 19(22):6151-6162 (Nov. 1, 2013).
Morales-Kastresana, A., et al., "Essential complicity of perforin-granzyme and FAS-L mechanisms to achieve tumor rejection following treatment with anti-CD137 mAb" J Immunother Cancer 1(3):1-6 (May 29, 2013).
Mueller, D. et al., "A Novel Antibody-4-1BBL Fusion Protein for Targeted Costimulation in Cancer Immunotherapy" J Immunother 31(8):714-722 (Oct. 1, 2008).
Murillo, O., et al., "In vivo depletion of DC impairs the anti-tumor effect of agonistic anti-CD137 mAb" Eur J Immunol 39(9):2424-2436 (Sep. 1, 2009).
Nakamoto, N., et al., "Synergistic Reversal of Intrahepatic HCV-Specific CD8 T Cell Exhaustion by Combined PD-1/CTLA-4 Blockade" PLOS PATHOG 5(2):e1000313, 1-13 (Feb. 1, 2009).
Narazaki, H., et al., "CD137 agonist antibody prevents cancer recurrence: contribution of CD137 on both hematopoietic and nonhematopoietic cells" Blood 115(10):1941-1948 (Mar. 11, 2010).
Ngiow, S., et al., "Review: Prospects for TIM3-Targeted Antitumor Immunotherapy" Cancer Res 71(21):6567-6571 (Nov 1, 2011).
Nishimoto, H., et al., "Costimulation of mast cells by 4-1BB, a member of the tumoe necrosis factor receptor superfamily, with the high-affinity IgE receptor" Blood 106(13):4241-4248 (Dec. 15, 2005).
Ohaegbulam, K., et al., "Human cancer immunotherapy with antibodies to the PD-1 and Pd-L1 pathway" Trends Mol Med 21(1):24-33 (Jan. 1, 2015).
Okazaki, T., et al., "New regulatory co-receptors: inducible co-stimulator and Pd-1" Curr Opin Immunol 14(6):779-782 (Dec. 1, 2002).
Olofsson, P. et al., "CD137 Is Expressed in Human Atherosclerosis and Promotes Development of Plaque Inflammation in Hypercholesterolemic Mice" Circulation 117(10):1292-1301 (Mar. 11, 2008).
Palazon, A., et al., "Agonist Anti-CD137 mAb Act on Tumor Endothelial Cells to Enhance Recruitment of Activated T Lymphocytes" Cancer Res 71:801-811 (Feb. 1, 2011).
Philips, G., et al., "Therapeutic uses of anti-PD-1 and anti-PD-L1 antibodies" Int Immunol 27(1):39-46 (Oct. 16, 2014).
Rudikoff, S., et al., "Single amino acid substitution altering antigen-binding specificity" PNAS USA 79(6):1979-1983 (Mar. 1, 1982).
Sakuishi, K., et al., "Targeting Tim-3 and PD-1 pathways to reverse T cell exhaustion and restore anti-tumor immunity" J Exp Med 207(10):2187-2194 (Sep. 27, 2010).
Sakuishi, K., et al., "TIM3+FOXP3+regulatory T cells are tissue-specific promoters of T-cell dysfunction in cancer" Oncoimmunology 2(4):e23849, 1-9 (Apr. 1, 2013).
Schwarz, H., et al., "ILA, the Human 4-1BB Homologue, Is Inducible in Lymphoid and Other Cell Lineages" Blood 85(4):1043-1052 (Feb. 15, 1995) .
Shao, Z., et al., "Mini-Review: CD137 ligand, a member of the tumor necrosis factor family, regulated immune responses via reverse signal transduction" J Leukocyte Biol 89(1):21-29 (Jan. 1, 2011).
Sheridan, C., et al., "Cautious optimism surrounds early clinical data for PD-1 blocker" !Nat Biotechnol 30(8):729-730 (Aug. 1, 2012).
Shi, W., et al., "Augmented antitumor effects of radiation therapy by 4-1BB antibody (BMS-469492) treatment" Anticancer Res 26(5A):3445-3453 (Sep. 2006).
Shindo, Y., et al., "Combination Immunotherapy with 4-1BB activation and PD-1 blockade enhances antitumor efficacy in a mouse model of subcutaneous tumor" Anticancer Res 35(1):129-136 (Jan. 1, 2015).
Sierro, S., et al., "The CD4-like molecule LAG-3, biology and therapeutic applications" Expert Opin Ther Tar 15(1):91-101 (Jan. 1, 2011).
Simeone, E. et al., "Immunomodulating antibodies in the treatment of metastatic melanoma: The experience with anti-CTLA-4, anti-CD137, and anti-PD1" J Immunotoxcity 9(3):241-247 (Jul. 1, 2012).

(56) References Cited

OTHER PUBLICATIONS

Singer, M. et al.,"Structure of Proteins" Genes & Genomes (Geny 1 genomy Moscow: Mir, 1998), 1:63-64 ( 1998).
Skosyrev, V.S., et al., "The Dependence of Stability of the Green Fluorescent Protein—Obelin Hybrids on the Nature of Their Constituent Modules and the Structure of the Amino Acid Linker" Bioorg Khim (Russ. J Bioorg Chem) 27(5):323-329 (Sep. 30, 2001).
Snell, L., et al., "T-cell intrinsic effects of GITR and 4-1BB during viral infection and cancer immunotherapy" Immunol Rev 244(1):197-217 (Nov. 1, 2011).
Song, J. et al., "Activation of NF-kB1 by OX40 Contributes to Antigen-Driven T Cell Expansion and Survival" J Immunol 180(11):7240-7248 (Jun. 1, 2008).
Stagg, J., et al., "Anti—ErbB-2 mAb therapy requires type I and II interferons and synergizes with anti—PD-1 or anti-CD137 mAb therapy" PNAS USA 108(17):7142-7147 (Apr. 26, 2011).
Strome, S., et al., "A Mechanistic Perspective of Monoclonal Antibodies in Cancer Therapy Beyond Target-Related Effects" Oncologist 12(9):1084-1095 (Sep. 1, 2007).
Takamura, S., et al., "Premature Terminal Exhaustion of Friend Virus-Specific Effector CD8 + T Cells by Rapid Induction of Multiple Inhibitory Receptors" J Immunol 184(9):4696-4707 (May 1, 2010).
Tan, S., et al., "An unexpected N-terminal loop in Pd-1 dominates binding by nivolumab" !Nat Commun 8(14369):1-10 (Feb. 6, 2017).
Teng, M., et al., "CD1d-Based Combination Therapy Eradicates Established Tumors in. Mice" J Immunol 183(3):1911-1920 (Aug. 1, 2009).
Tokuriki, N. et al., "Stability effects of mutations and protein evolvability" Curr Opin Struct Biol 19(5):596-604 (Oct. 1, 2009).
Topalian, S., et al., "Survival, Durable Tumor Remission, and Long-Term Safety in Patients With Advanced Melanoma Receiving Nivolumab" J Clin Oncol 32(10):1020-1030 (Apr. 1, 2014).
Tribel, F., et al., "A soluble lymphocyte activation gene-3 (sLAG-3) protein as a prognostic factor in human breast cancer expressing estrogen or progesterone receptors" Cancer Lett 235(1):147-153 (Apr. 8, 2006).
Von Kempis, J., et al., "Differentiation-dependent and stimulus-specific expression of ILA, the human 4-1BB-homologue, in cells of mesenchymal origin" Steoarthr Cartilage (5(6):394-406 (Nov. 1, 1997).
Wang, S-C, et al., "PD-1 and Tim-3 pathways are associated with regulatory CD8+ T-cell function in decidua and maintenance of normal pregnancy" Cell Death Dis, 6(5):e1738, 1-10 (May 1, 2015).
Watts, T., "TNF/TNFR family members in costimulation of T cell responses" Annu Rev Immunol 23:23-68 (Sep. 2005).
Wei, H. et al., "Dual targeting of CD137 co-stimulatory and PD-1 co-inhibitory molecules for ovarian cancer immunotherapy" Oncoimmunology 3(4):e28248, 1-3 (Mar. 28, 2014).
Wei, H., et al., "Combinatorial PD-1 blockade and CD137 activation has therapeutic efficacy in murine cancer models and synergizes with cisplatin" Plos One 8(12):e84927, 1-11 (Dec. 19, 2013).
Weinberg, A., et al., "Engagement of the OX-40 Receptor in Vivo Enhances Antitumor Immunity" J Immunol 164(4):2160-2169 (Feb. 15, 2000).
Wilcox, R., et al., "Cutting Edge: Expression of Functional CD137 Receptor by Dendritic Cells" J Immunol 168(9):4262-4267 (May 1, 2002).
Wilcox, R., et al., "Ligation of CD137 receptor prevents and reverses established anergy of CD8+ cytolytic T lymphocytes in vivo" Blood 103(1):177-184 (Jan. 1, 2004).
Xu, Z., et al., "Membrane-type TIM3 Promotes Anti-tumor Immunity in Tumor Bearing Mice" Chinese J Med Mol Biol 4(3):200-203 (Jan. 31, 2007).
Zhang, N. et al., "Targeted and untargeted CD137L fusion proteins for the immunotherapy of experimental solid tumors " Clin Cancer Res 13(9):2758-2767 (May 1, 2007).
Zhang, X., et al., "CD137 Promotes Proliferation and Survival of Human B Cells" L Immunol 184(2):787-795 (Jan. 15, 2010).
Zhou, Q., et al., "Coexpression of Tim-3 and PD-1 identifies a CD8+ T-cell exhaustion phenotype in mice with disseminated acute myelogenous leukemia" Blood 117(17):4501-4510 (Apr. 28, 2011).
Zitvogel, L. et al., "Targeting PD-1/PD-L1 interactions for cancer immunotherapy" Oncoimmunology 1(8):1223-1225 (Nov. 1, 2012).
Zitvogel, L., et al., "Cancer despite immunosurveillance: immunoselection and immunosubversion" Nat Rev Immunol 6(10):715-727 (Oct. 1, 2006).
Kikushige et al., "TIM-3 as a novel therapeutic target for eradicating acute myelogenous leukemia stem cells" Intl J Hematol 98:627-633 ( 2013).
Anderson et al., "Promotion of tissue inflammation by the immune receptor Tim-3 expressed on innate immune cells" Science 318(5853):1141-1143 ( 2007).
Mallender et al., "Inter-Active-Site Distance and Solution Dynamics of a Bivalent-Bispecific Single-Chain Antibody Molecule" Biochemistry 33:10100-10108 ( 1994).
Chen, X. et al., "Fusion Protein Linkers: Property, Design and Functionality" Adv Drug Deliv Rev 65(10):1357-1369 (Oct. 15, 2013).
Beiboer, S.H., et al., "Guided selection of a pan carcinoma specific antibody reveals similar binding characteristics yet structural divergence between the original murine antibody and its human equivalent" J Mol Biol 296(3):833-849 (Feb. 25, 2000).
De Genst, E., et al., "Antibody repertoire development in camelids" Dev Comp Immunol 30(1-2):187-198 ( 2006).
Malia, T., et al., "Epitope mapping and structural basis for the recognition of phosphorylated tau by the anti—tau antibody AT8" Proteins 84(4):427-484 (Apr. 1, 2016).
Barthelemy, P., et al., "Comprehensive Analysis of the Factors Contributing to the Stability and Solubility of Autonomous Human Vh Domains" J Biol Chem 283(6):3639-3654 (Feb. 8, 2008).
Beechem, J., Methods in Enzymology "Chapter 2: Global Analysis of Biochemical And Biophysical Data" Brand, L, and Johnson, M., eds, San Diego, CA-USA:Academic Press, vol. 210:37-54 ( 1992).
Chames, P., et al., "Therapeutic antibodies: successes, limitations and hopes for the future" Br J Pharmacol 157(2):220-233 (May 1, 2009).
Choi, Y., et al., "Predicting antibody complementarity determining region structures without classification" Mol Biosyst 7(12):3327-3334 (Dec. 1, 2011).
Dashivets, T., et al., "Oxidation in the complementarity-determining regions differentially influences the properties of therapeutic antibodies" MABS 8(8):1525-1535 (Nov. 1, 2016).
Dempke, W.C.M., et al., "Second-and third-generation drugs for immuno-oncology treatment—the more the better?" Eur J Cancer 74:55-72 (Mar. 1, 2017).
Dong, X, et al., "Time-resolved FRET reveals the structural mechanism of SSERCA-PLB regulation" Biochem Biophys Res Commun 449(2):196-201 (Jun. 27, 2014).
Gakamsky, D., et al., "Use of fluorescence lifetime technology to provide efficient protection from false hits in screening applications" Anal Biochem 409(1):89-97 (Feb. 1, 2011).
Gribbon, P., et al., "Fluorescence readouts in HTS: no. gain without pain?" Drug Discov Today 8(22):1035-1043 (Nov. 15, 2003).
Griffiths, A., et al., "Human anti-self antibodies with high specificity from phage display libraries" EMBO J 12(2):725-734 (Feb. 1, 1993).
"International Preliminary Report on Patentability—PCT/EP2016/073248" (dated Apr. 3, 2018, Chapter I),:pp. 1-13 (Apr. 12, 2018).
"International Preliminary Report on Patentability—PCT/EP2016/073186" (dated Apr. 3, 2018, Chapter I),:pp. 1-6 (Apr. 18, 2018).
"International Preliminary Report on Patentability—PCT/EP2017/061241" (dated Nov. 13, 2018, Chapter I),:pp. 1-9 (Nov. 22, 2018).
"International Preliminary Report on Patentability—PCT/EP2018/058382" (dated Oct. 17, 2019, Chapter I),:pp. 1-12 (Oct. 17, 2019).
"International Preliminary Report on Patentability—PCT/EP2018/058034" (dated Oct. 8, 2019, Chapter I),:pp. 1-10 (Oct. 17, 2019).
"International Preliminary Report on Patentability—PCT/EP2018/058385" (dated Oct. 8, 2019, Chapter I),:pp. 1-12 (Oct. 17, 2019).
"International Preliminary Report on Patentability-PCT/EP2018/058037" (dated Oct. 8, 2019, Chapter I),:pp. 1-10 (Oct. 17, 2019).

(56) References Cited

OTHER PUBLICATIONS

"International Search Report—PCT/EP2016/073186" (w/Written Opinion),:pp. 1-10 (dated Dec. 9, 2016).
"International Search Report—PCT/EP2017/061241" (w/Written Opinion),:pp. 1-18 (dated Aug. 3, 2017).
"International Search Report—PCT/EP2018/058034" (w/Written Opinion),:pp. 1-18 (dated Jun. 6, 2018).
"International Search Report—PCT/EP2018/058037" (w/Written Opinion),:pp. 1-18 (dated Jun. 6, 2018).
"International Search Report—PCT/EP2018/058382" (w/Written Opinion),:pp. 1-20 (dated. Jul 17, 2018).
"International Search Report—PCT/EP2018/058385" (w/Written Opinion),:pp. 1-24 (dated. Jun 6, ;2018).
Isenberg, I., et al., "The Analysis of Fluorescence Decay by a Method of Moments" Biophys J 9(11):1337-1350 (Nov 1, 1969).
Jamieson, D.M. et al., "Investigations of protein-protein interactions using time-resolved fluorescence and phasors" Methods 59(3):278-286 (Mar 1, 2013).
Klimka, A. et al., "Human anti-CD30 recombinant antibodies by guided phage antibody selection using cell panning" Brit J Cancer 83(2):252-260 (Jun. 15, 2000).
Knutson, J.R., et al., "Simultaneous analysis of multiple fluorescence decay curves: A global approach" Chem Phys Lett 102(6):501-507 (Dec. 9, 1983).
Lebakken, C.S., et al., "A fluorescence lifetime based binding assay to characterize kinase inhibitors" J Biomol Screen 12(6):828-841 (Sep. 1, 2007).
Maeda, Y., et al., "Engineering of functional chimeric protein G-Vargula luciferase" Anal Biochem 249(2):147-152 (Jul. 1, 1997).
Maltman, B., et al., "9-Aminoacridine peptide derivatives as versatile reporter systems for use in fluorescence lifetime assays" Chem Commun [CAMB] 46(37):6929-6931 (Oct. 7, 2010).
Moger, J., et al., "The Application of Fluorescence Lifetime Readouts in High-Throughput Screening" J Biomol Screen 11(7):765-772 (Oct. 1, 2006).
Muretta, J., et al., "High-performance time-resolved fluorescence by direct waveform recording." Rev Sci Instrum 81(10 Suppl 103101):1-8 (Oct. 1, 2010).
Padlan, E., "Anatomy of the Antibody Molecule" Mol Immunol 31(3):169-217 (Feb. 1, 1994).
Paterson, M.J., et al., "A fluorescence lifetime-based assay for serine and threonine kinases that is suitable for high-throughput screening" Anal Biochem 402(1):54-64 (Jul. 1, 2010).
Philips, G.K., et al., "Therapeutic uses of anti-PD-1 and anti-PD-L1 antibodies" Int Imiviunol 27(1):39-46 (Jan. 1, 2015).
Roitt, I., "Different antigen antibody binding is ensured by hypervariable sequences of antigen-recognizing centers" Immunologiya:110-111 ( 2000).
Shen, L., et al., "Construction and Expression of Anti-B7-1/B7-2-BsAb for Feature Analysis of its binding with antigen" Chinese J Immunol (w/Eng. Abstract), 31:927-931 (Jul. 14, 2015)
Thorne, N., et al., "Apparent activity in high-throughput screening: origins of compound-dependent assay interference" Curr Opin Chem Biol 14(3):315-324 (Jun. 1, 2010)
Vajdos, F.F., et at, "Comprehensive functional maps of the antigen-binding site of an-anti-ErbB2 antibody obtained with shotgun scanning mutagenesis" J Mol Biol !320(2):415-428 (Jul. 5, 2002).
Vig, B., et al., "Amino acids as promoieties in prodrug design and development" Adv Drug Deliv Rev 65(10):1370-1385 (Oct. 15, 2013).
Ward, E., et al., "Binding activities of a repertoire of single immunoglobulin variable domains" Nature 341(6242):544-546 (Oct. 12, 1989).
Woo, S., et al., "Immune inhibitory molecules LAG-3 and PD-1 synergistically regulate T cell function to promote tumoral immune escape" Cancer Res 72(4):917-927 (Feb. 15, 2012).
Wozney, J., Methods in Enzymology: Guide to Protein Purification "55: Using Purified Protein to Clone its Gene" Deutscher, Murray, ed., San Diego, CA-US:Academic Press, Inc.-Harcourt Brace Jovanivich, Publishers, vol. 182:738-751 ( 1990).

\* cited by examiner

SEQUENCE LISTING

```
<160> NUMBER OF SEQ ID NOS: 94

<210> SEQ ID NO 1
<211> LENGTH: 9
<212> TYPE: PRT
<213> ORGANISM: Mus musculus
```

```
<400> SEQUENCE: 1

Gly Phe Ser Leu Ser Thr Ser Gly Met
1               5

<210> SEQ ID NO 2
<211> LENGTH: 3
<212> TYPE: PRT
<213> ORGANISM: Mus musculus

<400> SEQUENCE: 2

Leu Asn Asp
1

<210> SEQ ID NO 3
<211> LENGTH: 8
<212> TYPE: PRT
<213> ORGANISM: Mus musculus

<400> SEQUENCE: 3

Asn Gly Tyr Leu Tyr Ala Leu Asp
1               5

<210> SEQ ID NO 4
<211> LENGTH: 6
<212> TYPE: PRT
<213> ORGANISM: Mus musculus

<400> SEQUENCE: 4

Ser Ser Ser Val Asn Tyr
1               5

<210> SEQ ID NO 5
<211> LENGTH: 3
<212> TYPE: PRT
<213> ORGANISM: Mus musculus

<400> SEQUENCE: 5

Asp Ala Phe
1

<210> SEQ ID NO 6
<211> LENGTH: 7
<212> TYPE: PRT
<213> ORGANISM: Mus musculus

<400> SEQUENCE: 6

Trp Ser Ser Tyr Pro Trp Thr
1               5

<210> SEQ ID NO 7
<211> LENGTH: 120
<212> TYPE: PRT
<213> ORGANISM: Mus musculus

<400> SEQUENCE: 7

Gln Val Thr Leu Lys Glu Ser Gly Pro Gly Ile Leu Gln Pro Ser Gln
1               5                   10                  15

Thr Leu Arg Leu Thr Cys Ser Phe Ser Gly Phe Ser Leu Ser Thr Ser
            20                  25                  30

Gly Met Ser Val Gly Trp Ile Arg Gln Pro Ser Gly Lys Gly Leu Glu
        35                  40                  45

Trp Leu Ala His Ile Trp Leu Asn Asp Asp Val Phe Phe Asn Pro Ala
```

```
                50                  55                  60
Leu Lys Ser Arg Leu Thr Ile Ser Lys Asp Thr Ser Asn Asn Gln Val
 65                  70                  75                  80

Phe Leu Gln Ile Ala Ser Val Val Thr Ala Asp Thr Ala Thr Tyr Tyr
                 85                  90                  95

Cys Val Arg Ala Asn Gly Tyr Leu Tyr Ala Leu Asp Tyr Trp Gly Gln
                100                 105                 110

Gly Thr Ser Val Thr Val Ser Ser
            115                 120

<210> SEQ ID NO 8
<211> LENGTH: 106
<212> TYPE: PRT
<213> ORGANISM: Mus musculus

<400> SEQUENCE: 8

Gln Ile Val Leu Thr Gln Ser Pro Ala Ile Met Ser Ala Ser Pro Gly
 1               5                  10                  15

Gln Lys Val Thr Ile Thr Cys Ser Ala Ser Ser Ser Val Asn Tyr Thr
                 20                  25                  30

Gln Trp Tyr Gln Gln Lys Leu Gly Ser Ser Pro Lys Leu Trp Ile Tyr
             35                  40                  45

Asp Ala Phe Lys Leu Ala Pro Gly Val Pro Ala Arg Phe Ser Gly Ser
 50                  55                  60

Gly Thr Gly Thr Ser Tyr Ser Leu Thr Ile Ser Ser Met Glu Ala Glu
 65                  70                  75                  80

Asp Ala Ala Ser Tyr Phe Cys His Gln Trp Ser Tyr Pro Trp Thr
                 85                  90                  95

Phe Gly Gly Gly Thr Lys Leu Glu Ile Lys
            100                 105

<210> SEQ ID NO 9
<211> LENGTH: 120
<212> TYPE: PRT
<213> ORGANISM: Mus musculus

<400> SEQUENCE: 9

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
                 20                  25                  30

Gly Met Ser Val Gly Trp Ile Arg Gln Pro Ser Gly Lys Gly Leu Glu
             35                  40                  45

Trp Leu Ala His Ile Trp Leu Asn Asp Asp Val Phe Phe Asn Pro Ala
 50                  55                  60

Leu Lys Arg Arg Leu Thr Ile Ser Lys Asp Thr Ser Asn Asn Gln Val
 65                  70                  75                  80

Phe Leu Gln Ile Ala Ser Val Val Thr Ala Asp Thr Ala Thr Tyr Tyr
                 85                  90                  95

Cys Val Arg Ala Asn Gly Tyr Leu Tyr Ala Leu Asp Tyr Trp Gly Gln
                100                 105                 110

Gly Ile Ser Val Thr Val Ser Ser
            115                 120

<210> SEQ ID NO 10
<211> LENGTH: 106
<212> TYPE: PRT
```

<213> ORGANISM: Mus musculus

<400> SEQUENCE: 10

Gln Ile Val Leu Thr Gln Ser Pro Ala Ile Met Ser Ala Ser Pro Gly
1               5                   10                  15
Gln Lys Val Thr Ile Thr Cys Ser Ala Ser Ser Val Asn Tyr Thr
            20                  25                  30
Gln Trp Tyr Gln Gln Lys Leu Gly Ser Ser Pro Lys Leu Trp Ile Tyr
        35                  40                  45
Asp Ala Phe Lys Leu Ala Pro Gly Val Pro Ala Arg Phe Ser Gly Ser
    50                  55                  60
Gly Thr Gly Thr Ser Tyr Ser Leu Thr Ile Ser Ser Met Glu Ala Glu
65                  70                  75                  80
Asp Ala Ala Ser Tyr Phe Cys His Gln Trp Ser Ser Tyr Pro Trp Thr
                85                  90                  95
Phe Gly Gly Gly Thr Lys Leu Glu Ile Lys
            100                 105

<210> SEQ ID NO 11
<211> LENGTH: 6
<212> TYPE: PRT
<213> ORGANISM: Mus musculus

<400> SEQUENCE: 11

Ser Ser Ser Val Gln Tyr
1               5

<210> SEQ ID NO 12
<211> LENGTH: 6
<212> TYPE: PRT
<213> ORGANISM: Mus musculus

<400> SEQUENCE: 12

Ser Ser Ser Val Ser Tyr
1               5

<210> SEQ ID NO 13
<211> LENGTH: 120
<212> TYPE: PRT
<213> ORGANISM: Artificial
<220> FEATURE:
<223> OTHER INFORMATION: VH humanized version of Tim3_0016 variant
      (0018) (= Tim3-0433)

<400> SEQUENCE: 13

Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Ser Val Gly Trp Ile Arg Gln Pro Pro Gly Lys Gly Leu Glu
        35                  40                  45
Trp Leu Ala His Ile Trp Leu Asn Asp Val Phe Phe Asn Pro Ala
    50                  55                  60
Leu Lys Ser Arg Leu Thr Ile Thr Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Val Arg Ala Asn Gly Tyr Leu Tyr Ala Leu Asp Tyr Trp Gly Gln
            100                 105                 110

Gly Thr Leu Val Thr Val Ser Ser
            115                 120

<210> SEQ ID NO 14
<211> LENGTH: 106
<212> TYPE: PRT
<213> ORGANISM: Artificial
<220> FEATURE:
<223> OTHER INFORMATION: VL humanized version of Tim3_0016 variant
      (0018) (= Tim3-0433)

<400> SEQUENCE: 14

Glu Thr Thr Leu Thr Gln Ser Pro Ala Phe Met Ser Ala Thr Pro Gly
1               5                   10                  15

Asp Lys Val Asn Ile Ala Cys Ser Ala Ser Ser Ser Val Ser Tyr Thr
            20                  25                  30

Gln Trp Tyr Gln Gln Lys Pro Gly Glu Ala Pro Lys Leu Trp Ile Tyr
        35                  40                  45

Asp Ala Phe Lys Leu Ala Pro Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys His Gln Trp Ser Ser Tyr Pro Trp Thr
                85                  90                  95

Phe Gly Gln Gly Thr Lys Leu Glu Ile Lys
            100                 105

<210> SEQ ID NO 15
<211> LENGTH: 120
<212> TYPE: PRT
<213> ORGANISM: Artificial
<220> FEATURE:
<223> OTHER INFORMATION: VH humanized version of Tim3_0016 variant
      (0018) (= Tim3-0434)

<400> SEQUENCE: 15

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Gly Leu Glu
        35                  40                  45

Trp Leu Ala His Ile Trp Leu Asn Asp Val Phe Phe Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Thr Leu Val Thr Val Ser Ser
            115                 120

<210> SEQ ID NO 16
<211> LENGTH: 106
<212> TYPE: PRT
<213> ORGANISM: Artificial
<220> FEATURE:
<223> OTHER INFORMATION: VL humanized version of Tim3_0016 variant
      (0018) (= Tim3-0434)

<400> SEQUENCE: 16

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Ser Tyr Thr
            20                  25                  30

Gln Trp Tyr Gln Gln Lys Pro Gly Lys Ala Pro Lys Leu Trp Ile Tyr
        35                  40                  45

Asp Ala Phe Lys Leu Ala Pro Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Phe Cys His Gln Trp Ser Ser Tyr Pro Trp Thr
                85                  90                  95

Phe Gly Gln Gly Thr Lys Leu Glu Ile Lys
            100                 105

<210> SEQ ID NO 17
<211> LENGTH: 7
<212> TYPE: PRT
<213> ORGANISM: Mus musculus

<400> SEQUENCE: 17

Gly Phe Asn Ile Lys Thr Thr
1               5

<210> SEQ ID NO 18
<211> LENGTH: 3
<212> TYPE: PRT
<213> ORGANISM: Mus musculus

<400> SEQUENCE: 18

Ala Asp Asp
1

<210> SEQ ID NO 19
<211> LENGTH: 8
<212> TYPE: PRT
<213> ORGANISM: Mus musculus

<400> SEQUENCE: 19

Phe Gly Tyr Val Ala Trp Phe Ala
1               5

<210> SEQ ID NO 20
<211> LENGTH: 7
<212> TYPE: PRT
<213> ORGANISM: Mus musculus

<400> SEQUENCE: 20

Ser Gln Ser Val Asp Asn Tyr
1               5

<210> SEQ ID NO 21
<211> LENGTH: 3
<212> TYPE: PRT
<213> ORGANISM: Mus musculus

<400> SEQUENCE: 21

Tyr Ala Ser
1

```
<210> SEQ ID NO 22
<211> LENGTH: 6
<212> TYPE: PRT
<213> ORGANISM: Mus musculus

<400> SEQUENCE: 22

His Tyr Ser Ser Pro Tyr
1               5

<210> SEQ ID NO 23
<211> LENGTH: 119
<212> TYPE: PRT
<213> ORGANISM: Mus musculus

<400> SEQUENCE: 23

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Asp Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ala Ala Ile Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Phe Ser Ala
        115

<210> SEQ ID NO 24
<211> LENGTH: 107
<212> TYPE: PRT
<213> ORGANISM: Mus musculus

<400> SEQUENCE: 24

Asn Ile Val Met Thr Pro Thr Pro Lys Phe Leu Pro Val Ser Ser Gly
1               5                   10                  15

Asp Arg Val Thr Met Thr Cys Arg Ala Ser Gln Ser Val Asp Asn Tyr
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu Ile Lys
            100                 105

<210> SEQ ID NO 25
<211> LENGTH: 119
<212> TYPE: PRT
<213> ORGANISM: Artificial
<220> FEATURE:
<223> OTHER INFORMATION: VH humanized version of Tim3-0028 (= Tim3-0438)
```

```
<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Thr Thr
            20                  25                  30

Tyr Met His Trp Val Arg Gln Ala Pro Gly Lys Gly Leu Glu Trp Val
        35                  40                  45

Gly Arg Ile Asp Pro Ala Asp Asp Asn Thr Lys Tyr Ala Pro Lys Phe
50                  55                  60

Gln Gly Lys Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Val Ser Ser
        115

<210> SEQ ID NO 26
<211> LENGTH: 107
<212> TYPE: PRT
<213> ORGANISM: Artificial
<220> FEATURE:
<223> OTHER INFORMATION: VL humanized version of Tim3-0028 (= Tim3-0438)

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Asp Asn Tyr
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Ile Gly Val Pro Asp Arg Phe Ser Gly
50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His Tyr Ser Ser Pro Tyr
                85                  90                  95

Thr Phe Gly Gln Gly Thr Lys Val Glu Ile Lys
            100                 105

<210> SEQ ID NO 27
<211> LENGTH: 119
<212> TYPE: PRT
<213> ORGANISM: Artificial
<220> FEATURE:
<223> OTHER INFORMATION: VH humanized version of Tim3-0028 (= Tim3-0443)

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Thr Thr
            20                  25                  30

Tyr Met His Trp Val Arg Gln Ala Pro Gly Lys Gly Leu Glu Trp Val
        35                  40                  45

Gly Arg Ile Asp Pro Ala Asp Asp Asn Thr Lys Tyr Ala Pro Lys Phe
50                  55                  60
```

```
Gln Gly Lys Ala Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Val Arg Asp Phe Gly Tyr Val Ala Trp Phe Ala Tyr Trp Gly Gln Gly
            100                 105                 110

Thr Leu Val Thr Phe Ser Ser
            115

<210> SEQ ID NO 28
<211> LENGTH: 107
<212> TYPE: PRT
<213> ORGANISM: Artificial
<220> FEATURE:
<223> OTHER INFORMATION: VL humanized version of Tim3-0028 (= Tim3-0443)

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Asp Asn Tyr
                20                  25                  30

Val Ala Trp Tyr Leu Gln Lys Pro Gly Gln Ser Pro Gln Leu Leu Ile
            35                  40                  45

Tyr Tyr Ala Ser Asn Arg Tyr Ile Gly Val Pro Asp Arg Phe Ser Gly
 50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Gln Gln His Tyr Ser Ser Pro Tyr
                 85                  90                  95

Thr Phe Gly Gln Gly Thr Lys Val Glu Ile Lys
            100                 105

<210> SEQ ID NO 29
<211> LENGTH: 7
<212> TYPE: PRT
<213> ORGANISM: Mus musculus

<400> SEQUENCE: 29

Gly Phe Asn Ile Lys Asp Tyr
1               5

<210> SEQ ID NO 30
<211> LENGTH: 3
<212> TYPE: PRT
<213> ORGANISM: Mus musculus

<400> SEQUENCE: 30

Glu Asp Gly
1

<210> SEQ ID NO 31
<211> LENGTH: 8
<212> TYPE: PRT
<213> ORGANISM: Mus musculus

<400> SEQUENCE: 31

His Gly Tyr Val Gly Trp Phe Ala
1               5

<210> SEQ ID NO 32
<211> LENGTH: 8
```

```
<212> TYPE: PRT
<213> ORGANISM: Mus musculus

<400> SEQUENCE: 32

Ala Ser Glu Asn Val Asp Thr Tyr
1               5

<210> SEQ ID NO 33
<211> LENGTH: 3
<212> TYPE: PRT
<213> ORGANISM: Mus musculus

<400> SEQUENCE: 33

Gly Ala Ser
1

<210> SEQ ID NO 34
<211> LENGTH: 6
<212> TYPE: PRT
<213> ORGANISM: Mus musculus

<400> SEQUENCE: 34

Ser Tyr Ser Tyr Pro Trp
1               5

<210> SEQ ID NO 35
<211> LENGTH: 119
<212> TYPE: PRT
<213> ORGANISM: Mus musculus

<400> SEQUENCE: 35

Glu Val Gln Leu Gln Gln Ser Gly Ala Glu Pro Leu Lys Pro Gly Ala
1               5                   10                  15

Ser Val Lys Leu Thr Cys Thr Thr Ser Gly Phe Asn Ile Lys Asp Tyr
            20                  25                  30

Tyr Ile His Trp Val Lys Gln Arg Ser Asp Gln Gly Leu Glu Trp Ile
        35                  40                  45

Gly Arg Ile Asp Pro Glu Asp Gly Glu Leu Ile Tyr Ala Pro Lys Phe
    50                  55                  60

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
            100                 105                 110

Thr Leu Val Thr Val Ser Ala
        115

<210> SEQ ID NO 36
<211> LENGTH: 107
<212> TYPE: PRT
<213> ORGANISM: Mus musculus

<400> SEQUENCE: 36

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45
```

```
Tyr Gly Ala Ser Asn Arg Tyr Thr Gly Val Pro Asp Arg Phe Thr Gly
            50                  55                  60
Ser Arg Ser Ala Thr Asp Phe Thr Leu Thr Ile Ser Ser Val Gln Ala
 65                  70                  75                  80
Glu Asp Leu Ala Val Tyr Tyr Cys Gly Gln Ser Tyr Ser Tyr Pro Trp
                 85                  90                  95
Thr Phe Gly Gly Gly Thr Lys Leu Glu Phe Arg
            100                 105
```

<210> SEQ ID NO 37
<211> LENGTH: 7
<212> TYPE: PRT
<213> ORGANISM: Mus Musculus

<400> SEQUENCE: 37

```
Gly Phe Ser Phe Ser Ser Tyr
 1               5
```

<210> SEQ ID NO 38
<211> LENGTH: 3
<212> TYPE: PRT
<213> ORGANISM: Mus Musculus

<400> SEQUENCE: 38

```
Gly Gly Arg
 1
```

<210> SEQ ID NO 39
<211> LENGTH: 9
<212> TYPE: PRT
<213> ORGANISM: Mus Musculus

<400> SEQUENCE: 39

```
Thr Gly Arg Val Tyr Phe Ala Leu Asp
 1               5
```

<210> SEQ ID NO 40
<211> LENGTH: 11
<212> TYPE: PRT
<213> ORGANISM: Mus Musculus

<400> SEQUENCE: 40

```
Ser Glu Ser Val Asp Thr Ser Asp Asn Ser Phe
 1               5                  10
```

<210> SEQ ID NO 41
<211> LENGTH: 3
<212> TYPE: PRT
<213> ORGANISM: Mus Musculus

<400> SEQUENCE: 41

```
Arg Ser Ser
 1
```

<210> SEQ ID NO 42
<211> LENGTH: 6
<212> TYPE: PRT
<213> ORGANISM: Mus Musculus

<400> SEQUENCE: 42

```
Asn Tyr Asp Val Pro Trp
 1               5
```

<210> SEQ ID NO 43
<211> LENGTH: 120
<212> TYPE: PRT
<213> ORGANISM: Mus Musculus

<400> SEQUENCE: 43

Glu Val Ile Leu Val Glu Ser Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser
        115                 120

<210> SEQ ID NO 44
<211> LENGTH: 111
<212> TYPE: PRT
<213> ORGANISM: Mus Musculus

<400> SEQUENCE: 44

Lys Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Thr Ser
            20                  25                  30

Asp Asn Ser Phe Ile His Trp Tyr Gln Gln Arg Pro Gly Gln Ser Pro
        35                  40                  45

Lys Leu Leu Ile Tyr Arg Ser Ser Thr Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Asn Tyr
                85                  90                  95

Asp Val Pro Trp Thr Phe Gly Gly Gly Thr Lys Leu Glu Ile Lys
            100                 105                 110

<210> SEQ ID NO 45
<211> LENGTH: 120
<212> TYPE: PRT
<213> ORGANISM: Artificial
<220> FEATURE:
<223> OTHER INFORMATION: humanized variant -heavy chain variable domain
      VH of PD1-0103_01

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

```
Ala Thr Ile Ser Gly Gly Arg Asp Ile Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Leu Leu Thr Gly Arg Val Tyr Phe Ala Leu Asp Ser Trp Gly Gln
            100                 105                 110

Gly Thr Leu Val Thr Val Ser Ser
            115                 120

<210> SEQ ID NO 46
<211> LENGTH: 111
<212> TYPE: PRT
<213> ORGANISM: Artificial
<220> FEATURE:
<223> OTHER INFORMATION: humanized variant -light chain variable domain
      VL of PD1-0103_01

<400> SEQUENCE: 46

Asp Ile Val Met Thr Gln Ser Pro Asp Ser Leu Ala Val Ser Leu Gly
 1               5                  10                  15

Glu Arg Ala Thr Ile Asn Cys Lys Ala Ser Glu Ser Val Asp Thr Ser
                20                  25                  30

Asp Asn Ser Phe Ile His Trp Tyr Gln Gln Lys Pro Gly Gln Ser Pro
            35                  40                  45

Lys Leu Leu Ile Tyr Arg Ser Ser Thr Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Tyr
                 85                  90                  95

Asp Val Pro Trp Thr Phe Gly Gln Gly Thr Lys Val Glu Ile Lys
            100                 105                 110

<210> SEQ ID NO 47
<211> LENGTH: 111
<212> TYPE: PRT
<213> ORGANISM: Artificial
<220> FEATURE:
<223> OTHER INFORMATION: humanized variant -light chain variable domain
      VL of PD1-0103_02

<400> SEQUENCE: 47

Asp Val Val Met Thr Gln Ser Pro Leu Ser Leu Pro Val Thr Leu Gly
 1               5                  10                  15

Gln Pro Ala Ser Ile Ser Cys Arg Ala Ser Glu Ser Val Asp Thr Ser
                20                  25                  30

Asp Asn Ser Phe Ile His Trp Tyr Gln Gln Arg Pro Gly Gln Ser Pro
            35                  40                  45

Arg Leu Leu Ile Tyr Arg Ser Ser Thr Leu Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Asn Tyr
                 85                  90                  95

Asp Val Pro Trp Thr Phe Gly Gln Gly Thr Lys Val Glu Ile Lys
            100                 105                 110
```

<210> SEQ ID NO 48
<211> LENGTH: 111
<212> TYPE: PRT
<213> ORGANISM: Artificial
<220> FEATURE:
<223> OTHER INFORMATION: humanized variant -light chain variable domain
      VL of PD1-0103_03

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Arg Leu Leu Ile Tyr Arg Ser Ser Thr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Asn Tyr
                85                  90                  95

Asp Val Pro Trp Thr Phe Gly Gln Gly Thr Lys Val Glu Ile Lys
            100                 105                 110

<210> SEQ ID NO 49
<211> LENGTH: 111
<212> TYPE: PRT
<213> ORGANISM: Artificial
<220> FEATURE:
<223> OTHER INFORMATION: humanized variant -light chain variable domain
      VL of PD1-0103_04

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Arg Leu Leu Ile Tyr Arg Ser Ser Thr Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Asn Tyr
                85                  90                  95

Asp Val Pro Trp Thr Phe Gly Gln Gly Thr Lys Val Glu Ile Lys
            100                 105                 110

<210> SEQ ID NO 50
<211> LENGTH: 443
<212> TYPE: PRT
<213> ORGANISM: Artificial
<220> FEATURE:
<223> OTHER INFORMATION: heavy chain 1 of 1+1 PD1TIM3_0389 (based on
      chimeric PD1-0103 / Tim3-0028)

<400> SEQUENCE: 50

Lys Ile Val Leu Thr Gln Ser Pro Ala Ser Leu Pro Val Ser Leu Gly
1               5                   10                  15

```
Gln Arg Ala Thr Ile Ser Cys Arg Ala Ser Glu Ser Val Asp Thr Ser
             20                  25                  30
Asp Asn Ser Phe Ile His Trp Tyr Gln Gln Arg Pro Gly Gln Ser Pro
         35                  40                  45
Lys Leu Leu Ile Tyr Arg Ser Ser Thr Leu Glu Ser Gly Val Pro Ala
     50                  55                  60
Arg Phe Ser Gly Ser Gly Ser Arg Thr Asp Phe Thr Leu Thr Ile Asp
 65                  70                  75                  80
Pro Val Glu Ala Asp Asp Val Ala Thr Tyr Tyr Cys Gln Gln Asn Tyr
                 85                  90                  95
Asp Val Pro Trp Thr Phe Gly Gly Gly Thr Lys Leu Glu Ile Lys Ser
             100                 105                 110
Ser Ala Ser Thr Lys Gly Pro Ser Val Phe Pro Leu Ala Pro Ser Ser
         115                 120                 125
Lys Ser Thr Ser Gly Gly Thr Ala Ala Leu Gly Cys Leu Val Lys Asp
     130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
        195                 200                 205
Lys Lys Val Glu Pro Lys Ser Cys Asp Lys Thr His Thr Cys Pro Pro
    210                 215                 220
Cys Pro Ala Pro Glu Ala Ala Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
        275                 280                 285
Glu Glu Gln Tyr Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Ala Leu Gly Ala Pro Ile Glu Lys Thr Ile Ser Lys Ala Lys
                325                 330                 335
Gly Gln Pro Arg Glu Pro Gln Val Tyr Thr Leu Pro Pro Cys Arg Asp
            340                 345                 350
Glu Leu Thr Lys Asn Gln Val Ser Leu Trp Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
```

<210> SEQ ID NO 51
<211> LENGTH: 449
<212> TYPE: PRT
<213> ORGANISM: Artificial
<220> FEATURE:
<223> OTHER INFORMATION: heavy chain 2 of 1+1 PD1TIM3_0389

<400> SEQUENCE: 51

```
Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Asp Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Ala Ala Ile Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Phe Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
```

```
                     355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
                435                 440                 445

Lys

<210> SEQ ID NO 52
<211> LENGTH: 227
<212> TYPE: PRT
<213> ORGANISM: Artificial
<220> FEATURE:
<223> OTHER INFORMATION: light chain 1 of 1+1 PD1TIM3_0389

<400> SEQUENCE: 52

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 53
<211> LENGTH: 214
<212> TYPE: PRT
<213> ORGANISM: Artificial
```

<220> FEATURE:
<223> OTHER INFORMATION: light chain 2 of 1+1 PD1TIM3_0389

<400> SEQUENCE: 53

Asn Ile Val Met Thr Pro Thr Pro Lys Phe Leu Pro Val Ser Ser Gly
1               5                   10                  15

Asp Arg Val Thr Met Thr Cys Arg Ala Ser Gln Ser Val Asp Asn Tyr
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Ile Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 443
<212> TYPE: PRT
<213> ORGANISM: Artificial
<220> FEATURE:
<223> OTHER INFORMATION: heavy chain 1 of 1+1 PD1TIM3_0168 (based on
      chimeric PD1-0103 / Tim3-0018)

<400> SEQUENCE: 54

Lys Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Thr Ser
            20                  25                  30

Asp Asn Ser Phe Ile His Trp Tyr Gln Gln Arg Pro Gly Gln Ser Pro
        35                  40                  45

Lys Leu Leu Ile Tyr Arg Ser Ser Thr Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Asn Tyr
                85                  90                  95

Asp Val Pro Trp Thr Phe Gly Gly Gly Thr Lys Leu Glu Ile Lys Ser
            100                 105                 110

-continued

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 55
<211> LENGTH: 450
<212> TYPE: PRT
<213> ORGANISM: Artificial
<220> FEATURE:
<223> OTHER INFORMATION: heavy chain 2 of 1+1 PD1TIM3_0168

<400> SEQUENCE: 55

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

```
Gly Met Ser Val Gly Trp Ile Arg Gln Pro Ser Gly Lys Gly Leu Glu
            35                  40                  45

Trp Leu Ala His Ile Trp Leu Asn Asp Asp Val Phe Phe Asn Pro Ala
 50                  55                  60

Leu Lys Arg Arg Leu Thr Ile Ser Lys Asp Thr Ser Asn Asn Gln Val
 65                  70                  75                  80

Phe Leu Gln Ile Ala Ser Val Val Thr Ala Asp Thr Ala Thr Tyr Tyr
                 85                  90                  95

Cys Val Arg Ala Asn Gly Tyr Leu Tyr Ala Leu Asp Tyr Trp Gly Gln
            100                 105                 110

Gly Ile Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Glu Pro Lys Ser Cys Asp
            210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn Arg Phe Thr Gln Lys Ser Leu Ser Leu Ser Pro
            435                 440                 445

Gly Lys
```

<210> SEQ ID NO 56
<211> LENGTH: 227
<212> TYPE: PRT
<213> ORGANISM: Artificial
<220> FEATURE:
<223> OTHER INFORMATION: light chain 1 of 1+1 PD1TIM3_0168

<400> SEQUENCE: 56

```
Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225
```

<210> SEQ ID NO 57
<211> LENGTH: 213
<212> TYPE: PRT
<213> ORGANISM: Artificial
<220> FEATURE:
<223> OTHER INFORMATION: light chain 2 of 1+1 PD1TIM3_0168

<400> SEQUENCE: 57

```
Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Thr
            20                  25                  30

Gln Trp Tyr Gln Gln Lys Leu Gly Ser Ser Pro Lys Leu Trp Ile Tyr
        35                  40                  45

Asp Ala Phe Lys Leu Ala Pro Gly Val Pro Ala Arg Phe Ser Gly Ser
    50                  55                  60
```

```
Gly Thr Gly Thr Ser Tyr Ser Leu Thr Ile Ser Ser Met Glu Ala Glu
 65                  70                  75                  80

Asp Ala Ala Ser Tyr Phe Cys His Gln Trp Ser Ser Tyr Pro Trp Thr
                 85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 58
<211> LENGTH: 443
<212> TYPE: PRT
<213> ORGANISM: Artificial
<220> FEATURE:
<223> OTHER INFORMATION: heavy chain 1 of 1+1 PD1TIM3_0166: ( based on chimeric PD1-0103 / Tim3-0038

<400> SEQUENCE: 58

```
Lys Ile Val Leu Thr Gln Ser Pro Ala Ser Leu Pro Val Ser Leu Gly
 1               5                  10                  15

Gln Arg Ala Thr Ile Ser Cys Arg Ala Ser Glu Ser Val Asp Thr Ser
             20                  25                  30

Asp Asn Ser Phe Ile His Trp Tyr Gln Gln Arg Pro Gly Gln Ser Pro
         35                  40                  45

Lys Leu Leu Ile Tyr Arg Ser Ser Thr Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Val Ala Thr Tyr Tyr Cys Gln Gln Asn Tyr
                 85                  90                  95

Asp Val Pro Trp Thr Phe Gly Gly Gly Thr Lys Leu Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205
```

Lys Lys Val Glu Pro Lys Ser Cys Asp Lys Thr His Thr Cys Pro Pro
            210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
            325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 59
<211> LENGTH: 449
<212> TYPE: PRT
<213> ORGANISM: Artificial
<220> FEATURE:
<223> OTHER INFORMATION: heavy chain 2 of 1+1 PD1TIM3_0166

<400> SEQUENCE: 59

Glu Val Gln Leu Gln Gln Ser Gly Ala Glu Pro Leu Lys Pro Gly Ala
1               5                   10                  15

Ser Val Lys Leu Thr Cys Thr Thr Ser Gly Phe Asn Ile Lys Asp Tyr
            20                  25                  30

Tyr Ile His Trp Val Lys Gln Arg Ser Asp Gln Gly Leu Glu Trp Ile
        35                  40                  45

Gly Arg Ile Asp Pro Glu Asp Gly Glu Leu Ile Tyr Ala Pro Lys Phe
    50                  55                  60

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
            130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Phe Thr Gln Lys Ser Leu Ser Leu Ser Pro Gly
            435                 440                 445

Lys

<210> SEQ ID NO 60
<211> LENGTH: 227
<212> TYPE: PRT
<213> ORGANISM: Artificial
<220> FEATURE:
<223> OTHER INFORMATION: light chain 1 of 1+1 PD1TIM3_0166

<400> SEQUENCE: 60

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Arg Asp Ile Tyr Tyr Pro Asp Ser Val
 50                  55                  60

Lys Gly Arg Phe Thr Ile Ser Arg Asp Asn Ala Lys Asn Thr Leu Tyr
 65                  70                  75                  80

Leu Glu Met Ser Ser Leu Met Ser Glu Asp Thr Ala Leu Tyr Tyr Cys
                 85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
            115                 120                 125

Phe Ile Phe Pro Pro Ser Asp Glu Gln Leu Lys Ser Gly Thr Ala Ser
130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 61
<211> LENGTH: 214
<212> TYPE: PRT
<213> ORGANISM: Artificial
<220> FEATURE:
<223> OTHER INFORMATION: light chain 2 of 1+1 PD1TIM3_0166

<400> SEQUENCE: 61

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
 50                  55                  60

Ser Arg Ser Ala Thr Asp Phe Thr Leu Thr Ile Ser Ser Val Gln Ala
65                  70                  75                  80

Glu Asp Leu Ala Val Tyr Tyr Cys Gly Gln Ser Tyr Ser Tyr Pro Trp
                85                  90                  95

Thr Phe Gly Gly Gly Thr Lys Leu Glu Phe Arg Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 443
<212> TYPE: PRT
<213> ORGANISM: Artificial
<220> FEATURE:
<223> OTHER INFORMATION: heavy chain 1 of 1+1 PD1TIM3_0476: (based on
      humanized PD1-0103_0312)/ Tim3-0438)

<400> SEQUENCE: 62

Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300
```

```
Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 63
<211> LENGTH: 449
<212> TYPE: PRT
<213> ORGANISM: Artificial
<220> FEATURE:
<223> OTHER INFORMATION: heavy chain 2 of 1+1 PD1TIM3_0476

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Thr Thr
            20                  25                  30

Tyr Met His Trp Val Arg Gln Ala Pro Gly Lys Gly Leu Glu Trp Val
        35                  40                  45

Gly Arg Ile Asp Pro Ala Asp Asp Asn Thr Lys Tyr Ala Pro Lys Phe
    50                  55                  60

Gln Gly Lys Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Val Arg Asp Phe Gly Tyr Val Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220
```

```
Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 64
<211> LENGTH: 227
<212> TYPE: PRT
<213> ORGANISM: Artificial
<220> FEATURE:
<223> OTHER INFORMATION: light chain 1 of 1+1 PD1TIM3_0476

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Val Ala Ala Pro Ser Val
        115                 120                 125
```

```
Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
            195                 200                 205

Val Thr His Gln Gly Leu Ser Ser Pro Val Thr Lys Ser Phe Asn Arg
210                 215                 220

Gly Glu Cys
225

<210> SEQ ID NO 65
<211> LENGTH: 214
<212> TYPE: PRT
<213> ORGANISM: Artificial
<220> FEATURE:
<223> OTHER INFORMATION: light chain 2 of 1+1 PD1TIM3_0476

<400> SEQUENCE: 65

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Ser Val Asp Asn Tyr
            20                  25                  30

Val Ala Trp Tyr Leu Gln Lys Pro Gly Gln Ser Pro Gln Leu Leu Ile
        35                  40                  45

Tyr Tyr Ala Ser Asn Arg Tyr Ile Gly Val Pro Asp Arg Phe Ser Gly
50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln His Tyr Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 443
<212> TYPE: PRT
<213> ORGANISM: Artificial
<220> FEATURE:
```

<223> OTHER INFORMATION: heavy chain 1 of 1+1 PD1TIM3_0477: (based on humanized PD1-0103_0312) / Tim3-0434)

<400> SEQUENCE: 66

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Glu Ser Val Asp Thr Ser
            20                  25                  30

Asp Asn Ser Phe Ile His Trp Tyr Gln Gln Lys Pro Gly Gln Ser Pro
        35                  40                  45

Lys Leu Leu Ile Tyr Arg Ser Ser Thr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Asp Val Pro Trp Thr Phe Gly Gln Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Gly Ala Pro Ile Glu Lys Thr Ile Ser Lys Ala Lys
                325                 330                 335

Gly Gln Pro Arg Glu Pro Gln Val Tyr Thr Leu Pro Pro Cys Arg Asp
            340                 345                 350

Glu Leu Thr Lys Asn Gln Val Ser Leu Trp Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 67
<211> LENGTH: 450
<212> TYPE: PRT
<213> ORGANISM: Artificial
<220> FEATURE:
<223> OTHER INFORMATION: heavy chain 2 of 1+1 PD1TIM3_0477

<400> SEQUENCE: 67

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Gly Leu Glu
        35                  40                  45

Trp Leu Ala His Ile Trp Leu Asn Asp Asp Val Phe Phe Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Ala Asn Gly Tyr Leu Tyr Ala Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Glu Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

-continued

```
Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 68
<211> LENGTH: 227
<212> TYPE: PRT
<213> ORGANISM: Artificial
<220> FEATURE:
<223> OTHER INFORMATION: light chain 1 of 1+1 PD1TIM3_0477

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Leu Leu Thr Gly Arg Val Tyr Phe Ala Leu Asp Ser Trp Gly Gln
            100                 105                 110

Gly Thr Leu Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220
```

Gly Glu Cys
225

<210> SEQ ID NO 69
<211> LENGTH: 213
<212> TYPE: PRT
<213> ORGANISM: Artificial
<220> FEATURE:
<223> OTHER INFORMATION: light chain 2 of 1+1 PD1TIM3_0477

<400> SEQUENCE: 69

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Ser Tyr Thr
            20                  25                  30

Gln Trp Tyr Gln Gln Lys Pro Gly Lys Ala Pro Lys Leu Trp Ile Tyr
        35                  40                  45

Asp Ala Phe Lys Leu Ala Pro Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Phe Cys His Gln Trp Ser Ser Tyr Pro Trp Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Arg Lys Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 70
<211> LENGTH: 685
<212> TYPE: PRT
<213> ORGANISM: Artificial
<220> FEATURE:
<223> OTHER INFORMATION: heavy chain of 2+2 PD1TIM3_0358: chimeric
      PD1-0103 / Tim3-0028

<400> SEQUENCE: 70

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Thr Thr
            20                  25                  30

Tyr Met His Trp Val Lys Gln Arg Pro Glu Gln Gly Leu Glu Trp Ile
        35                  40                  45

Gly Arg Ile Asp Pro Ala Asp Asp Asn Thr Lys Tyr Ala Pro Lys Phe
    50                  55                  60

-continued

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Ala Ala Ile Tyr Tyr Cys
             85                  90                  95

Val Arg Asp Phe Gly Tyr Val Ala Trp Phe Ala Tyr Trp Gly Gln Gly
            100                 105                 110

Thr Leu Val Thr Phe Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Lys
            210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Gly Gly Gly Gly Ser Gly Gly Gly Gly Ser Gly Gly Gly Gly Ser Gly
            450                 455                 460

Gly Gly Gly Ser Lys Ile Val Leu Thr Gln Ser Pro Ala Ser Leu Pro
465                 470                 475                 480

Val Ser Leu Gly Gln Arg Ala Thr Ile Ser Cys Arg Ala Ser Glu Ser

```
                    485                 490                 495
Val Asp Thr Ser Asp Asn Ser Phe Ile His Trp Tyr Gln Gln Arg Pro
                500                 505                 510

Gly Gln Ser Pro Lys Leu Leu Ile Tyr Arg Ser Ser Thr Leu Glu Ser
                515                 520                 525

Gly Val Pro Ala Arg Phe Ser Gly Ser Gly Ser Arg Thr Asp Phe Thr
                530                 535                 540

Leu Thr Ile Asp Pro Val Glu Ala Asp Val Ala Thr Tyr Tyr Cys
545                 550                 555                 560

Gln Gln Asn Tyr Asp Val Pro Trp Thr Phe Gly Gly Gly Thr Lys Leu
                565                 570                 575

Glu Ile Lys Ser Ser Ala Ser Thr Lys Gly Pro Ser Val Phe Pro Leu
                580                 585                 590

Ala Pro Ser Ser Lys Ser Thr Ser Gly Gly Thr Ala Ala Leu Gly Cys
                595                 600                 605

Leu Val Lys Asp Tyr Phe Pro Glu Pro Val Thr Val Ser Trp Asn Ser
                610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
                645                 650                 655

Leu Gly Thr Gln Thr Tyr Ile Cys Asn Val Asn His Lys Pro Ser Asn
                660                 665                 670

Thr Lys Val Asp Lys Lys Val Glu Pro Lys Ser Cys Asp
                675                 680                 685

<210> SEQ ID NO 71
<211> LENGTH: 200
<212> TYPE: PRT
<213> ORGANISM: Artificial
<220> FEATURE:
<223> OTHER INFORMATION: light chain 1 of 2+2 PD1TIM3_0358

<400> SEQUENCE: 71

Asn Ile Val Met Thr Pro Thr Pro Lys Phe Leu Pro Val Ser Ser Gly
1               5                   10                  15

Asp Arg Val Thr Met Thr Cys Arg Ala Ser Gln Ser Val Asp Asn Tyr
                20                  25                  30

Val Ala Trp Tyr Gln Gln Lys Pro Gly Gln Ser Pro Lys Leu Leu Ile
                35                  40                  45

Tyr Tyr Ala Ser Asn Arg Tyr Ile Gly Val Pro Asp Arg Phe Thr Gly
                50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Tyr
                85                  90                  95

Thr Phe Gly Ser Gly Thr Lys Leu Glu Ile Lys Arg Thr Val Ala Ala
                100                 105                 110

Pro Ser Val Phe Ile Phe Pro Pro Ser Asp Arg Lys Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly
        195                 200

<210> SEQ ID NO 72
<211> LENGTH: 227
<212> TYPE: PRT
<213> ORGANISM: Artificial
<220> FEATURE:
<223> OTHER INFORMATION: light chain 2 of 2+2 PD1TIM3_0358

<400> SEQUENCE: 72

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 73
<211> LENGTH: 686
<212> TYPE: PRT
<213> ORGANISM: Artificial
<220> FEATURE:
<223> OTHER INFORMATION: heavy chain of 2+2 PD1TIM3_0359: chimeric
      PD1-0103 / Tim3-0018

<400> SEQUENCE: 73

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30
```

-continued

Gly Met Ser Val Gly Trp Ile Arg Gln Pro Ser Gly Lys Gly Leu Glu
         35                  40                  45

Trp Leu Ala His Ile Trp Leu Asn Asp Asp Val Phe Phe Asn Pro Ala
 50                  55                  60

Leu Lys Arg Arg Leu Thr Ile Ser Lys Asp Thr Ser Asn Asn Gln Val
 65                  70                  75                  80

Phe Leu Gln Ile Ala Ser Val Val Thr Ala Asp Thr Ala Thr Tyr Tyr
                 85                  90                  95

Cys Val Arg Ala Asn Gly Tyr Leu Tyr Ala Leu Asp Tyr Trp Gly Gln
                100                 105                 110

Gly Ile Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Glu Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Glu Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Ser Gly Gly Gly Ser Gly Gly Gly Ser
450             455             460

Gly Gly Gly Ser Lys Ile Val Leu Thr Gln Ser Pro Ala Ser Leu
465             470             475             480

Pro Val Ser Leu Gly Gln Arg Ala Thr Ile Ser Cys Arg Ala Ser Glu
            485             490             495

Ser Val Asp Thr Ser Asp Asn Ser Phe Ile His Trp Tyr Gln Gln Arg
            500             505             510

Pro Gly Gln Ser Pro Lys Leu Leu Ile Tyr Arg Ser Ser Thr Leu Glu
            515             520             525

Ser Gly Val Pro Ala Arg Phe Ser Gly Ser Gly Ser Arg Thr Asp Phe
530             535             540

Thr Leu Thr Ile Asp Pro Val Glu Ala Asp Asp Val Ala Thr Tyr Tyr
545             550             555             560

Cys Gln Gln Asn Tyr Asp Val Pro Trp Thr Phe Gly Gly Gly Thr Lys
            565             570             575

Leu Glu Ile Lys Ser Ser Ala Ser Thr Lys Gly Pro Ser Val Phe Pro
            580             585             590

Leu Ala Pro Ser Ser Lys Ser Thr Ser Gly Gly Thr Ala Ala Leu Gly
            595             600             605

Cys Leu Val Lys Asp Tyr Phe Pro Glu Pro Val Thr Val Ser Trp Asn
610             615             620

Ser Gly Ala Leu Thr Ser Gly Val His Thr Phe Pro Ala Val Leu Gln
625             630             635             640

Ser Ser Gly Leu Tyr Ser Leu Ser Ser Val Val Thr Val Pro Ser Ser
            645             650             655

Ser Leu Gly Thr Gln Thr Tyr Ile Cys Asn Val Asn His Lys Pro Ser
            660             665             670

Asn Thr Lys Val Asp Lys Lys Val Glu Pro Lys Ser Cys Asp
            675             680             685

<210> SEQ ID NO 74
<211> LENGTH: 213
<212> TYPE: PRT
<213> ORGANISM: Artificial
<220> FEATURE:
<223> OTHER INFORMATION: light chain 1 of 2+2 PD1TIM3_0359

<400> SEQUENCE: 74

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Ser Val Asn Tyr Thr
                20                  25                  30

Gln Trp Tyr Gln Gln Lys Leu Gly Ser Ser Pro Lys Leu Trp Ile Tyr
            35                  40                  45

Asp Ala Phe Lys Leu Ala Pro Gly Val Pro Ala Arg Phe Ser Gly Ser
        50                  55                  60

Gly Thr Gly Thr Ser Tyr Ser Leu Thr Ile Ser Ser Met Glu Ala Glu
65                  70                  75                  80

Asp Ala Ala Ser Tyr Phe Cys His Gln Trp Ser Ser Tyr Pro Trp Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Arg Lys Leu Lys Ser Gly Thr
            115                 120                 125

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 75
<211> LENGTH: 227
<212> TYPE: PRT
<213> ORGANISM: Artificial
<220> FEATURE:
<223> OTHER INFORMATION: light chain 2 of 2+2 PD1TIM3_0359

<400> SEQUENCE: 75

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
                20                  25                  30

Thr Met Ser Trp Val Arg Gln Thr Pro Glu Lys Arg Leu Asp Trp Val
            35                  40                  45

Ala Thr Ile Ser Gly Gly Gly Arg Asp Ile Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 76
<211> LENGTH: 685
<212> TYPE: PRT
<213> ORGANISM: Artificial
<220> FEATURE:
```

<223> OTHER INFORMATION: heavy chain of 2+2 PD1TIM3_0321: chimeric
PD1-0103 / Tim3-0038

<400> SEQUENCE: 76

Glu Val Gln Leu Gln Gln Ser Gly Ala Glu Pro Leu Lys Pro Gly Ala
1               5                   10                  15

Ser Val Lys Leu Thr Cys Thr Thr Ser Gly Phe Asn Ile Lys Asp Tyr
            20                  25                  30

Tyr Ile His Trp Val Lys Gln Arg Ser Asp Gln Gly Leu Glu Trp Ile
        35                  40                  45

Gly Arg Ile Asp Pro Glu Asp Gly Glu Leu Ile Tyr Ala Pro Lys Phe
    50                  55                  60

Gln Asp Lys Ala Thr Ile Thr Val Asp Thr Ser Ser Asn Ile Ala Tyr
65                  70                  75                  80

Leu Gln Leu Asn Ser Leu Thr Ser Glu Asp Thr Ala Val Tyr Tyr Cys
                85                  90                  95

Ser Arg Asp His Gly Tyr Val Gly Trp Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Gly Gly Gly Gly Ser Gly Gly Gly Ser Gly Gly Gly Gly Ser Gly
450                 455                 460

Gly Gly Gly Ser Lys Ile Val Leu Thr Gln Ser Pro Ala Ser Leu Pro
465                 470                 475                 480

Val Ser Leu Gly Gln Arg Ala Thr Ile Ser Cys Arg Ala Ser Glu Ser
                485                 490                 495

Val Asp Thr Ser Asp Asn Ser Phe Ile His Trp Tyr Gln Gln Arg Pro
            500                 505                 510

Gly Gln Ser Pro Lys Leu Leu Ile Tyr Arg Ser Ser Thr Leu Glu Ser
        515                 520                 525

Gly Val Pro Ala Arg Phe Ser Gly Ser Gly Ser Arg Thr Asp Phe Thr
    530                 535                 540

Leu Thr Ile Asp Pro Val Glu Ala Asp Val Ala Thr Tyr Tyr Cys
545                 550                 555                 560

Gln Gln Asn Tyr Asp Val Pro Trp Thr Phe Gly Gly Gly Thr Lys Leu
                565                 570                 575

Glu Ile Lys Ser Ser Ala Ser Thr Lys Gly Pro Ser Val Phe Pro Leu
            580                 585                 590

Ala Pro Ser Ser Lys Ser Thr Ser Gly Gly Thr Ala Ala Leu Gly Cys
        595                 600                 605

Leu Val Lys Asp Tyr Phe Pro Glu Pro Val Thr Val Ser Trp Asn Ser
    610                 615                 620

Gly Ala Leu Thr Ser Gly Val His Thr Phe Pro Ala Val Leu Gln Ser
625                 630                 635                 640

Ser Gly Leu Tyr Ser Leu Ser Ser Val Val Thr Val Pro Ser Ser Ser
                645                 650                 655

Leu Gly Thr Gln Thr Tyr Ile Cys Asn Val Asn His Lys Pro Ser Asn
            660                 665                 670

Thr Lys Val Asp Lys Lys Val Glu Pro Lys Ser Cys Asp
        675                 680                 685

<210> SEQ ID NO 77
<211> LENGTH: 214
<212> TYPE: PRT
<213> ORGANISM: Artificial
<220> FEATURE:
<223> OTHER INFORMATION: light chain 1 of 2+2 PD1TIM3_0321

<400> SEQUENCE: 77

Asn Val Val Met Thr Gln Ser Pro Lys Ser Met Ile Met Ser Val Gly
1               5                   10                  15

Gln Arg Val Thr Leu Asn Cys Lys Ala Ser Glu Asn Val Asp Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Arg Ser Ala Thr Asp Phe Thr Leu Thr Ile Ser Ser Val Gln Ala
65                  70                  75                  80

-continued

Glu Asp Leu Ala Val Tyr Tyr Cys Gly Gln Ser Tyr Ser Tyr Pro Trp
                85                  90                  95

Thr Phe Gly Gly Gly Thr Lys Leu Glu Phe Arg Arg Thr Val Ala Ala
            100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 78
<211> LENGTH: 227
<212> TYPE: PRT
<213> ORGANISM: Artificial
<220> FEATURE:
<223> OTHER INFORMATION: light chain 2 of 2+2 PD1TIM3_0321

<400> SEQUENCE: 78

Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Thr Met Ser Trp Val Arg Gln Thr Pro Glu Lys Arg Leu Asp Trp Val
        35                  40                  45

Ala Thr Ile Ser Gly Gly Gly Arg Asp Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Met Ser Glu Asp Thr Ala Leu Tyr Tyr Cys
                85                  90                  95

Val Leu Leu Thr Gly Arg Val Tyr Phe Ala Leu Asp Ser Trp Gly Gln
            100                 105                 110

Gly Thr Ser Val Thr Val Ser Ser Ala Ser Val Ala Ala Pro Ser Val
            115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
            165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
            195                 200                 205

Val Thr His Gln Gly Leu Ser Ser Pro Val Thr Lys Ser Phe Asn Arg
    210                 215                 220

Gly Glu Cys
225

<210> SEQ ID NO 79
<211> LENGTH: 107
<212> TYPE: PRT
<213> ORGANISM: Homo Sapiens

<400> SEQUENCE: 79

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 80
<211> LENGTH: 105
<212> TYPE: PRT
<213> ORGANISM: Homo Sapiens

<400> SEQUENCE: 80

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 81
<211> LENGTH: 330
<212> TYPE: PRT
<213> ORGANISM: Homo Sapiens

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 82
<211> LENGTH: 330
<212> TYPE: PRT
<213> ORGANISM: homo sapiens

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                    85                  90                  95

```
Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 330
<212> TYPE: PRT
<213> ORGANISM: homo sapiens

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
```

```
                130             135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Gly Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 84
<211> LENGTH: 327
<212> TYPE: PRT
<213> ORGANISM: Homo Sapiens

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

Asn Ser Thr Tyr Arg Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 280
<212> TYPE: PRT
<213> ORGANISM: homo sapiens

<400> SEQUENCE: 85

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
                100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
        130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly Ile Tyr Ile Gly Ala Gly Ile Cys Ala Gly Leu
            180                 185                 190

Ala Leu Ala Leu Ile Phe Gly Ala Leu Ile Phe Lys Trp Tyr Ser His
        195                 200                 205

Ser Lys Glu Lys Ile Gln Asn Leu Ser Leu Ile Ser Leu Ala Asn Leu
        210                 215                 220

```
Pro Pro Ser Gly Leu Ala Asn Ala Val Ala Glu Gly Ile Arg Ser Glu
225                 230                 235                 240

Glu Asn Ile Tyr Thr Ile Glu Glu Asn Val Tyr Glu Val Glu Pro
                245                 250                 255

Asn Glu Tyr Tyr Cys Tyr Val Ser Ser Arg Gln Gln Pro Ser Gln Pro
            260                 265                 270

Leu Gly Cys Arg Phe Ala Met Pro
        275                 280

<210> SEQ ID NO 86
<211> LENGTH: 181
<212> TYPE: PRT
<213> ORGANISM: homo sapiens

<400> SEQUENCE: 86

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
        115                 120                 125

Arg Met Leu Thr Thr Arg Gly His Gly Pro Ala Glu Thr Gln Thr Leu
    130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
            180

<210> SEQ ID NO 87
<211> LENGTH: 268
<212> TYPE: PRT
<213> ORGANISM: Homo Sapiens

<400> SEQUENCE: 87

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80
```

-continued

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265

<210> SEQ ID NO 88
<211> LENGTH: 150
<212> TYPE: PRT
<213> ORGANISM: Homo Sapiens

<400> SEQUENCE: 88

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 89
<211> LENGTH: 288
<212> TYPE: PRT

<213> ORGANISM: Homo sapiens

<400> SEQUENCE: 89

Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
        35                  40                  45
Asn Ala Thr Phe Thr Cys Ser Phe Ser Asn Thr Ser Glu Ser Phe Val
    50                  55                  60
Leu Asn Trp Tyr Arg Met Ser Pro Ser Asn Gln Thr Asp Lys Leu Ala
65                  70                  75                  80
Ala Phe Pro Glu Asp Arg Ser Gln Pro Gly Gln Asp Cys Arg Phe Arg
                85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
        115                 120                 125
Ala Pro Lys Ala Gln Ile Lys Glu Ser Leu Arg Ala Glu Leu Arg Val
    130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
        195                 200                 205
Leu Lys Glu Asp Pro Ser Ala Val Pro Val Phe Ser Val Asp Tyr Gly
    210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
        275                 280                 285

<210> SEQ ID NO 90
<211> LENGTH: 5
<212> TYPE: PRT
<213> ORGANISM: Artificial Sequence
<220> FEATURE:
<223> OTHER INFORMATION: GGGGS spacer

<400> SEQUENCE: 90

Gly Gly Gly Gly Ser
1               5

<210> SEQ ID NO 91
<211> LENGTH: 192
<212> TYPE: PRT
<213> ORGANISM: Artificial Sequence
<220> FEATURE:
<223> OTHER INFORMATION: SNAP-tag

<400> SEQUENCE: 91

```
Asp Lys Asp Cys Glu Met Lys Arg Thr Thr Leu Asp Ser Pro Leu Gly
1               5                   10                  15
Lys Leu Glu Leu Ser Gly Cys Glu Gln Gly Leu His Glu Ile Lys Leu
            20                  25                  30
Leu Gly Lys Gly Thr Ser Ala Ala Asp Ala Val Glu Val Pro Ala Pro
        35                  40                  45
Ala Ala Val Leu Gly Gly Pro Glu Pro Leu Met Gln Ala Thr Ala Trp
    50                  55                  60
Leu Asn Ala Tyr Phe His Gln Pro Glu Ala Ile Glu Glu Phe Pro Val
65                  70                  75                  80
Pro Ala Leu His His Pro Val Phe Gln Gln Glu Ser Phe Thr Arg Gln
                85                  90                  95
Val Leu Trp Lys Leu Leu Lys Val Val Lys Phe Gly Glu Val Ile Ser
            100                 105                 110
Tyr Gln Gln Leu Ala Ala Leu Ala Gly Asn Pro Ala Ala Thr Ala Ala
        115                 120                 125
Val Lys Thr Ala Leu Ser Gly Asn Pro Val Pro Ile Leu Ile Pro Cys
    130                 135                 140
His Arg Val Val Ser Ser Ser Gly Ala Val Gly Gly Tyr Glu Gly Gly
145                 150                 155                 160
Leu Ala Val Lys Glu Trp Leu Leu Ala His Glu Gly His Arg Leu Gly
                165                 170                 175
Lys Pro Gly Leu Gly Pro Ala Gly Gly Ser Pro Gly Leu Glu Val Asn
            180                 185                 190
```

<210> SEQ ID NO 92
<211> LENGTH: 8
<212> TYPE: PRT
<213> ORGANISM: Artificial Sequence
<220> FEATURE:
<223> OTHER INFORMATION: Flag-tag

<400> SEQUENCE: 92

```
Asp Tyr Lys Asp Asp Asp Asp Lys
1               5
```

<210> SEQ ID NO 93
<211> LENGTH: 300
<212> TYPE: PRT
<213> ORGANISM: Homo sapiens

<400> SEQUENCE: 93

```
Met Phe Ser His Leu Pro Phe Asp Cys Val Leu Leu Leu Leu Leu Leu
1               5                   10                  15
Leu Leu Thr Arg Ser Ser Glu Val Glu Tyr Arg Ala Glu Val Gly Gln
            20                  25                  30
Asn Ala Tyr Leu Pro Cys Phe Tyr Thr Pro Ala Ala Pro Gly Asn Leu
        35                  40                  45
Val Pro Val Cys Trp Gly Lys Gly Ala Cys Pro Val Phe Glu Cys Gly
    50                  55                  60
Asn Val Val Leu Arg Thr Asp Glu Arg Asp Val Asn Tyr Trp Thr Ser
65                  70                  75                  80
Arg Tyr Trp Leu Asn Gly Asp Phe Arg Lys Gly Asp Val Ser Leu Thr
                85                  90                  95
Ile Glu Asn Val Thr Leu Ala Asp Ser Gly Ile Tyr Cys Cys Arg Ile
            100                 105                 110
```

```
Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
195                 200                 205

Ile Cys Ala Gly Leu Ala Leu Ala Leu Ile Phe Gly Ala Leu Ile Phe
            210                 215                 220

Lys Trp Tyr Ser His Ser Lys Glu Lys Ile Gln Asn Leu Ser Leu Ile
225                 230                 235                 240

Ser Leu Ala Asn Leu Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
275                 280                 285

Gln Pro Ser Gln Pro Leu Gly Cys Arg Phe Ala Met
            290                 295                 300

<210> SEQ ID NO 94
<211> LENGTH: 181
<212> TYPE: PRT
<213> ORGANISM: Artificial Sequence
<220> FEATURE:
<223> OTHER INFORMATION: Clip-tag

<400> SEQUENCE: 94

Asp Lys Asp Cys Glu Met Lys Arg Thr Thr Leu Asp Ser Pro Leu Gly
1               5                   10                  15

Lys Leu Glu Leu Ser Gly Cys Glu Gln Gly Leu His Arg Ile Ile Phe
                20                  25                  30

Leu Gly Lys Gly Thr Ser Ala Ala Asp Ala Val Glu Val Pro Ala Pro
            35                  40                  45

Ala Ala Val Leu Gly Gly Pro Glu Pro Leu Ile Gln Ala Thr Ala Trp
50                  55                  60

Leu Asn Ala Tyr Phe His Gln Pro Glu Ala Ile Glu Glu Phe Pro Val
65                  70                  75                  80

Pro Ala Leu His His Pro Val Phe Gln Gln Glu Ser Phe Thr Arg Gln
                85                  90                  95

Val Leu Trp Lys Leu Leu Lys Val Val Lys Phe Gly Glu Val Ile Ser
            100                 105                 110

Glu Ser His Leu Ala Ala Leu Val Gly Asn Pro Ala Ala Thr Ala Ala
                115                 120                 125

Val Asn Thr Ala Leu Asp Gly Asn Pro Val Pro Ile Leu Ile Pro Cys
130                 135                 140

His Arg Val Val Gln Gly Asp Ser Asp Val Gly Pro Tyr Leu Gly Gly
145                 150                 155                 160
```

```
Leu Ala Val Lys Glu Trp Leu Leu Ala His Glu Gly His Arg Leu Gly
            165                 170                 175
Lys Pro Gly Leu Gly
        180
```

BISPECIFIC ANTIBODIES SPECIFIC FOR PD1 AND TIM3

CROSS REFERENCE TO RELATED APPLICATIONS

This application is a divisional of U.S. application Ser. No. 15/280,372, filed Sep. 29, 2016, now pending, which claims the benefit of priority under 35 U.S.C § 119 to European Patent Application No. 15188036.6, filed Oct. 2, 2015, and European Patent Application No. 15188065.5, filed Oct. 2, 2015, which applications are hereby incorporated by reference in their entirety.

SEQUENCE LISTING

The instant application contains a Sequence Listing submitted via EFS-Web and is hereby incorporated by reference in its entirety. Said ASCII copy, created on Dec. 13, 2018, is named P33115-US-1_SeqList.txt, and is 147,646 bytes in size.

FIELD OF THE INVENTION

The invention relates to bispecific antibodies comprising a first antigen-binding site that specifically binds to PD1 and a second antigen-binding site that specifically binds to TIM3, in particular to bispecific antibodies, wherein the bispecific antibody binds to TIM3 with a lower binding affinity when compared to the binding to PD1. The invention further relates to methods of producing these molecules and to methods of using the same.

BACKGROUND

The importance of the immune system in protection against cancer is based on its capacity to detect and destroy abnormal cells. However, some tumor cells are able to escape the immune system by engendering a state of immunosuppression (Zitvogel et al., Nature Reviews Immunology 6 (2006), 715-727). One example of a mechanism of immunosuppression present in tumor-bearing hosts is the promotion of T cell dysfunction or exhaustion. T cells have been the major focus of efforts to therapeutically manipulate endogenous antitumour immunity owing to their capacity for the selective recognition of peptides derived from proteins in all cellular compartments; their capacity to directly recognize and kill antigen-expressing cells (by CD8+ effector T cells; also known as cytotoxic T lymphocytes (CTLs)) and their ability to orchestrate diverse immune responses (by CD4+ helper T cells), which integrates adaptive and innate effector mechanisms. Exhausted T cells fail to proliferate and exert effector functions such as cytotoxicity and cytokine secretion in response to antigen stimulation. Further studies identified that exhausted T cells are characterized by sustained expression of the inhibitory molecule PD-1 (programmed cell death protein 1) and that blockade of PD-1 and PD-L1 (PD-1 ligand) interactions can reverse T cell exhaustion and restore antigen-specific T cell responses in LCMV-infected mice (Barber et al., Nature 439 (2006), 682-687). However, targeting the PD-1-PD-L1 pathway alone does not always result in reversal of T cell exhaustion (Gehring et al., Gastroenterology 137 (2009), 682-690), indicating that other molecules are likely involved in T cell exhaustion (Sakuishi, J. Experimental Med. 207 (2010), 2187-2194).

TIM-3 is a molecule originally identified as being selectively expressed on IFN-γ-secreting Th1 and Tc1 cells (Monney et al., Nature 415 (2002), 536-541). The interaction of TIM-3 with its ligand, galectin-9, triggers cell death in TIM-3+ T cells. Thus, both TIM-3 and PD-1 can function as negative regulators of T cell responses. It has been shown that TIM-3 marks the most suppressed or dysfunctional population of CD8+ T cells in preclinical models of both solid and hematologic malignancy (Sakuishi, J. Experimental Med. 207 (2010), 2187-2194; Zhou, Blood 117 (2011), 4501-4510; Majeti R et al., PNAS, 106 (2009), 3396-3401). In these models, all of the CD8+ TIM-3+ T cells coexpress PD1, and these dual-expressing cells exhibit greater defects in both cell-cycle progression and effector cytokine production [interleukin (IL)-2, TNF, and IFN-γ] than cells that express PD1 alone. Thus, the TIM-3 pathway may cooperate with the PD-1 pathway to promote the development of a severe dysfunctional phenotype in CD8+ T cells in cancer. The combined targeting of the TIM-3 and PD1 pathways is thus expected to be highly effective in controlling tumor growth.

TIM3 is a human protein which belongs to the immunoglobulin superfamily, and TIM family of proteins. In humans, as similar to mice, TIM-3 is expressed on T-cells as well as phagocytic cells such as macrophages and dendritic cells. Binding of TIM3 to a protein ligand (e.g., galectin-9) can inhibit the Th1 response via mechanism of apoptosis induction, and therefore lead to such as induction of peripheral tolerance. The reduction in expression of human TIM3 with siRNA or the inhibition of human TIM3 by blocking-antibody increased the secretion of interferon alpha from CD4 positive T-cells, supporting the inhibitory role of TIM3 in human T cells. In phagocytes, TIM3 also functions as a receptor for recognizing the apoptosis cells. Analysis of clinical samples from autoimmune disease patients showed no expression of TIM3 in CD4 positive cells. In particular, in T cell clones derived from the cerebrospinal fluid of patients with multiple sclerosis, the expression level of TIM3 was lower and the secretion level of IFN-gamma was higher than those of clones derived from normal healthy persons (Koguchi K et al., J Exp Med. 203 (2006), 1413-1418). There are reports on relation of TIM-3 with allergic diseases or asthma (WO 96/27603 and WO2003/063792).

Examples of the anti-TIM3 monoclonal antibodies include anti-human TIM3 rat monoclonal antibody (Clone 344823, manufactured by R&D Systems) and anti-human TIM-3 mouse monoclonal antibody (Clone F38-2E2, manufactured by R&D Systems). WO2013/06490 relates to anti-TIM3 antibodies which show rapid internalization and immunoconjugates thereof for treating cancer and reducing inflammation. US2012/189617 relates to anti-TIM-3 antibodies which exhibit higher effector activity such as an antibody-dependent cellular cytotoxicity (ADCC activity) for diseases relating to a human TIM3 expressing cell.

Programmed cell death protein 1 (PD-1 or CD279) is an inhibitory member of the CD28 family of receptors, that also includes CD28, CTLA-4, ICOS and BTLA. PD-1 is a cell surface receptor and is expressed on activated B cells, T cells, and myeloid cells (Okazaki et al (2002) Curr. Opin. Immunol. 14: 391779-82; Bennett et al. (2003) J Immunol 170:711-8). The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Activated T cells transiently express PD1, but sustained hyperexpression of PD1 and its ligand PDL1 promote immune exhaustion, leading to persistence of viral infections, tumor evasion, increased infections and mortality. PD1 expression is induced by antigen recognition via the T-cell receptor and its expression is maintained primarily through continuous T-cell receptor signaling. After prolonged antigen exposure, the PD1 locus fails to be remethylated, which promotes continuous hyperexpression. Blocking the PD1 pathway can restore the exhausted T-cell functionality in cancer and chronic viral infections (Sheridan, Nature Biotechnology 30 (2012), 729-730). Monoclonal antibodies to PD-1 have been described, for example, in WO 2003/042402, WO 2004/004771, WO 2004/056875, WO 2004/072286, WO 2004/087196, WO 2006/121168, WO 2006/133396, WO 2007/005874, WO 2008/083174, WO 2008/156712, WO 2009/024531, WO 2009/014708, WO 2009/101611, WO 2009/114335, WO 2009/154335, WO 2010/027828, WO 2010/027423, WO 2010/029434, WO 2010/029435, WO 2010/036959, WO 2010/063011, WO 2010/089411, WO 2011/066342, WO 2011/110604, WO 2011/110621, WO 2012/145493, WO 2013/014668, WO 2014/179664, and WO 2015/112900.

It has also been shown that blocking both PD1 and TIM3 can restore the antibacterial immune responses, for instance in patients with acute alcoholic hepatitis (AAH). Lymphocytes from these patients express high levels of immune inhibitory receptors, produce lower levels of interferon gamma, and have increased IL10 production due to chronic endotoxin exposure. These effects can be reversed by blocking PD1 and TIM3, which increase the antimicrobial activities of T cells and neutrophils (Markwick et al, Gastroenterology 148 (2015), 590-602).

Bispecific antibodies against TIM3 and PD1 for immunotherapy in chronic immune conditions have already been described in WO 2011/159877. However, there is a need of providing new bispecific antibodies that not only simultaneously bind to PD1 and TIM3 and thus selectively target T cells expressing both PD1 and TIM3, but that also avoid blocking of TIM3 on other cells such as innate immune cells, for example naive dendritic cells (DCs) and monocytes. The bispecific antibodies of the present invention do not only effectively block PD1 and Tim3 on T cells overexpressing both PD1 and TIM3, they are very selective for these cells and thereby side effects by administering highly active TIM3 antibodies may be avoided.

SUMMARY OF THE INVENTION

In one aspect, the invention provides a bispecific antibody comprising a first antigen-binding site that specifically binds to PD1 and a second antigen-binding site that specifically binds to TIM3, wherein
said first antigen-binding site specifically binding to PD1 comprises
a VH domain comprising
(i) HVR-H1 comprising the amino acid sequence of SEQ ID NO:37,
(ii) HVR-H2 comprising the amino acid sequence of SEQ ID NO:38, and
(iii) HVR-H3 comprising an amino acid sequence of SEQ ID NO:39; and
a VL domain comprising
(i) HVR-L1 comprising the amino acid sequence of SEQ ID NO:40;
(ii) HVR-L2 comprising the amino acid sequence of SEQ ID NO:41, and
(iii) HVR-L3 comprising the amino acid sequence of SEQ ID NO:42; and
said second antigen-binding site specifically binding to TIM3 comprises (a) a VH domain comprising
(i) HVR-H1 comprising the amino acid sequence of SEQ ID NO:1,
(ii) HVR-H2 comprising the amino acid sequence of SEQ ID NO:2, and
(iii) HVR-H3 comprising an amino acid sequence of SEQ ID NO:3; and
a VL domain comprising
(i) HVR-L1 comprising the amino acid sequence of SEQ ID NO:4 or SEQ ID NO:11 or SEQ ID NO:12,
(ii) HVR-L2 comprising the amino acid sequence of SEQ ID NO:5, and
(iii) HVR-L3 comprising the amino acid sequence of SEQ ID NO:6; or
(b) a VH domain comprising
(i) HVR-H1 comprising the amino acid sequence of SEQ ID NO:17,
(ii) HVR-H2 comprising the amino acid sequence of SEQ ID NO:18, and
(iii) HVR-H3 comprising an amino acid sequence of SEQ ID NO:19; and
a VL domain comprising
(i) HVR-L1 comprising the amino acid sequence of SEQ ID NO:20,
(ii) HVR-L2 comprising the amino acid sequence of SEQ ID NO:21, and
(iii) HVR-L3 comprising the amino acid sequence of SEQ ID NO:22; or
(c) a VH domain comprising
(i) HVR-H1 comprising the amino acid sequence of SEQ ID NO:29,
(ii) HVR-H2 comprising the amino acid sequence of SEQ ID NO:30, and
(iii) HVR-H3 comprising an amino acid sequence of SEQ ID NO:31; and
a VL domain comprising
(i) HVR-L1 comprising the amino acid sequence of SEQ ID NO:32,
(ii) HVR-L2 comprising the amino acid sequence of SEQ ID NO:33, and
(iii) HVR-L3 comprising the amino acid sequence of SEQ ID NO:34.

In one aspect, the bispecific antibody comprising a first antigen-binding site that specifically binds to PD1 and a second antigen-binding site that specifically binds to TIM3 is bivalent.

In another aspect, provided is a bispecific antibody comprising a first antigen-binding site that specifically binds to PD1 and a second antigen-binding site that specifically binds to TIM3, wherein the bispecific antibody binds to TIM3 with low affinity and binds to PD1 with high affinity. In a particular aspect, the invention provides a bispecific antibody comprising a first antigen-binding site that specifically binds to PD1 and a second antigen-binding site that specifically binds to TIM3, wherein the bispecific antibody binds to TIM3 with an at least 50 fold lower binding affinity when compared to the binding to PD1, more particularly with an at least 100 fold lower binding affinity when compared to the binding to PD1. In one preferred embodiment the binding affinity (KD) is determined with Surface Plasmon Resoncance Assay (as described e.g. in Example 12.)

In a further aspect, provided is a bispecific antibody comprising a first antigen-binding site that specifically binds to PD1 and a second antigen-binding site that specifically binds to TIM3, wherein
said first antigen-binding site specifically binding to PD1 comprises (a) a VH domain comprising the amino acid sequence of SEQ ID NO: 43 and a VL domain comprising the amino acid sequence of SEQ ID NO: 44, or
(b) a VH domain comprising the amino acid sequence of SEQ ID NO: 45 and a VL domain comprising the amino acid sequence of SEQ ID NO: 46, or
(c) a VH domain comprising the amino acid sequence of SEQ ID NO: 45 and a VL domain comprising the amino acid sequence of SEQ ID NO: 47, or
(d) a VH domain comprising the amino acid sequence of SEQ ID NO: 45 and a VL domain comprising the amino acid sequence of SEQ ID NO: 48, or
(e) a VH domain comprising the amino acid sequence of SEQ ID NO: 45 and a VL domain comprising the amino acid sequence of SEQ ID NO: 49, and said second antigen-binding site specifically binding to TIM3 comprises
(a) a VH domain comprising the amino acid sequence of SEQ ID NO: 7 and a VL domain comprising the amino acid sequence of SEQ ID NO: 8, or
(b) a VH domain comprising the amino acid sequence of SEQ ID NO: 9 and a VL domain comprising the amino acid sequence of SEQ ID NO: 10, or
(c) a VH domain comprising the amino acid sequence of SEQ ID NO: 13 and a VL domain comprising the amino acid sequence of SEQ ID NO: 14, or
(d) a VH domain comprising the amino acid sequence of SEQ ID NO: 15 and a VL domain comprising the amino acid sequence of SEQ ID NO: 16, or
(e) a VH domain comprising the amino acid sequence of SEQ ID NO: 23 and a VL domain comprising the amino acid sequence of SEQ ID NO: 24, or
(f) a VH domain comprising the amino acid sequence of SEQ ID NO: 25 and a VL domain comprising the amino acid sequence of SEQ ID NO: 26, or
(g) a VH domain comprising the amino acid sequence of SEQ ID NO: 27 and a VL domain comprising the amino acid sequence of SEQ ID NO: 28, or
(h) a VH domain comprising the amino acid sequence of SEQ ID NO: 35 and a VL domain comprising the amino acid sequence of SEQ ID NO: 36.

In a particular aspect, provided is a bispecific antibody comprising a first antigen-binding site that specifically binds to PD1 and a second antigen-binding site that specifically binds to TIM3, wherein
said first antigen-binding site specifically binding to PD1 comprises a VH domain comprising the amino acid sequence of SEQ ID NO: 45 and a VL domain comprising the amino acid sequence of SEQ ID NO: 46,
and said second antigen-binding site specifically binding to TIM3 comprises a VH domain comprising the amino acid sequence of SEQ ID NO: 15 and a VL domain comprising the amino acid sequence of SEQ ID NO: 16 or a VH domain comprising the amino acid sequence of SEQ ID NO: 25 and a VL domain comprising the amino acid sequence of SEQ ID NO: 26.

Particularly, the invention provides a bispecific antibody comprising a first antigen-binding site that specifically binds to PD1 and a second antigen-binding site that specifically binds to TIM3, wherein
said first antigen-binding site specifically binding to PD1 comprises
a VH domain comprising
(i) HVR-H1 comprising the amino acid sequence of SEQ ID NO:37,
(ii) HVR-H2 comprising the amino acid sequence of SEQ ID NO:38, and
(iii) HVR-H3 comprising an amino acid sequence of SEQ ID NO:39; and
a VL domain comprising
(i) HVR-L1 comprising the amino acid sequence of SEQ ID NO:40;
(ii) HVR-L2 comprising the amino acid sequence of SEQ ID NO:41, and
(iii) HVR-L3 comprising the amino acid sequence of SEQ ID NO:42; and
said second antigen-binding site specifically binding to TIM3 comprises a VH domain comprising
(i) HVR-H1 comprising the amino acid sequence of SEQ ID NO:17,
(ii) HVR-H2 comprising the amino acid sequence of SEQ ID NO:18, and
(iii) HVR-H3 comprising an amino acid sequence of SEQ ID NO:19; and
a VL domain comprising
(i) HVR-L1 comprising the amino acid sequence of SEQ ID NO:20,
(ii) HVR-L2 comprising the amino acid sequence of SEQ ID NO:21, and
(iii) HVR-L3 comprising the amino acid sequence of SEQ ID NO:22.

More particularly, provided is a bispecific antibody comprising a first antigen-binding site that specifically binds to PD1 and a second antigen-binding site that specifically binds to TIM3, wherein said first antigen-binding site specifically binding to PD1 comprises a VH domain comprising the amino acid sequence of SEQ ID NO: 45 and a VL domain comprising the amino acid sequence of SEQ ID NO: 46, and said second antigen-binding site specifically binding to TIM3 comprises a VH domain comprising the amino acid sequence of SEQ ID NO: 25 and a VL domain comprising the amino acid sequence of SEQ ID NO: 26.

In a particular aspect, the invention provides a bispecific antibody comprising a first antigen-binding site that specifically binds to PD1 and a second antigen-binding site that specifically binds to TIM3, wherein the bispecific antibody binds to TIM3 with an at least 50 fold lower binding affinity when compared to the binding to PD1, more particularly with an at least 100 fold lower binding affinity when compared to the binding to PD1.

In a further aspect, the bispecific antibody comprising a first antigen-binding site that specifically binds to PD1 and a second antigen-binding site that specifically binds to TIM3 is a human, humanized or chimeric antibody. In particular, it is a humanized or chimeric antibody.

In another aspect, the invention relates to a bispecific antibody comprising a first antigen-binding site that specifically binds to PD1 and a second antigen-binding site that specifically binds to TIM3, wherein the bispecific antibody comprises an Fc domain, a first Fab fragment comprising the antigen-binding site that specifically binds to PD1 and a second Fab fragment comprising the antigen-binding site that specifically binds to TIM3.

In particular, the Fc domain is an IgG domain, more particularly an IgG1 Fc domain or an IgG4 Fc domain.

In one aspect, the invention relates to a bispecific antibody comprising a first antigen-binding site that specifically binds to PD1 and a second antigen-binding site that specifically binds to TIM3, wherein the Fc domain comprises one or more amino acid substitution that reduces binding to an Fc receptor, in particular towards Fcγ receptor. In particular, the Fc domain is of human IgG1 subclass with the amino acid mutations L234A, L235A and P329G (numbering according to Kabat EU index).

In another aspect, the invention relates to a bispecific antibody comprising a first antigen-binding site that specifically binds to PD1 and a second antigen-binding site that specifically binds to TIM3, wherein the Fc domain comprises a modification promoting the association of the first and second subunit of the Fc domain.

In one aspect, the invention relates to a bispecific antibody comprising a first antigen-binding site that specifically binds to PD1 and a second antigen-binding site that specifically binds to TIM3, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an additional aspect, the invention relates to a bispecific antibody comprising a first antigen-binding site that specifically binds to PD1 and a second antigen-binding site that specifically binds to TIM3, wherein in one of the Fab fragments the variable domains VL and VH are replaced by each other so that the VH domain is part of the light chain and the VL domain is part of the heavy chain. In a particular aspect, the bispecific antibody is one, wherein in the first Fab fragment comprising the antigen-binding site that specifically binds to PD1 the variable domains VL and VH are replaced by each other.

In a further aspect, the invention is concerned with a bispecific antibody comprising a first antigen-binding site that specifically binds to PD1 and a second antigen-binding site that specifically binds to TIM3, wherein in one of the Fab fragments in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index). In a particular aspect, the bispecific antibody is one, wherein in the second Fab fragment comprising the antigen-binding site that specifically binds to TIM3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

In another aspect, the invention provides a bispecific antibody comprising a first antigen-binding site that specifically binds to PD1 and a second antigen-binding site that specifically binds to TIM3, comprising
(a) a first heavy chain comprising an amino acid sequence with at least 95% sequence identity to the sequence of SEQ ID NO: 50, a first light chain comprising an amino acid sequence with at least 95% sequence identity to the sequence of SEQ ID NO: 52,
a second heavy chain comprising an amino acid sequence with at least 95% sequence identity to the sequence of SEQ ID NO: 51, and a second light chain comprising an amino acid sequence with at least 95% sequence identity to the sequence of SEQ ID NO:53, or
(b) a first heavy chain comprising an amino acid sequence with at least 95% sequence identity to the sequence of SEQ ID NO: 54, a first light chain comprising an amino acid sequence with at least 95% sequence identity to the sequence of SEQ ID NO: 56,
a second heavy chain comprising an amino acid sequence with at least 95% sequence identity to the sequence of SEQ ID NO: 55, and a second light chain comprising an amino acid sequence with at least 95% sequence identity to the sequence of SEQ ID NO:57, or
(c) a first heavy chain comprising an amino acid sequence with at least 95% sequence identity to the sequence of SEQ ID NO: 58, a first light chain comprising an amino acid sequence with at least 95% sequence identity to the sequence of SEQ ID NO: 60,
a second heavy chain comprising an amino acid sequence with at least 95% sequence identity to the sequence of SEQ ID NO: 59, and a second light chain comprising an amino acid sequence with at least 95% sequence identity to the sequence of SEQ ID NO:61, or
(d) a first heavy chain comprising an amino acid sequence with at least 95% sequence identity to the sequence of SEQ ID NO: 62, a first light chain comprising an amino acid sequence with at least 95% sequence identity to the sequence of SEQ ID NO: 64,
a second heavy chain comprising an amino acid sequence with at least 95% sequence identity to the sequence of SEQ ID NO: 63, and a second light chain comprising an amino acid sequence with at least 95% sequence identity to the sequence of SEQ ID NO:65, or
(e) a first heavy chain comprising an amino acid sequence with at least 95% sequence identity to the sequence of SEQ ID NO: 66, a first light chain comprising an amino acid sequence with at least 95% sequence identity to the sequence of SEQ ID NO: 68,
a second heavy chain comprising an amino acid sequence with at least 95% sequence identity to the sequence of SEQ ID NO: 67, and a second light chain comprising an amino acid sequence with at least 95% sequence identity to the sequence of SEQ ID NO:69.

In a particular aspect, the invention provides a bispecific antibody comprising a first antigen-binding site that specifically binds to PD1 and a second antigen-binding site that specifically binds to TIM3, comprising
(a) a first heavy chain comprising the amino acid sequence of SEQ ID NO: 50, a first light chain comprising the amino acid sequence of SEQ ID NO: 52,
a second heavy chain comprising the amino acid sequence of SEQ ID NO: 51, and a second light chain comprising the amino acid sequence of SEQ ID NO:53, or
(b) a first heavy chain comprising the amino acid sequence of SEQ ID NO: 54, a first light chain comprising the amino acid sequence of SEQ ID NO: 56,
a second heavy chain comprising the amino acid sequence of SEQ ID NO: 55, and a second light chain comprising the amino acid sequence of SEQ ID NO:57, or
(c) a first heavy chain comprising the amino acid sequence of SEQ ID NO: 58, a first light chain comprising the amino acid sequence of SEQ ID NO: 60,
a second heavy chain comprising the amino acid sequence of SEQ ID NO: 59, and a second light chain comprising the amino acid sequence of SEQ ID NO:61, or
(d) a first heavy chain comprising the amino acid sequence of SEQ ID NO: 62, a first light chain comprising the amino acid sequence of SEQ ID NO: 64,
a second heavy chain comprising the amino acid sequence of SEQ ID NO: 63, and a second light chain comprising the amino acid sequence of SEQ ID NO:65, or
(e) a first heavy chain comprising the amino acid sequence of SEQ ID NO: 66, a first light chain comprising the amino acid sequence of SEQ ID NO: 68, a second heavy chain comprising the amino acid sequence of SEQ ID NO: 67, and a second light chain comprising the amino acid sequence of SEQ ID NO:69.

According to another aspect of the invention, there is provided a polynucleotide encoding the bispecific antibody as described herein before. The invention further provides a vector, particularly an expression vector, comprising a polynucleotide of the invention and a prokaryotic or eukaryotic host cell comprising the polynucleotide or the vector of the invention. In some embodiments the host cell is a eukaryotic cell, particularly a mammalian cell.

In another aspect, provided is a method for producing a bispecific antibody comprising a first antigen-binding site that specifically binds to PD1 and a second antigen-binding site that specifically binds to TIM3 as described herein, comprising the steps of a) transforming a host cell with vectors comprising polynucleotides encoding said bispecific antibody, b) culturing the host cell according under conditions suitable for the expression of the bispecific antibody and c) recovering the bispecific antibody from the culture. The invention also encompasses a bispecific antibody produced by the method of the invention.

The invention further provides a pharmaceutical composition comprising a bispecific antibody comprising a first antigen-binding site that specifically binds to PD1 and a second antigen-binding site that specifically binds to TIM3 as described herein, and at least one pharmaceutically acceptable excipient.

Also encompassed by the invention is the bispecific antibody comprising a first antigen-binding site that specifically binds to PD1 and a second antigen-binding site that specifically binds to TIM3 as described herein, or the pharmaceutical composition comprising the bispecific antibody, for use as a medicament.

In another aspect, the invention provides a bispecific antibody comprising a first antigen-binding site that specifically binds to PD1 and a second antigen-binding site that specifically binds to TIM3 as described herein, or the pharmaceutical composition comprising the bispecific antibody, for use
i) in the modulation of immune responses, such as restoring T cell activity,
ii) in stimulating an immune response or function,
iii) in the treatment of infections,
iv) in the treatment of cancer,
v) in delaying progression of cancer,
vi) in prolonging the survival of a patient suffering from cancer.

In one aspect provided is the bispecific antibody comprising a first antigen-binding site that specifically binds to PD1 and a second antigen-binding site that specifically binds to TIM3 as described herein, or the pharmaceutical composition comprising the bispecific antibody, for use in the treatment of a disease in an individual in need thereof. In a specific aspect, the invention provides a bispecific antibody comprising a first antigen-binding site that specifically binds to PD1 and a second antigen-binding site that specifically binds to TIM3, or the pharmaceutical composition comprising the bispecific antibody, for use in the treatment of cancer. In a further specific aspect, a bispecific antibody comprising a first antigen-binding site that specifically binds to PD1 and a second antigen-binding site that specifically binds to TIM3, or the pharmaceutical composition comprising the bispecific antibody, for use in the modulation of immune responses is provided. In another aspect, a bispecific antibody comprising a first antigen-binding site that specifically binds to PD1 and a second antigen-binding site that specifically binds to TIM3, or a pharmaceutical composition comprising the bispecific antibody for use in the treatment of a chronic viral infection is provided.

Also provided is the use of the bispecific antibody comprising a first antigen-binding site that specifically binds to PD1 and a second antigen-binding site that specifically binds to TIM3 as described herein for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the bispecific antibody comprising a first antigen-binding site that specifically binds to PD1 and a second antigen-binding site that specifically binds to TIM3 as described herein in a pharmaceutically acceptable form. In a specific aspect, the disease is cancer. In another specific aspect, the disease is a chronic viral infection. In another aspect, a method of modulating of immune responses in an individual, comprising administering to said individual a therapeutically effective amount of a composition comprising the bispecific antibody comprising a first antigen-binding site that specifically binds to PD1 and a second antigen-binding site that specifically binds to TIM3 as described herein in a pharmaceutically acceptable form is provided. In any of the above aspects the individual is preferably a mammal, particularly a human.

The invention also provides a bispecific antibody comprising a first antigen-binding site that specifically binds to PD1 and a second antigen-binding site that specifically binds to TIM3 as described herein, or a pharmaceutical composition comprising the bispecific antibody for use in the prevention or treatment of cancer, wherein the bispecific antibody is administered in combination with a chemotherapeutic agent, radiation and/or other agents for use in cancer immunotherapy.

Furthermore, provided is a method of inhibiting the growth of tumor cells in an individual comprising administering to the individual an effective amount of a bispecific antibody comprising a first antigen-binding site that specifically binds to PD1 and a second antigen-binding site that specifically binds to TIM3 as described herein to inhibit the growth of the tumor cells. The individual is preferably a mammal, particularly a human.

BRIEF DESCRIPTION OF THE DRAWINGS

FIG. 4A: frequency of CD4 T cells producing Granzyme B; and FIG. 4B: Amount of IFN-γ detected by absorbance (Optical Density, O.D.) in the supernatant of the MLR in presence of increasing concentrations of different anti-PD-1 antibodies FIG. 5A: Impact of PD1/PD-L1 blockade on reactivation of suppressed T cell receptor signalig in presence of different anti-PD-1 antibodies; FIG. 5B:) Impact of PD1/PD-L1 blockade on reactivation of suppressed T cell receptor signalig in presence of different anti-PD-1 antibodies FIG. 7A: 1+1 formats (antibodies PD1TIM3_0389 and PD1TIM3_0168) compared to 2+2 constructs (PD1TIM3_0358+PD1TIM3_0359). FIG. 7B: humanized bispecific variants (PD1TIM3_0476 and PD1TIM3_477).

FIG. 8A) or an anti-TIM3-blocking antibody (#0018, FIG. 8B) were added for competition resulting in an almost complete prevention of the FRET signal (grey curves). Treatment with an anti-PD1 antibody alone did not result in FRET induction (dotted lines).

The anti-PD1 and the bispecific 1+1 PD1TIM3_0389 (Bispec 0389) show only very slow internalization, even after 3 h, whereas the internalization for the other bispecific 1+1 PD1TIM3_0168 (Bispec 0168) is stronger. Stronger internalization is shown the aTIM3 Ab 0028; the most internalization is shown by aTIM3-0018.

Figure 11A:
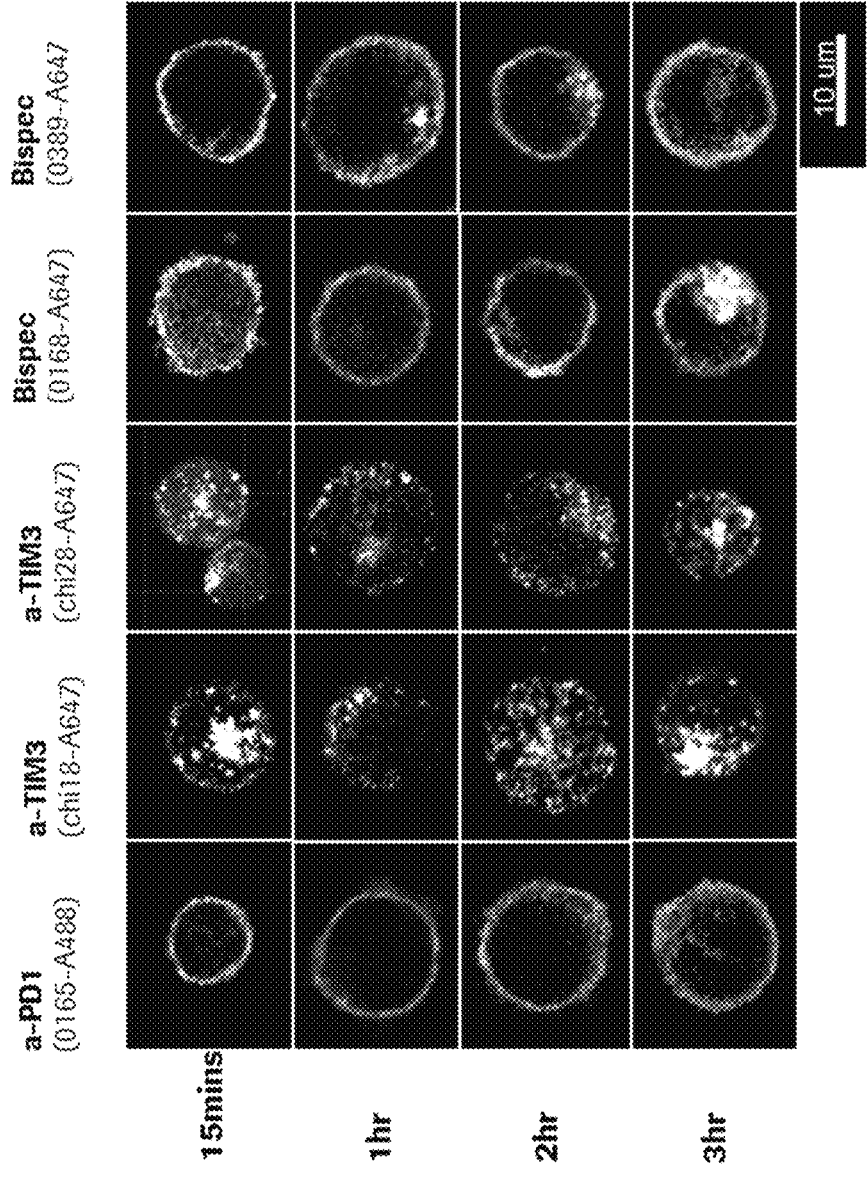
FIG. 11A: Analysis over time shows higher membrane localization in both bispecific and PD1 antibodies when compared to intracellular clustering of TIM3 antibodies. Antibody designations in Figure: TIM3 (chi18-A647=chimeric TIM3_0018 labeled with AlexaA647), a-TIM3 (chi28-A647=chimeric TIM3_0028 labeled with AlexaA647), Bispec (0168-A647=1+1 PD1TIM3_0168 (based on chimeric PD1-0103/TIM3-0018) labeled with AlexaA647) Bispec (0389-A647=1+1 PD1TIM3_0389 (based on chimeric PD1-0103/TIM3-0028) labeled with Alexa 647) and a-PD1 (0165-A488=chimeric PD1-0103 labeled with Alexa488).
Figure 11B:
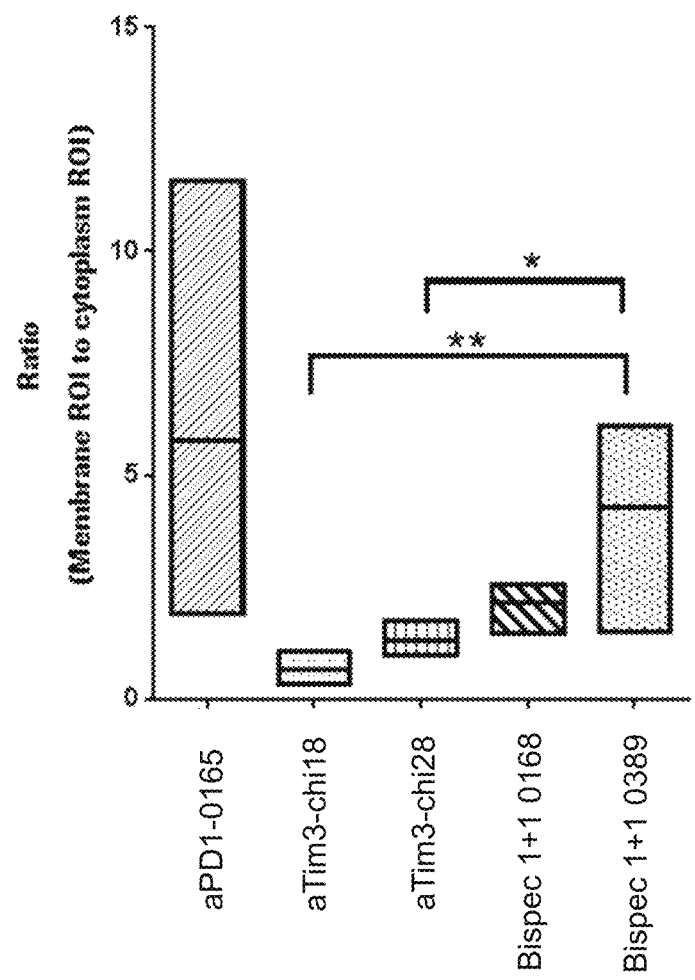

FIG. 11B: Chimeric PD1-0103 (aPD1-0165) shows only poor internalization, whereas the high affinity chimeric TIM3_0018 (aTim3-chi18) is strongly internalized upon TIM3-binding, even after 15 minutes. Internalization for the low affinity binder chimeric TIM3_0028 (aTIM3-chi28) is slightly reduced. The bispecific 1+1 AB 0168 (composed of high affinity binder aPD1-0165 and high affinity aTIM3-0018) shows more reduced internalization. The bispecific 1+1 AB 0389 (composed of high affinity binder chimeric PD1-0103 (aPD1-0165) and low affinity chimeric TIM3_0028 (aTIM3-0028) shows very strong reduced internalization. This could be due to the bivalent binding to PD1 and TIM3, where the high affinity binding to PD1 retains the antibody at the cell surface.

Figure 12A:
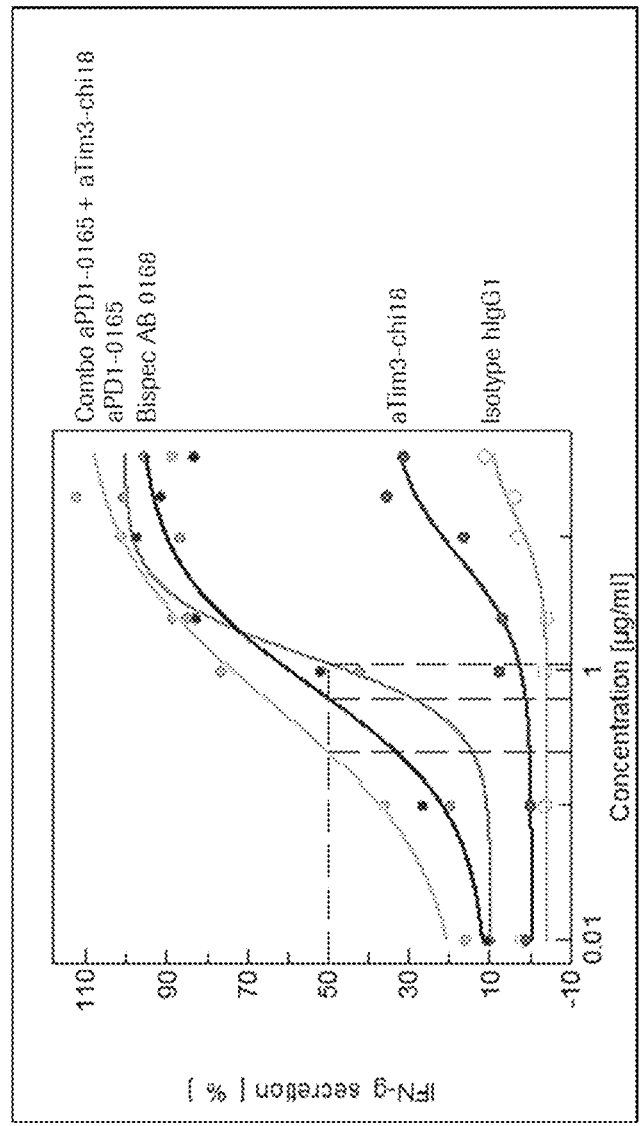

FIG. 12A: Potency of PD1-TIM3 Bispecific Antibody 1+1 PD1TIM3_0168 (based on chimeric PD1-0103/TIM3-0018 (=AB 0168) in comparison with chimeric PD1-0103 (=PD1-0165) and chimeric TIM3_0018 (=TIM3-chi18) and combinations thereof.

Figure 12B:
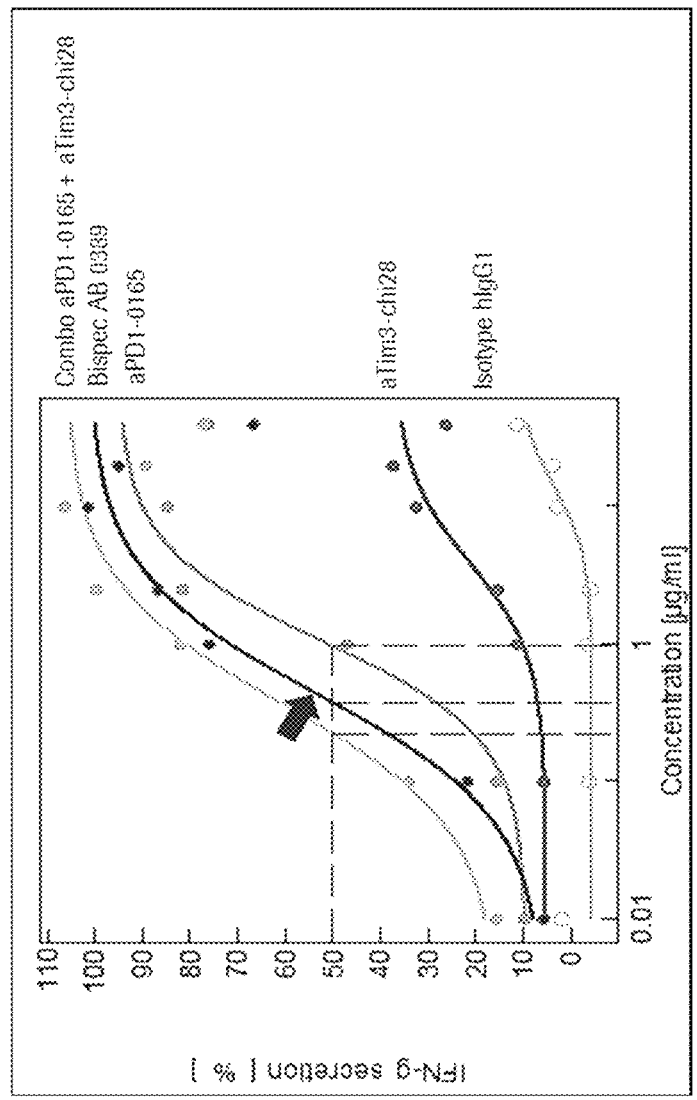

FIG. 12B: Potency of PD1-TIM3 Bispecific Antibody 1+1 PD1TIM3_0389 (based on chimeric PD1-0103/TIM3-0028 (=Bispec AB 0389) in comparison with chimeric PD1-0103 (=PD1-0165) and chimeric TIM3_0028 (=TIM3-chi28) and combinations thereof.

Figure 12C:
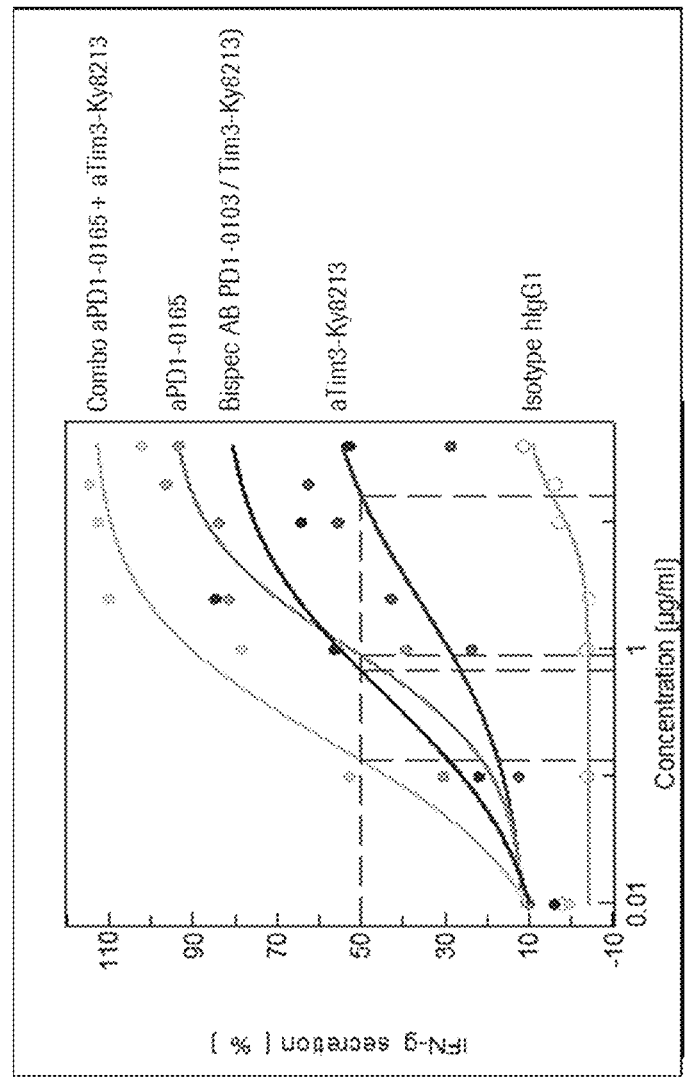

FIG. 12C: Potency of PD1-TIM3 Bispecific Antibody 1+1 PD1-0103/Ky8213 (based on chimeric PD1-0103/and anti-TIM3 Ky8213 from US20120189617 (see antibody 8213 e.g. Example 33) which produced anlalougously as described in Example 1 as a 1+1 CrossMab) in comparison with chimeric PD1-0103 (=PD1-0165) and anti-TIM3-Ky8213 (from US20120189617 (see antibody 8213) e.g. Example 33) and combinations thereof.

Figure 12D:
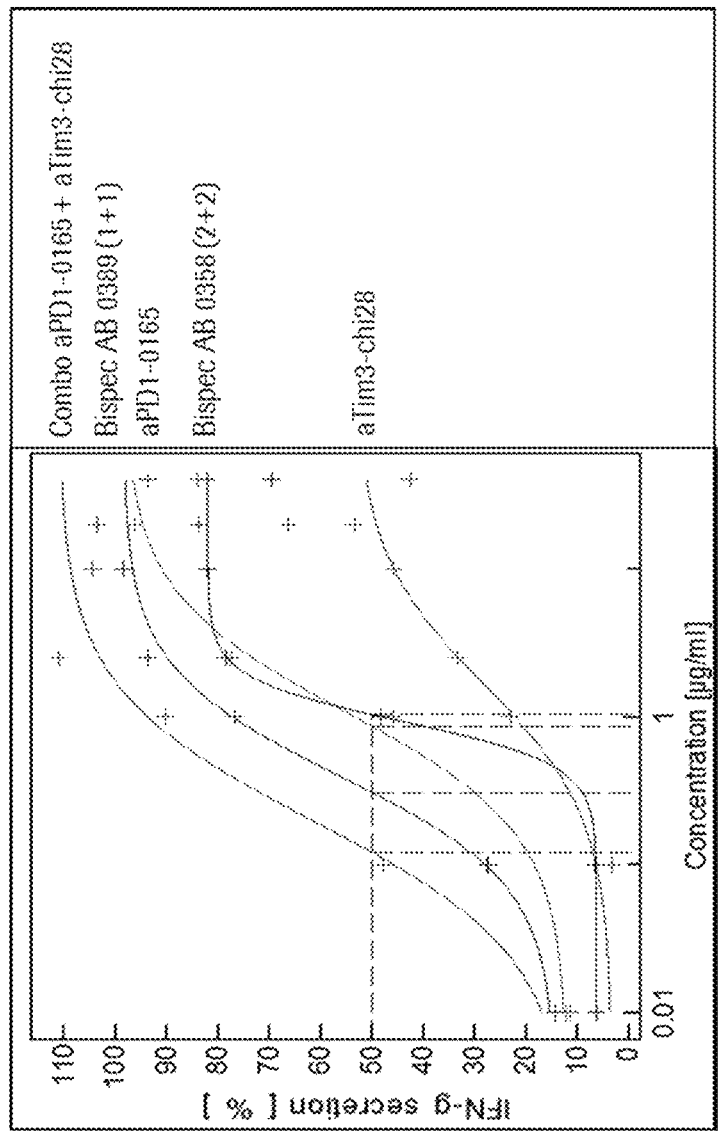

FIG. 12D: Potency of PD1-TIM3 Bispecific Antibody 1+1 PD1TIM3_0389 (based on chimeric PD1-0103/TIM3-0028 (=Bispec AB 0389 (1+1))) in comparison with PD1-TIM3 Bispecific Antibody 2+2 PD1TIM3_0358 based on chimeric PD1-0103/TIM3-0028 (=Bispec AB 0358 (2+2)), and chimeric PD1-0103 (=PD1-0165) and chimeric TIM3_0028 (=TIIM3-chi28) and combinations thereof.

Figure 13:
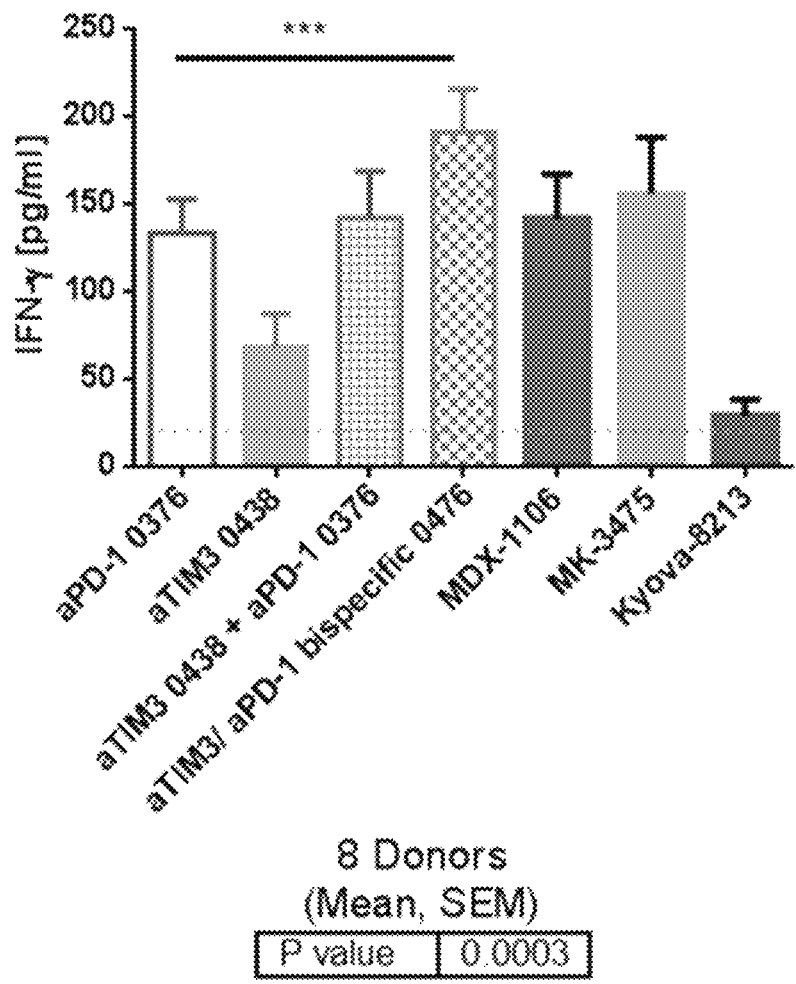

FIG. 13: Treatment with PD1-TIM3 Bispecific Antibody 1+1 PD1TIM3_0476 significantly increased the ability of CD4 T cells to release IFN-gamma compared to treatment with PD1 or TIM3 antibodies alone and even compared to treatment with a combination of the parent antibody PD1_0376 and antibody TIM3_0438. CD4 T cells were co-cultured with a MHCII-expressing tumor cell line. PD1-Tim3 Bispecific Antibody 1+1 PD1TIM3_0476 was tested against the PD1 antibodies aPD1_0376, MDX-1106 (nivolumab) and MK-3475 (pembrolizumab), against the TIM3 antibodies aTIM3_0438 and Kyowa-8213 (as disclosed in WO 2011/155697) and against the combination of anti-PD1 antibody aPD1-0376 and anti-TIM3 antibody aTIM3_0438.

Figure 14A:
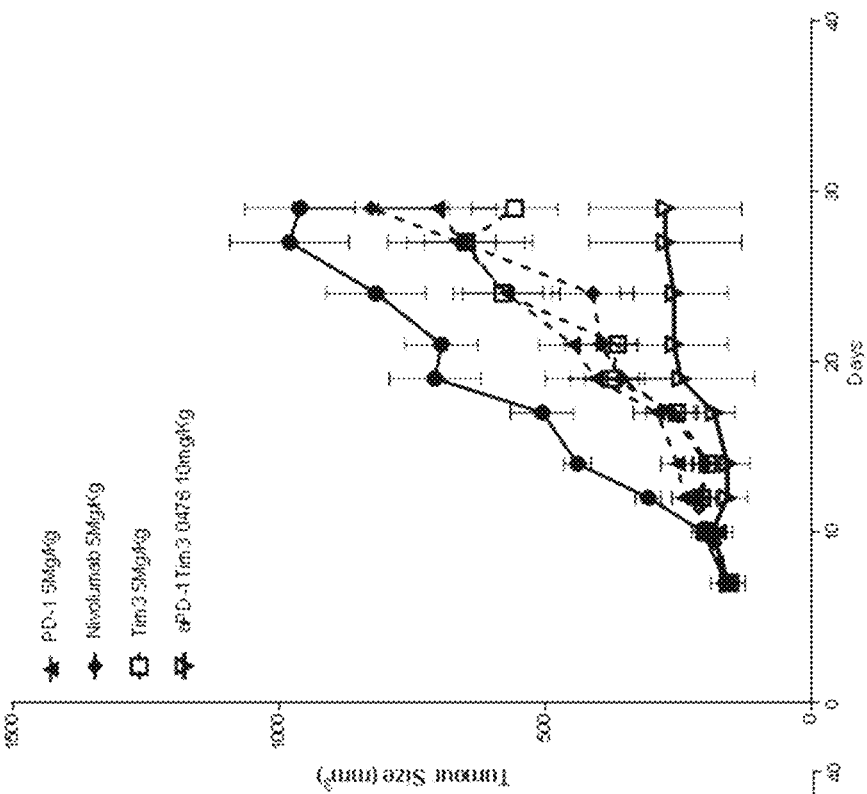
Figure 14B:
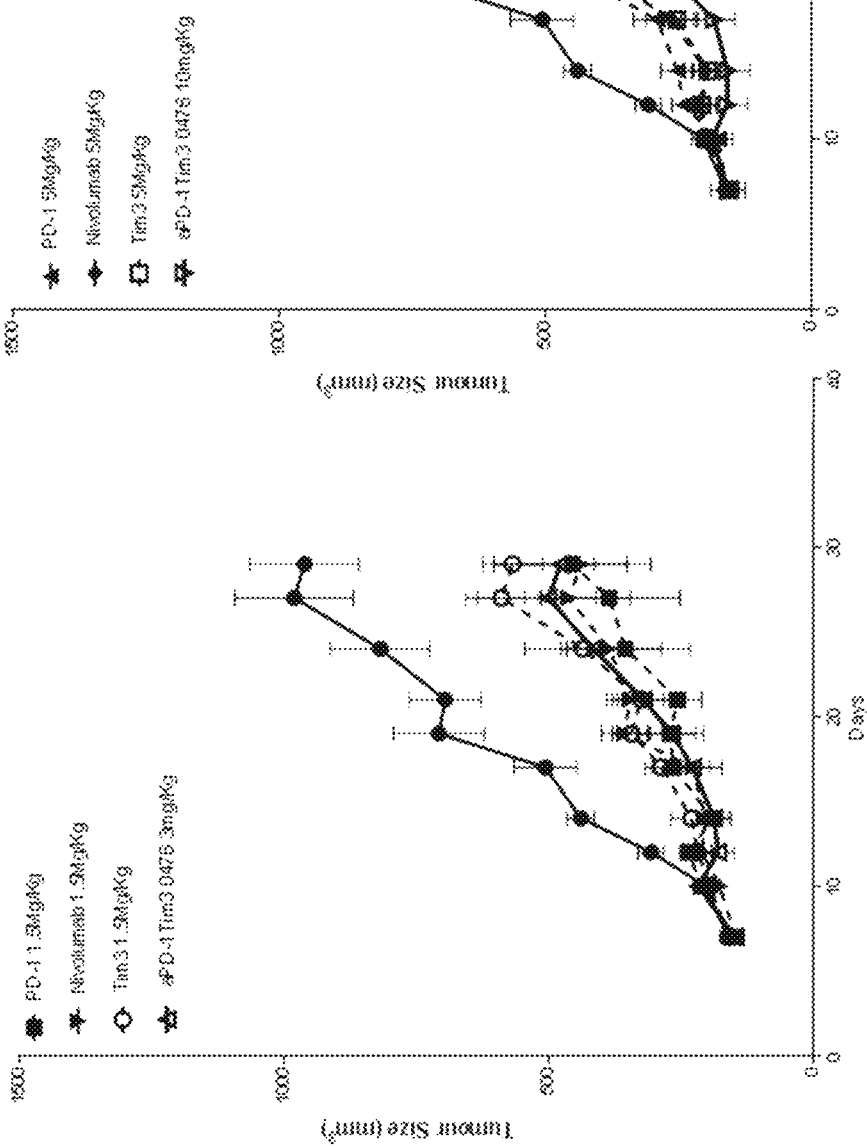

FIGS. 14A and 14B: The results of an Efficacy Experiment comparing PD1-TIM3 Bispecific Antibody 1+1 (0476) with PD1 or TIM3 antibodies alone in immune supressed female mice (NOG) challenged with MKN45 cells and provided with PBMC from a healthy human donor are shown in FIGS. 14A and 14B. The plots represent the measurement mean of tumour size (within a treatment group) including the standard error of the tumour size mean over the period of 30 days. The curves with the filled circle correspond to tumour size growth without treatment (vehicle). In FIG. 14A the tumour growth with lower dose treatment is shown (1.5 mg/kg antibody PD1_0376, 1.5 mg/kg nivolumab, 1.5 mg/kg antibody TIM3_0438 or 3 mg/kg bispecific antibody 1+1 PD1TIM3_0476); in FIG. 14B the tumor growth at higher doses (5 mg/kg antibody PD1_0376, 5 mg/kg nivolumab, 5 mg/kg antibody Tim3_0438 or 10 mg/kg bispecific antibody 1+1 PD1TIM3_0476) is shown.

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antibody is able to specifically bind to at least two distinct antigenic determinants, for example two binding sites each formed by a pair of an antibody heavy chain variable domain (VH) and an antibody light chain variable domain (VL) binding to different antigens or to different epitopes on the same antigen. Such a bispecific antibody is an 1+1 format. Other bispecific antibody formats are 2+1 formats (comprising two binding sites for a first antigen or epitope and one binding site for a second antigen or epitope) or 2+2 formats (comprising two binding sites for a first antigen or epitope and two binding sites for a second antigen or epitope). Typically, a bispecific antibody comprises two antigen binding sites, each of which is specific for a different antigenic determinant.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule. The bispecific antibodies according to the invention are at least "bivalent" and may be "trivalent" or "multivalent" (e.g. "tetravalent" or "hexavalent"). In a particular aspect, the antibodies of the present invention have two or more binding sites and are bispecific. That is, the antibodies may be bispecific even in cases where there are more than two binding sites (i.e. that the antibody is trivalent or multivalent). In particular, the invention relates to bispecific bivalent antibodies, having one binding site for each antigen they specifically bind to.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); multispecific antibodies formed from antibody fragments and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies. Antibody fragments can be made by various techniques, including but not limited to proteolytic digestion of an intact antibody as well as production by recombinant host cells (e.g. *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an $F(ab')_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as $CrossFab_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as $CrossFab_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin).

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domains were derived from the variable domain of the antibody heavy chain from camelids (nanobodies or $V_H H$ fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

As used herein, the term "antigen-binding site" refers to the part of the antigen binding molecule that specifically binds to an antigenic determinant. More particularly, the term "antigen-binding site" refers the part of an antibody that comprises the area which specifically binds to and is complementary to part or all of an antigen. Where an antigen is large, an antigen binding molecule may only bind to a particular part of the antigen, which part is termed an epitope. An antigen-binding site may be provided by, for example, one or more variable domains (also called variable regions). Preferably, an antigen-binding site comprises an antibody light chain variable region (VL) and an antibody heavy chain variable region (VH). In one aspect, the antigen-binding site is able to bind to its antigen and block or partly block its function. Antigen-binding sites that specifically bind to PD1 or to TIM-3 include antibodies and fragments thereof as further defined herein. In addition, antigen-binding sites may include scaffold antigen binding proteins, e.g. binding domains which are based on designed repeat proteins or designed repeat domains (see e.g. WO 2002/020565).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 µM, ≤100 nM, ≤10 nM, ≤1 nM, ≤0.1 nM, ≤0.01 nM, or ≤0.001 nM (e.g. $10^{-7}$ M or less, e.g. from $10^{-7}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

As used herein, the term "high affinity" of an antibody refers to an antibody having a Kd of $10^{-9}$ M or less and even more particularly $10^{-10}$ M or less for a target antigen. The term "low affinity" of an antibody refers to an antibody having a Kd of $10^{-8}$ or higher.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "a bispecific antibody comprising a first antigen-binding site that specifically binds to PD1 and a second antigen-binding site that specifically binds to TIM-3" "a bispecific antibody that specifically binds PD1 and TIM-3", "bispecific antigen binding molecule specific for PD1 and TIM-3" are used interchangeably herein and refer to a bispecific antibody that is capable of binding PD1 and TIM-3 with sufficient affinity such that the antibody is useful as a diagnostic and/or therapeutic agent in targeting PD1 and TIM-3.

The term "PD1", also known as Programmed cell death protein 1, is a type I membrane protein of 288 amino acids that was first described in 1992 (Ishida et al., EMBO J., 11 (1992), 3887-3895). PD-1 is a member of the extended CD28/CTLA-4 family of T cell regulators and has two ligands, PD-L1 (B7-H1, CD274) and PD-L2 (B7-DC, CD273). The protein's structure includes an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals. This is consistent with binding of SHP-1 and SHP-2 phosphatases to the cytoplasmic tail of PD-1 upon ligand binding. While PD-1 is not expressed on naïve T cells, it is upregulated following T cell receptor (TCR)-mediated activation and is observed on both activated and exhausted T cells (Agata et al., Int. Immunology 8 (1996), 765-772). These exhausted T-cells have a dysfunctional phenotype and are unable to respond appropriately. Although PD-1 has a relatively wide expression pattern its most important role is likely as a coinhibitory receptor on T cells (Chinai et al, Trends in Pharmacological Sciences 36 (2015), 587-595). Current therapeutic approaches thus focus on blocking the interaction of PD-1 with its ligands to enhance T cell response. The terms "Programmed Death 1," "Programmed Cell Death 1," "Protein PD-1," "PD-1," PD1," "PDCD1," "hPD-1" and "hPD-I" can be used interchangeably, and include variants, isoforms, species homologs of human PD-1, and analogs having at least one common epitope with PD-1. The amino acid sequence of human PD1 is shown in UniProt (www.uniprot.org) accession no. Q15116 (SEQ ID NO:89).

The terms "anti-PD1 antibody" and "an antibody comprising an antigen-binding site that binds to PD1" refer to an antibody that is capable of binding PD1, especially a PD1 polypeptide expressed on a cell surface, with sufficient affinity such that the antibody is useful as a diagnostic and/or therapeutic agent in targeting PD1. In one embodiment, the extent of binding of an anti-PD1 antibody to an unrelated, non-PD1 protein is less than about 10% of the binding of the antibody to PD1 as measured, e.g., by radioimmunoassay (RIA) or flow cytometry (FACS) or by a Surface Plasmon Resonance assay using a biosensor system such as a Biacore® system. In certain embodiments, an antigen binding protein that binds to human PD1 has a KD value of the binding affinity for binding to human PD1 of ≤1 µM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). In one preferred embodiment the respective KD value of the binding affinities is determined in a Surface Plasmon Resonance assay using the Extracellular domain (ECD) of human PD1 (PD1-ECD) for the PD1 binding affinity. The term "anti-PD1 antibody" also encompasses bispecific antibodies that are capable of binding PD1 and a second antigen.

The term "TIM3", the abbreviation for "T cell Immunoglobulin- and Mucin domain-containing molecule 3", also known as TIM-3, HAVCR2, KIM-3, TIMD3, and FLJ14428, refers to a T helper cell type 1-specific cell surface protein that regulates macrophage activation and the severity of inflammatory conditions. TIM3 is also associated with cancer, in particular, with cancer stem cells. The nucleotide and protein sequences of TIM3 are known for many species. For example, the human amino acid sequence can be found under Uniprot accession number Q8TDQ0 (SEQ ID NO:93). The human protein is characterized by an extracellular domain comprising an Ig like domain and a mucin domain (further comprising O-linked and N-linked glycosylation sites) comprising approximately amino acids 22-202, a transmembrane domain (amino acids 203-223), and an intracellular (cytoplasmic) domain (amino acids 224-301). For the human TIM3 protein shown as SEQ ID NO: 93, the extracellular domain comprises approximately amino acids 22-202, the transmembrane domain comprises approximately amino acids 203-223, and the cytoplasmic domain comprises approximately amino acids 224-301. The term "TIM3" includes variants, isoforms, species homologs of human TIM3, and analogs having at least one common epitope with TIM3.

The terms "anti-TIM3 antibody" and "an antibody comprising an antigen-binding site that binds to TIM3" refer to an antibody that is capable of binding TIM3, especially a TIM3 polypeptide expressed on a cell surface, with sufficient affinity such that the antibody is useful as a diagnostic and/or therapeutic agent in targeting TIM3. In one embodiment, the extent of binding of an anti-TIM3 antibody to an unrelated, non-TIM3 protein is less than about 10% of the binding of the antibody to TIM3 as measured, e.g., by radioimmunoassay (RIA) or flow cytometry (FACS) or by a Surface Plasmon Resonance assay using a biosensor system such as a Biacore® system. In certain embodiments, an antigen binding protein that binds to human TIM3 has a KD value of the binding affinity for binding to human TIM3 of ≤1 µM, ≤100 nM, ≤10 nM, ≤1 nM, ≤0.1 nM, ≤0.01 nM, or ≤0.001 nM (e.g. 10-8 M or less, e.g. from 10-7 M to 10-13 M, e.g., from 10-9 M to 10-13 M). In one preferred embodiment the respective KD value of the binding affinities is determined in a Surface Plasmon Resonance assay using the Extracellular domain (ECD) of human TIM3 (TIM3-ECD) for the TIM3 binding affinity. The term "anti-TIM3 antibody" also encompasses bispecific antibodies that are capable of binding TIM3 and a second antigen.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. For example, the bispecific antibodies of the invention block the signaling through PD-1 and TIM-3 so as to restore a functional response by T cells (e.g., proliferation, cytokine production, target cell killing) from a dysfunctional state to antigen stimulation.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc domain" or "Fc region" herein is used to define a C-terminal region of an antibody heavy chain that contains at least a portion of the constant region. The term includes native sequence Fc regions and variant Fc regions. Particularly, a human IgG heavy chain Fc region extends from Cys226, or from Pro230, to the carboxyl-terminus of the heavy chain. However, the C-terminal lysine (Lys447) of the Fc region may or may not be present. The amino acid sequences of the heavy chains are always presented with the C-terminal lysine, however variants without the C-terminal lysine are included in the invention.

An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2.

By "fused" or "connected" is meant that the components (e.g. an antigen-binding site and a FC domain) are linked by peptide bonds, either directly or via one or more peptide linkers.

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain aspects, amino acid sequence variants of the bispecific antibodies of the invention provided herein are contemplated. For example, it may be desirable to improve the binding affinity and/or other biological properties of the bispecific antibodies. Amino acid sequence variants of the bispecific antibodies may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |

TABLE B-continued

| Original Residue | Exemplary Substitutions | Preferred Substitutions |
|---|---|---|
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antibodies with an N-terminal methionyl residue. Other insertional variants of the molecule include the fusion to the N- or C-terminus to a polypeptide which increases the serum half-life of the bispecific antibody.

In certain aspects, the bispecific antibodies provided herein are altered to increase or decrease the extent to which the antibody is glycosylated. Glycosylation variants of the molecules may be conveniently obtained by altering the amino acid sequence such that one or more glycosylation sites is created or removed, e.g. the carbohydrates attached to the Fc domain may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the bispecific antibodies of the invention may be made in order to create variants with certain improved properties. In one aspect, variants of bispecific antibodies are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of the bispecific antibodies of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antibodies of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the bispecific antibodies provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the bispecific antibody derivative will be used in a therapy under defined conditions, etc.

In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

An "immunoconjugate" is an antibody conjugated to one or more heterologous molecule(s), including but not limited to a cytotoxic agent.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. In particular, the host cell is a prokaryotic or eukaryotic host cell. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Bispecific Antibodies of the Invention

The invention provides novel bispecific antibodies comprising a first antigen-binding site that specifically binds to PD1 and a second antigen-binding site that specifically binds to TIM-3, with particularly advantageous properties such as producibility, stability, binding affinity, biological activity, specific targeting of certain T cells, targeting efficiency and reduced toxicity. In particular, these are bispecific antibodies, wherein the bispecific antibody binds to PD1 with high affinity and to TIM3 with low affinity.

A. Exemplary Bispecific Antibodies that Bind to PD1 and TIM-3

In one aspect, the invention provides a bispecific antibody comprising a first antigen-binding site that specifically binds to PD1 and a second antigen-binding site that specifically binds to TIM3, wherein said first antigen-binding site specifically binding to PD1 comprises
  a VH domain comprising
    (i) HVR-H1 comprising the amino acid sequence of SEQ ID NO:37,
    (ii) HVR-H2 comprising the amino acid sequence of SEQ ID NO:38, and
    (iii) HVR-H3 comprising an amino acid sequence of SEQ ID NO:39; and
  a VL domain comprising
    (i) HVR-L1 comprising the amino acid sequence of SEQ ID NO:40;
    (ii) HVR-L2 comprising the amino acid sequence of SEQ ID NO:41, and
    (iii) HVR-L3 comprising the amino acid sequence of SEQ ID NO:42; and
said second antigen-binding site specifically binding to TIM3 comprises
  (a) a VH domain comprising
    (i) HVR-H1 comprising the amino acid sequence of SEQ ID NO:1,
    (ii) HVR-H2 comprising the amino acid sequence of SEQ ID NO:2, and
    (iii) HVR-H3 comprising an amino acid sequence of SEQ ID NO:3; and
  a VL domain comprising
    (i) HVR-L1 comprising the amino acid sequence of SEQ ID NO:4 or SEQ ID NO:11 or SEQ ID NO:12,
    (ii) HVR-L2 comprising the amino acid sequence of SEQ ID NO:5, and
    (iii) HVR-L3 comprising the amino acid sequence of SEQ ID NO:6; or
  (b) a VH domain comprising
    (i) HVR-H1 comprising the amino acid sequence of SEQ ID NO:17,
    (ii) HVR-H2 comprising the amino acid sequence of SEQ ID NO:18, and
    (iii) HVR-H3 comprising an amino acid sequence of SEQ ID NO:19; and
  a VL domain comprising
    (i) HVR-L1 comprising the amino acid sequence of SEQ ID NO:20, (ii) HVR-L2 comprising the amino acid sequence of SEQ ID NO:21, and
(iii) HVR-L3 comprising the amino acid sequence of SEQ ID NO:22; or
(c) a VH domain comprising
(i) HVR-H1 comprising the amino acid sequence of SEQ ID NO:29,
(ii) HVR-H2 comprising the amino acid sequence of SEQ ID NO:30, and
(iii) HVR-H3 comprising an amino acid sequence of SEQ ID NO:31; and
a VL domain comprising
(i) HVR-L1 comprising the amino acid sequence of SEQ ID NO:32,
(ii) HVR-L2 comprising the amino acid sequence of SEQ ID NO:33, and
(iii) HVR-L3 comprising the amino acid sequence of SEQ ID NO:34.

In a particular aspect, provided is a bispecific antibody comprising a first antigen-binding site that specifically binds to PD1 and a second antigen-binding site that specifically binds to TIM3, wherein
said first antigen-binding site specifically binding to PD1 comprises
a VH domain comprising
(i) HVR-H1 comprising the amino acid sequence of SEQ ID NO:37,
(ii) HVR-H2 comprising the amino acid sequence of SEQ ID NO:38, and
(iii) HVR-H3 comprising an amino acid sequence of SEQ ID NO:39; and
a VL domain comprising
(i) HVR-L1 comprising the amino acid sequence of SEQ ID NO:40;
(ii) HVR-L2 comprising the amino acid sequence of SEQ ID NO:41, and
(iii) HVR-L3 comprising the amino acid sequence of SEQ ID NO:42; and
said second antigen-binding site specifically binding to TIM3 comprises
a VH domain comprising
(i) HVR-H1 comprising the amino acid sequence of SEQ ID NO:1,
(ii) HVR-H2 comprising the amino acid sequence of SEQ ID NO:2, and
(iii) HVR-H3 comprising an amino acid sequence of SEQ ID NO:3; and
a VL domain comprising
(i) HVR-L1 comprising the amino acid sequence of SEQ ID NO:12,
(ii) HVR-L2 comprising the amino acid sequence of SEQ ID NO:5, and
(iii) HVR-L3 comprising the amino acid sequence of SEQ ID NO:6.

In another particular aspect, provided is a bispecific antibody comprising a first antigen-binding site that specifically binds to PD1 and a second antigen-binding site that specifically binds to TIM3, wherein
said first antigen-binding site specifically binding to PD1 comprises
a VH domain comprising
(i) HVR-H1 comprising the amino acid sequence of SEQ ID NO:37,
(ii) HVR-H2 comprising the amino acid sequence of SEQ ID NO:38, and
(iii) HVR-H3 comprising an amino acid sequence of SEQ ID NO:39; and
a VL domain comprising
(i) HVR-L1 comprising the amino acid sequence of SEQ ID NO:40;
(ii) HVR-L2 comprising the amino acid sequence of SEQ ID NO:41, and
(iii) HVR-L3 comprising the amino acid sequence of SEQ ID NO:42; and
said second antigen-binding site specifically binding to TIM3 comprises
a VH domain comprising
(i) HVR-H1 comprising the amino acid sequence of SEQ ID NO:17,
(ii) HVR-H2 comprising the amino acid sequence of SEQ ID NO:18, and
(iii) HVR-H3 comprising an amino acid sequence of SEQ ID NO:19; and
a VL domain comprising
(i) HVR-L1 comprising the amino acid sequence of SEQ ID NO:20,
(ii) HVR-L2 comprising the amino acid sequence of SEQ ID NO:21, and
(iii) HVR-L3 comprising the amino acid sequence of SEQ ID NO:22.

In a further aspect, provided is a bispecific antibody comprising a first antigen-binding site that specifically binds to PD1 and a second antigen-binding site that specifically binds to TIM3, wherein
said first antigen-binding site specifically binding to PD1 comprises
(a) a VH domain comprising the amino acid sequence of SEQ ID NO: 43 and a VL domain comprising the amino acid sequence of SEQ ID NO: 44, or
(b) a VH domain comprising the amino acid sequence of SEQ ID NO: 45 and a VL domain comprising the amino acid sequence of SEQ ID NO: 46, or
(c) a VH domain comprising the amino acid sequence of SEQ ID NO: 45 and a VL domain comprising the amino acid sequence of SEQ ID NO: 47, or
(d) a VH domain comprising the amino acid sequence of SEQ ID NO: 45 and a VL domain comprising the amino acid sequence of SEQ ID NO: 48, or
(e) a VH domain comprising the amino acid sequence of SEQ ID NO: 45 and a VL domain comprising the amino acid sequence of SEQ ID NO: 49,
and said second antigen-binding site specifically binding to TIM3 comprises
(a) a VH domain comprising the amino acid sequence of SEQ ID NO: 7 and a VL domain comprising the amino acid sequence of SEQ ID NO: 8, or
(b) a VH domain comprising the amino acid sequence of SEQ ID NO: 9 and a VL domain comprising the amino acid sequence of SEQ ID NO: 10, or
(c) a VH domain comprising the amino acid sequence of SEQ ID NO: 13 and a VL domain comprising the amino acid sequence of SEQ ID NO: 14, or
(d) a VH domain comprising the amino acid sequence of SEQ ID NO: 15 and a VL domain comprising the amino acid sequence of SEQ ID NO: 16, or
(e) a VH domain comprising the amino acid sequence of SEQ ID NO: 23 and a VL domain comprising the amino acid sequence of SEQ ID NO: 24, or
(f) a VH domain comprising the amino acid sequence of SEQ ID NO: 25 and a VL domain comprising the amino acid sequence of SEQ ID NO: 26, or
(g) a VH domain comprising the amino acid sequence of SEQ ID NO: 27 and a VL domain comprising the amino acid sequence of SEQ ID NO: 28, or (h) a VH domain comprising the amino acid sequence of SEQ ID NO: 35 and a VL domain comprising the amino acid sequence of SEQ ID NO: 36.

In a further aspect, the bispecific antibody comprising a first antigen-binding site that specifically binds to PD1 and a second antigen-binding site that specifically binds to TIM3 is a human, humanized or chimeric antibody. In particular, it is a humanized antibody.

In one aspect, provided is a humanized, bispecific antibody comprising a first antigen-binding site that specifically binds to PD1 and a second antigen-binding site that specifically binds to TIM3, wherein
said first antigen-binding site specifically binding to PD1 comprises
(a) a VH domain comprising the amino acid sequence of SEQ ID NO: 45 and a VL domain comprising the amino acid sequence of SEQ ID NO: 46, or
(b) a VH domain comprising the amino acid sequence of SEQ ID NO: 45 and a VL domain comprising the amino acid sequence of SEQ ID NO: 47, or
(c) a VH domain comprising the amino acid sequence of SEQ ID NO: 45 and a VL domain comprising the amino acid sequence of SEQ ID NO: 48, or
(d) a VH domain comprising the amino acid sequence of SEQ ID NO: 45 and a VL domain comprising the amino acid sequence of SEQ ID NO: 49,
and said second antigen-binding site specifically binding to TIM3 comprises
(a) a VH domain comprising the amino acid sequence of SEQ ID NO: 13 and a VL domain comprising the amino acid sequence of SEQ ID NO: 14, or
(b) a VH domain comprising the amino acid sequence of SEQ ID NO: 15 and a VL domain comprising the amino acid sequence of SEQ ID NO: 16, or
(c) a VH domain comprising the amino acid sequence of SEQ ID NO: 25 and a VL domain comprising the amino acid sequence of SEQ ID NO: 26, or
(d) a VH domain comprising the amino acid sequence of SEQ ID NO: 27 and a VL domain comprising the amino acid sequence of SEQ ID NO: 28.

In a particular aspect, provided is a bispecific antibody comprising a first antigen-binding site that specifically binds to PD1 and a second antigen-binding site that specifically binds to TIM3, wherein
said first antigen-binding site specifically binding to PD1 comprises a VH domain comprising the amino acid sequence of SEQ ID NO: 45 and a VL domain comprising the amino acid sequence of SEQ ID NO: 46,
and said second antigen-binding site specifically binding to TIM3 comprises a VH domain comprising the amino acid sequence of SEQ ID NO: 15 and a VL domain comprising the amino acid sequence of SEQ ID NO: 16 or a VH domain comprising the amino acid sequence of SEQ ID NO: 25 and a VL domain comprising the amino acid sequence of SEQ ID NO: 26.

Particularly, the invention provides a bispecific antibody comprising a first antigen-binding site that specifically binds to PD1 and a second antigen-binding site that specifically binds to TIM3, wherein
said first antigen-binding site specifically binding to PD1 comprises
a VH domain comprising
(i) HVR-H1 comprising the amino acid sequence of SEQ ID NO:37,
(ii) HVR-H2 comprising the amino acid sequence of SEQ ID NO:38, and
(iii) HVR-H3 comprising an amino acid sequence of SEQ ID NO:39; and
a VL domain comprising
(i) HVR-L1 comprising the amino acid sequence of SEQ ID NO:40;
(ii) HVR-L2 comprising the amino acid sequence of SEQ ID NO:41, and
(iii) HVR-L3 comprising the amino acid sequence of SEQ ID NO:42; and
said second antigen-binding site specifically binding to TIM3 comprises a VH domain comprising
(i) HVR-H1 comprising the amino acid sequence of SEQ ID NO:17,
(ii) HVR-H2 comprising the amino acid sequence of SEQ ID NO:18, and
(iii) HVR-H3 comprising an amino acid sequence of SEQ ID NO:19; and
a VL domain comprising
(i) HVR-L1 comprising the amino acid sequence of SEQ ID NO:20,
(ii) HVR-L2 comprising the amino acid sequence of SEQ ID NO:21, and
(iii) HVR-L3 comprising the amino acid sequence of SEQ ID NO:22.

More particularly, provided is a bispecific antibody comprising a first antigen-binding site that specifically binds to PD1 and a second antigen-binding site that specifically binds to TIM3, wherein said first antigen-binding site specifically binding to PD1 comprises a VH domain comprising the amino acid sequence of SEQ ID NO: 45 and a VL domain comprising the amino acid sequence selected from the group consisting of SEQ ID NO: 46, SEQ ID NO:47, SEQ ID NO:48 and SEQ ID NO:49, and said second antigen-binding site specifically binding to TIM3 comprises a VH domain comprising the amino acid sequence of SEQ ID NO: 25 and a VL domain comprising the amino acid sequence of SEQ ID NO: 26.

More specifically, provided is a bispecific antibody comprising a first antigen-binding site that specifically binds to PD1 and a second antigen-binding site that specifically binds to TIM3, wherein said first antigen-binding site specifically binding to PD1 comprises a VH domain comprising the amino acid sequence of SEQ ID NO: 45 and a VL domain comprising the amino acid sequence of SEQ ID NO: 46, and said second antigen-binding site specifically binding to TIM3 comprises a VH domain comprising the amino acid sequence of SEQ ID NO: 25 and a VL domain comprising the amino acid sequence of SEQ ID NO: 26.

In a further aspect, provided is a bispecific antibody comprising a first antigen-binding site that specifically binds to PD1 and a second antigen-binding site that specifically binds to TIM3, wherein said first antigen-binding site specifically binding to PD1 comprises a VH domain comprising the amino acid sequence of SEQ ID NO: 45 and a VL domain comprising the amino acid sequence selected from the group consisting of SEQ ID NO: 46, SEQ ID NO:47, SEQ ID NO:48 and SEQ ID NO:49, and said second antigen-binding site specifically binding to TIM3 comprises a VH domain comprising the amino acid sequence of SEQ ID NO: 27 and a VL domain comprising the amino acid sequence of SEQ ID NO: 28.

In one aspect, the bispecific antibody comprising a first antigen-binding site that specifically binds to PD1 and a second antigen-binding site that specifically binds to TIM3 is bivalent. This means that the bispecific antibody comprises one antigen-binding site that specifically binds to PD1 and one antigen-binding site that specifically binds to TIM3 (1+1 format).

In another aspect, provided is a bispecific antibody comprising a first antigen-binding site that specifically binds to PD1 and a second antigen-binding site that specifically binds to TIM3, wherein the bispecific antibody binds to TIM3 with low affinity and binds to PD1 with high affinity. In a particular aspect, the invention provides a bispecific antibody comprising a first antigen-binding site that specifically binds to PD1 and a second antigen-binding site that specifically binds to TIM3, wherein the bispecific antibody binds to TIM3 with an at least 50 fold lower binding affinity when compared to the binding to PD1, more particularly with an at least 100 fold lower binding affinity when compared to the binding to PD1. In one preferred embodiment the binding affinity (KD) is determined with Surface Plasmon Resoncance Assay (as described e.g. in Example 12.)

In one aspect, thus provided is a bispecific antibody comprising a first antigen-binding site that specifically binds to PD1 and a second antigen-binding site that specifically binds to TIM3, wherein
    said first antigen-binding site specifically binding to PD1 with high affinity comprises
        (a) a VH domain comprising the amino acid sequence of SEQ ID NO: 43 and a VL domain comprising the amino acid sequence of SEQ ID NO: 44, or
        (b) a VH domain comprising the amino acid sequence of SEQ ID NO: 45 and a VL domain comprising the amino acid sequence of SEQ ID NO: 46, or
        (c) a VH domain comprising the amino acid sequence of SEQ ID NO: 45 and a VL domain comprising the amino acid sequence of SEQ ID NO: 47, or
        (d) a VH domain comprising the amino acid sequence of SEQ ID NO: 45 and a VL domain comprising the amino acid sequence of SEQ ID NO: 48, or
        (d) a VH domain comprising the amino acid sequence of SEQ ID NO: 45 and a VL domain comprising the amino acid sequence of SEQ ID NO: 49,
    and said second antigen-binding site specifically binding to TIM3 with low affinity comprises
        (a) a VH domain comprising the amino acid sequence of SEQ ID NO: 23 and a VL domain comprising the amino acid sequence of SEQ ID NO: 24, or
        (c) a VH domain comprising the amino acid sequence of SEQ ID NO: 25 and a VL domain comprising the amino acid sequence of SEQ ID NO: 26, or
        (d) a VH domain comprising the amino acid sequence of SEQ ID NO: 27 and a VL domain comprising the amino acid sequence of SEQ ID NO: 28.

In a specific aspect, provided is a bispecific antibody comprising a first antigen-binding site that specifically binds to PD1 and a second antigen-binding site that specifically binds to TIM3, wherein said first antigen-binding site specifically binding to PD1 with high affinity comprises a VH domain comprising the amino acid sequence of SEQ ID NO: 45 and a VL domain comprising the amino acid sequence of SEQ ID NO: 46, and said second antigen-binding site specifically binding to TIM3 with low affinity comprises a VH domain comprising the amino acid sequence of SEQ ID NO: 25 and a VL domain comprising the amino acid sequence of SEQ ID NO: 26.

In another aspect, the invention relates to a bispecific antibody comprising a first antigen-binding site that specifically binds to PD1 and a second antigen-binding site that specifically binds to TIM3, wherein the bispecific antibody comprises an Fc domain, a first Fab fragment comprising the antigen-binding site that specifically binds to PD1 and a second Fab fragment comprising the antigen-binding site that specifically binds to TIM3.

In particular, the Fc domain is an IgG domain, more particularly an IgG1 Fc domain or an IgG4 Fc domain.

In another aspect, the invention provides a bispecific antibody comprising a first antigen-binding site that specifically binds to PD1 and a second antigen-binding site that specifically binds to TIM3, comprising
(a) a first heavy chain comprising an amino acid sequence with at least 95% sequence identity to the sequence of SEQ ID NO: 50, a first light chain comprising an amino acid sequence with at least 95% sequence identity to the sequence of SEQ ID NO: 52,
    a second heavy chain comprising an amino acid sequence with at least 95% sequence identity to the sequence of SEQ ID NO: 51, and a second light chain comprising an amino acid sequence with at least 95% sequence identity to the sequence of SEQ ID NO:53, or
(b) a first heavy chain comprising an amino acid sequence with at least 95% sequence identity to the sequence of SEQ ID NO: 54, a first light chain comprising an amino acid sequence with at least 95% sequence identity to the sequence of SEQ ID NO: 56,
    a second heavy chain comprising an amino acid sequence with at least 95% sequence identity to the sequence of SEQ ID NO: 55, and a second light chain comprising an amino acid sequence with at least 95% sequence identity to the sequence of SEQ ID NO:57, or
(c) a first heavy chain comprising an amino acid sequence with at least 95% sequence identity to the sequence of SEQ ID NO: 58, a first light chain comprising an amino acid sequence with at least 95% sequence identity to the sequence of SEQ ID NO: 60,
    a second heavy chain comprising an amino acid sequence with at least 95% sequence identity to the sequence of SEQ ID NO: 59, and a second light chain comprising an amino acid sequence with at least 95% sequence identity to the sequence of SEQ ID NO:61, or
(d) a first heavy chain comprising an amino acid sequence with at least 95% sequence identity to the sequence of SEQ ID NO: 62, a first light chain comprising an amino acid sequence with at least 95% sequence identity to the sequence of SEQ ID NO: 64,
    a second heavy chain comprising an amino acid sequence with at least 95% sequence identity to the sequence of SEQ ID NO: 63, and a second light chain comprising an amino acid sequence with at least 95% sequence identity to the sequence of SEQ ID NO:65, or
(e) a first heavy chain comprising an amino acid sequence with at least 95% sequence identity to the sequence of SEQ ID NO: 66, a first light chain comprising an amino acid sequence with at least 95% sequence identity to the sequence of SEQ ID NO: 68,
    a second heavy chain comprising an amino acid sequence with at least 95% sequence identity to the sequence of SEQ ID NO: 67, and a second light chain comprising an amino acid sequence with at least 95% sequence identity to the sequence of SEQ ID NO:69.

In a particular aspect, the invention provides a bispecific antibody comprising a first antigen-binding site that specifically binds to PD1 and a second antigen-binding site that specifically binds to TIM3, comprising
(a) a first heavy chain comprising the amino acid sequence of SEQ ID NO: 50, a first light chain comprising the amino acid sequence of SEQ ID NO: 52, a second heavy chain comprising the amino acid sequence of SEQ ID NO: 51, and a second light chain comprising the amino acid sequence of SEQ ID NO:53, or (b) a first heavy chain comprising the amino acid sequence of SEQ ID NO: 54, a first light chain comprising the amino acid sequence of SEQ ID NO: 56, a second heavy chain comprising the amino acid sequence of SEQ ID NO: 55, and a second light chain comprising the amino acid sequence of SEQ ID NO:57, or (c) a first heavy chain comprising the amino acid sequence of SEQ ID NO: 58, a first light chain comprising the amino acid sequence of SEQ ID NO: 60, a second heavy chain comprising the amino acid sequence of SEQ ID NO: 59, and a second light chain comprising the amino acid sequence of SEQ ID NO:61, or (d) a first heavy chain comprising the amino acid sequence of SEQ ID NO: 62, a first light chain comprising the amino acid sequence of SEQ ID NO: 64, a second heavy chain comprising the amino acid sequence of SEQ ID NO: 63, and a second light chain comprising the amino acid sequence of SEQ ID NO:65, or (e) a first heavy chain comprising the amino acid sequence of SEQ ID NO: 66, a first light chain comprising the amino acid sequence of SEQ ID NO: 68, a second heavy chain comprising the amino acid sequence of SEQ ID NO: 67, and a second light chain comprising the amino acid sequence of SEQ ID NO:69.

More particularly, the invention provides a bispecific antibody comprising a first antigen-binding site that specifically binds to PD1 and a second antigen-binding site that specifically binds to TIM3, comprising a first heavy chain comprising the amino acid sequence of SEQ ID NO: 62, a first light chain comprising the amino acid sequence of SEQ ID NO: 64, a second heavy chain comprising the amino acid sequence of SEQ ID NO: 63, and a second light chain comprising the amino acid sequence of SEQ ID NO:65.

In another particular aspect, provided is a bispecific antibody comprising a first antigen-binding site that specifically binds to PD1 and a second antigen-binding site that specifically binds to TIM3, a first heavy chain comprising the amino acid sequence of SEQ ID NO: 66, a first light chain comprising the amino acid sequence of SEQ ID NO: 68, a second heavy chain comprising the amino acid sequence of SEQ ID NO: 67, and a second light chain comprising the amino acid sequence of SEQ ID NO:69.

In another aspect, the bispecific antibody comprising a first antigen-binding site that specifically binds to PD1 and a second antigen-binding site that specifically binds to TIM3 is tetravalent. In one aspect, the bispecific antibody comprises two antigen-binding sites that specifically bind to PD1 and two antigen-binding sites that specifically bind to TIM3 (2+2 format).

In one aspect, the bispecific antibody of the invention comprises (a) two light chains and two heavy chains of an antibody comprising two Fab fragments comprising the antigen-binding sites that specifically bind to TIM3, and (b) two additional Fab fragments comprising the antigen-binding sites that specifically bind to PD1, wherein said additional Fab fragments are each connected via a peptide linker to the C-terminus of the heavy chains of (a).

In a particular aspect, the peptide linker is $(G4S)_4$. In another aspect, the two additional Fab fragments comprising the antigen-binding sites that specifically bind to PD1 are crossover Fab fragments wherein the variable domains VL and VH are replaced by each other and the VL-CH chains are each connected via a peptide linker to the C-terminus of the heavy chains of (a).

In a particular aspect, the invention provides a bispecific antibody comprising a first antigen-binding site that specifically binds to PD1 and a second antigen-binding site that specifically binds to TIM3, comprising (a) two heavy chains, each comprising the amino acid sequence of SEQ ID NO: 70, a first light chain comprising the amino acid sequence of SEQ ID NO: 71, and a second light chain comprising the amino acid sequence of SEQ ID NO:72, or (b) two heavy chains, each comprising the amino acid sequence of SEQ ID NO: 73, a first light chain comprising the amino acid sequence of SEQ ID NO: 74, and a second light chain comprising the amino acid sequence of SEQ ID NO:75, or (c) two heavy chains, each comprising the amino acid sequence of SEQ ID NO: 76, a first light chain comprising the amino acid sequence of SEQ ID NO: 77, and a second light chain comprising the amino acid sequence of SEQ ID NO:78.

Fc Domain Modifications Reducing Fc Receptor Binding and/or Effector Function

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The following section describes preferred aspects of the bispecific antigen binding molecules of the invention comprising Fc domain modifications reducing Fc receptor binding and/or effector function. In one aspect, the invention relates to a bispecific antibody comprising a first antigen-binding site that specifically binds to PD1 and a second antigen-binding site that specifically binds to TIM3, wherein the Fc domain comprises one or more amino acid substitution that reduces binding to an Fc receptor, in particular towards Fcγ receptor. In particular, the Fc domain is of human IgG1 subclass with the amino acid mutations L234A, L235A and P329G (numbering according to Kabat EU index).

The Fc domain confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc domain of the bispecific antibodies of the invention exhibits reduced binding affinity to an Fc receptor and/or reduced effector function, as compared to a native IgG Fc domain, in particular an IgG1 FC domain or an IgG4 Fc domain. More particularly, the Fc domain is an IgG1 FC domain.

In one such aspect the Fc domain (or the bispecific antigen binding molecule of the invention comprising said Fc domain) exhibits less than 50%, preferably less than 20%, more preferably less than 10% and most preferably less than 5% of the binding affinity to an Fc receptor, as compared to a native IgG1 Fc domain (or the bispecific antigen binding molecule of the invention comprising a native IgG1 Fc domain), and/or less than 50%, preferably less than 20%, more preferably less than 10% and most preferably less than 5% of the effector function, as compared to a native IgG1 Fc domain (or the bispecific antigen binding molecule of the invention comprising a native IgG1 Fc domain). In one aspect, the Fc domain (or the bispecific antigen binding molecule of the invention comprising said Fc domain) does not substantially bind to an Fc receptor and/or induce effector function. In a particular aspect the Fc receptor is an Fcγ receptor. In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human FcγRIIB. In one aspect the effector function is one or more of CDC, ADCC, ADCP, and cytokine secretion. In a particular aspect, the effector function is ADCC. In one aspect, the Fc domain domain exhibits substantially similar binding affinity to neonatal Fc receptor (FcRn), as compared to a native IgG1 Fc domain. Substantially similar binding to FcRn is achieved when the Fc domain (or the bispecific antigen binding molecule of the invention comprising said Fc domain) exhibits greater than about 70%, particularly greater than about 80%, more particularly greater than about 90% of the binding affinity of a native IgG1 Fc domain (or the bispecific antigen binding molecule of the invention comprising a native IgG1 Fc domain) to FcRn.

In a particular aspect, the Fc domain is engineered to have reduced binding affinity to an Fc receptor and/or reduced effector function, as compared to a non-engineered Fc domain. In a particular aspect, the Fc domain of the bispecific antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In another aspect, the amino acid mutation reduces the binding affinity of the Fc domain to an Fc receptor by at least 2-fold, at least 5-fold, or at least 10-fold. In one aspect, the bispecific antigen binding molecule of the invention comprising an engineered Fc domain exhibits less than 20%, particularly less than 10%, more particularly less than 5% of the binding affinity to an Fc receptor as compared to bispecific antibodies of the invention comprising a non-engineered Fc domain. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human FcγRIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the bispecific antigen binding molecule of the invention comprising said Fc domain) exhibits greater than about 70% of the binding affinity of a non-engineered form of the Fc domain (or the bispecific antigen binding molecule of the invention comprising said non-engineered form of the Fc domain) to FcRn. The Fc domain, or the bispecific antigen binding molecule of the invention comprising said Fc domain, may exhibit greater than about 80% and even greater than about 90% of such affinity. In certain embodiments the Fc domain of the bispecific antigen binding molecule of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect of the invention, the Fc domain comprises an amino acid substitution at a position of E233, L234, L235, N297, P331 and P329. In some aspects, the Fc domain comprises the amino acid substitutions L234A and L235A ("LALA"). In one such embodiment, the Fc domain is an IgG1 Fc domain, particularly a human IgG1 Fc domain. In one aspect, the Fc domain comprises an amino acid substitution at position P329. In a more specific aspect, the amino acid substitution is P329A or P329G, particularly P329G. In one embodiment the Fc domain comprises an amino acid substitution at position P329 and a further amino acid substitution selected from the group consisting of E233P, L234A, L235A, L235E, N297A, N297D or P331S. In more particular embodiments the Fc domain comprises the amino acid mutations L234A, L235A and P329G ("P329G LALA"). The "P329G LALA" combination of amino acid substitutions almost completely abolishes Fcγ receptor binding of a human IgG1 Fc domain, as described in PCT Patent Application No. WO 2012/130831 A1. Said document also describes methods of preparing such mutant Fc domains and methods for determining its properties such as Fc receptor binding or effector functions such antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, Md., 1991).

In one aspect, the bispecific antibody of the invention comprises (all positions according to EU index of Kabat) (i) a homodimeric Fc-region of the human IgG1 subclass optionally with the mutations P329G, L234A and L235A, or (ii) a homodimeric Fc-region of the human IgG4 subclass optionally with the mutations P329G, S228P and L235E, or (iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or (iv) a heterodimeric Fc-region wherein one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C, or (v) a heterodimeric Fc-region of the human IgG1 subclass wherein both Fc-region polypeptides comprise the mutations P329G, L234A and L235A and one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C.

In one aspect, the Fc domain is an IgG4 Fc domain. In a more specific embodiment, the Fc domain is an IgG4 Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)). Thus, in one aspect, provided is a bispecific antibody, comprising (all positions according to EU index of Kabat) a heterodimeric Fc-region of the human IgG4 subclass wherein both Fc-region polypeptides comprise the mutations P329G, S228P and L235E and one Fc-region polypeptide comprises the mutation T366W, and the other Fc-region polypeptide comprises the mutations T366S, L368A and Y407V, or wherein one Fc-region polypeptide comprises the mutations T366W and Y349C, and the other Fc-region polypeptide comprises the mutations T366S, L368A, Y407V, and S354C, or wherein one Fc-region polypeptide comprises the mutations T366W and S354C, and the other Fc-region polypeptide comprises the mutations T366S, L368A, Y407V and Y349C.

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor. Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

Fc Domain Modifications Promoting Heterodimerization

The bispecific antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antigen binding molecules of the invention a modification promoting the association of the desired polypeptides.

Accordingly, in particular aspects the invention relates to a bispecific antibody comprising a first antigen-binding site that specifically binds to PD1 and a second antigen-binding site that specifically binds to TIM3, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to a bispecific antibody comprising a first antigen-binding site that specifically binds to PD1 and a second antigen-binding site that specifically binds to TIM3, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

But also other knobs-in-holes technologies as described by EP 1 870 459, can be used alternatively or additionally. In one embodiment the multispecific antibody comprises the mutations R409D and K370E in the CH3 domain of the "knobs chain" and the mutations D399K and E357K in the CH3 domain of the "hole-chain" (numbering according to Kabat EU index).

In one aspect, the bispecific antibody comprises a T366W mutation in the CH3 domain of the "knobs chain" and the mutations T366S, L368A and Y407V in the CH3 domain of the "hole chain" and additionally the mutations R409D and K370E in the CH3 domain of the "knobs chain" and the mutations D399K and E357K in the CH3 domain of the "hole chain" (numbering according to the Kabat EU index).

In one aspect, the bispecific antibody comprises the mutations Y349C and T366W in one of the two CH3 domains and the mutations S354C, T366S, L368A and Y407V in the other of the two CH3 domains, or the multispecific antibody comprises the mutations Y349C and T366W in one of the two CH3 domains and the mutations S354C, T366S, L368A and Y407V in the other of the two CH3 domains and additionally the mutations R409D and K370E in the CH3 domain of the "knobs chain" and the mutations D399K and E357K in the CH3 domain of the "hole chain" (numbering according to the Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Apart from the "knob-into-hole technology" other techniques for modifying the CH3 domains of the heavy chains of a multispecific antibody to enforce heterodimerization are known in the art. These technologies, especially the ones described in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291 are contemplated herein as alternatives to the "knob-into-hole technology" in combination with a bispecific antibody.

In one aspect, in the bispecific antibody the approach described in EP 1870459 is used to support heterodimerization of the first heavy chain and the second heavy chain of the multispecific antibody. This approach is based on the introduction of charged amino acids with opposite charges at specific amino acid positions in the CH3/CH3-domain-interface between both, the first and the second heavy chain.

Accordingly, in this aspect in the tertiary structure of the multispecific antibody the CH3 domain of the first heavy chain and the CH3 domain of the second heavy chain form an interface that is located between the respective antibody CH3 domains, wherein the respective amino acid sequences of the CH3 domain of the first heavy chain and the amino acid sequence of the CH3 domain of the second heavy chain each comprise a set of amino acids that is located within said interface in the tertiary structure of the antibody, wherein from the set of amino acids that is located in the interface in the CH3 domain of one heavy chain a first amino acid is substituted by a positively charged amino acid and from the set of amino acids that is located in the interface in the CH3 domain of the other heavy chain a second amino acid is substituted by a negatively charged amino acid. The bispecific antibody according to this aspect is herein also referred to as "CH3(+/−)-engineered bispecific antibody" (wherein the abbreviation "+/−" stands for the oppositely charged amino acids that were introduced in the respective CH3 domains).

In one aspect, in the CH3(+/−)-engineered bispecific antibody the positively charged amino acid is selected from K, R and H, and the negatively charged amino acid is selected from E or D.

In one aspect, in the CH3(+/−)-engineered bispecific antibody the positively charged amino acid is selected from K and R, and the negatively charged amino acid is selected from E or D.

In one aspect, in the CH3(+/−)-engineered bispecific antibody the positively charged amino acid is K, and the negatively charged amino acid is E.

In one aspect, in the CH3(+/−)-engineered bispecific antibody in the CH3 domain of one heavy chain the amino acid R at position 409 is substituted by D and the amino acid K at position is substituted by E, and in the CH3 domain of the other heavy chain the amino acid D at position 399 is substituted by K and the amino acid E at position 357 is substituted by K (numbering according to Kabat EU index).

In one aspect, the approach described in WO 2013/157953 is used to support heterodimerization of the first heavy chain and the second heavy chain of the multispecific antibody. In one embodiment in the CH3 domain of one heavy chain the amino acid T at position 366 is substituted by K, and in the CH3 domain of the other heavy chain the amino acid L at position 351 is substituted by D (numbering according to Kabat EU index). In another embodiment in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index).

In another aspect, in the CH3 domain of one heavy chain the amino acid T at position 366 is substituted by K and the amino acid L at position 351 is substituted by K, and in the CH3 domain of the other heavy chain the amino acid L at position 351 is substituted by D (numbering according to Kabat EU index). Additionally at least one of the following substitutions is comprised in the CH3 domain of the other heavy chain: the amino acid Y at position 349 is substituted by E, the amino acid Y at position 349 is substituted by D and the amino acid L at position 368 is substituted by E (numbering according to Kabat EU index). In one embodiment the amino acid L at position 368 is substituted by E (numbering according to Kabat EU index).

In one aspect, the approach described in WO 2012/058768 is used to support heterodimerization of the first heavy chain and the second heavy chain of the multispecific antibody. In one aspect, in the CH3 domain of one heavy chain the amino acid L at position 351 is substituted by Y and the amino acid Y at position 407 is substituted by A, and in the CH3 domain of the other heavy chain the amino acid T at position 366 is substituted by A and the amino acid K at position 409 is substituted by F (numbering according to Kabat EU index). In another embodiment, in addition to the aforementioned substitutions, in the CH3 domain of the other heavy chain at least one of the amino acids at positions 411 (originally T), 399 (originally D), 400 (originally S), 405 (originally F), 390 (originally N) and 392 (originally K) is substituted (numbering according to Kabat EU index). Preferred substitutions are:
  substituting the amino acid T at position 411 by an amino acid selected from N, R, Q, K, D, E and W (numbering according to Kabat EU index),
  substituting the amino acid D at position 399 by an amino acid selected from R, W, Y, and K (numbering according to Kabat EU index),
  substituting the amino acid S at position 400 by an amino acid selected from E, D, R and K (numbering according to Kabat EU index),
  substituting the amino acid F at position 405 by an amino acid selected from I, M, T, S, V and W (numbering according to Kabat EU index;
  substituting the amino acid N at position 390 by an amino acid selected from R, K and D (numbering according to Kabat EU index; and
  substituting the amino acid K at position 392 by an amino acid selected from V, M, R, L, F and E (numbering according to Kabat EU index).

In another aspect, the bispecific antibody is engineered according to WO 2012/058768), i.e. in the CH3 domain of one heavy chain the amino acid L at position 351 is substituted by Y and the amino acid Y at position 407 is substituted by A, and in the CH3 domain of the other heavy chain the amino acid T at position 366 is substituted by V and the amino acid K at position 409 is substituted by F (numbering according to Kabat EU index). In another embodiment of the multispecific antibody, in the CH3 domain of one heavy chain the amino acid Y at position 407 is substituted by A, and in the CH3 domain of the other heavy chain the amino acid T at position 366 is substituted by A and the amino acid K at position 409 is substituted by F (numbering according to Kabat EU index). In the last aforementioned embodiment, in the CH3 domain of the other heavy chain the amino acid K at position 392 is substituted by E, the amino acid T at position 411 is substituted by E, the amino acid D at position 399 is substituted by R and the amino acid S at position 400 is substituted by R (numbering according to Kabat EU index).

In one aspect, the approach described in WO 2011/143545 is used to support heterodimerization of the first heavy chain and the second heavy chain of the multispecific antibody. In one aspect, amino acid modifications in the CH3 domains of both heavy chains are introduced at positions 368 and/or 409 (numbering according to Kabat EU index).

In one aspect, the approach described in WO 2011/090762 is used to support heterodimerization of the first heavy chain and the second heavy chain of the bispecific antibody. WO 2011/090762 relates to amino acid modifications according to the "knob-into-hole" (KiH) technology. In one embodiment in the CH3 domain of one heavy chain the amino acid T at position 366 is substituted by W, and in the CH3 domain of the other heavy chain the amino acid Y at position 407 is substituted by A (numbering according to Kabat EU index). In another embodiment in the CH3 domain of one heavy chain the amino acid T at position 366 is substituted by Y, and in the CH3 domain of the other heavy chain the amino acid Y at position 407 is substituted by T (numbering according to Kabat EU index).

In one aspect, the approach described in WO 2009/089004 is used to support heterodimerization of the first heavy chain and the second heavy chain of the bispecific antibody. In one embodiment in the CH3 domain of one heavy chain the amino acid K or N at position 392 is substituted by a negatively charged amino acid (in one embodiment by E or D, in one preferred embodiment by D), and in the CH3 domain of the other heavy chain the amino acid D at position 399 the amino acid E or D at position 356 or the amino acid E at position 357 is substituted by a positively charged amino acid (in one embodiment K or R, in one preferred embodiment by K, in one preferred embodiment the amino acids at positions 399 or 356 are substituted by K) (numbering according to Kabat EU index). In one further embodiment, in addition to the aforementioned substitutions, in the CH3 domain of the one heavy chain the amino acid K or R at position 409 is substituted by a negatively charged amino acid (in one embodiment by E or D, in one preferred embodiment by D) (numbering according to Kabat EU index). In one even further aspect, in addition to or alternatively to the aforementioned substitutions, in the CH3 domain of the one heavy chain the amino acid K at position 439 and/or the amino acid K at position 370 is substituted independently from each other by a negatively charged amino acid (in one embodiment by E or D, in one preferred embodiment by D) (numbering according to Kabat EU index).

In one aspect, the approach described in WO 2007/147901 is used to support heterodimerization of the first heavy chain and the second heavy chain of the multispecific antibody. In one embodiment in the CH3 domain of one heavy chain the amino acid K at position 253 is substituted by E, the amino acid D at position 282 is substituted by K and the amino acid K at position 322 is substituted by D, and in the CH3 domain of the other heavy chain the amino acid D at position 239 is substituted by K, the amino acid E at position 240 is substituted by K and the amino acid K at position 292 is substituted by D (numbering according to Kabat EU index).

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG.

In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific antibody comprising a first Fab fragment that specifically binds to PD1 and a second Fab fragment that specifically binds to TIM3, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In a particular aspect, the invention relates to a bispecific antibody comprising a first Fab fragment that specifically binds to PD1 and a second Fab fragment that specifically binds to TIM3, wherein in one of the Fab fragments the variable domains VL and VH are replaced by each other so that the VH domain is part of the light chain and the VL domain is part of the heavy chain. In a particular aspect, the bispecific antibody is one, wherein in the first Fab fragment comprising the antigen-binding site that specifically binds to PD1 the variable domains VL and VH are replaced by each other.

In another aspect, and to further improve correct pairing, the bispecific antibody comprising a first Fab fragment that specifically binds to PD1 and a second Fab fragment that specifically binds to TIM3, can contain different charged amino acid substitutions (so-called "charged residues"). These modifications are introduced in the crossed or non-crossed CH1 and CL domains.

In a particular aspect, the invention is concerned with a bispecific antibody comprising a first Fab fragment that specifically binds to PD1 and a second Fab fragment that specifically binds to TIM3, wherein in one of the Fab fragments in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index). In a particular aspect, the bispecific antibody is one, wherein in the second Fab fragment comprising the antigen-binding site that specifically binds to TIM3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

In a particular aspect, the invention relates to a bispecific antibody comprising a first Fab fragment that specifically binds to PD1 and a second Fab fragment that specifically binds to TIM3, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E). In a particular aspect, the bispecific antibody is one, wherein in the second Fab fragment comprising the antigen-binding site that specifically binds to TIM3 the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

In a further aspect, the bispecific antibody is a bivalent antibody comprising a) a first light chain and a first heavy chain of an antibody specifically binding to a first antigen, and b) a second light chain and a second heavy chain of an antibody specifically binding to a second antigen, wherein the variable domains VL and VH of the second light chain and the second heavy chain are replaced by each other.

The antibody under a) does not contain a modification as reported under b) and the heavy chain and the light chain under a) are isolated chains.

In the antibody under b) within the light chain the variable light chain domain VL is replaced by the variable heavy chain domain VH of said antibody, and within the heavy chain the variable heavy chain domain VH is replaced by the variable light chain domain VL of said antibody.

In one aspect, (i) in the constant domain CL of the first light chain under a) the amino acid at position 124 (numbering according to Kabat) is substituted by a positively charged amino acid, and wherein in the constant domain CH1 of the first heavy chain under a) the amino acid at position 147 or the amino acid at position 213 (numbering according to Kabat EU index) is substituted by a negatively charged amino acid, or (ii) in the constant domain CL of the second light chain under b) the amino acid at position 124 (numbering according to Kabat) is substituted by a positively charged amino acid, and wherein in the constant domain CH1 of the second heavy chain under b) the amino acid at position 147 or the amino acid at position 213 (numbering according to Kabat EU index) is substituted by a negatively charged amino acid.

In another aspect, (i) in the constant domain CL of the first light chain under a) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the first heavy chain under a) the amino acid at position 147 or the amino acid at position 213 is substituted independently by glutamic acid (E) or aspartic acid (D) (numbering according to Kabat EU index), or (ii) in the constant domain CL of the second light chain under b) the amino acid at position 124 is substituted independently by lysine (K), arginine (R) or histidine (H) (numbering according to Kabat) (in one preferred embodiment independently by lysine (K) or arginine (R)), and wherein in the constant domain CH1 of the second heavy chain under b) the amino acid at position 147 or the amino acid at position 213 is substituted independently by glutamic acid (E) or aspartic acid (D) (numbering according to Kabat EU index).

In one aspect, in the constant domain CL of the second heavy chain the amino acids at position 124 and 123 are substituted by K (numbering according to Kabat EU index).

In one aspect, in the constant domain CL of the second heavy chain the amino acid at position 123 is substituted by R and the amino acid as position 124 is substituted by K (numbering according to Kabat EU index).

In one aspect, in the constant domain CH1 of the second light chain the amino acids at position 147 and 213 are substituted by E (numbering according to EU index of Kabat).

In one aspect, in the constant domain CL of the first light chain the amino acids at position 124 and 123 are substituted by K, and in the constant domain CH1 of the first heavy chain the amino acids at position 147 and 213 are substituted by E (numbering according to Kabat EU index).

In one aspect, in the constant domain CL of the first light chain the amino acid at position 123 is substituted by R and the amino acid at position 124 is substituted by K, and in the constant domain CH1 of the first heavy chain the amino acids at position 147 and 213 are both substituted by E (numbering according to Kabat EU index).

In one aspect, in the constant domain CL of the second heavy chain the amino acids at position 124 and 123 are substituted by K, and wherein in the constant domain CH1 of the second light chain the amino acids at position 147 and 213 are substituted by E, and in the variable domain VL of the first light chain the amino acid at position 38 is substituted by K, in the variable domain VH of the first heavy chain the amino acid at position 39 is substituted by E, in the variable domain VL of the second heavy chain the amino acid at position 38 is substituted by K, and in the variable domain VH of the second light chain the amino acid at position 39 is substituted by E (numbering according to Kabat EU index).

In one aspect, the bispecific antibody is a bivalent antibody comprising a) a first light chain and a first heavy chain of an antibody specifically binding to a first antigen, and b) a second light chain and a second heavy chain of an antibody specifically binding to a second antigen, wherein the variable domains VL and VH of the second light chain and the second heavy chain are replaced by each other, and wherein the constant domains CL and CH1 of the second light chain and the second heavy chain are replaced by each other.

The antibody under a) does not contain a modification as reported under b) and the heavy chain and the light chain and a) are isolated chains. In the antibody under b) within the light chain the variable light chain domain VL is replaced by the variable heavy chain domain VH of said antibody, and the constant light chain domain CL is replaced by the constant heavy chain domain CH1 of said antibody; and within the heavy chain the variable heavy chain domain VH is replaced by the variable light chain domain VL of said antibody, and the constant heavy chain domain CH1 is replaced by the constant light chain domain CL of said antibody.

In one aspect, the bispecific antibody is a bivalent antibody comprising a) a first light chain and a first heavy chain of an antibody specifically binding to a first antigen, and b) a second light chain and a second heavy chain of an antibody specifically binding to a second antigen, wherein the constant domains CL and CH1 of the second light chain and the second heavy chain are replaced by each other.

The antibody under a) does not contain a modification as reported under b) and the heavy chain and the light chain under a) are isolated chains. In the antibody under b) within the light chain the constant light chain domain CL is replaced by the constant heavy chain domain CH1 of said antibody; and within the heavy chain the constant heavy chain domain CH1 is replaced by the constant light chain domain CL of said antibody.

In one aspect, the multispecific antibody is a multispecific antibody comprising a) a full length antibody specifically binding to a first antigen and consisting of two antibody heavy chains and two antibody light chains, and b) one, two, three or four single chain Fab fragments specifically binding to one to four further antigens (i.e. a second and/or third and/or fourth and/or fifth antigen, preferably specifically binding to one further antigen, i.e. a second antigen), wherein said single chain Fab fragments under b) are fused to said full length antibody under a) via a peptidic linker at the C- or N-terminus of the heavy or light chain of said full length antibody.

In one aspect, one or two identical single chain Fab fragments binding to a second antigen are fused to the full length antibody via a peptidic linker at the C terminus of the heavy or light chains of said full length antibody.

In one aspect, one or two identical single chain Fab fragments binding to a second antigen are fused to the full length antibody via a peptidic linker at the C terminus of the heavy chains of said full length antibody.

In one aspect, one or two identical single chain Fab fragments binding to a second antigen are fused to the full length antibody via a peptidic linker at the C terminus of the light chains of said full length antibody.

In one aspect, two identical single chain Fab fragments binding to a second antigen are fused to the full length antibody via a peptidic linker at the C-terminus of each heavy or light chain of said full length antibody.

In one aspect, two identical single chain Fab fragments binding to a second antigen are fused to the full length antibody via a peptidic linker at the C-terminus of each heavy chain of said full length antibody.

In one aspect, two identical single chain Fab fragments binding to a second antigen are fused to the full length antibody via a peptidic linker at the C-terminus of each light chain of said full length antibody.

In one aspect, the bispecific antibody is a trivalent antibody comprising a) a full length antibody specifically binding to a first antigen and consisting of two antibody heavy chains and two antibody light chains, b) a first polypeptide consisting of
ba) an antibody heavy chain variable domain (VH), or
bb) an antibody heavy chain variable domain (VH) and an antibody constant domain 1 (CH1),
wherein said first polypeptide is fused with the N-terminus of its VH domain via a peptidic linker to the C-terminus of one of the two heavy chains of said full length antibody,
c) a second polypeptide consisting of
ca) an antibody light chain variable domain (VL), or
cb) an antibody light chain variable domain (VL) and an antibody light chain constant domain (CL),
wherein said second polypeptide is fused with the N-terminus of the VL domain via a peptidic linker to the C-terminus of the other of the two heavy chains of said full length antibody, and
wherein the antibody heavy chain variable domain (VH) of the first polypeptide and the antibody light chain variable domain (VL) of the second polypeptide together form an antigen-binding site specifically binding to a second antigen.

In one aspect, the antibody heavy chain variable domain (VH) of the polypeptide under b) and the antibody light chain variable domain (VL) of the polypeptide under c) are linked and stabilized via an interchain disulfide bridge by introduction of a disulfide bond between the following positions:
(i) heavy chain variable domain position 44 to light chain variable domain position 100, or
(ii) heavy chain variable domain position 105 to light chain variable domain position 43, or
(iii) heavy chain variable domain position 101 to light chain variable domain position 100 (numbering always according to Kabat EU index).

Techniques to introduce unnatural disulfide bridges for stabilization are described e.g. in WO 94/029350, Rajagopal, V., et al., Prot. Eng. (1997) 1453-1459; Kobayashi, H., et al., Nucl. Med. Biol. 25 (1998) 387-393; and Schmidt, M., et al., Oncogene 18 (1999) 1711-1721. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to Kabat). In one embodiment a trivalent, bispecific antibody without said optional disulfide stabilization between the variable domains VH and VL of the single chain Fab fragments is preferred.

In one aspect, the bispecific antibody is a trispecific or tetraspecific antibody, comprising
a) a first light chain and a first heavy chain of a full length antibody which specifically binds to a first antigen, and
b) a second (modified) light chain and a second (modified) heavy chain of a full length antibody which specifically binds to a second antigen, wherein the variable domains VL and VH are replaced by each other, and/or wherein the constant domains CL and CH1 are replaced by each other, and
c) wherein one to four antigen binding peptides which specifically bind to one or two further antigens (i.e. to a third and/or fourth antigen) are fused via a peptidic linker to the C- or N-terminus of the light chains or heavy chains of a) and/or b).

The antibody under a) does not contain a modification as reported under b) and the heavy chain and the light chain and a) are isolated chains.

In one aspect, the trispecific or tetraspecific antibody comprises under c) one or two antigen binding peptides which specifically bind to one or two further antigens.

In one aspect, the antigen binding peptides are selected from the group of a scFv fragment and a scFab fragment.

In one aspect, the antigen binding peptides are scFv fragments.

In one aspect, the antigen binding peptides are scFab fragments.

In one aspect, the antigen binding peptides are fused to the C-terminus of the heavy chains of a) and/or b).

In one aspect, the trispecific or tetraspecific antibody comprises under c) one or two antigen binding peptides which specifically bind to one further antigen.

In one aspect, the trispecific or tetraspecific antibody comprises under c) two identical antigen binding peptides which specifically bind to a third antigen. In one preferred embodiment such two identical antigen binding peptides are fused both via the same peptidic linker to the C-terminus of the heavy chains of a) and b). In one preferred embodiment the two identical antigen binding peptides are either a scFv fragment or a scFab fragment.

In one aspect, the trispecific or tetraspecific antibody comprises under c) two antigen binding peptides which specifically bind to a third and a fourth antigen. In one embodiment said two antigen binding peptides are fused both via the same peptide connector to the C-terminus of the heavy chains of a) and b). In one preferred embodiment said two antigen binding peptides are either a scFv fragment or a scFab fragment.

In one aspect, the bispecific antibody is a bispecific, tetravalent antibody comprising
a) two light chains and two heavy chains of an antibody, which specifically bind to a first antigen (and comprise two Fab fragments),
b) two additional Fab fragments of an antibody, which specifically bind to a second antigen, wherein said additional Fab fragments are fused both via a peptidic linker either to the C- or N-termini of the heavy chains of a), and
wherein in the Fab fragments the following modifications were performed
(i) in both Fab fragments of a), or in both Fab fragments of b), the variable domains VL and VH are replaced by each other, and/or the constant domains CL and CH1 are replaced by each other, or
(ii) in both Fab fragments of a) the variable domains VL and VH are replaced by each other, and the constant domains CL and CH1 are replaced by each other, and in both Fab fragments of b) the variable domains VL and VH are replaced by each other, or the constant domains CL and CH1 are replaced by each other, or
(iii) in both Fab fragments of a) the variable domains VL and VH are replaced by each other, or the constant domains CL and CH1 are replaced by each other, and in both Fab fragments of b) the variable domains VL and VH are replaced by each other, and the constant domains CL and CH1 are replaced by each other, or
(iv) in both Fab fragments of a) the variable domains VL and VH are replaced by each other, and in both Fab fragments of b) the constant domains CL and CH1 are replaced by each other, or
(v) in both Fab fragments of a) the constant domains CL and CH1 are replaced by each other, and in both Fab fragments of b) the variable domains VL and VH are replaced by each other.

In one aspect, said additional Fab fragments are fused both via a peptidic linker either to the C-termini of the heavy chains of a), or to the N-termini of the heavy chains of a).

In one aspect, said additional Fab fragments are fused both via a peptidic linker either to the C-termini of the heavy chains of a).

In one aspect, said additional Fab fragments are fused both via a peptide connector to the N-termini of the heavy chains of a).

In one aspect, in the Fab fragments the following modifications are performed: in both Fab fragments of a), or in both Fab fragments of b), the variable domains VL and VH are replaced by each other, and/or the constant domains CL and CH1 are replaced by each other.

In one aspect, the bispecific antibody is a tetravalent antibody comprising:
  a) a (modified) heavy chain of a first antibody, which specifically binds to a first antigen and comprises a first VH-CH1 domain pair, wherein to the C terminus of said heavy chain the N-terminus of a second VH-CH1 domain pair of said first antibody is fused via a peptidic linker,
  b) two light chains of said first antibody of a),
  c) a (modified) heavy chain of a second antibody, which specifically binds to a second antigen and comprises a first VH-CL domain pair, wherein to the C-terminus of said heavy chain the N-terminus of a second VH-CL domain pair of said second antibody is fused via a peptidic linker, and
  d) two (modified) light chains of said second antibody of c), each comprising a CL-CH1 domain pair.

In one aspect, the bispecific antibody comprises
  a) the heavy chain and the light chain of a first full length antibody that specifically binds to a first antigen, and
  b) the heavy chain and the light chain of a second full length antibody that specifically binds to a second antigen, wherein the N-terminus of the heavy chain is connected to the C-terminus of the light chain via a peptidic linker.

The antibody under a) does not contain a modification as reported under b) and the heavy chain and the light chain are isolated chains.

In one aspect, the bispecific antibody comprises
  a) a full length antibody specifically binding to a first antigen and consisting of two antibody heavy chains and two antibody light chains, and
  b) an Fv fragment specifically binding to a second antigen comprising a VH2 domain and a VL2 domain, wherein both domains are connected to each other via a disulfide bridge,
  wherein only either the VH2 domain or the VL2 domain is fused via a peptidic linker to the heavy or light chain of the full length antibody specifically binding to a first antigen.

In the bispecific antibody the heavy chains and the light chains under a) are isolated chains.

In one aspect, the other of the VH2 domain or the VL2 domain is not fused via a peptide linker to the heavy or light chain of the full length antibody specifically binding to a first antigen.

In all aspects as reported herein the first light chain comprises a VL domain and a CL domain and the first heavy chain comprises a VH domain, a CH1 domain, a hinge region, a CH2 domain and a CH3 domain.

In one aspect, the bispecific antibody is a trivalent antibody comprising
  a) two Fab fragments that specifically binds to a first antigen,
  b) one CrossFab fragment that specifically binds to a second antigen in which the CH1 and the CL domain are exchanged for each other,
  c) one Fc-region comprising a first Fc-region heavy chain and a second Fc region heavy chain,
  wherein the C-terminus of CH1 domains of the two Fab fragments are connected to the N-terminus of the heavy chain Fc-region polypeptides, and wherein the C-terminus of the CL domain of the CrossFab fragment is connected to the N-terminus of the VH domain of one of the Fab fragments.

In one aspect, the bispecific antibody is a trivalent antibody comprising
  a) two Fab fragments that specifically binds to a first antigen,
  b) one CrossFab fragment that specifically binds to a second antigen in which the CH1 and the CL domain are exchanged for each other,
  c) one Fc-region comprising a first Fc-region heavy chain and a second Fc region heavy chain,
  wherein the C-terminus of CH1 domain of the first Fab fragment is connected to the N-terminus of one of the heavy chain Fc-region polypeptides and the C-terminus of the CL-domain of the CrossFab fragment is connected to the N-terminus of the other heavy chain Fc-region polypeptide, and wherein the C-terminus of the CH1 domain of the second Fab fragment is connected to the N-terminus of the VH domain of the first Fab fragment or to the N-terminus of the VH domain of the CrossFab fragment.

In one aspect, the bispecific antibody comprises
  a) a full length antibody specifically binding to a first antigen and consisting of two antibody heavy chains and two antibody light chains, and
  b) a Fab fragment specifically binding to a second antigen comprising a VH2 domain and a VL2 domain comprising a heavy chain fragment and a light chain fragment, wherein within the light chain fragment the variable light chain domain VL2 is replaced by the variable heavy chain domain VH2 of said antibody, and within the heavy chain fragment the variable heavy chain domain VH2 is replaced by the variable light chain domain VL2 of said antibody
  wherein the heavy chain Fab fragment is inserted between the CH1 domain of one of the heavy chains of the full length antibody and the respective Fc-region of the full length antibody, and the N-terminus of the light chain Fab fragment is conjugated to the C-terminus of the light chain of the full length antibody that is paired with the heavy chain of the full length antibody into which the heavy chain Fab fragment has been inserted.

In one aspect, the bispecific antibody comprises
  a) a full length antibody specifically binding to a first antigen and consisting of two antibody heavy chains and two antibody light chains, and
  b) a Fab fragment specifically binding to a second antigen comprising a VH2 domain and a VL2 domain comprising a heavy chain fragment and a light chain fragment, wherein within the light chain fragment the variable light chain domain VL2 is replaced by the variable heavy chain domain VH2 of said antibody, and within the heavy chain fragment the variable heavy chain domain VH2 is replaced by the variable light chain domain VL2 of said antibody and
  wherein the C-terminus of the heavy chain fragment of the Fab fragment is conjugated to the N-terminus of one of the heavy chains of the full length antibody and the C-terminus of the light chain fragment of the Fab fragment is conjugated to the N-terminus of the light chain of the full length antibody that pairs with the heavy chain of the full length antibody to which the heavy chain fragment of the Fab fragment is conjugated.

Polynucleotides

The invention further provides isolated polynucleotides encoding a bispecific antibody as described herein or a fragment thereof.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

B. Recombinant Methods

The bispecific antibodies provided herein may be produced using recombinant methods and compositions, e.g., as described in U.S. Pat. No. 4,816,567. In one aspect, isolated nucleic acid encoding an bispecific antibody described herein is provided. Such nucleic acid may encode an amino acid sequence comprising the VL and/or an amino acid sequence comprising the VH of the antigen-binding sites that specifically bind to PD1 and TIM-3, respectively (e.g., in the light and/or heavy chains of the antibody). In a further aspect, one or more vectors (e.g., expression vectors) comprising such nucleic acid are provided. In a further aspect, a host cell comprising such nucleic acid is provided. In one such aspect, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one aspect, the host cell is eukaryotic, e.g. a Chinese Hamster Ovary (CHO) cell or lymphoid cell (e.g., Y0, NS0, Sp20 cell). In one aspect, a method of making a bispecific antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of the bispecific antibodies comprising a first antigen-binding site that specifically binds to PD1 and a second antigen-binding site that specifically binds to TIM-3 as described herein, nucleic acid encoding the bispecific antibodies, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

The bispecific antibodies comprising a first antigen-binding site that specifically binds to PD1 and a second antigen-binding site that specifically binds to TIM-3 provided herein may be identified, screened for, or characterized for their physical/chemical properties and/or biological activities by various assays known in the art.

1. Affinity Assays

The affinity of the bispecific antigen binding molecules, antibodies and antibody fragments provided herein for the corresponding antigens can be determined in accordance with the methods set forth in the Examples by surface plasmon resonance (SPR), using standard instrumentation such as a Biacore® instrument (GE Healthcare), and receptors or target proteins such as may be obtained by recombinant expression. A specific illustrative and exemplary embodiment for measuring binding affinity is described in Examples 1b, 5 or 12. According to one aspect, KD is measured by surface plasmon resonance using a BIACORE® T100 machine (GE Healthcare) at 25° C.

2. Binding Assays and Other Assays

In one aspect, an antibody of the invention is tested for its antigen binding activity, e.g., by known methods such as ELISA, Western blot, etc. Binding of the bispecific antibodies provided herein to the corresponding recombinant antigen or to antigen-expressing cells may be evaluated by ELISA as described in Example 12.

In another aspect, the invention provides a cell-based TR-FRET assay to determine the simultaneous binding of bispecific antibody formats to two different receptors present on one cell. The chosen Tag-lite technology is a combination of a classical TR-FRET (time-resolved fluorescence resonance energy transfer) and SNAP-tag technology (e.g. New England Biolabs, CISBIO), which allows antigens present on the cell surface to be labeled with a fluorescent donor or acceptor dye. The assay is described in Example 13.

In a further aspect, fresh peripheral blood mononuclear cells (PBMCs) are used in binding assays to show binding to different peripheral blood mononuclear cells (PBMC) such as monocytes, NK cells and T cells.

In another aspect, competition assays may be used to identify an antibody that competes with a specific antibody or antigen binding site for binding to the target, respectively. In certain embodiments, such a competing antibody binds to the same epitope (e.g., a linear or a conformational epitope) that is bound by a bispecific antibody comprising a first antigen-binding site that specifically binds to PD1 and a second antigen-binding site that specifically binds to TIM3 according to the invention. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized PD1 or TIM3 is incubated in a solution comprising a first labeled antibody that binds to PD1 or TIM3 and a second unlabeled antibody that is being tested for its ability to compete with the first antibody for binding to PD1 or TIM3. The second antibody may be present in a hybridoma supernatant. As a control, immobilized PD1 or TIM3 is incubated in a solution comprising the first labeled antibody but not the second unlabeled antibody. After incubation under conditions permissive for binding of the first antibody to PD1 or TIM3, excess unbound antibody is removed, and the amount of label associated with immobilized PD1 or TIM3 is measured. If the amount of label associated with immobilized PD1 or TIM3 is substantially reduced in the test sample relative to the control sample, then that indicates that the second antibody is competing with the first antibody for binding to PD1 or TIM3. See Harlow and Lane (1988) Antibodies: A Laboratory Manual ch.14 (Cold Spring Harbor Laboratory, Cold Spring Harbor, N.Y.).

3. Activity Assays

In one aspect, assays are provided for identifying a bispecific antibody comprising a first antigen-binding site that specifically binds to PD1 and a second antigen-binding site that specifically binds to TIM3 having biological activity. Biological activity may include, e.g., the ability to enhance the activation and/or proliferation of different immune cells, especially T-cells, secretion of immune-modulating cytokines such IFNγ or TNF-alpha, blocking the PD1 pathway, blocking the TIM3 pathway, killing of tumor cells. Antibodies having such biological activity in vivo and/or in vitro are also provided.

In certain aspects, an antibody of the invention is tested for such biological activity. In one aspect, provided is an immune cell assay which measures the activation of lymphocytes from one individual (donor X) to lymphocytes from another individual (donor Y). The mixed lymphocyte reaction (MLR) can demonstrate the effect of blocking the PD1 pathway to lymphocyte effector cells. T cells in the assay were tested for activation and their IFN-gamma secretion in the presence or absence of bispecific antibodies of the invention. The assay is described in more detail in Example 16.

D. Immunoconjugates

The invention also provides immunoconjugates comprising a bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one aspect, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At211, I131, I125, Y90, Re186, Re188, Sm153, Bi212, P32, Pb212 and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinyl sulfone)benzoate) which are commercially available (e.g., from Pierce Biotechnology, Inc., Rockford, Ill., U.S.A).

E. Methods and Compositions for Diagnostics and Detection

In certain aspects, any of the bispecific antibodies comprising a first antigen-binding site that specifically binds to PD1 and a second antigen-binding site that specifically binds to TIM-3 provided herein may be useful for detecting the presence of both PD1 and TIM3 in a biological sample. The term "detecting" as used herein encompasses quantitative or qualitative detection. In certain embodiments, a biological sample comprises a cell or tissue, such as AML stem cancer cells.

In one aspect, a bispecific antibody for use in a method of diagnosis or detection is provided. In a further aspect, a method of detecting the presence of both PD1 and TIM3 in a biological sample is provided. In certain embodiments, the method comprises contacting the biological sample with a bispecific antibody as described herein under conditions permissive for binding of the bispecific antibody to both PD1 and TIM3, and detecting whether a complex is formed between the bispecific antibody and both antigens. Such method may be an in vitro or in vivo method. In one embodiment, the bispecific antibody is used to select subjects eligible for therapy with a bispecific antibody comprising a first antigen-binding site that specifically binds to PD1 and a second antigen-binding site that specifically binds to TIM-3 antibody, e.g. where PD1 and TIM3 are biomarkers for selection of patients.

In certain aspects, labeled bispecific antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels or stable free radicals.

F. Pharmaceutical Compositions, Formulations and Routes of Administation

In a further aspect, the invention provides pharmaceutical compositions comprising any of the bispecific antibodies comprising a first antigen-binding site that specifically binds to PD1 and a second antigen-binding site that specifically binds to TIM-3 provided herein, e.g., for use in any of the below therapeutic methods. In one embodiment, a pharmaceutical composition comprises any of the bispecific antibodies provided herein and at least one pharmaceutically acceptable excipient. In another embodiment, a pharmaceutical composition comprises any of the bispecific antibodies provided herein and at least one additional therapeutic agent, e.g., as described below.

Pharmaceutical compositions of the present invention comprise a therapeutically effective amount of one or more bispecific antibodies dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antibody and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the bispecific antibodies of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the bispecific antibodies may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the bispecific antibodies may also be formulated as a depot preparation. Such long acting formulations may be administered by implantation (for example subcutaneously or intramuscularly) or by intramuscular injection. Thus, for example, the bispecific antibodies may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the bispecific antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antibodies may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

G. Therapeutic Methods and Compositions

Any of the bispecific antibodies comprising a first antigen-binding site that specifically binds to PD1 and a second antigen-binding site that specifically binds to TIM-3 provided herein may be used in therapeutic methods.

For use in therapeutic methods, bispecific antibodies comprising a first antigen-binding site that specifically binds to PD1 and a second antigen-binding site that specifically binds to TIM-3 as defined herein before can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, bispecific antibodies comprising a first antigen-binding site that specifically binds to PD1 and a second antigen-binding site that specifically binds to TIM-3 as defined herein for use as a medicament are provided. In further aspects, bispecific antibodies comprising a first antigen-binding site that specifically binds to PD1 and a second antigen-binding site that specifically binds to TIM-3 as defined herein for use in treating a disease, in particular for use in the treatment of cancer, are provided. In certain embodiments, bispecific antibodies comprising a first antigen-binding site that specifically binds to PD1 and a second antigen-binding site that specifically binds to TIM-3 for use in a method of treatment are provided. In one embodiment, the invention provides bispecific antibodies comprising a first antigen-binding site that specifically binds to PD1 and a second antigen-binding site that specifically binds to TIM-3 as described herein for use in the treatment of a disease in an individual in need thereof. In certain embodiments, the invention provides bispecific antibodies comprising a first antigen-binding site that specifically binds to PD1 and a second antigen-binding site that specifically binds to TIM-3 for use in a method of treating an individual having a disease comprising administering to the individual a therapeutically effective amount of the bispecific antibody. In certain embodiments the disease to be treated is cancer. In another aspect, the disease to be treated is a chronic viral infection like HIV, HBV, HCV, HSV1, CMV, LCMV or EBV. The subject, patient, or "individual" in need of treatment is typically a mammal, more specifically a human.

In a further aspect, the invention provides for the use of bispecific antibodies comprising a first antigen-binding site that specifically binds to PD1 and a second antigen-binding site that specifically binds to TIM-3 as defined herein before in the manufacture or preparation of a medicament for the treatment of a disease in an individual in need thereof. In one embodiment, the medicament is for use in a method of treating a disease comprising administering to an individual having the disease a therapeutically effective amount of the medicament.

In certain aspects, the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using bispecific antibodies comprising a first antigen-binding site that specifically binds to PD1 and a second antigen-binding site that specifically binds to TIM-3 according to the invention include, but are not limited to neoplasms located in the abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain aspects, the cancer is chosen from the group consisting of renal cell cancer, skin cancer, lung cancer, colorectal cancer, breast cancer, brain cancer, head and neck cancer. In further aspects, the cancer is chosen from carcinoma, lymphoma (e.g., Hodgkin's and non-Hodgkin's lymphoma), blastoma, sarcoma, and leukemia. In another aspect, the cancer is to be treated is selected from squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

In a further aspect, the disease to be treated is a chronic viral infection. The term "chronic viral infection" refers to a subject afflicted or infected with a chronic virus. Examples for chronic viral infections are human immunodeficiency virus (HIV), hepatitis B viral infection (HBV), hepatitis C viral infection (HCV), herpes simplex virus 1 (HSV1), cytomegalovirus (CMV), lymphocytic choriomeningitis virus (LCMV) or Epstein-Barr virus (EBV).

A skilled artisan readily recognizes that in many cases the bispecific molecule may not provide a cure but may only provide partial benefit. In some embodiments, a physiological change having some benefit is also considered therapeutically beneficial. Thus, in some embodiments, an amount of the bispecific antibody that provides a physiological change is considered an "effective amount" or a "therapeutically effective amount".

In a further aspect, the invention provides a method for treating a disease in an individual, comprising administering to said individual a therapeutically effective amount of bispecific antibodies comprising a first antigen-binding site that specifically binds to PD1 and a second antigen-binding site that specifically binds to TIM-3 of the invention. In one embodiment a composition is administered to said individual, comprising a bispecific antibody of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g. an anti-cancer agent if the disease to be treated is cancer. In another aspect, the disease is a chronic viral infection. An "individual" according to any of the above embodiments may be a mammal, preferably a human.

For the prevention or treatment of disease, the appropriate dosage of a bispecific antibodies comprising a first antigen-binding site that specifically binds to PD1 and a second antigen-binding site that specifically binds to TIM-3 of the invention (when used alone or in combination with one or more other additional therapeutic agents) will depend on the type of disease to be treated, the route of administration, the body weight of the patient, the type of fusion protein, the severity and course of the disease, whether the bispecific antibody is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antibody comprising a first antigen-binding site that specifically binds to PD1 and a second antigen-binding site that specifically binds to TIM-3 as defined herein is suitably administered to the patient at one time or over a series of treatments. Depending on the type and severity of the disease, about 1 μg/kg to 15 mg/kg (e.g. 0.1 mg/kg-10 mg/kg) of the bispecific antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antibody would be in the range from about 0.005 mg/kg to about 10 mg/kg. In other examples, a dose may also comprise from about 1 µg/kg body weight, about 5 µg/kg body weight, about 10 µg/kg body weight, about 50 µg/kg body weight, about 100 µg/kg body weight, about 200 µg/kg body weight, about 350 µg/kg body weight, about 500 µg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 µg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). An initial higher loading dose, followed by one or more lower doses may be administered. However, other dosage regimens may be useful. The progress of this therapy is easily monitored by conventional techniques and assays.

The bispecific antibodies comprising a first antigen-binding site that specifically binds to PD1 and a second antigen-binding site that specifically binds to TIM-3 as defined herein will generally be used in an amount effective to achieve the intended purpose. For use to treat or prevent a disease condition, the bispecific antibodies of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the bispecific antibody which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the bispecific antibody may not be related to plasma concentration. One skilled in the art will be able to optimize therapeutically effective local dosages without undue experimentation.

A therapeutically effective dose of the bispecific antibodies described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antibodies that exhibit large therapeutic indices are preferred. In one embodiment, the bispecific antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with bispecific antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antibodies comprising a first antigen-binding site that specifically binds to PD1 and a second antigen-binding site that specifically binds to TIM-3 as described herein before may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The TNF family ligand trimer-containing antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antibody can occur prior to, simultaneously, and/or following, administration of the additional therapeutic agent and/or adjuvant.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen-binding site that specifically binds to PD1 and a second antigen-binding site that specifically binds to TIM-3 as defined herein before.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C (Sequences):

| SEQ ID NO: | Name | Sequence |
|---|---|---|
| 1 | heavy chain HVR-H1, Tim3_0016 | GFSLSTSGM |
| 2 | heavy chain HVR-H2, Tim3_0016 | LND |
| 3 | heavy chain HVR-H3, Tim3_0016 | NGYLYALD |
| 4 | light chain HVR-L1, Tim3_0016 | SSSVNY |
| 5 | light chain HVR-L2, Tim3_0016 | DAF |
| 6 | light chain HVR-L3, Tim3_0016 | WSSYPWT |
| 7 | heavy chain variable domain VH, Tim3_0016 | QVTLKESGPG ILQPSQTLRL TCSFSGFSLS TSGMSVGWIR QPSGKGLEWL AHIWLNDDVF FNPALKSRLT ISKDTSNNQV FLQIASVVTA DTATYYCVRA NGYLYALDYW GQGTSVTVSS |
| 8 | light chain variable domain VL, Tim3_0016 | QIVLTQSPAI MSASPGQKVT ITCSASSSVN YTQWYQQKLG SSPKLWIYDA FKLAPGVPAR FSGSGTGTSY SLTISSMEAE DAASYFCHQW SSYPWTFGGG TKLEIK |
| 9 | heavy chain variable domain VH, Tim3_0016 variant (0018) | QVTLKESGPG ILQPSQTLSL TCSFSGFSLS TSGMSVGWIR QPSGKGLEWL AHIWLNDDVF FNPALKRRLT ISKDTSNNQV FLQIASVVTA DTATYYCVRA NGYLYALDYW GQGISVTVSS |
| 10 | light chain variable domain VL, Tim3_0016 variant (0018) | QIVLTQSPAI MSASPGQKVT ITCSASSSVN YTQWYQQKLG SSPKLWIYDA FKLAPGVPAR FSGSGTGTSY SLTISSMEAE DAASYFCHQW SSYPWTFGGG TKLEIK |
| 11 | light chain HVR-L1, Tim3_0016 HVR-L1 variant 1_NQ (removal of glycosylation site by N to Q mutation) | SSSVQY |
| 12 | light chain HVR-L1, Tim3_0016 HVR-L1 variant 2_NS (removal of glycosylation site by N to S mutation) | SSSVSY |

TABLE C-continued (Sequences):

| SEQ ID NO: | Name | Sequence |
|---|---|---|
| 13 | VH humanized version of Tim3_0016 variant (0018)(= Tim3-0433) | QITLKESGPT LVKPTQTLTL TCTFSGFSLS TSGMSVGWIR QPPGKGLEWL AHIWLNDDVF FNPALKSRLT ITKDTSKNQV VLTMTNMDPV DTATYYCVRA NGYLYALDYW GQGTLVTVSS |
| 14 | VL humanized version of Tim3_0016 variant (0018)(= Tim3-0433) | ETTLTQSPAF MSATPGDKVN IACSASSSVS YTQWYQQKPG EAPKLWIYDA FKLAPGIPPR FSGSGYGTDF TLTINNIESE DAAYYFCHQW SSYPWTFGQG TKLEIK |
| 15 | VH humanized version of Tim3_0016 variant (0018)(= Tim3-0434) | QITLKESGPT LVKPTQTLTL TCTFSGFSLS TSGMSVGWIR QPPGKGLEWL AHIWLNDDVF FNPALKSRLT ITKDTSKNQV VLTMTNMDPV DTATYYCVRA NGYLYALDYW GQGTLVTVSS |
| 16 | VL humanized version of Tim3_0016 variant (0018)(= Tim3-0434) | DIQLTQSPSF LSASVGDRVT ITCSASSSVS YTQWYQQKPG KAPKLWIYDA FKLAPGVPSR 60 FSGSGSGTEF TLTISSLQPE DFATYFCHQW SSYPWTFGQG TKLEIK |
| 17 | heavy chain HVR-H1, Tim3_0028 | GFNIKTT |
| 18 | heavy chain HVR-H2, Tim3_0028 | ADD |
| 19 | heavy chain HVR-H3, Tim3_0028 | FGYVAWFA |
| 20 | light chain HVR-L1, Tim3_0028 | SQSVDNY |
| 21 | light chain HVR-L2, Tim3_0028 | YAS |
| 22 | light chain HVR-L3, Tim_0028 | HYSSPY |
| 23 | heavy chain variable domain VH, Tim3_0028 | EVQLQQSVAE LVRPGASVKL SCTASGFNIK TTYMHWVKQR PEQGLEWIGR IDPADDNTKY APKFQGKATI TADTSSNTAY LQLSSLTSED AAIYYCVRDF GYVAWFAYWG QGTLVTFSA |
| 24 | light chain variable domain VL, Tim3_0028 | NIVMTPTPKF LPVSSGDRVT MTCRASQSVD NYVAWYQQKP GQSPKLLIYY ASNRYIGVPD RFTGSGSGTD FTFTISSVQV EDLAVYFCQQ HYSSPYTFGS GTKLEIK |
| 25 | VH humanized version of Tim3-0028 (= Tim3-0438) | EVQLVESGGG LVQPGGSLRL SCAASGFNIK TTYMHWVRQA PGKGLEWVGR IDPADDNTKY APKFQGKATI SADTSKNTAY LQMNSLRAED TAVYYCVRDF GYVAWFAYWG QGTLVTVSS |
| 26 | VL humanized version of Tim3-0028 (= Tim3-0438) | DIVMTQSPLS LPVTPGEPAS ISCRASQSVD NYVAWYLQKP GQSPQLLIYY ASNRYIGVPD RFSGSGSGTD FTLKISRVEA EDVGVYYCQQ HYSSPYTFGQ GTKVEIK |
| 27 | VH humanized version of Tim3-0028 (= Tim3-0443) | EVQLVESGGG LVQPGGSLRL SCAASGFNIK TTYMHWVRQA PGKGLEWVGR IDPADDNTKY APKFQGKATI SADTSKNTAY LQMNSLRAED TAVYYCVRDF GYVAWFAYWG QGTLVTFSS |
| 28 | VL humanized version of Tim3-0028 (= Tim3-0443) | DIVMTQSPLS LPVTPGEPAS ISCRASQSVD NYVAWYLQKP GQSPQLLIYY ASNRYIGVPD RFSGSGSGTD FTLKISRVEA EDVGVYYCQQ HYSSPYTFGQ GTKVEIK |
| 29 | heavy chain HVR-H1, Tim3_0038 | GFNIKDY |
| 30 | heavy chain HVR-H2, Tim3_0038 | EDG |
| 31 | heavy chain HVR-H3, Tim3_0038 | HGYVGWFA |
| 32 | light chain HVR-L1, Tim3_0038 | ASENVDTY |
| 33 | light chain HVR-L2, Tim3_0038 | GAS |
| 34 | light chain HVR-L3, Tim3_0038 | SYSYPW |

TABLE C-continued (Sequences):

| SEQ ID NO: | Name | Sequence |
|---|---|---|
| 35 | heavy chain variable domain VH, Tim3_0038 | EVQLQQSGAE PLKPGASVKL TCTTSGFNIK DYYIHWVKQR SDQGLEWIGR IDPEDGELIY APKFQDKATI TVDTSSNIAY LQLNSLTSED TAVYYCSRDH GYVGWFAYWG QGTLVTVSA |
| 36 | light chain variable domain VL, Tim3_0038 | NVVMTQSPKS MIMSVGQRVT LNCKASENVD TYVSWYQQKP EQSPKLLIYG ASNRYTGVPD RFTGSRSATD FTLTISSVQA EDLAVYYCGQ SYSYPWTFGG GTKLEFR |
| 37 | heavy chain HVR-H1, PD1-0103 | GFSFSSY |
| 38 | heavy chain HVR-H2, PD1-0103 | GGR |
| 39 | heavy chain HVR-H3, PD1-0103 | TGRVYFALD |
| 40 | light chain HVR-L1, PD1-0103 | SESVDTSDNSF |
| 41 | light chain HVR-L2, PD1-0103 | RSS |
| 42 | light chain HVR-L3, PD1-0103 | NYDVPW |
| 43 | heavy chain variable domain VH, PD1-0103 | EVILVESGGGLVKPGGSLKLSCAASGFSFSSY TMSWVRQTPEKRLDWVATISGGGRDIYYPDSV KGRFTISRDNAKNTLYLEMSSLMSEDTALYYC VLLTGRVYFALDSWGQGTSVTVSS |
| 44 | light chain variable domain VL, PD1-0103 | KIVLTQSPASLPVSLGQRATISCRASESVDTS DNSFIHWYQQRPGQSPKLLIYRSSTLESGVPA RFSGSGSRTDFTLTIDPVEADDVATYYCQQNY DVPWTFGGGTKLEIK |
| 45 | humanized variant -heavy chain variable domain VH of PD1-0103_01 | EVQLLESGGGLVQPGGSLRLSCAASGFSFSSY TMSWVRQAPGKGLEWVATISGGGRDIYYPDSV KGRFTISRDNSKNTLYLQMNSLRAEDTAVYYC VLLTGRVYFALDSWGQGTLVTVSS |
| 46 | humanized variant -light chain variable domain VL of PD1-0103_01 | DIVMTQSPDSLAVSLGERATINCKASESVDTS DNSFIHWYQQKPGQSPKLLIYRSSTLESGVPD RFSGSGSGTDFTLTISSLQAEDVAVYYCQQNY DVPWTFGQGTKVEIK |
| 47 | humanized variant -light chain variable domain VL of PD1-0103_02 | DVVMTQSPLSLPVTLGQPASISCRASESVDTS DNSFIHWYQQRPGQSPRLLIYRSSTLESGVPD RFSGSGSGTDFTLKISRVEAEDVGVYYCQQNY DVPWTFGQGTKVEIK |
| 48 | humanized variant -light chain variable domain VL of PD1-0103_03 | EIVLTQSPATLSLSPGERATLSCRASESVDTS DNSFIHWYQQKPGQSPRLLIYRSSTLESGIPA RFSGSGSGTDFTLTISSLEPEDFAVYYCQQNY DVPWTFGQGTKVEIK |
| 49 | humanized variant -light chain variable domain VL of PD1-0103_04 | EIVLTQSPATLSLSPGERATLSCRASESVDTS DNSFIHWYQQKPGQSPRLLIYRSSTLESGIPA RFSGSGSGTDFTLTISSLEPEDFAVYYCQQNY DVPWTFGQGTKVEIK |
| 50 | heavy chain 1 of 1 + 1 PD1TIM3_0389 (based on chimeric PD1-0103 / Tim3-0028) | KIVLTQSPAS LPVSLGQRAT ISCRASESVD TSDNSFIHWY QQRPGQSPKL LIYRSSTLES GVPARFSGSG SRTDFTLTID PVEADDVATY YCQQNYDVPW TFGGGTKLEI KSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALGAPIEK TISKAKGQPR EPQVYTLPPC RDELTKNQVS LWCLVKGFYP SDIAVEWESN GQPENNYKTT PPVLDSDGSF FLYSKLTVDK SRWQQGNVFS CSVMHEALHN HYTQKSLSLS PGK |

TABLE C-continued (Sequences):

| SEQ ID NO: | Name | Sequence |
|---|---|---|
| 51 | heavy chain 2 of 1 + 1 PD1TIM3_0389 | EVQLQQSVAE LVRPGASVKL SCTASGFNIK TTYMHWVKQR PEQGLEWIGR IDPADDNTKY APKFQGKATI TADTSSNTAY LQLSSLTSED AAIYYCVRDF GYVAWFAYWG QGTLVTFSAA STKGPSVFPL APSSKSTSGG TAALGCLVED YFPEPVTVSW NSGALTSGVH TFPAVLQSSG LYSLSSVVTV PSSSLGTQTY ICNVNHKPSN TKVDEKVEPK SCDKTHTCPP CPAPEAAGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL GAPIEKTISK AKGQPREPQV CTLPPSRDEL TKNQVSLSCA VKGFYPSDIA VEWESNGQPE NNYKTTPPVL DSDGSFFLVS KLTVDKSRWQ QGNVFSCSVM HEALHNRFTQ KSLSLSPGK |
| 52 | light chain 1 of 1 + 1 PD1TIM3_0389 | EVILVESGGG LVKPGGSLKL SCAASGFSFS SYTMSWVRQT PEKRLDWVAT ISGGGRDIYY PDSVKGRFTI SRDNAKNTLY LEMSSLMSED TALYYCVLLT GRVYFALDSW GQGTSVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 53 | light chain 2 of 1 + 1 PD1TIM3_0389 | NIVMTPTPKF LPVSSGDRVT MTCRASQSVD NYVAWYQQKP GQSPKLLIYY ASNRYIGVPD RFTGSGSGTD FTFTISSVQV EDLAVYFCQQ HYSSPYTFGS GTKLEIKRTV AAPSVFIFPP SDRKLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 54 | heavy chain 1 of 1 + 1 PD1TIM3_0168 (based on chimeric PD1-0103 / Tim3-0018) | KIVLTQSPAS LPVSLGQRAT ISCRASESVD TSDNSFIHWY QQRPGQSPKL LIYRSSTLES GVPARFSGSG SRTDFTLTID PVEADDVATY YCQQNYDVPW TFGGGTKLEI KSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALGAPIEK TISKAKGQPR EPQVYTLPPC RDELTKNQVS LWCLVKGFYP SDIAVEWESN GQPENNYKTT PPVLDSDGSF FLYSKLTVDK SRWQQGNVFS CSVMHEALHN HYTQKSLSLS PGK |
| 55 | heavy chain 2 of 1 + 1 PD1TIM3_0168 | QVTLKESGPG ILQPSQTLSL TCSFSGFSLS TSGMSVGWIR QPSGKGLEWL AHIWLNDDVF FNPALKRRLT ISKDTSNNQV FLQIASVVTA DTATYYCVRA NGYLYALDYW GQGISVTVSS ASTKGPSVFP LAPSSKSTSG GTAALGCLVE DYFPEPVTVS WNSGALTSGV HTFPAVLQSS GLYSLSSVVT VPSSSLGTQT YICNVNHKPS NTKVDEKVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LGAPIEKTIS KAKGQPREPQ VCTLPPSRDE LTKNQVSLSC AVKGFYPSDI AVEWESNGQP ENNYKTTPPV LDSDGSFFLV SKLTVDKSRW QQGNVFSCSV MHEALHNRFT QKSLSLSPGK |
| 56 | light chain 1 of 1 + 1 PD1TIM3_0168 | EVILVESGGG LVKPGGSLKL SCAASGFSFS SYTMSWVRQT PEKRLDWVAT ISGGGRDIYY PDSVKGRFTI SRDNAKNTLY LEMSSLMSED TALYYCVLLT GRVYFALDSW GQGTSVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |

TABLE C-continued (Sequences):

| SEQ ID NO: | Name | Sequence |
|---|---|---|
| 57 | light chain 2 of 1 + 1 PD1TIM3_0168 | QIVLTQSPAI MSASPGQKVT ITCSASSSVN YTQWYQQKLG SSPKLWIYDA FKLAPGVPAR FSGSGTGTSY SLTISSMEAE DAASYFCHQW SSYPWTFGGG TKLEIKRTVA APSVFIFPPS DRKLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 58 | heavy chain 1 of 1 + 1 PD1TIM3_0166: (based on chimeric PD1-0103 / Tim3-0038 | KIVLTQSPAS LPVSLGQRAT ISCRASESVD TSDNSFIHWY QQRPGQSPKL LIYRSSTLES GVPARFSGSG SRTDFTLTID PVEADDVATY YCQQNYDVPW TFGGGTKLEI KSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALGAPIEK TISKAKGQPR EPQVYTLPPC RDELTKNQVS LWCLVKGFYP SDIAVEWESN GQPENNYKTT PPVLDSDGSF FLYSKLTVDK SRWQQGNVFS CSVMHEALHN HYTQKSLSLS PGK |
| 59 | heavy chain 2 of 1 + 1 PD1TIM3_0166 | EVQLQQSGAE PLKPGASVKL TCTTSGFNIK DYYIHWVKQR SDQGLEWIGR IDPEDGELIY APKFQDKATI TVDTSSNIAY LQLNSLTSED TAVYYCSRDH GYVGWFAYWG QGTLVTVSAA STKGPSVFPL APSSKSTSGG TAALGCLVED YPEPVTVSW NSGALTSGVH TFPAVLQSSG LYSLSSVVTV PSSSLGTQTY ICNVNHKPSN TKVDEKVEPK SCDKTHTCPP CPAPEAAGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL GAPIEKTISK AKGQPREPQV CTLPPSRDEL TKNQVSLSCA VKGFYPSDIA VEWESNGQPE NNYKTTPPVL DSDGSFFLVS KLTVDKSRWQ QGNVFSCSVM HEALHNRFTQ KSLSLSPGK |
| 60 | light chain 1 of 1 + 1 PD1TIM3_0166 | EVILVESGGG LVKPGGSLKL SCAASGFSFS SYTMSWVRQT PEKRLDWVAT ISGGGRDIYY PDSVKGRFTI SRDNAKNTLY LEMSSLMSED TALYYCVLLT GRVYFALDSW GQGTSVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 61 | light chain 2 of 1 + 1 PD1TIM3_0166 | NVVMTQSPKS MIMSVGQRVT LNCKASENVD TYVSWYQQKP EQSPKLLIYG ASNRYTGVPD RFTGSRSATD FTLTISSVQA EDLAVYYCGQ SYSYPWTFGG GTKLEFRRTV AAPSVFIFPP SDRKLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 62 | heavy chain 1 of 1 + 1 PD1TIM3_0476: (based on humanized PD1-0103_0312)/ Tim3-0438) | DIVMTQSPDS LAVSLGERAT INCKASESVD TSDNSFIHWY QQKPGQSPKL LIYRSSTLES GVPDRFSGSG SGTDFTLTIS SLQAEDVAVY YCQQNYDVPW TFGQGTKVEI KSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALGAPIEK TISKAKGQPR EPQVYTLPPC RDELTKNQVS LWCLVKGFYP SDIAVEWESN GQPENNYKTT PPVLDSDGSF FLYSKLTVDK SRWQQGNVFS CSVMHEALHN HYTQKSLSLS PGK |

TABLE C-continued (Sequences):

| SEQ ID NO: | Name | Sequence |
|---|---|---|
| 63 | heavy chain 2 of 1 + 1 PD1TIM3_0476 | EVQLVESGGG LVQPGGSLRL SCAASGFNIK TTYMHWVRQA PGKGLEWVGR IDPADDNTKY APKFQGKATI SADTSKNTAY LQMNSLRAED TAVYYCVRDF GYVAWFAYWG QGTLVTVSSA STKGPSVFPL APSSKSTSGG TAALGCLVED YFPEPVTVSW NSGALTSGVH TFPAVLQSSG LYSLSSVVTV PSSSLGTQTY ICNVNHKPSN TKVDEKVEPK SCDKTHTCPP CPAPEAAGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL GAPIEKTISK AKGQPREPQV CTLPPSRDEL TKNQVSLSCA VKGFYPSDIA VEWESNGQPE NNYKTTPPVL DSDGSFFLVS KLTVDKSRWQ QGNVFSCSVM HEALHNHYTQ KSLSLSPGK |
| 64 | light chain 1 of 1 + 1 PD1TIM3_0476 | EVQLLESGGG LVQPGGSLRL SCAASGFSFS SYTMSWVRQA PGKGLEWVAT ISGGGRDIYY PDSVKGRFTI SRDNSKNTLY LQMNSLRAED TAVYYCVLLT GRVYFALDSW GQGTLVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 65 | light chain 2 of 1 + 1 PD1TIM3_0476 | DIVMTQSPLS LPVTPGEPAS ISCRASQSVD NYVAWYLQKP GQSPQLLIYY ASNRYIGVPD RFSGSGSGTD FTLKISRVEA EDVGVYYCQQ HYSSPYTFGQ GTKVEIKRTV AAPSVFIFPP SDRKLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 66 | heavy chain 1 of 1 + 1 PD1TIM3_0477: (based on humanized PD1-0103_0312) / Tim3-0434) | DIVMTQSPDS LAVSLGERAT INCKASESVD TSDNSFIHWY QQKPGQSPKL LIYRSSTLES GVPDRFSGSG SGTDFTLTIS SLQAEDVAVY YCQQNYDVPW TFGQGTKVEI KSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALGAPIEK TISKAKGQPR EPQVYTLPPC RDELTKNQVS LWCLVKGFYP SDIAVEWESN GQPENNYKTT PPVLDSDGSF FLYSKLTVDK SRWQQGNVFS CSVMHEALHN HYTQKSLSLS PGK |
| 67 | heavy chain 2 of 1 + 1 PD1TIM3_0477 | QITLKESGPT LVKPTQTLTL TCTFSGFSLS TSGMSVGWIR QPPGKGLEWL AHIWLNDDVF FNPALKSRLT ITKDTSKNQV VLTMTNMDPV DTATYYCVRA NGYLYALDYW GQGTLVTVSS ASTKGPSVFP LAPSSKSTSG GTAALGCLVE DYFPEPVTVS WNSGALTSGV HTFPAVLQSS GLYSLSSVVT VPSSSLGTQT YICNVNHKPS NTKVDEKVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LGAPIEKTIS KAKGQPREPQ VCTLPPSRDE LTKNQVSLSC AVKGFYPSDI AVEWESNGQP ENNYKTTPPV LDSDGSFFLV SKLTVDKSRW QQGNVFSCSV MHEALHNHYT QKSLSLSPGK |
| 68 | light chain 1 of 1 + 1 PD1TIM3_0477 | EVQLLESGGG LVQPGGSLRL SCAASGFSFS SYTMSWVRQA PGKGLEWVAT ISGGGRDIYY PDSVKGRFTI SRDNSKNTLY LQMNSLRAED TAVYYCVLLT GRVYFALDSW GQGTLVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |

TABLE C-continued (Sequences):

| SEQ ID NO: | Name | Sequence |
|---|---|---|
| 69 | light chain 2 of 1 + 1 PD1TIM3_0477 | DIQLTQSPSF LSASVGDRVT ITCSASSSVS YTQWYQQKPG KAPKLWIYDA FKLAPGVPSR FSGSGSGTEF TLTISSLQPE DFATYFCHQW SSYPWTFGQG TKLEIKRTVA APSVFIFPPS DRKLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 70 | heavy chain of 2 + 2 PD1TIM3_0358: chimeric PD1-0103 / Tim3-0028 | EVQLQQSVAE LVRPGASVKL SCTASGFNIK TTYMHWVKQR PEQGLEWIGR IDPADDNTKY APKFQGKATI TADTSSNTAY LQLSSLTSED AAIYYCVRDF GYVAWFAYWG QGTLVTFSAA STKGPSVFPL APSSKSTSGG TAALGCLVED YFPEPVTVSW NSGALTSGVH TFPAVLQSSG LYSLSSVVTV PSSSLGTQTY ICNVNHKPSN TKVDEKVEPK SCDKTHTCPP CPAPEAAGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL GAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGGG GGSGGGGSGG GGSGGGGSKI VLTQSPASLP VSLGQRATIS CRASESVDTS DNSFIHWYQQ RPGQSPKLLI YRSSTLESGV PARFSGSGSR TDFTLTIDPV EADDVATYYC QQNYDVPWTF GGGTKLEIKS SASTKGPSVF PLAPSSKSTS GGTAALGCLV KDYFPEPVTV SWNSGALTSG VHTFPAVLQS SGLYSLSSVV TVPSSLGTQ TYICNVNHKP SNTKVDKKVE PKSCD |
| 71 | light chain 1 of 2 + 2 PD1TIM3_0358 | NIVMTPTPKF LPVSSGDRVT MTCRASQSVD NYVAWYQQKP GQSPKLLIYY ASNRYIGVPD RFTGSGSGTD FTFTISSVQV EDLAVYFCQQ HYSSPYTFGS GTKLEIKRTV AAPSVFIFPP SDRKLKSGTA SVVCLLNNFY PREAKVQWKV DNALQSGNSQ ESVTEQDSKD STYSLSSTLT LSKADYEKHK VYACEVTHQG |
| 72 | light chain 2 of 2 + 2 PD1TIM3_0358 | EVILVESGGG LVKPGGSLKL SCAASGFSFS SYTMSWVRQT PEKRLDWVAT ISGGGRDIYY PDSVKGRFTI SRDNAKNTLY LEMSSLMSED TALYYCVLLT GRVYFALDSW GQGTSVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 73 | heavy chain of 2 + 2 PD1TIM3_0359: chimeric PD1-0103 / Tim3-0018 | QVTLKESGPG ILQPSQTLSL TCSFSGFSLS TSGMSVGWIR QPSGKGLEWL AHIWLNDDVF FNPALKRRLT ISKDTSNNQV FLQIASVVTA DTATYYCVRA NGYLYALDYW GQGISVTVSS ASTKGPSVFP LAPSSKSTSG GTAALGCLVE DYFPEPVTVS WNSGALTSGV HTFPAVLQSS GLYSLSSVVT VPSSSLGTQT YICNVNHKPS NTKVDEKVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LGAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGG GGGSGGGGSG GGGSGGGGSK IVLTQSPASL PVSLGQRATI SCRASESVDT SDNSFIHWYQ QRPGQSPKLL IYRSSTLESG VPARFSGSGS RTDFTLTIDP VEADDVATYY CQQNYDVPWT FGGGTKLEIK SSASTKGPSV FPLAPSSKST SGGTAALGCL VKDYFPEPVT VSWNSGALTS GVHTFPAVLQ SSGLYSLSSV VTVPSSLGT QTYICNVNHK PSNTKVDKKV EPKSCD |

TABLE C-continued (Sequences):

| SEQ ID NO: | Name | Sequence |
|---|---|---|
| 74 | light chain 1 of 2 + 2 PD1TIM3_0359 | QIVLTQSPAI MSASPGQKVT ITCSASSSVN YTQWYQQKLG SSPKLWIYDA FKLAPGVPAR FSGSGTGTSY SLTISSMEAE DAASYFCHQW SSYPWTFGGG TKLEIKRTVA APSVFIFPPS DRKLKSGTAS VVCLLNNFYP REAKVQWKVD NALQSGNSQE SVTEQDSKDS TYSLSSTLTL SKADYEKHKV YACEVTHQGL SSPVTKSFNR GEC |
| 75 | light chain 2 of 2 + 2 PD1TIM3_0359 | EVILVESGGG LVKPGGSLKL SCAASGFSFS SYTMSWVRQT PEKRLDWVAT ISGGGRDIYY PDSVKGRFTI SRDNAKNTLY LEMSSLMSED TALYYCVLLT GRVYFALDSW GQGTSVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 76 | heavy chain of 2 + 2 PD1TIM3_0321: chimeric PD1-0103 / Tim3-0038 | EVQLQQSGAE PLKPGASVKL TCTTSGFNIK DYYIHWVKQR SDQGLEWIGR IDPEDGELIY APKFQDKATI TVDTSSNIAY LQLNSLTSED TAVYYCSRDH GYVGWPAYWG QGTLVTVSAA STKGPSVFPL APSSKSTSGG TAALGCLVED YPEPVTVSW NSGALTSGVH TFPAVLQSSG LYSLSSVVTV PSSSLGTQTY ICNVNHKPSN TKVDEKVEPK SCDKTHTCPP CPAPEAAGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL GAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGGG GGSGGGGSGG GGSGGGGSKI VLTQSPASLP VSLGQRATIS CRASESVDTS DNSFIHWYQQ RPGQSPKLLI YRSSTLESGV PARFSGSGSR TDFTLTIDPV EADDVATYYC QQNYDVPWTF GGGTKLEIKS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCD |
| 77 | light chain 1 of 2 + 2 PD1TIM3_0321 | NVVMTQSPKS MIMSVGQRVT LNCKASENVD TYVSWYQQKP EQSPKLLIYG ASNRYTGVPD RFTGSRSATD FTLTISSVQA EDLAVYYCGQ SYSYPWTFGG GTKLEFRRTV AAPSVFIFPP SDRKLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 78 | light chain 2 of 2 + 2 PD1TIM3_0321 | EVILVESGGG LVKPGGSLKL SCAASGFSFS SYTMSWVRQT PEKRLDWVAT ISGGGRDIYY PDSVKGRFTI SRDNAKNTLY LEMSSLMSED TALYYCVLLT GRVYFALDSW GQGTSVTVSS ASVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 79 | human kappa light chain constant region | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 80 | human lambda light chain constant region | QPKAAPSVTL FPPSSEELQA NKATLVCLIS DFYPGAVTVA WKADSSPVKA GVETTTPSKQ SNNKYAASSY LSLTPEQWKS HRSYSCQVTH EGSTVEKTVA PTECS |
| 81 | human heavy chain constant region derived from IgG1 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS |

TABLE C-continued (Sequences):

| SEQ ID NO: | Name | Sequence |
|---|---|---|
| | | HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 82 | human heavy chain constant region derived from IgG1 with mutations L234A and L235A | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 83 | human heavy chain constant region derived from IgG1 with mutations L234A, L235A and P329G | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPEAAGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LGAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 84 | human heavy chain constant region derived from IgG4 | ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKRVES KYGPPCPSCP APEFLGGPSV FLFPPKPKDT LMISRTPEVT CVVVDVSQED PEVQFNWYVD GVEVHNAKTK PREEQFNSTY RVVSVLTVLH QDWLNGKEYK CKVSNKGLPS SIEKTISKAK GQPREPQVYT LPPSQEEMTK NQVSLTCLVK GFYPSDIAVE WESNGQPENN YKTTPPVLDS DGSFFLYSRL TVDKSRWQEG NVFSCSVMHE ALHNHYTQKS LSLSLGK |
| 85 | exemplary human TIM3 sequences | SEVEYRAEVG QNAYLPCFYT PAAPGNLVPV CWGKGACPVF ECGNVVLRTD ERDVNYWTSR YWLNGDFRKG DVSLTIENVT LADSGIYCCR IQIPGIMNDE KFNLKLVIKP AKVTPAPTRQ RDFTAAFPRM LTTRGHGPAE TQTLGSLPDI NLTQISTLAN ELRDSRLAND LRDSGATIRI GIYIGAGICA GLALALIFGA LIFKWYSHSK EKIQNLSLIS LANLPPSGLA NAVAEGIRSE ENIYTIEENV YEVEEPNEYY CYVSSRQQPS QPLGCRFAMP |
| 86 | human TIM3 Extracellular Domain (ECD) | SEVEYRAEVG QNAYLPCFYT PAAPGNLVPV CWGKGACPVF ECGNVVLRTD ERDVNYWTSR YWLNGDFRKG DVSLTIENVT LADSGIYCCR IQIPGIMNDE KFNLKLVIKP AKVTPAPTRQ RDFTAAFPRM LTTRGHGPAE TQTLGSLPDI NLTQISTLAN ELRDSRLAND LRDSGATIRI G |
| 87 | exemplary human PD1 sequence | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 88 | human PD1 Extracellular Domain (ECD) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV |

TABLE C-continued (Sequences):

| SEQ ID NO: | Name | Sequence |
|---|---|---|
| | | VRARRNDSGT YLCGAISLAP KAQIKESLRA ELRVTERRAE VPTAHPSPSP RPAGQFQTLV |
| 89 | human PD1 Extracellular Domain (ECD) including the signal peptide | MQIPQAPWPVVWAVLQLGWRPGWFLDSPDRPW NPPTFSPALLVVTEGDNATFTCSFSNTSESFV LNWYRMSPSNQTDKLAAFPEDRSQPGQDCRFR VTQLPNGRDFHMSVVRARRNDSGTYLCGAISL APKAQIKESLRAELRVTERRAEVPTAHPSPSP RPAGQFQTLVVGVVGGLLGSLVLLVWVLAVIC SRAARGTIGARRTGQPLKEDPSAVPVFSVDYG ELDFQWREKTPEPPVPCVPEQTEYATIVFPSG MGTSSPARRGSADGPRSAQPLRPEDGHCSWPL |
| 90 | GGGGS spacer | GGGGS |
| 91 | SNAP-tag | DKDCEMKRTTLDSPLGKLELSGCEQGLHEIKL LGKGTSAADAVEVPAPAAVLGGPEPLMQATAW LNAYFHQPEAIEEFPVPALHHPVFQQESFTRQ VLWKLLKVVKFGEVISYQQLAALAGNPAATAA VKTALSGNPVPILIPCHRVVSSSGAVGGYEGG LAVKEWLLAHEGHRLGKPGLGPAGGSPGLEVN |
| 92 | Flag-tag | DYKDDDDK |
| 93 | human TIM3 Extracellular Domain (ECD) including signal peptide | MFSHLPFDCVLLLLLLLLTRSSEVEYRAEVGQ NAYLPCFYTPAAPGNLVPVCWGKGACPVFECG NVVLRTDERDVNYWTSRYWLNGDFRKGDVSLT IENVTLADSGIYCCRIQIPGIMNDEKFNLKLV IKPAKVTPAPTRQRDFTAAFPRMLTTRGHGPA ETQTLGSLPDINLTQISTLANELRDSRLANDL RDSGATIRIGIYIGAGICAGLALALIFGALIF KWYSHSKEKIQNLSLISLANLPPSGLANAVAE GIRSEENIYTIEENVYEVEEPNEYYCYVSSRQ QPSQPLGCRFAM |
| 94 | Clip-tag | DKDCEMKRTTLDSPLGKLELSGCEQGLHRIIF LGKGTSAADAVEVPAPAAVLGGPEPLIQATAW LNAYFHQPEAIEEFPVPALHHPVFQQESFTRQ VLWKLLKVVKFGEVISESHLAALVGNPAATAA VNTALDGNPVPILIPCHRVVQGDSDVGPYLGG LAVKEWLLAHEGHRLGKPGLG |

In the following specific embodiments of the invention are listed:

1. A bispecific antibody comprising a first antigen-binding site that specifically binds to PD1 and a second antigen-binding site that specifically binds to TIM3, wherein said first antigen-binding site specifically binding to PD1 comprises
   a VH domain comprising
   (i) HVR-H1 comprising the amino acid sequence of SEQ ID NO:37,
   (ii) HVR-H2 comprising the amino acid sequence of SEQ ID NO:38, and
   (iii) HVR-H3 comprising an amino acid sequence of SEQ ID NO:39; and
   a VL domain comprising
   (i) HVR-L1 comprising the amino acid sequence of SEQ ID NO:40;
   (ii) HVR-L2 comprising the amino acid sequence of SEQ ID NO:41, and
   (iii) HVR-L3 comprising the amino acid sequence of SEQ ID NO:42; and
   said second antigen-binding site specifically binding to TIM3 comprises
   (a) a VH domain comprising
   (i) HVR-H1 comprising the amino acid sequence of SEQ ID NO:1,
   (ii) HVR-H2 comprising the amino acid sequence of SEQ ID NO:2, and
   (iii) HVR-H3 comprising an amino acid sequence of SEQ ID NO:3; and
   a VL domain comprising
   (i) HVR-L1 comprising the amino acid sequence of SEQ ID NO:4 or SEQ ID NO:11 or SEQ ID NO:12,
   (ii) HVR-L2 comprising the amino acid sequence of SEQ ID NO:5, and
   (iii) HVR-L3 comprising the amino acid sequence of SEQ ID NO:6; or
   (b) a VH domain comprising
   (i) HVR-H1 comprising the amino acid sequence of SEQ ID NO:17,
   (ii) HVR-H2 comprising the amino acid sequence of SEQ ID NO:18, and
   (iii) HVR-H3 comprising an amino acid sequence of SEQ ID NO:19; and
   a VL domain comprising
   (i) HVR-L1 comprising the amino acid sequence of SEQ ID NO:20,
   (ii) HVR-L2 comprising the amino acid sequence of SEQ ID NO:21, and
   (iii) HVR-L3 comprising the amino acid sequence of SEQ ID NO:22; or (c) a VH domain comprising
  (i) HVR-H1 comprising the amino acid sequence of SEQ ID NO:29,
  (ii) HVR-H2 comprising the amino acid sequence of SEQ ID NO:30, and
  (iii) HVR-H3 comprising an amino acid sequence of SEQ ID NO:31; and
a VL domain comprising
  (i) HVR-L1 comprising the amino acid sequence of SEQ ID NO:32,
  (ii) HVR-L2 comprising the amino acid sequence of SEQ ID NO:33, and
  (iii) HVR-L3 comprising the amino acid sequence of SEQ ID NO:34.

2. A bispecific antibody comprising a first antigen-binding site that specifically binds to PD1 and a second antigen-binding site that specifically binds to TIM3, wherein the bispecific antibody binds to TIM3 with an at least 50 fold lower binding affinity when compared to the binding to PD1, more particularly with an at least 100 fold lower binding affinity when compared to the binding to PD1.

3. The bispecific antibody according as defined herein before, wherein
said first antigen-binding site specifically binding to PD1 comprises
  (a) a VH domain comprising the amino acid sequence of SEQ ID NO: 43 and a VL domain comprising the amino acid sequence of SEQ ID NO: 44, or
  (b) a VH domain comprising the amino acid sequence of SEQ ID NO: 45 and a VL domain comprising the amino acid sequence of SEQ ID NO: 46, or
  (c) a VH domain comprising the amino acid sequence of SEQ ID NO: 45 and a VL domain comprising the amino acid sequence of SEQ ID NO: 47, or
  (d) a VH domain comprising the amino acid sequence of SEQ ID NO: 45 and a VL domain comprising the amino acid sequence of SEQ ID NO: 48, or
  (e) a VH domain comprising the amino acid sequence of SEQ ID NO: 45 and a VL domain comprising the amino acid sequence of SEQ ID NO: 49,
and said second antigen-binding site specifically binding to TIM3 comprises
  (a) a VH domain comprising the amino acid sequence of SEQ ID NO: 7 and a VL domain comprising the amino acid sequence of SEQ ID NO: 8, or
  (b) a VH domain comprising the amino acid sequence of SEQ ID NO: 9 and a VL domain comprising the amino acid sequence of SEQ ID NO: 10, or
  (c) a VH domain comprising the amino acid sequence of SEQ ID NO: 13 and a VL domain comprising the amino acid sequence of SEQ ID NO: 14, or
  (d) a VH domain comprising the amino acid sequence of SEQ ID NO: 15 and a VL domain comprising the amino acid sequence of SEQ ID NO: 16, or
  (e) a VH domain comprising the amino acid sequence of SEQ ID NO: 23 and a VL domain comprising the amino acid sequence of SEQ ID NO: 24, or
  (f) a VH domain comprising the amino acid sequence of SEQ ID NO: 25 and a VL domain comprising the amino acid sequence of SEQ ID NO: 26, or
  (g) a VH domain comprising the amino acid sequence of SEQ ID NO: 27 and a VL domain comprising the amino acid sequence of SEQ ID NO: 28, or
  (h) a VH domain comprising the amino acid sequence of SEQ ID NO: 35 and a VL domain comprising the amino acid sequence of SEQ ID NO: 36.

4. The bispecific antibody as defined hereinbefore, wherein said first antigen-binding site specifically binding to PD1 comprises a VH domain comprising the amino acid sequence of SEQ ID NO: 45 and a VL domain comprising the amino acid sequence of SEQ ID NO: 46,
and said second antigen-binding site specifically binding to TIM3 comprises a VH domain comprising the amino acid sequence of SEQ ID NO: 15 and a VL domain comprising the amino acid sequence of SEQ ID NO: 16 or a VH domain comprising the amino acid sequence of SEQ ID NO: 25 and a VL domain comprising the amino acid sequence of SEQ ID NO: 26.

5. The bispecific antibody as defined herein before, wherein said first antigen-binding site specifically binding to PD1 comprises a VH domain comprising the amino acid sequence of SEQ ID NO: 45 and a VL domain comprising the amino acid sequence of SEQ ID NO: 46,
and said second antigen-binding site specifically binding to TIM3 comprises a VH domain comprising the amino acid sequence of SEQ ID NO: 25 and a VL domain comprising the amino acid sequence of SEQ ID NO: 26.

6. The bispecific antibody as defined herein before, wherein the bispecific antibody is a human, humanized or chimeric antibody.

7. The bispecific antibody as defined herein before, wherein the bispecific antibody comprises an Fc domain, a first Fab fragment comprising the antigen-binding site that specifically binds to PD1 and a second Fab fragment comprising the antigen-binding site that specifically binds to TIM3.

8. The bispecific antibody as defined herein before, wherein the Fc domain is an IgG, particularly an IgG1 Fc domain or an IgG4 Fc domain.

9. The bispecific antibody as defined herein before, wherein the Fc domain comprises one or more amino acid substitution that reduces binding to an Fc receptor, in particular towards Fcγ receptor.

10. The bispecific antibody as defined herein before, wherein the Fc domain is of human IgG1 subclass with the amino acid mutations L234A, L235A and P329G (numbering according to Kabat EU index).

11. The bispecific antibody as defined herein before, wherein the Fc domain comprises a modification promoting the association of the first and second subunit of the Fc domain.

12. The bispecific antibody as defined herein before, wherein the first subunit of the Fc domain comprises knobs and the second subunit of the Fc domain comprises holes according to the knobs into holes method.

13. The bispecific antibody as defined herein before, wherein the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

14. The bispecific antibody as defined herein before, wherein in one of the Fab fragments the variable domains VL and VH are replaced by each other so that the VH domain is part of the light chain and the VL domain is part of the heavy chain.

15. The bispecific antibody as defined herein before, wherein in the first Fab fragment comprising the antigen-binding site that specifically binds to PD1 the variable domains VL and VH are replaced by each other.

16. The bispecific antibody as defined herein before, wherein in one of the Fab fragments in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

17. The bispecific antibody as defined herein before, wherein in the second Fab fragment comprising the antigen-binding site that specifically binds to TIM3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

18. The bispecific antibody as defined herein before, comprising
    (a) a first heavy chain comprising an amino acid sequence with at least 95% sequence identity to the sequence of SEQ ID NO: 50, a first light chain comprising an amino acid sequence with at least 95% sequence identity to the sequence of SEQ ID NO: 52,
       a second heavy chain comprising an amino acid sequence with at least 95% sequence identity to the sequence of SEQ ID NO: 51, and a second light chain comprising an amino acid sequence with at least 95% sequence identity to the sequence of SEQ ID NO:53, or
    (b) a first heavy chain comprising an amino acid sequence with at least 95% sequence identity to the sequence of SEQ ID NO: 54, a first light chain comprising an amino acid sequence with at least 95% sequence identity to the sequence of SEQ ID NO: 56,
       a second heavy chain comprising an amino acid sequence with at least 95% sequence identity to the sequence of SEQ ID NO: 55, and a second light chain comprising an amino acid sequence with at least 95% sequence identity to the sequence of SEQ ID NO:57, or
    (c) a first heavy chain comprising an amino acid sequence with at least 95% sequence identity to the sequence of SEQ ID NO: 58, a first light chain comprising an amino acid sequence with at least 95% sequence identity to the sequence of SEQ ID NO: 60,
       a second heavy chain comprising an amino acid sequence with at least 95% sequence identity to the sequence of SEQ ID NO: 59, and a second light chain comprising an amino acid sequence with at least 95% sequence identity to the sequence of SEQ ID NO:61, or
    (d) a first heavy chain comprising an amino acid sequence with at least 95% sequence identity to the sequence of SEQ ID NO: 62, a first light chain comprising an amino acid sequence with at least 95% sequence identity to the sequence of SEQ ID NO: 64,
       a second heavy chain comprising an amino acid sequence with at least 95% sequence identity to the sequence of SEQ ID NO: 63, and a second light chain comprising an amino acid sequence with at least 95% sequence identity to the sequence of SEQ ID NO:65, or
    (e) a first heavy chain comprising an amino acid sequence with at least 95% sequence identity to the sequence of SEQ ID NO: 66, a first light chain comprising an amino acid sequence with at least 95% sequence identity to the sequence of SEQ ID NO: 68,
       a second heavy chain comprising an amino acid sequence with at least 95% sequence identity to the sequence of SEQ ID NO: 67, and a second light chain comprising an amino acid sequence with at least 95% sequence identity to the sequence of SEQ ID NO:69.

19. The bispecific antibody as defined herein before, comprising
    (a) a first heavy chain comprising the amino acid sequence of SEQ ID NO: 50, a first light chain comprising the amino acid sequence of SEQ ID NO: 52,
       a second heavy chain comprising the amino acid sequence of SEQ ID NO: 51, and a second light chain comprising the amino acid sequence of SEQ ID NO:53, or
    (b) a first heavy chain comprising the amino acid sequence of SEQ ID NO: 54, a first light chain comprising the amino acid sequence of SEQ ID NO: 56,
       a second heavy chain comprising the amino acid sequence of SEQ ID NO: 55, and a second light chain comprising the amino acid sequence of SEQ ID NO:57, or
    (c) a first heavy chain comprising the amino acid sequence of SEQ ID NO: 58, a first light chain comprising the amino acid sequence of SEQ ID NO: 60,
       a second heavy chain comprising the amino acid sequence of SEQ ID NO: 59, and a second light chain comprising the amino acid sequence of SEQ ID NO:61, or
    (d) a first heavy chain comprising the amino acid sequence of SEQ ID NO: 62, a first light chain comprising the amino acid sequence of SEQ ID NO: 64,
       a second heavy chain comprising the amino acid sequence of SEQ ID NO: 63, and a second light chain comprising the amino acid sequence of SEQ ID NO:65, or
    (e) a first heavy chain comprising the amino acid sequence of SEQ ID NO: 66, a first light chain comprising the amino acid sequence of SEQ ID NO: 68,
       a second heavy chain comprising the amino acid sequence of SEQ ID NO: 67, and a second light chain comprising the amino acid sequence of SEQ ID NO:69.

20. A polynucleotide encoding the bispecific antibody as defined herein before.

21. A vector, particularly an expression vector, comprising the polynucleotide as defined herein before.

22. A prokaryotic or eukaryotic host cell comprising the polynucleotide as defined herein before or the vector as defined herein before.

23. A method of producing the bispecific antibody as defined herein before, comprising the steps of
    a) transforming a host cell with vectors comprising polynucleotides encoding said bispecific antibody, b) culturing the host cell according under conditions suitable for the expression of the bispecific antibody and c) recovering the bispecific antibody from the culture.

24. A pharmaceutical composition comprising the bispecific antibody as defined herein before and at least one pharmaceutically acceptable excipient.

25. The bispecific antibody as defined herein before or the pharmaceutical composition as defined herein before for use as a medicament.

26. The bispecific antibody as defined herein before or the pharmaceutical composition as defined herein before for use i) in the modulation of immune responses, such as restoring T cell activity,
ii) in stimulating an immune response or function,
iii) in the treatment of infections,
iv) in the treatment of cancer,
v) in delaying progression of cancer,
vi) in prolonging the survival of a patient suffering from cancer.

27. The bispecific antibody as defined herein before or the pharmaceutical composition as defined herein before for use in the prevention or treatment of cancer.
28. The bispecific antibody as defined herein before or the pharmaceutical composition as defined herein before for use in the treatment of a chronic viral infection.
29. The bispecific antibody as defined herein before or the pharmaceutical composition as defined herein before for use in the prevention or treatment of cancer, wherein the bispecific antibody is administered in combination with a chemotherapeutic agent, radiation and/or other agents for use in cancer immunotherapy.
30. A method of inhibiting the growth of tumor cells in an individual comprising administering to the individual an effective amount of the bispecific antibody as defined herein before to inhibit the growth of the tumor cells.

EXAMPLES

The following are examples of methods and compositions of the invention. It is understood that various other embodiments may be practiced, given the general description provided above.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to the numbering systems according to Kabat (Kabat, E. A., et al., Sequences of Proteins of Immunological Interest, 5th ed., Public Health Service, National Institutes of Health, Bethesda, Md. (1991)) as defined above.

Recombinant DNA Techniques

Standard methods were used to manipulate DNA as described in Sambrook, J. et al., Molecular Cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The 600-1800 bp long gene segments, which were flanked by singular restriction endonuclease cleavage sites, were assembled by annealing and ligating oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany).

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors

For the expression of the described antibodies, variants of expression plasmids for transient expression (e.g. in HEK293) cells based either on a cDNA organization with or without a CMV-Intron A promoter or on a genomic organization with a CMV promoter were applied.

Beside the antibody expression cassette the vectors contained:
an origin of replication which allows replication of this plasmid in E. coli, and
a ß-lactamase gene which confers ampicillin resistance in E. coli.

The transcription unit of the antibody gene was composed of the following elements:
unique restriction site(s) at the 5' end
the immediate early enhancer and promoter from the human cytomegalovirus,
followed by the Intron A sequence in the case of the cDNA organization,
a 5'-untranslated region of a human antibody gene,
an immunoglobulin heavy chain signal sequence,
the human antibody chain (wildtype or with domain exchange) either as cDNA or as genomic organization with the immunoglobulin exon-intron organization
a 3' untranslated region with a polyadenylation signal sequence, and
unique restriction site(s) at the 3' end.

The fusion genes comprising the antibody chains as described below were generated by PCR and/or gene synthesis and assembled by known recombinant methods and techniques by connection of the according nucleic acid segments e.g. using unique restriction sites in the respective vectors. The subcloned nucleic acid sequences were verified by DNA sequencing. For transient transfections larger quantities of the plasmids were prepared by plasmid preparation from transformed E. coli cultures (Nucleobond AX, Macherey-Nagel).

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Multi specific antibodies were expressed by transient co-transfection of the respective expression plasmids in adherently growing HEK293-EBNA or in HEK29-F cells growing in suspension as described below.

Transient Transfections in HEK293 System

All antibodies and bispecific antibodies were generated by transient transfection of 293F cells using the Freestyle system (ThermoFisher). Here the 293F cells were cultivated in F17 Medium, transfected with 293Free (Novagene) and feeded after 4 hours with VPA 4 mM and Feed 7 and 0.6% Glucose after 16 h. Further the Expi293F™ Expression System Kit (ThermoFisher) was used. Here the Expi293F™ cells were cultivated in Expi293™ Expression Medium and transfected using ExpiFectamine™ 293 Transfection Kit according manufactuer's instructions. Due to the improved stability and purity and reduced aggregation tendency of the CrossMAb$^{Vh-VL}$ bispecific antibodies with additionally introduced charged pairs of amino acids in th CH1/CL interface (see positions in the respective sequences for further detail) no adjustments of plasmid ratio have been employed. Therefore the relative plasmid ratio of 1:1:1:1 for 1+1 CrossMab or 1:1:1 for 2+2 CrossMab was used for the co-transfection of LC, HC, crossed LC and crossed HC plasmids. Cell supernatants were harvested after 7 days and purified by standard methods.

Protein Determination

The protein concentration of purified antibodies and derivatives was determined by determining the optical density (OD) at 280 nm, using the molar extinction coefficient calculated on the basis of the amino acid sequence according to Pace, et al., Protein Science, 1995, 4, 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads were washed three times in TBS-NP40 (50 mM Tris, pH 7.5, 150 mM NaCl, 1% Nonidet-P40). Subsequently, 1-15 mL cell culture supernatant was applied to the Protein A Agarose beads pre-equilibrated in TBS-NP40. After incubation for at 1 hour at room temperature the beads were washed on an Ultrafree-MC-filter column (Amicon) once with 0.5 mL TBS-NP40, twice with 0.5 mL 2× phosphate buffered saline (2×PBS, Roche) and briefly four times with 0.5 mL 100 mM Na-citrate pH 5.0. Bound antibody was eluted by addition of 35 µl NuPAGE® LDS Sample Buffer (Invitrogen). Half of the sample was combined with NuPAGE® Sample Reducing Agent or left unreduced, respectively, and heated for 10 min at 70° C. Consequently, 5-30 µl were applied to a 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was quantitatively measured by affinity HPLC chromatography. Briefly, cell culture supernatants containing antibodies and derivatives that bind to Protein A were applied to an Applied Biosystems Poros A/20 column in 200 mM KH2PO4, 100 mM sodium citrate, pH 7.4 and eluted from the matrix with 200 mM NaCl, 100 mM citric acid, pH 2.5 on an Agilent HPLC 1100 system. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) are coated with 100 µL/well biotinylated anti-human IgG capture molecule F(ab')2<h-Fcγ>BI (Dianova) at 0.1 µg/mL for 1 hour at room temperature or alternatively overnight at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 hour on a microtiterplate shaker at room temperature. The wells were washed three times with 200 µL/well PBST and bound antibody was detected with 100 µl F(ab') 2<hFcγ>POD (Dianova) at 0.1 µg/mL as the detection antibody for 1-2 hours on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 µg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multispecific Antibodies to the Respective Antigens Using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). Briefly, for affinity measurements Goat-Anti-Human IgG, JIR 109-005-098 antibodies are immobilized on a CM5 chip via amine coupling for presentation of the antibodies against the respective antigen. Binding is measured in HBS buffer (HBS-P (10 mM HEPES, 150 mM NaCl, 0.005% Tween 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective Biacore Evaluation Software is used for analysis of sensorgrams and for calculation of affinity data.

TIM3 Antibodies

Example 1a: Generation of Anti-TIM3 Antibodies

Immunization of Mice

NMRI mice were immunized genetically, using a plasmid expression vector coding for full-length human Tim-3 by intradermal application of 100 ug vector DNA (plasmid 15304_hTIM3-fl), followed by Electroporation (2 square pulses of 1000 V/cm, duration 0.1 ms, interval 0.125 s; followed by 4 square pulses of 287.5 V/cm, duration 10 ms, interval 0.125 s. Mice received either 6 consecutive immunizations at days 0, 14, 28, 42, 56, 70, and 84. Blood was taken at days 36, 78 and 92 and serum prepared, which was used for titer determination by ELISA (see below). Animals with highest titers were selected for boosting at day 96, by intravenous injection of 50 ug of recombinant human Tim-3 human Fc chimera, and monoclonal antibodies were isolated by hybridoma technology, by fusion of splenocytes to myeloma cell line 3 days after boost.

Determination of Serum Titers (ELISA)

Human recombinant Tim-3 human Fc chimera was immobilized on a 96-well NUNC Maxisorp plate at 0.3 ug/ml, 100 µl/well, in PBS, followed by: blocking of the plate with 2% Crotein C in PBS, 200 µl/well; application of serial dilutions of antisera, in duplicates, in 0.5% Crotein C in PBS, 100 µl/well; detection with HRP-conjugated goat anti-mouse antibody (Jackson Immunoresearch/Dianova 115-036-071; 1/16 000). For all steps, plates were incubated for 1 h at 37° C. Between all steps, plates were washed 3 times with 0.05% Tween 20 in PBS. Signal was developed by addition of BM Blue POD Substrate soluble (Roche), 100 ul/well; and stopped by addition of 1 M HCl, 100 ul/well. Absorbance was read out at 450 nm, against 690 nm as reference. Titer was defined as dilution of antisera resulting in half-maximal signal.

Example 1b: Characterization Anti-TIM3 Antibodies

ELISA for TIM3

Nunc-Maxi Sorp Streptavidine plates (MicroCoat #11974998/MC1099) were coated by 25 µl/well with Tim3-ECD-His-Biotin (biotinylated with BirA Ligase) and incubated at RT for 1 h while shaking at 400 rpm rotation. After washing (3×90 µl/well with PBST-buffer) 25 µl aTim3 samples or diluted (1:2 steps) reference antibody aTim3 F38-2E2 (Biolegend) was added and incubated 1 h at RT. After washing (3×90 µl/well with PBST-buffer) 25 µl/well sheep-anti-mouse-POD (GE NA9310V) was added in 1:9000 dilution and incubated at RT for 1 h while shaking at 400 rpm rotation. After washing (4×90 µl/well with PBST-buffer) 25 µl/well TMB substrate (Calbiochem, #CL07) was added and incubated until OD 1.5-2.5. Then the reaction was stopped by addition of 25 µl/well 1N HCL-solution. Measurement took place at 370/492 nm.

ELISA results are listed as $EC_{50}$-values [ng/ml] in Summary Table 1 below.

Cell ELISA for TIM3

Adherent CHO-K1 cell line stably transfected with plasmid 15312_hTIM3-fl_pUC_Neo coding for full-length human Tim3 and selection with G418 (Neomycin resistance marker on plasmid) were seeded at a concentration of 1.2×10E6 cells/ml into 384-well flat bottom plates and grown over night.

At the next day 25 µl/well Tim3 sample or aTim3 reference antibody F38-2E2 Azide free (Biolegend, 354004) was added and incubated for 2 h at 4° C. (to avoid internalization). After washing (3×90 µl/well PBST (BIOTEK Washer: Prog. 29, 1×90) cells were fixed by flicking out residual buffer and addition of 50 µl/well 0.05% Glutaraldehyde: Dilution 1:500 of 25% Glutaraldehyde (Sigma Cat. No: G5882) in 1×PBS-buffer and incubated for 1 h at RT. After washing (3×90 µl/well PBST (BIOTEK Washer: Prog. 21, 3×90 GreinLysin) 25 µl/well secondary antibody was added for detection (Sheep-anti-mouse-POD; Horseradish POD linked F(ab')$_2$ Fragment; GE NA9310) followed by 2 h incubation at RT while shaking at 400 rpm. After washing (3×90 µl/well PBST (BIOTEK Washer: Prog. 21, 3×90 GreinLysin) 25 µl/well TMB substrate solution (Roche 11835033001) was added and incubated until OD 1.5-2.5. Then the reaction was stopped by addition of 25 µl/well 1N HCL-solution. Measurement took place at 370/492 nm.

Cell ELISA results are listed as "$EC_{50}$ CHO-Tim3"-values [ng/ml] in summary Table 1 below.

TABLE 1

Binding affinities of exemplary antibodies (ELISA and BIACORE)

| Assay | Tim3_0018 | Tim3_0021 | Tim3_0028 | Tim3_0026 | Tim3-0033 | Tim3_0038 |
|---|---|---|---|---|---|---|
| Affinity KD [nM] | | | | | | |
| monomer/dimer Tim3 | 3.4/1.1 | 204/4.1 | 173/2.8 | 6.2/1.5 | n.f./3.1 | 7.6/0.6 |
| $EC_{50}$ ELISA [nM] | 0.56 | | 0.22 | | | 0.501 |
| $EC_{50}$ ELISA [ng/ml] | 94 | 47 | 37 | 47 | 1321 | 83 |
| $EC_{50}$ CHO-Tim3 [nM] | 0.52 | | 0.32 | | | 0.17 |
| $EC_{50}$ CHO-Tim3 [ng/ml] | 87 | 73 | 53 | 69 | 3710 | 29 |

BIAcore Characterization of the TIM3 Antibodies

A surface plasmon resonance (SPR) based assay has been used to determine the kinetic parameters of the binding between several murine Tim3 binders as well as commercial human Tim3 binding references. Therefore, an anti-mouse IgG was immobilized by amine coupling to the surface of a (BIAcore) CM5 sensor chip. The samples were then captured and monomeric hu/cy Tim3-ECD as well as a Fc-tagged human Tim3-ECD dimer was bound to them. The sensor chip surface was regenerated after each analysis cycle. The equilibrium constant KD was finally gained by fitting the data to a 1:1 Langmuir interaction model.

About 12000 response units (RU) of 30 µg/ml anti-mouse IgG (GE Healthcare #BR-1008-38) were coupled onto the spots 1, 2, 4 and 5 of the flow cells 1-4 (spots 1, 5 are active and spots 2, 4 are reference spots) of a CM5 sensor chip in a BIAcore B4000 at pH 5.0 by using an amine coupling kit supplied by GE Healthcare.

The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

The samples were injected for 30 seconds with a concentration of 200 µg/ml and bound to the spots 1 and 5 of each flow cell, allowing the measurement of eight samples in parallel. Then a complete set of different (monomeric cyno, monomeric human and huFc fused dimeric human Tim3-ECD) concentrations was injected over each sample for 240 s followed by a dissociation time of 30/1800 s. Each analysis cycle (sample capture, spot 1 and 5-Tim3 ECD injection) was then regenerated with a 30 seconds long injection of Glycine-HCl pH 1.7. The flow rate was set to 30 µl/min for the whole run.

Finally the double referenced data was fitted to a 1:1 Langmuir interaction model with the BIAcore B4000 Evaluation Software. Resulting affinities to monomeric human, cyno Tim3 and huFc fused dimeric human Tim3 are shown in Table 2a. The affinity to the hu Tim3 dimer is most likely affected by avidity and therefore apparently stronger than the affinity to the monomeric huTim3.

TABLE 2a

Binding affinities determined by BIAcore-KD values gained by a kinetic SPR measurement.

| Sample | huTim3 $K_D$ (25° C.) [M] | huTim3Fc $K_D$ (25° C.) [M] | cyTim3 $K_D$ (25° C.) [M] |
| --- | --- | --- | --- |
| TIM3-0016 | 3.29E-09 | 1.09E-09 | 2.16E-08 |
| TIM3-0016 variant (0018) | 3.40E-09 | 1.11E-09 | 4.19E-08 |
| TIM3-0021 | 2.04E-07 | 4.07E-09 | n.f. |
| TIM3-0022 | 1.26E-07 | 1.52E-09 | 2.84E-08 |
| TIM3-0026 | 6.23E-09 | 1.52E-09 | n.f. |
| TIM3-0028 | 1.73E-07 | 2.77E-09 | n.f. |
| TIM3-0030 | 3.11E-09 | 1.28E-09 | n.f. |
| TIM3-0033 | n.f. | 3.05E-09 | n.f. |
| TIM3-0038 | 7.56E-09 | 5.69E-10 | n.f. |
| Reference antibody Biolegend F38-2E2 | 1.36E-08 | 7.50E-09 | 1.68E-07 |
| Reference antibody USB 11E365 | 1.34E-08 | 7.73E-09 | 1.41E-07 | n.f. means no fit possible, most likely due to no or weak binding.

Determination of the Affinity to Tim3 Via SPR (Chimeric TIM3-0016 Variant (0018) and Humanized Versions)

Protein A was immobilized by amine coupling to the surface of a (Biacore) CM5 sensor chip. The samples were then captured and hu Tim3-ECD was bound to them. The sensor chip surface was regenerated after each analysis cycle. The equilibrium constant and kinetic rate constants were finally gained by fitting the data to a 1:1 Langmuir interaction model.

About 2000 response units (RU) of 20 µg/ml Protein A were coupled onto the spots 1, 2, 4 and 5 of all flow cells of a CM5 sensor chip in a Biacore B4000 instrument using an amine coupling kit supplied by GE Healthcare.

The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

Different samples were injected for 30 seconds with a concentration of 10 nM and bound consecutively to the spots 1 and 5 in all flow cells. Then a complete set of monomeric human Tim3-ECD dilutions (600 nM, 200 nM, 66.7 nM, 2×22.2 nM, 7.4 nM, 2.5 nM and 2×0 nM) was consecutively injected over each sample for 300 s. Each antigen injection was followed by a dissociation time of 12 s/1000 s and two 30 s regeneration steps with a Glycine-HCl pH 1.5 solution, of which the last one contained a stabilization period after injection of 20 seconds.

Finally the double referenced data was fitted to a 1:1 Langmuir interaction model using the Biacore B4000 Evaluation Software. Resulting $K_D$ values are shown in Table 2b. Determination of the Affinity to Tim3 Via SPR ((Chimeric TIM3-0028 and Humanized Versions))

Anti-human Fc IgG was immobilized by amine coupling to the surface of a (Biacore) CM5 sensor chip. The samples were then captured and hu Tim3-ECD was bound to them. The sensor chip surface was regenerated after each analysis cycle. The equilibrium constant and kinetic rate constants were finally gained by fitting the data to a 1:1 Langmuir interaction model.

About 2500 response units (RU) of 10 µg/ml anti-human Fc IgG (GE Healthcare #BR-1008-39) were coupled onto the spots 1, 2, 4 and 5 of all flow cells of a CM5 sensor chip in a Biacore B4000 instrument using an amine coupling kit supplied by GE Healthcare.

The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

Different samples were injected for 30 seconds with a concentration of 10 nM and bound consecutively to the spots 1 and 5 in all flow cells. Then a complete set of monomeric human Tim3-ECD dilutions (600 nM, 200 nM, 66.7 nM, 2×22.2 nM, 7.4 nM, 2.5 nM and 2×0 nM) was consecutively injected over each sample for 300 s. Each antigen injection was followed by a dissociation time of 12 s/700 s and two 30 s regeneration steps with a 3 M $MgCl_2$ solution, of which the last one contained an "extra wash after injection" with running buffer.

Finally the double referenced data was fitted to a 1:1 langmuir interaction model using the Biacore B4000 Evaluation Software. Resulting KD values are shown in Table 2b.

TABLE 2b

Binding affinities determined by BIAcore-KD values gained by a kinetic SPR measurement

| Sample | huTim3 $K_D$ (25° C.) [M] |
| --- | --- |
| Chimeric TIM3-0016 variant (0018) | 2.78E-09 |
| TIM3-0433 | 5.74E-09 |
| TIM3-0434 | 5.76E-09 |
| Chimeric TIM3-0028 | 2.35E-07 |
| TIM3-0438 | 3.05E-07 |
| TIM3-0443 | 2.87E-07 |

Example 2: Generation of Anti-TIM3 Antibody Derivatives

Chimeric Antibody Derivatives

Chimeric Tim3 antibodies were generated by amplifying the variable heavy and light chain regions of the anti-TIM3 mouse antibodies Tim3-0016, Tim3-0016 variant (0018), Tim3-0021, Tim3-0022, Tim3-0026, Tim3-0028, Tim3-0030, and Tim3-0033, Tim3-0038 from via PCR and cloning them into heavy chain expression vectors as fusion proteins with human IgG1 backbones/human CH1-Hinge-CH2-CH3 with LALA and PG mutations (Leucine 234 to Alanine, Leucine 235 to Alanine, Proline 329 to Glycine) abrogating effector functions and light chain expression vectors as fusion proteins to human C-kappa. LC and HC Plasmids were then cotransfected into HEK293 and purified after 7 days from supernatants by standard methods for antibody purification.

Removal of Glycosylation Site NYT: Modifying 1 HVR-L1 Position in Tim3-0016, Tim3_0016 Variant (Named 0018 or Tim3_0018) by Substitution of N by Q or S Mutations within the variable light chain region of Tim3_0016 and Tim3_0016 variant (0018) were generated by in vitro mutagenesis using Agilent "Quick Change Lightning Site-directed Mutagenesis Kit" according manufacturer's instructions. By this method the asparagine (N) of the glycosylation site motif NYT in the light chain HVR-L1 (SEQ ID NO: 4) was replaced by glutamine (Q) (resulting in SEQ ID NO: 11=Tim3_0016 HVR-L1 variant 1_NQ) or, alternatively, the asparagine (N) was replaced by serine (S) (resulting in SEQ ID NO: 12=Tim3_0016_HVR-L1 variant 2_NS). In both, the glycosylation site motif NYT was successfully modified. LC and HC Plasmids coding for the variants were then cotransfected into HEK293 and purified after 7 days from supernatants by standard methods for antibody purification.

The generated mutants were tested by ELISA on human Tim3, ELISA on cynomolgus Tim3 and cellular ELISA on adherent CHO-K1 cells expressing full-length human Tim3.

TABLE 3

| Antibodies and mutant antibodies tested | Biochem Human | | Biochem Cyno | | Cellular binding CHO-TIM3 | |
|---|---|---|---|---|---|---|
| | $EC_{50}$ [ng/ml] values in relation to the samples max value | Inflexion point [ng/ml] | $EC_{50}$ [ng/ml] values in relation to the samples max value | Inflexion point [ng/ml] | $EC_{50}$ [ng/ml] values in relation to the samples max value | Inflexion point [ng/ml] |
| Anti Tim3 F38-2E2 | 73.2 | 88.3 | 423.0 | 209871.3 | 150.2 | 224.3 |
| Tim3_0018 (TIM3-0016 variant) | 15.1 | 15.3 | 14.6 | 14.6 | 26.4 | 29.4 |
| Tim3_0018MutNQ | 12.0 | 10.8 | 13.2 | 10.8 | 13.4 | 12.8 |
| Tim3_0018MutNS | 10.3 | 6.5 | 11.9 | 6.5 | 11.2 | 11.1 |
| Tim3_0016MutNQ | 7.6 | 5.7 | 8.3 | 5.7 | 6.3 | 5.4 |
| Tim3_0016MutNS | 8.5 | 5.5 | 9.7 | 5.5 | 9.1 | 8.5 |

All mutants generated were found to show even more functional binding to human TIM3 (human), cyno TIM3 (cyno) or human TIMR on CHO cells than the parental antibodies Tim3_0016 or the Tim3_0016 antibody variant Tim3_0018 respectively.

Humanized Antibody Derivatives

Humanization of the VH and VL Domains of Murine Anti-Tim3-0016 Variant (0018) and Anti-Tim3_0028

Based upon the amino acid sequence of the VH and VL domains of a) anti-Tim3 antibody Tim3_0016 variant (0018) (with the amino acid sequences of the 6 HVRs wherein in the light chain the HVR-L1 variant 2_NS (removal of glycosylation site by N to S mutation) was used humanized anti-Tim3 antibody variants Tim3-0433 and Tim3-0434 were generated and based upon the amino acid sequence of the VH and VL domains of b) anti-Tim3 antibody Tim3_0028 humanized anti-Tim3 antibody variants Tim3-0438 and Tim3-0443 were generated.

The humanized amino acid sequences for heavy and light chain variable regions of were backtranslated in to DNA and the resulting cNDA were synthesized (GenArt) and then cloned into heavy chain expression vectors as fusion proteins with human IgG1 backbones/human CH1-Hinge-CH2-CH3 with LALA and PG mutations (Leucine 234 to Alanine, Leucine 235 to Alanine, Proline 329 to Glycine) abrogating effector functions or into light chain expression vectors as fusion proteins to human C-kappa. LC and HC Plasmids were then cotransfected into HEK293 and purified after 7 days from supernatants by standard methods for antibody purification. The resulting humanized Tim3-antibodies are named as follows:

TABLE 4

VH and VL sequences of humanized antibodies

| | VH/SEQ ID NO: | VL/SEQ ID NO: |
|---|---|---|
| Humanized antibodies of Tim3__0016 variant (0018) | | |
| Tim3-0433 | SEQ ID NO: 13 | SEQ ID NO: 14 |
| Tim3-0434 | SEQ ID NO: 15 | SEQ ID NO: 16 |
| Humanized antibodies of Tim3__0028 | | |
| Tim3-0438 | SEQ ID NO: 25 | SEQ ID NO: 26 |
| Tim3-0443 | SEQ ID NO: 27 | SEQ ID NO: 28 |

TABLE 5

HVR sequences of humanized antibodies

| | HVR-H1, HVR-H2, and HVR-H3/SEQ ID NOs: | HVR-L1, HVR-L2, and HVR-L3 t/SEQ ID NOs: |
|---|---|---|
| Humanized antibodies of Tim3__0016 variant (0018) | | |
| Tim3-0433 | SEQ ID NOs: 1, 2 and 3 | SEQ ID NOs: 12, 5 and 6 |
| Tim3-0434 | SEQ ID NOs: 1, 2 and 3 | SEQ ID NOs: 12, 5 and 6 |
| Humanized antibodies of Tim3__0028 | | |
| Tim3-0438 | SEQ ID NOs: 17, 18 and 19 | SEQ ID NOs: 20, 21 and 22 |
| Tim3-0443 | SEQ ID NOs: 17, 18 and 19 | SEQ ID NOs: 20, 21 and 22 |

Example 3: Effect of Human Anti-TIM-3 Antibodies on Cytokine Production in a Mixed Lymphocyte Reaction (MLR)

A mixed lymphocyte reaction was used to demonstrate the effect of blocking the TIM-3 pathway to lymphocyte effector cells. T cells in the assay were tested for activation and IFN-gamma secretion in the presence or absence of an anti-TIM-3 mAbs.

Human Lymphocytes were isolated from peripheral blood of healthy donor by density gradient centrifugation using Leukosep (Greiner Bio One, 227 288). Briefly, heparinized blood was diluted with the three fold volume of PBS and 25 ml aliquots of the diluted blood were layered in 50 ml Leukosep tubes. After centrifugation at 800×g for 15 min at room temperature (w/o break) the lymphocyte containing fractions were harvested, washed in PBS and used directly in functional assay or resuspended in freezing medium (10% DMSO, 90% FCS) at 1.0E+07 cells/ml and stored in liquid nitrogen. 1:1 target/responder cell ratio was used in MLR assay (i.e. each MLR culture contained—2.0E+05 PBMCs from each donor in a total volume of 200 µl. Anti-TIM3 monoclonal antibodies Tim3_0016, Tim3_0016 variant (Tim3_0018), Tim3_0021, Tim3_0022, Tim3_0026, Tim3_0028, Tim3_0030, Tim3_0033, Tim3_0038 and F38-2E2 (BioLegend), were added to each culture at different antibody concentrations. Either no antibody or an isotype control antibody was used as a negative control and rec hu IL-2 (20 EU/ml) was used as positive control. The cells were cultured for 6 days at 37° C. After day 6 100 µl of medium was taken from each culture for cytokine measurement. The levels of IFN-gamma were measured using OptEIA ELISA kit (BD Biosciences).

The results are shown in Table 6 (IFN-g secretion/release). The anti-TIM-3 monoclonal antibodies promoted T cell activation and IFN-gamma secretion in concentration dependent manner. The anti-TIM3 antibodies Tim3_0021, Tim3_0022, Tim3_0028, and Tim3_0038 reduce release of the inflammatory cytokine IFN-gamma) more than the F38-2E2 antibody. Tim3_0016, Tim3_0016 variant (Tim3_0018), Tim3_0033 and Tim3_0038 showed a similar release when compared the F38-2E2 antibody. In contrast, cultures containing the isotype control antibody did not show an increase in IFN-gamma secretion.

TABLE 6b $EC_{50}$ of anti-Tim3 antibody induced (IFN-g secretion/release)

| Antibody | $EC_{50}$ [nM] with donors D2 + D3 | $EC_{50}$ [nM] with donors D1 + D5 |
|---|---|---|
| chi_Tim3_018 | 3.1 | 4.2 |
| Tim3-433 | 3.0 | 2.4 |
| Tim3-434 | 1.7 | 2.6 |
| chi_Tim3_028 | 2.9 | 6.4 |
| Tim3-438 | 1.9 | 2.7 |
| Tim3-443 | 3.0 | 4.7 |

PD1 Antibodies

Example 4: Generation of Anti-PD-1 Antibodies

Immunization of Mice

NMRI mice were immunized genetically, using a plasmid expression vector coding for full-length human PD-1 by intradermal application of 100 ug vector DNA (plasmid15300_hPD1-fl), followed by Electroporation (2 square pulses of 1000 V/cm, duration 0.1 ms, interval 0.125 s; followed by 4 square pulses of 287.5 V/cm, duration 10 ms, interval 0.125 s. Mice received either 6 consecutive immunizations at days 0, 14, 28, 42, 56, 70, and 84. Blood was taken at days 36, 78 and 92 and serum prepared, which was used for titer determination by ELISA (see below). Animals with highest titers were selected for boosting at day 96, by intravenous injection of 50 ug of recombinant human PD1 human Fc chimera, and monoclonal antibodies were isolated by hybridoma technology, by fusion of splenocytes to myeloma cell line 3 days after boost.

Determination of Serum Titers (ELISA)

Human recombinant PD1 human Fc chimera was immobilized on a 96-well NUNC Maxisorp plate at 0.3 ug/ml, 100 ul/well, in PBS, followed by: blocking of the plate with 2% Crotein C in PBS, 200 ul/well; application of serial dilutions of antisera, in duplicates, in 0.5% Crotein C in PBS, 100 ul/well; detection with HRP-conjugated goat anti-mouse

TABLE 6a

Percentage of anti-Tim3 antibody induced IFNgamma release in comparison to rec hu IL-2 (20 EU/ml) ( =100%) as positive control and no antibody as negative control

| Compound concentration | MLR + IL-2 20 U/ml | Isotype IgG2a | F38-2E2 | Tim3 0016 | Tim3 0018 | Tim3 0021 | Tim3 0022 | Tim3 0026 | Tim3 0028 | Tim3 0030 | Tim3 0033 | Tim3 0038 | Isotype hIgG1 |
|---|---|---|---|---|---|---|---|---|---|---|---|---|---|
| 40 µg/ml |  | 2 | 36 | 33 | 36 | 112 | 58 | 25 | 40 | 14 | 35 | 51 | 0 |
| 10 µg/ml | 100 | 0 | 26 | 22 | 30 | 108 | 38 | 16 | 38 | 4 | 30 | 38 | 5 |
| 1 µg/ml |  | 0 | 7 | 7 | 12 | 101 | 18 | 18 | 12 | 3 | 0 | 1 | 0 |

In further experiments the EC50 values of the following chimeric and humanized antibodies (generated as described above) in combination with 0.1 µg/ml anti-PD1 mAb were measured: chimeric chi_Tim3_018 antibody and its humanized versions Tim3-433 and Tim3-434, chimeric chi_Tim3_028 antibody and its humanized versions Tim3-438 and Tim3-443 were measured with different lymphocyte donor mixtures (D2 and D3, or D1 and D5, respectively) Results are shown in Table 6b.

antibody (Jackson Immunoresearch/Dianova 115-036-071; 1/16 000). For all steps, plates were incubated for 1 h at 37° C. Between all steps, plates were washed 3 times with 0.05% Tween 20 in PBS. Signal was developed by addition of BM Blue POD Substrate soluble (Roche), 100 ul/well; and stopped by addition of 1 M HCl, 100 ul/well. Absorbance was read out at 450 nm, against 690 nm as reference. Titer was defined as dilution of antisera resulting in half-maximal signal.

Example 5: Characterization Anti-PD1 Antibodies/Binding of Anti-PD1 Antibodies to Human PD1

ELISA for hu PD1

Nunc maxisorp streptavidin coated plates (MicroCoat #11974998001) were coated with 25 µl/well biotinylated PD1-ECD-AviHis and incubated at 4° C. over night. After washing (3×90 µl/well with PBST-buffer) 25 µl anti PD1 samples or reference antibodies (human anti PD1; Roche/mouse anti PD1; Biolegend; cat.:329912) were added and incubated 1 h at RT. After washing (3×90 µl/well with PBST-buffer) 25 µl/well goat-anti-human H+L-POD (JIR, JIR109-036-088)/Sheep-anti-mouse-POD (GE Healthcare; NA9310) was added in 1:2000/1:1000 dilution and incubated at RT for 1 h on shaker. After washing (3×90 µl/well with PBST-buffer) 25 µl/well TMB substrate (Roche Catalogue No. 11835033001) was added and incubated until OD 2-3. Measurement took place at 370/492 nm.

ELISA results are listed as EC50-values [ng/ml] in summary Tables 7 and 8 below.

Cell ELISA for PD1

Adherent CHO-K1 cell line stably transfected with plasmid 15311_hPD1-fl_pUC_Neo coding for full-length human PD1 and selection with G418 (Neomycin restistance marker on plasmid) were seeded at a concentration of 0.01×10E6 cells/well in 384-well flat bottom plates and grown over night.

The next day 25 µl/well PD1 sample or human anti PD1 (Roche)/mouse anti PD1 (Biolegend; cat.:329912) reference antibody were added and incubated for 2 h at 4° C. (to avoid internalization). After washing carefully (1×90 µl/well PBST) cells were fixed by adding 30 µl/well 0.05% Glutaraldehyde (Sigma, Cat. No: G5882, 25%) diluted in 1×PBS-buffer and incubated for 10 min at RT. After washing (3×90 µl/well PBST) 25 µl/well secondary antibody was added for detection: goat-anti-human H+L-POD (JIR, JIR109-036-088)/Sheep-anti-mouse-POD (GE NA9310) followed by 1 h incubation at RT on shaker. After washing (3×90 µl/well PBST) 25 µl/well TMB substrate solution (Roche 11835033001) was added and incubated until OD 1.0-2.0. Plates were measured at 370/492 nm.

Cell ELISA results are listed as "EC50 CHO-PD1"-values [ng/ml] in summary table Table 8 below.

ELISA for Cyno PD1

Nunc maxisorp streptavidin coated plates (MicroCoat #11974998001) were coated with 25 µl/well biotinylated cynoPD1-ECD-Biotin and incubated at 4° C. over night. After washing (3×90 µl/well with PBST-buffer) 25 µl anti PD1 samples or reference antibodies (human anti PD1; Roche) were added and incubated 1 h at RT on shaker. After washing (3×90 µl/well with PBST-buffer) 25 µl/well goat-anti-human H+L-POD (JIR, JIR109-036-088) was added in 1:1000 dilution and incubated at RT for 1 h on shaker. After washing (3×90 µl/well with PBST-buffer) 25 µl/well TMB substrate (Roche, 11835033001) was added and incubated until OD 2-3. Measurement took place at 370/492 nm.

ELISA results are listed as EC50-values [ng/ml] in summary Table 7 and 8 below.

PD Ligand 1 Replacing Assay

Nunc maxisorp streptavidin coated plates (MicroCoat #11974998001) were coated with 25 µl/well biotinylated PD1-ECD-AviHis and incubated at 4° C. over night. After washing (3×90 µl/well with PBST-buffer) 25 µl anti PD1 samples or reference antibodies (mouse anti PD1; Biolegend; cat.:329912) were added and incubated 1 h at RT on shaker. After washing (3×90 µl/well with PBST-buffer) 25 µl/well PD-L1 (Recombinant human B7-H1/PD-L1 Fc Chimera; 156-B7, R&D) was added and incubated 1 h at RT on shaker. After washing (3×90 µl/well with PBST-buffer) 25 µl/well goat-anti-human H+L-POD (JIR, 109-036-088) was added in 1:1000 dilution and incubated at RT for 1 h on shaker. After washing (3×90 µl/well with PBST-buffer) 25 µl/well TMB substrate (Roche, 11835033001) was added and incubated until OD 2-3. Measurement took place at 370/492 nm.

ELISA results are listed as $IC_{50}$-values [ng/ml] in summary Table 7 below.

PD Ligand 2 Replacing Assay

Nunc maxisorp streptavidin coated plates (MicroCoat #11974998001) were coated with 25 µl/well biotinylated PD1-ECD-AviHis and incubated at 4° C. over night. After washing (3×90 µl/well with PBST-buffer) 25 µl anti PD1 samples or reference antibodies (mouse anti huPD1; Roche) were added and incubated 1 h at RT on shaker. After washing (3×90 µl/well with PBST-buffer) 25 µl/well PD-L2 (Recombinant human B7-DC/PD-L2 Fc Chimera; 1224-PL-100, R&D) was added and incubated 1 h at RT on shaker. After washing (3×90 µl/well with PBST-buffer) 25 µl/well goat-anti-human H+L-POD (JIR, 109-036-088) was added in 1:2000 dilution and incubated at RT for 1 h on shaker. After washing (3×90 µl/well with PBST-buffer) 25 µl/well TMB substrate (Roche, 11835033001) was added and incubated until OD 2-3. Measurement took place at 370/492 nm.

ELISA results are listed as $IC_{50}$-values [ng/ml] in summary Table 7 below.

Epitope Mapping ELISA/Binding Competition Assay

Nunc maxisorp plates (Nunc #464718) were coated with 25 µl/well capture antibody (goat anti mouse IgG; JIR; 115-006-071) and incubated for 1 h at RT on shaker. After washing (3×90 µl/well with PBST-buffer) plates were blocked for 1 h with 2% BSA containing PBS buffer at RT on shaker. After washing (3×90 µl/well with PBST-buffer) 25 µl mouse anti PD1 samples were added and incubated 1 h at RT on shaker. After washing (3×90 µl/well with PBST-buffer) capture antibody was blocked by 30 µl/well mouse IgG (JIR; 015-000-003) for 1 h at RT on shaker. At the same time biotinylated PD1-ECD-AviHis was preincubated with second sample antibody for 1 h at RT on shaker. After washing assay plate (3×90 µl/well with PBST-buffer) the PD1 antibody mix was transferred to assay plate and incubated at RT for 1 h on shaker. After washing (3×90 µl/well with PBST-buffer) 25 µl/well streptavidin POD (Roche, #11089153001) was added in 1:4000 dilution and incubated at RT for 1 h on shaker. After washing (3×90 µl/well with PBST-buffer) 25 µl/well TMB substrate (Roche, #11089153001) was added and incubated until OD 1.5-2.5. Measurement took place at 370/492 nm. Epitope groups were defined by hierarchical clustering against reference antibodies.

TABLE 7

Binding, PD-L1 inhibition and epitope region groups of exemplary antibodies (ELISA)

| Antibody | ELISA huPD1 $EC_{50}$ [ng/ml] | ELISA cyPD1 $EC_{50}$ [ng/ml] | ELISA PD-L1 inhibition $IC_{50}$ [ng/ml] | ELISA PD-L2 inhibition $IC_{50}$ [ng/ml] | Epitope region group By competion assay) |
|---|---|---|---|---|---|
| PD1- 0050 | 17.9 | 9.8 | 128 | 34 | 1 |
| PD1- 0069 | 45.7 | 22.7 | 225 | 89 | 6 |
| PD1- 0073 | 15.1 | 8.3 | 124 | 65 | 5 |

TABLE 7-continued

Binding, PD-L1 inhibition and epitope region groups of exemplary antibodies (ELISA)

| Antibody | ELISA huPD1 $EC_{50}$ [ng/ml] | ELISA cyPD1 $EC_{50}$ [ng/ml] | ELISA PD-L1 inhibition $IC_{50}$ [ng/ml] | ELISA PD-L2 inhibition $IC_{50}$ [ng/ml] | Epitope region group By competion assay) |
|---|---|---|---|---|---|
| PD1-0078 | 26.3 | 22.4 | x | 86 | 2 |
| PD1-0098 | 50.8 | 54.6 | 174 | 45 | 5 |
| PD1-0102 | 34.2 | 52.7 | >35.5 µg/ml | 140 | 4 |
| PD1-0103 | 33.7 | 36.9 | 182 | 51 | 5 |

TABLE 8

Biochemial- and Cell-binding of humanized PD1 antibodies derived from parental mouse antibody PD1-0103 (ELISA).

| antibody | ELISA huPD1 $EC_{50}$ [ng/ml] | ELISA cyPD1 $EC_{50}$ [ng/ml] | ELISA CHO-PD1 $EC_{50}$ [ng/ml] |
|---|---|---|---|
| PD1-103-0312 | 11 | 8.3 | 10.1 |
| PD1-103-0313 | 15 | 11 | 10.8 |
| PD1-103-0314 | 11 | 8.3 | 7.7 |
| PD1-103-0315 | 10 | 7.9 | 7.3 |

Biacore Characterization of the Humanized Anti-PD-1 Antibodies

A surface plasmon resonance (SPR) based assay has been used to determine the kinetic parameters of the binding between several murine PD1 binders as well as commercial human PD1 binding references. Therefore, an anti-human IgG was immobilized by amine coupling to the surface of a (Biacore) CM5 sensor chip. The samples were then captured and hu PD1-ECD was bound to them. The sensor chip surface was regenerated after each analysis cycle. The equilibrium constant and kinetic rate constants were finally gained by fitting the data to a 1:1 langmuir interaction model.

About 2000 response units (RU) of 20 µg/ml anti-human IgG (GE Healthcare #BR-1008-39) were coupled onto the flow cells 1 and 2 (alternatively: 3 and 4) of a CM5 sensor chip in a Biacore T200 at pH 5.0 by using an amine coupling kit supplied by GE Healthcare.

The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

The samples were injected for 20 seconds with a concentration of 10 nM and bound to the second flow cell. Then a complete set of human PD1-ECD concentrations (144 nM, 48 nM, 16 nM, 5.33 nM, 1.78 nM, 0.59 nM, 0.20 nM and 0 nM) was injected over each sample for 120 s followed by a dissociation time of 30/300 s and two 20 s regeneration steps with 3 M $MgCl_2$, of which the last one contained an "extra wash after injection" with running buffer.

Finally the double referenced data was fitted to a 1:1 langmuir interaction model with the Biacore T200 Evaluation Software. Resulting $K_D$, $k_a$ and $k_d$ values are shown in Table 9.

TABLE 9

Kinetic rate constants and equilibrium constant for chimeric PD1-0103 and humanized PD1-Abs determined by Biacore.

| Ligand | $k_a$ [$M^{-1}s^{-1}$] | $k_d$ [$s^{-1}$] | $K_D$ [nM] |
|---|---|---|---|
| chimeric PD1-0103 | 3.86E+05 | 3.07E−04 | 0.8 |
| PD1-0103-0312 | 1.95E+05 | 3.45E−04 | 1.8 |
| PD1-0103-0313 | 1.60E+05 | 3.67E−04 | 2.3 |
| PD1-0103-0314 | 1.87E+05 | 2.79E−04 | 1.5 |
| PD1-0103-0315 | 1.89E+05 | 2.91E−04 | 1.5 |

As shown in Table 9, all the humanized versions of chimeric PD1-0103 (generation see Example 6) display kinetic properties similar to the parental antibody (chimeric PD1-0103).

Kinetics

A CM5 sensor series S was mounted into the Biacore 4000 System and the detection spots were hydrodynamically addressed according to the manufacturer's instructions.

The polyclonal rabbit IgG antibody <IgGFCγM>R (Jackson ImmunoResearch Laboratories Inc.) was immobilized at 10 000 Ru on the detection spots 1 and 5 in the flow cells 1, 2, 3 and 4. Coupling was done via EDC/NHS chemistry according to the manufacturer's instructions. The remaining spots in the flow cells served as a reference. The sample buffer was the system buffer supplemented with 1 mg/ml carboxymethyldextrane.

In one embodiment the assay was driven at 25° C. In another embodiment the assay was driven at 37° C. 50 nM of each murine monoclonal antibody was captured on the sensor surface by a 1 min injection at 10 µl/min. Subsequently the respective antigens were injected in a concentration series of 100 nM, 2×33 nM, 11 nM, 4 nM, 1 nM and system buffer 0 nM at 30 µl/min for 4 min association phase time. The dissociation was monitored for another 4 min. The capture system was regenerated using a 3 min injection of 10 mM glycine pH 1.5 at 30 µl/min. Relevant kinetic data was calculated using the Biacore evaluation software according to the manufacturer's instructions.

Epitope Mapping

A Biacore 4000 instrument was mounted with a Biacore CAP sensor and was prepared like recommended by the manufacturer. The instrument buffer was HBS-ET (10 mM HEPES pH 7.4, 150 mM NaCl, 3 mM EDTA, 0.005% w/v Tween 20). The instrument was running at 25° C.

All samples were diluted in system buffer. A 35 kDa biotinylated antigen PD1-ECD-AviHis was captured at 200 RU on the CAP sensor surface by a 1 min injection at 30 µl/min in the flow cells 1, 2, 3 and 4 in the spots 1 and 5. Spots 2, 3 and 4 served as a reference. In another embodiment, a 35 kDa biotinylated antigen PD1-ECD-AviHis was captured at 200 RU on the CAP sensor in the same manner.

Subsequently a primary antibody was injected at 100 nM for 3 min at 30 µl/min followed by the injection of a secondary antibody at 100 nM for 3 min at 30 µl/min. The primary antibody was injected until full saturation of the surface presented antigen. At the end of the primary and secondary antibody injection phases report points "Binding Late" (BL) were set to monitor the binding response of the respective antibodies. The Molar Ratio, a quotient between the secondary antibody binding response "BL2" and the primary antibody response "BL1" was calculated. The Molar Ratio was used as an indicator of the antigen accessibility of the secondary antibody, when the antigen was already complexed by the primary antibody.

The complexes were completely removed from the sensor surface by an injection for 2 min at 30 µl/min 2M guanidine-HCL 250 mM NaOH regeneration buffer as recommended by the manufacturer, followed by a 1 min injection at 30 µl/min of system buffer.

Example 6: Effect of Different Anti-PD-1 Antibodies on Cytokine Production in a Mixed Lymphocyte Reaction (MLR)

3A) The Mixed Lymphocyte Reaction (MLR) is a immune cell assay which measures the activation of lymphocytes from one individual (donor X) to lymphocytes from another individual (donor Y). A mixed lymphocyte reaction was used to demonstrate the effect of blocking the PD1 pathway to lymphocyte effector cells. T cells in the assay were tested for activation and theier IFN-gamma secretion in the presence or absence of an anti-PD1 mAbs.

To perform an allogeneic MLR, peripheral blood mononuclear cells (PBMCs) from at least four healthy donors of unknown HLA type were isolated by density gradient centrifugation using Leukosep (Greiner Bio One, 227 288). Briefly, heparinized blood samples were diluted with the three fold volume of PBS and 25 ml aliquots of the diluted blood were layered in 50 ml Leukosep tubes. After centrifugation at 800×g for 15 min at room temperature (w/o break) the lymphocyte containing fractions were harvested, washed in PBS and used directly in functional assay or resuspended in freezing medium (10% DMSO, 90% FCS) at 1.0E+07 cells/ml and stored in liquid nitrogen. Individual 2-way MLR reactions were set up by mixing PBMCs from two different donors at a 1:1 stimulator/responder cell ratio and co-cultures were done at least in duplicate in flat-bottomed 96-well plates for 6 days at 37° C., 5% CO2, in the presence or w/o of a different concentration range of purified anti-PD1 monoclonal antibodies PD1-0050, PD1-0069, PD1-0073, PD1-0078, PD1-0098, PD1-0102, PD1-0103. As reference anti-PD1 antibodies, antibodies comprising the VH and VL domains of either nivolumab (also known as MDX-5C4 or MDX-1106) or pembrolizumab (also known as MK-3475 or Org 1.09A) were synthesized and cloned with backbones of human IgG1 (with mutations L234A, L235A and P329G (EU index of Kabat)). Either no antibody or an isotype control antibody was used as a negative control and rec hu IL-2 (20 EU/ml) was used as positive control. After day 6 100 µl of medium was taken from each culture for cytokine measurement. The levels of IFN-gamma were measured using OptEIA ELISA kit (BD Biosciences).

The results are shown in Table 10 (IFN-g secretion/release). The anti-PD1 monoclonal antibodies promoted T cell activation and IFN-gamma secretion in concentration dependent manner. The value of % increase of IFNg secretion was calculated in relation to IFN-g production of MLR w/o adding of any blocking mAbs (basal allogeneic stimulation induced IFNg value as E-c) and MLR with adding of 20 EU/ml rec hu IL-2 (positive control=100% IFNg value as E+c) and was calculated according to formula: Rel. Stimulation [%]=((Esampel−E−c)/(E+c−E−c)*100

TABLE 10

Percentage of of IFN gamma secretion after allogenic stimulation and treatment with anti-PD-1 antibody in comparison to effect of recombinant human IL-2 treatment (20 EU/ml) (=100% increase) as positive control

| | Concentration (µg/ml) | 1:12 | 1:120 | 1:1200 | Effect in MLR |
|---|---|---|---|---|---|
| PD1-0050 | 44 | 136 | 96 | 33 | +++ |
| PD1-0069 | 60 | 76 | 71 | 55 | +++ |
| PD1-0073 | 43 | 103 | 63 | 38 | ++ |
| PD1-0078 | 64 | 99 | 72 | 21 | ++ |

Several PD1 blocking antibodies PD1-0050, PD1-0069, PD1-0073, PD1-0078, PD1-0098, PD1-0102, PD1-0103 demonstrated strong immune modulating activity by enhancing secretion of interferon gamma (IFN-g) (data not shown for all antibodies).

Figure 1:
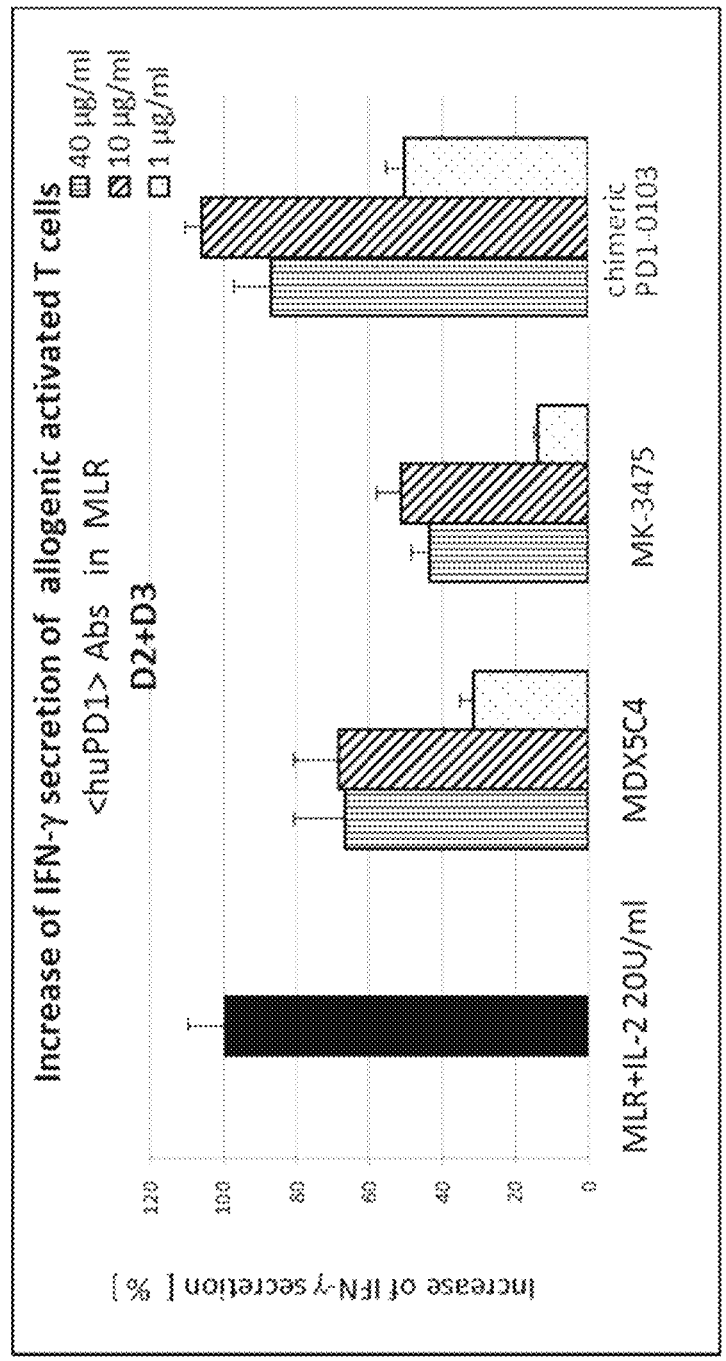
FIG. 1: Blockade of PD1 with chimeric PD1-0103 strongly enhances IFN-gamma secretion by allogenic stimulated primary human T cells.

3B) In a further experiment chimeric PD1-0103 (human IgG1 isotype with mutations L234A, L235A and P329G (EU index of Kabat)) was evaluated. Blockade of PD1 with chimeric PD1-0103 strongly enhances IFN-gamma secretion by allogenic stimulated primary human T cells. Chimeric PD1-0103 is more potent than reference anti-PD1 antibodies (see FIG. 1).

For comparison the reference anti-PD1 antibodies comprising the VH and VL domains of either nivolumab (also known as MDX5C4 or MDX-1106) and pembrolizumab (also known as MK-3475 or Org 1.09A) were synthesized and cloned with backbones of human IgG1 (with mutations L234A, L235A and P329G (EU index of Kabat)) were used.

3C) In additional experiments the immune modulating activity of the humanized variants of anti-PD-1 antibody PD1-0103 (humanized antibodies PD1-0103-0312, PD1-0103-0314, in FIGS. 2 and 3, see also Example 9 below) the a) IFN release (secretion) b) TNF-alpha release (secretion) was evaluated in MLR as described above. The effect of the chimeric PD1-0103 antibody and its humanized versions were compared to the reference anti-PD1 antibodies comprising the VH and VL domains of either nivolumab (also known as MDX5C4 or MDX-1106) and pembrolizumab (also known as MK-3475 or Org 1.09A) with backbones of human IgG1 (with mutations L234A, L235A and P329G (EU index of Kabat)). After 6 days of MLR culture 50 µl of supernatant was taken and multiple cytokines were measured in a single culture using Bio-Plex Pro™ Human Cytokine Th1/Th2 Assay (Bio-Rad Laboratories Inc.). (data not shown for all cytokines).

Figure 2:
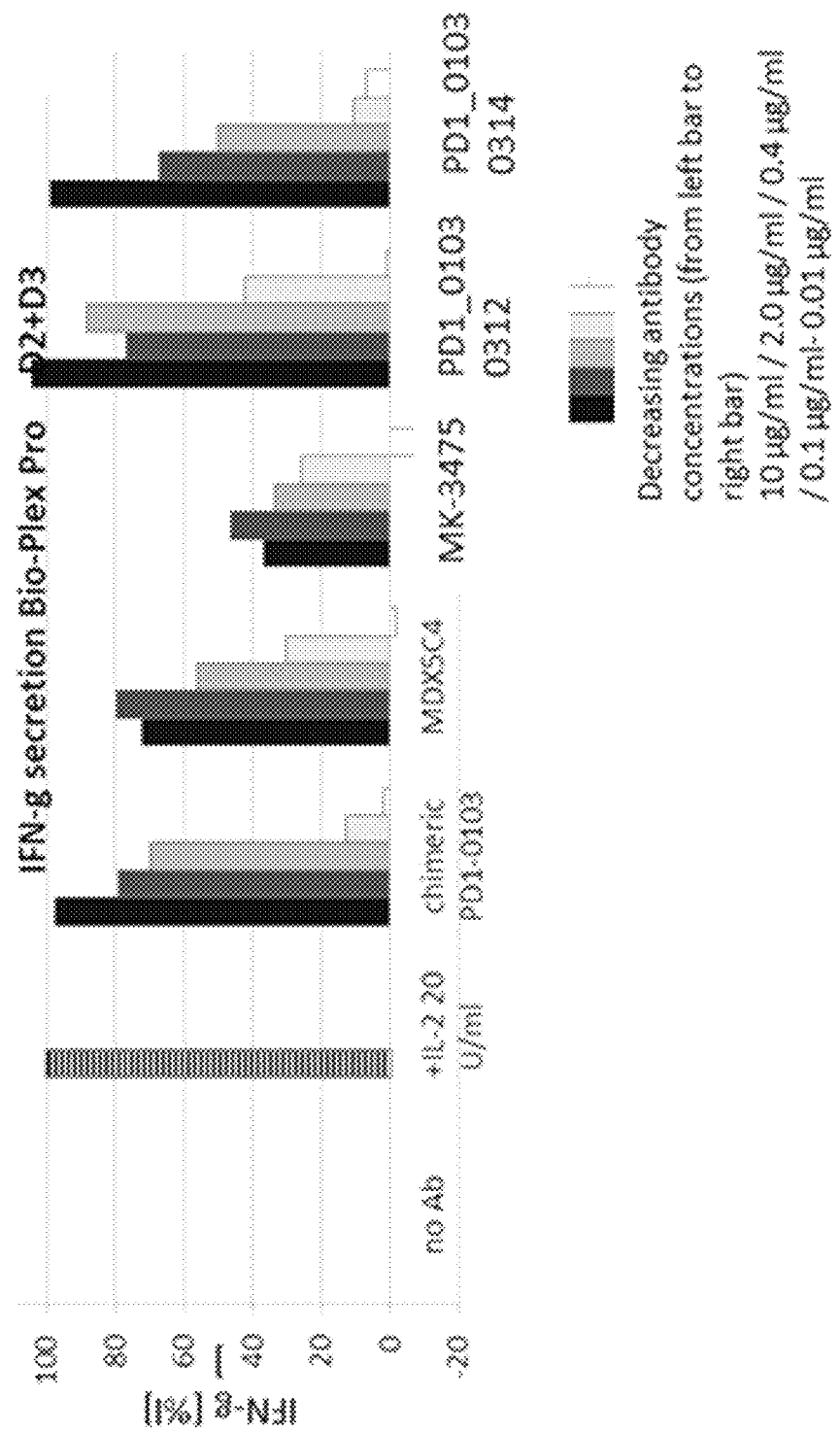
FIG. 2: Blockade of PD1 with chimeric PD1-0103 strongly increases interferon-gamma (IFN-γ) secretion by allogenic stimulated primary human T cells.
Figure 3:
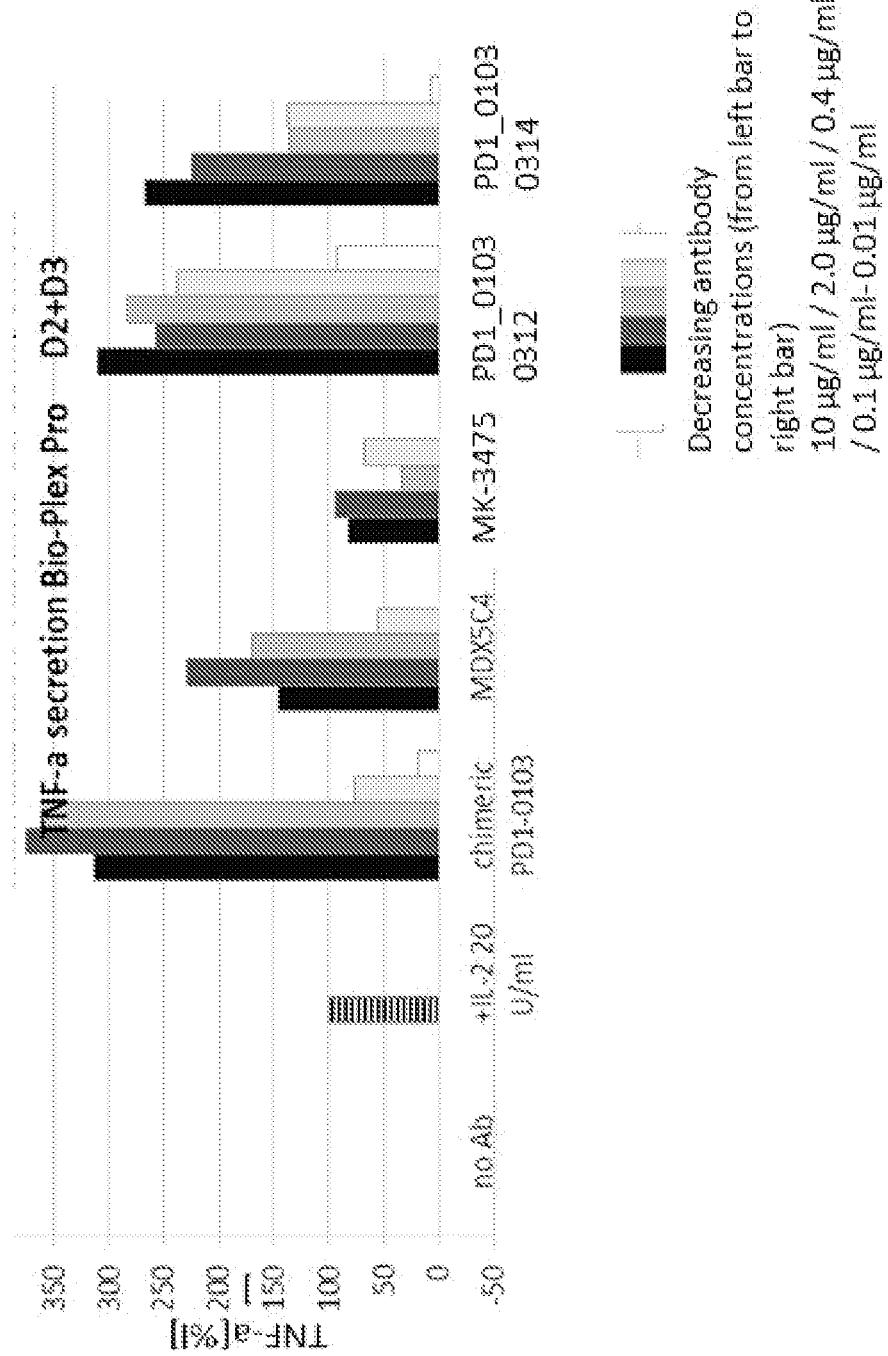
FIG. 3: Blockade of PD1 with chimeric PD1-0103 strongly increases tumor necrosis factor alpha (TNF) secretion by allogenic stimulated primary human T cells.

The chimeric PD1-0103 antibody and its humanized versions (PD1-0103_0312 and PD1-0103_0314) were more potent compared to the reference anti-PD1 antibodies in enhancing the T cell activation and IFN-gamma secretion (see FIG. 2).

Furthermore, the chimeric PD1-0103 antibody and its humanization variants increase tumor necrosis factor alpha (TNF alpha) (see FIG. 3) and IL-12 (data not shown) secretion by antigen presenting cells and encance capacity of monocytes/macrophages or antigen presenting cells to stimulate a T cell.

Example 7: Effect of Anti-PD-1 Blockade on Cytotoxic Granzyme B Release and IFN-γ Secretion by Human CD4 T Cells Cocultured with Allogeneic Mature Dendritic Cells To further investigate the effect of anti-PD-1 treatment in an allogeneic setting we developed an assay in which freshly purified CD4 T cells are cocultured for 5 days in presence of monocyte-derived allogeneic mature dendritic cells (mDCs). Monocytes were isolated from fresh PBMCs one week before through plastic adherence followed by the removal of the non-adherent cells. We then generated immature DCs from the monocytes by culturing them for 5 days in media containing GM-CSF (50 ng/ml) and IL-4 (100 ng/ml). To induce iDCs maturation, we added TNF-α, IL-1β and IL-6 (50 ng/ml each) to the culturing media for 2 additional days. We then assessed DCs maturation by measuring their surface expression of Major Histocompatibility Complex Class II (MHCII), CD80, CD83 and CD86 thorugh flow cytometry (LSRFortessa, BD Biosciences).

On the day of the minimal mixed lymphocyte reaction (mMLR), CD4 T cells were enriched via a microbead kit (Miltenyi Biotec) from $10^8$ PBMCs obtained from an unrelated donor. Prior culture, CD4 T cells were labeled with 5 μM of Carboxy-Fluorescein-Succinimidyl Esther (CFSE). $10^5$ CD4 T cells were then plated in a 96 well plate together with mature allo-DCs (5:1) in presence or absence of blocking anti-PD1 antibody (either PD1-0103, chimeric PD1-0103, or humanized antibodies PD1-0103-0312, PD1-0103-0313, PD1-0103-0314, PD1-0103-0315, abbreviated as 0312, 0313, 0314, 0315 in FIGS. 4A and 4B), at the concentration of 10 μg/ml if not differentely indicated in the figures.

Five days later we collected the cell-culture supernatants, used later to measure the IFN-γ levels by ELISA (R&D systems), and left the cells at 37 C degrees for additional 5 hours in presence of Golgi Plug (Brefeldin A) and Golgi Stop (Monensin). The cells were then washed, stained on the surface with anti-human CD4 antibody and the Live/Dead fixable dye Aqua (Invitrogen) before being fixed/permeabilized with Fix/Perm Buffer (BD Bioscience). We performed intracellular staining for Granzyme B (BD Bioscience), IFN-γ and IL-2 (both from eBioscience).

Figure 4A:
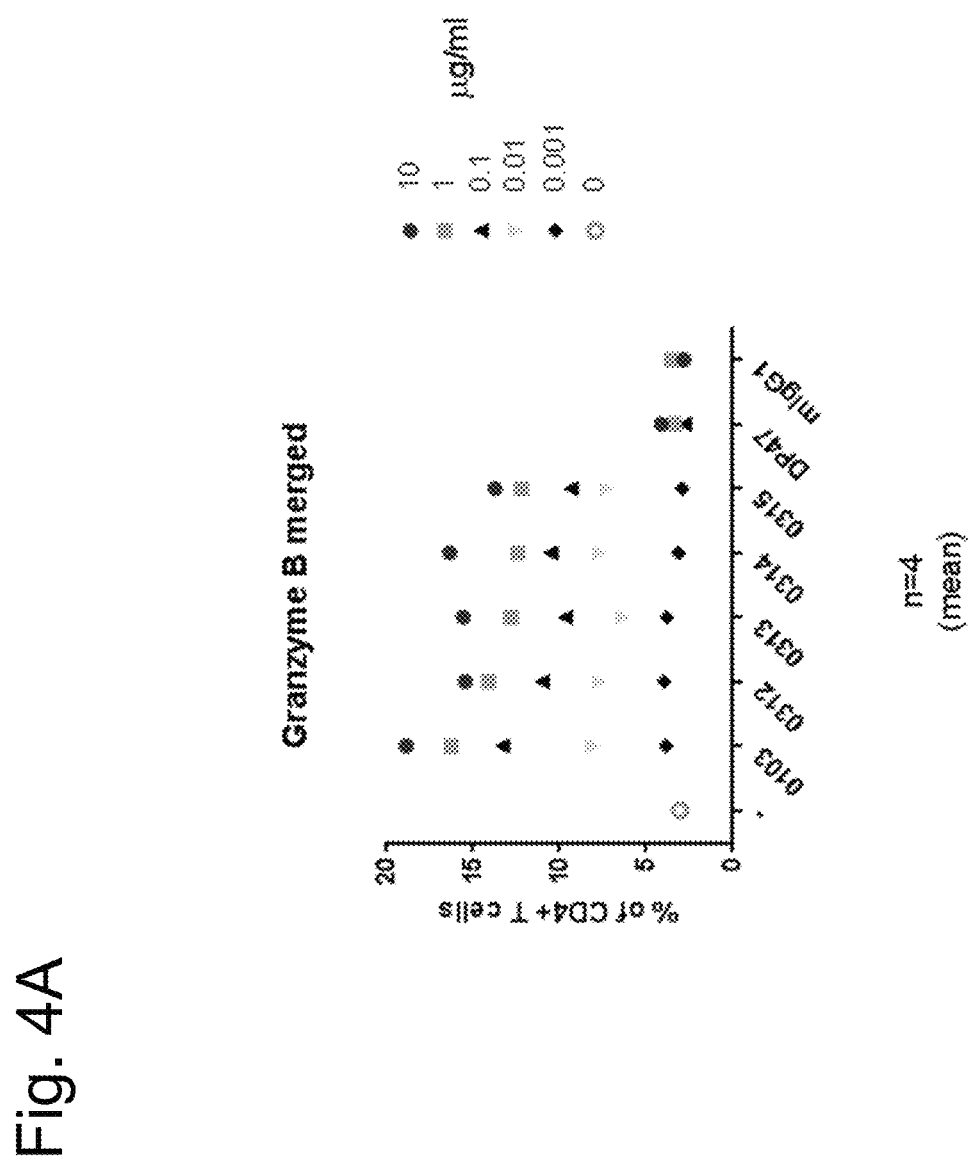
FIGS. 4A and 4B.
Figure 4B:
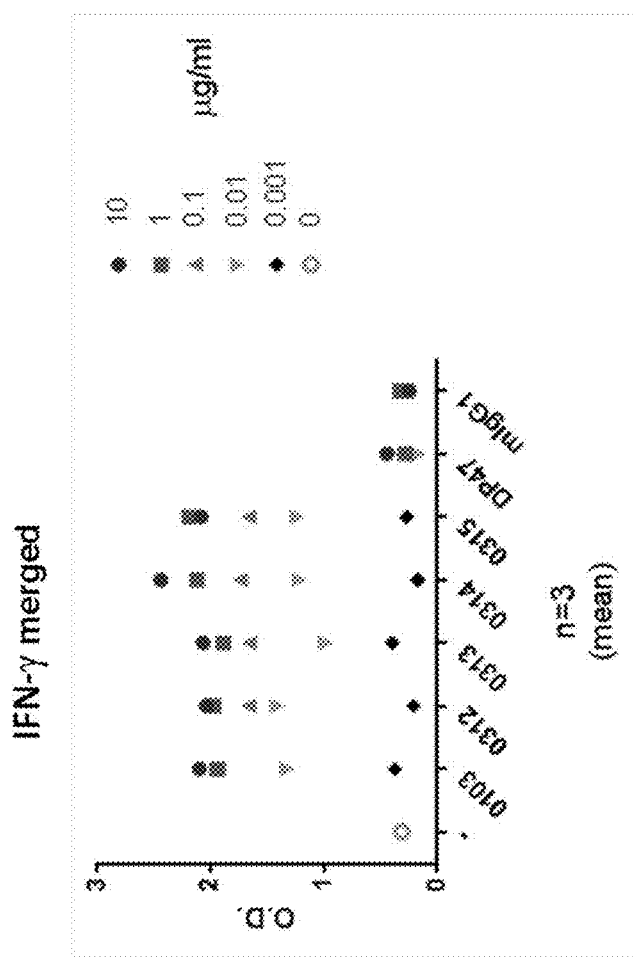

We also tested different concentrations of the humanized variants PD1-0103 (humanized antibodies PD1-0103-0312, PD1-0103-0313, PD1-0103-0314, PD1-0103-0315, abbreviated as 0312, 0313, 0314, 0315 in the figures, see also Example 9 below) and found them to be equally good in enhancing granzyme B and interferon gamma. DP47 is a non binding human IgG with a LALA mutation in the Fc portion to avoid recognition by FcγR and was used as negative control. Results are shown in FIGS. 4A and 4B.

Example 8: Chimeric Antibodies Derivatives

Chimeric PD1 antibodies were generated by amplifying the variable heavy and light chain regions of the anti-PD1 mouse antibodies PD1-0098, PD1-0103 via PCR and cloning them into heavy chain expression vectors as fusion proteins with human IgG1 backbones/human CH1-Hinge-CH2-CH3 with mutations L234A, L235A and P329G (EU index of Kabat)) (Leucine 234 to Alanine, Leucine 235 to Alanine, Proline 329 to Glycine) abrogating effector functions and light chain expression vectors as fusion proteins to human C-kappa. LC and HC Plasmids were then cotransfected into HEK293 and purified after 7 days from supertnatants by standard methods for antibody purification. The chimeric PD1-antibodies were renamed chimeric chiPD1-0098 (chiPD1-0098) and chimeric PD1-0103 (chiPD1-0103). For comparison the reference anti-PD1 antibodies comprising the VH and VL domains of either nivolumab (also known as MDX-5C4 or MDX-1106) and pembrolizumab (also known as MK-3475 or Org 1.09A) were synthesized and cloned with backbones of human IgG1 (with mutations L234A, L235A and P329G (EU index of Kabat)) were used.

Example 9: Generation, Expression and Purification of Humanized Variants of Anti-PD1 Antibody PD-0103 (huMab PD-0103) and Characterization Humanization of the VH and VL Domains of Murine Anti-PD1 Antibody 0103

Based upon the amino acid sequence of the murine VH and VL domains of murine anti-PD1 antibody PD1-0103 (SEQ ID NO: 43 and 44), humanized anti-anti-PD1 antibody variants were generated.

The humanized VH-variant is based on the human germline IMGT_hVH_3_23 in combination with the human J-element germline IGHJ5-01 with several mutations. (resulting in SEQ ID NO: 45).

The humanized variants of VL are based on the human germlines IMGT_hVK_4_1, IMGT_hVK_2_30, IMGT_hVK_3_11 and IMGT_hVK_1_39 in combination with the human J-element germline IGKJ1-01. Different muations resulted in humanized variants of SEQ ID NO: 46 to SEQ ID NO: 49.

The humanized amino acid sequences for heavy and light chain variable regions of PD1-0103 were backtranslated in to DNA and the resulting cNDA were synthesized (GenArt) and then cloned into heavy chain expression vectors as fusion proteins with human IgG1 backbones/human CH1-Hinge-CH2-CH3 with LALA and PG mutations (Leucine 234 to Alanine, Leucine 235 to Alanine, Proline 329 to Glycine) abrogating effector functions or into light chain expression vectors as fusion proteins to human C-kappa. LC and HC Plasmids were then cotransfected into HEK293 and purified after 7 days from supernatants by standard methods for antibody purification. The resulting humanized PD1-antibodies named as follows:

TABLE 11

VH and VL sequences of humanized variant antibodies of PD1-0103

| Humanized antibodies of PD1-0103 | humanized variant of VH/SEQ ID NO: | humanized variant of VL/SEQ ID NO: |
| --- | --- | --- |
| PD1-0103-0312 | SEQ ID NO: 45 | SEQ ID NO: 46 |
| PD1-0103-0313 | SEQ ID NO: 45 | SEQ ID NO: 47 |
| PD1-0103-0314 | SEQ ID NO: 45 | SEQ ID NO: 48 |
| PD1-0103-0315 | SEQ ID NO: 45 | SEQ ID NO: 49 |

TABLE 12

HVR sequences of humanized variant antibodies of PD1-0103

| Humanized antibodies of PD1-0103 | HVR-H1, HVR-H2, and HVR-H3 of humanized variant/SEQ ID NO: | HVR-L1, HVR-L2, and HVR-L3 of humanized variant/SEQ ID NO: |
| --- | --- | --- |
| PD-0103-0312 | SEQ ID NOs: 37, 38 and 39 | SEQ ID NOs: 40, 41 and 42 |
| PD-0103-0313 | SEQ ID NOs: 37, 38 and 39 | SEQ ID NOs: 40, 41 and 42 |
| PD-0103-0314 | SEQ ID NOs: 37, 38 and 39 | SEQ ID NOs: 40, 41 and 42 |
| PD-0103-0315 | SEQ ID NOs: 37, 38 and 39 | SEQ ID NOs: 40, 41 and 42 |

Humanized PD1-0103 antibody variants and parental chimeric PD1-0103 were characterized as described above. Results are shown in Table 13.

TABLE 13

Summary of results for humanized PD1-0103 antibody variants and parental chimeric PD1-0103

| Assay | chimeric PD1-0103 | PD-0103-0312 | PD-0103-0313 | PD-0103-0314 | PD-0103-0315 |
|---|---|---|---|---|---|
| Affinity $K_{D\ 37°C.}$ [nM] *) | 2.0/0.8 | 1.5/1.8 | 1.9/2.3 | 1.6/1.5 | 1.7/1.5 |
| ELISA $EC_{50}$ [nM] | 0.2 | 0.1 | 0.07 | 0.07 | 0.06 |
| CHO-PD1 $EC_{50}$ | + | + | + | + | + |
| $IC_{50}$ PD-L1, 2 [nM] | 1.35 | tbd | tbd | tbd | tbd |
| Mixed Lymphocyte Reaction assay | +++ | +++ | +++ | ++++ | ++ |
| cynomolgus cross-reactivity ($EC_{50}$ [nm]) | + | 0.08 | 0.06 | 0.05 | 0.04 |

Example 10: Neutralizing Potency of PD-1 Antibodies

To test the neutralizing potency of inhouse generated PD-1 antibodies in mimicking a restoration of a suppressed T cell response in vitro a commercially available PD1/PD-L1 reporter assay (Promega) was used. This system consists of PD1+ NFAT Jurkat cells and a PD-L1+ CHO counterpart, which also gives the activation signal. In principle, the reporter system is based on three steps: (1) TCR-mediated NFAT activation, (2) inhibition of NFAT signal upon activation by the PD-1/PD-L1 axis and (3) recovery of the NFAT signal by PD-1 blocking antibodies.

Material and Methods:
  PD-L1 Medium: PAN Biotech (#P04-03609); FBS (10%) and L-Gln (4 mM)
  Assay Medium: RPMI 1640 (#31870; Invitrogen), 25 mM HEPES, 2 mM L-Gln, FBS (2%)

Figure 5A:
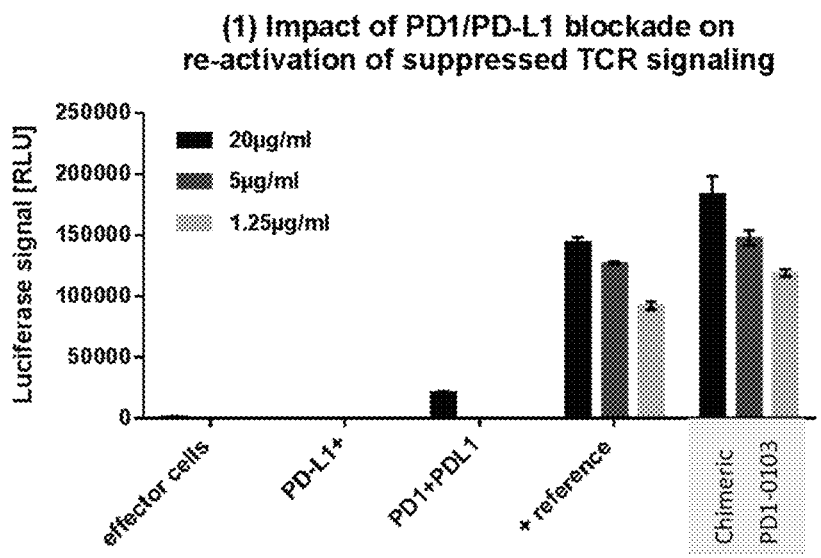
FIGS. 5A and 5B.
Figure 5B:
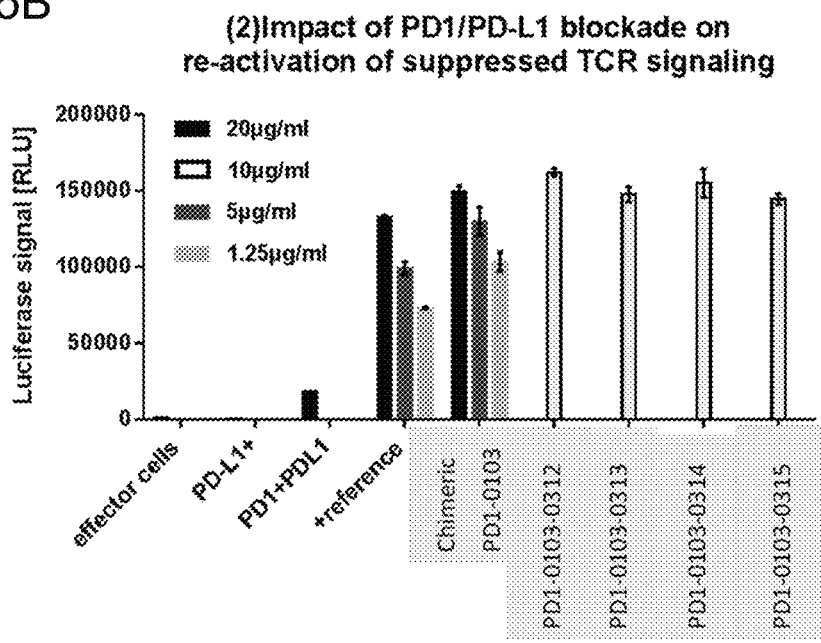

Cells used for this assay (both cell types purchased by Promega):
  PD-L1+ CHO cells (batch no. #139147): 2-3×10⁴ cells/96 well
  PD-1+ NFAT Jurkat cells (batch no. #133024: 3.5×10⁴ cells/well On day 1, PD-L1+ cells were thawed, seeded at the indicated cell concentration in the above mentioned medium and cultured over night at 37° C. and 5% $CO_2$. On the next day, medium was removed and PD-L1+ cells were incubated with the prepared antibodies at indicated concentrations (in Assay Medium). In parallel, PD-1+ NFAT Jurkat cells were thawed and above mentioned cell numbers were transferred to and co-cultured with the PD-L1+ cells. After an incubation of 6 hrs at 37° C. and 5% $CO_2$, Bio-Glo substrate was warmed to room temperature (1-2 hrs prior addition). The cell culture plate was removed from the incubator and adjusted to room temperature (10 min) before 80 µl Bio-Glo solution was added per well, incubated for 5-10 min before the luminescence was measured at a Tecan Infinite reader according to the kit's manufacturer's recommendation. Results can be seen in the FIGS. 5A and 5B where the restoration of a PD-1/PD-L1 mediated suppression of the NFAT signal by different PD-1 antibodies upon TCR stimulation is shown: FIG. 5A: Chimeric PD1_0103 showed a reproducibly superior effect when compared to a reference antibody. As reference an anti-PD1 antibody comprising the VH and VL domains nivolumab (also known as MDX-5C4 or MDX-1106) was synthesized and cloned with backbones of human IgG1 (with mutations L234A, L235A and P329G (EU index of Kabat)). FIG. 5B: The four humanized variants of PD1_0103 demonstrated a similar in vitro potency to the lead antibody and were also slightly superior to the reference antibody.

Bispecific PD1/TIM3 Antibodies

Example 11A

Production and Expression of Multispecific Antibodies which Bind to PD1 and TIM3 with VH/VL Domain Exchange/Replacement (CrossMAb$^{Vh-VL}$) in One Binding Arm and with Single Charged Amino Acid Substitutions in the CH1/CL Interface In an example multispecific antibodies which binds to human PD1 and human TIM3 were generated is described in the general methods section by classical molecular biology techniques and were expressed transiently in 293F of Expi293F cells as described above. The multispecific 1+1 CrossMAb$^{Vh-VL}$ antibodies are described also in WO 2009/080252. The multispecific antibodies were expressed using expression plasmids containing the nucleic acids encoding the amino acid sequences depicted in Table 14a.

TABLE 14a

Amino acid sequences of light chains (LC) and heavy chains (HC), with VH/VL domain exchange/replacement (1 + 1 CrossMAb$^{Vh-V}$)

| 1 + 1 Antibody | HC1 | HC2 | LC1 | LC2 |
|---|---|---|---|---|
| PD1TIM3_0389 | SEQ ID NO: 50 | SEQ ID NO: 51 | SEQ ID NO: 52 | SEQ ID NO: 53 |
| PD1TIM3-0168 | SEQ ID NO: 54 | SEQ ID NO: 55 | SEQ ID NO: 56 | SEQ ID NO: 57 |
| PD1TIM3-0476 | SEQ ID NO: 62 | SEQ ID NO: 63 | SEQ ID NO: 64 | SEQ ID NO: 65 |
| PD1TIM3-0477 | SEQ ID NO: 66 | SEQ ID NO: 67 | SEQ ID NO: 68 | SEQ ID NO: 69 |
| PD1TIM3_0166 | SEQ ID NO: 58 | SEQ ID NO: 59 | SEQ ID NO: 60 | SEQ ID NO: 61 |

For all constructs knobs into holes heterodimerization technology was used with a typical knob (T366W) substitution in the first CH3 domain and the corresponding hole substitutions (T366S, L368A and Y410V) in the second CH3 domain (as well as two additional introduced cysteine residues S354C/Y349'C) (contained in the respective corresponding heavy chain (HC) sequences depicted above).

Example 11B

Production and Expression of Multispecific Antibodies which Bind to PD1 and TIM3 with VH/VL Domain Exchange/Replacement (2+2 CrossMAb$^{Vh-VL}$) in Two Binding Arms and with Single Charged Amino Acid Substitutions in the CH1/CL Interfaces In an example multispecific antibodies which binds to human PD1 and human TIM3 were generated as described in the general methods section by classical molecular biology techniques and were expressed transiently in 293F of Expi293F cells as described above. The multispecific 2+2 CrossMAb$^{VH-VL}$ antibodies are described also in WO 2010/145792. The multispecific antibodies were expressed using expression plasmids containing the nucleic acids encoding the amino acid sequences depicted in Table 14b.

TABLE 14b

Amino acid sequences of light chains (LC) and heavy chains (HC), with VH/VL domain exchange/replacement (2 + 2 CrossMAb$^{Vh-VL}$)

| 2 + 2 Antibody | HC | LC1 | LC2 |
|---|---|---|---|
| PD1TIM3_0358 | SEQ ID NO: 70 | SEQ ID NO: 71 | SEQ ID NO: 72 |
| PD1TIM3_0359 | SEQ ID NO: 73 | SEQ ID NO: 74 | SEQ ID NO: 75 |
| PD1TIM3_0321 | SEQ ID NO: 76 | SEQ ID NO: 77 | SEQ ID NO: 80 | care). The total mass was determined via ESI-MS on a maXis 4G UHR-QTOF MS system (Bruker Daltonik) equipped with a TriVersa NanoMate source (Advion).

Stability of Multispecific Antibodies

In order to assess stability of the antibody constructs, thermal stability as well as aggregation onset temperatures were assessed according to the following procedure. Samples of the indicated antibodies were prepared at a concentration of 1 mg/mL in 20 mM Histidine/Histidine chloride, 140 mM NaCl, pH 6.0, transferred into a 10 μL micro-cuvette array and static light scattering data as well as fluorescence data upon excitation with a 266 nm laser were recorded with an Optim1000 instrument (Avacta Inc.), while the samples were heated at a rate of 0.1° C./min from 25° C. to 90° C.

The aggregation onset temperature ($T_{agg}$) is defined as the temperature at which the scattered light intensity starts to increase. The melting temperature ($T_m$) is defined as the inflection point in a fluorescence intensity vs. wavelength graph. Results are shown in Table 15.

TABLE 15

| | ProtA | | | ProtA + prep SEC | | | | |
|---|---|---|---|---|---|---|---|---|
| Antibody | Yield [mg/L] | CE-SDS main peak | SEC monomer | Yield [mg/L] | CE-SDS main peak | SEC monomer | T-agg | MS |
| PD1TIM3-0389 | 21 | 88.9 | 97.6 | 19 | 92.1% | 100% | | confirmed |
| PD1TIM3-0168 | 48 | 87.3 | 88.9 | 42 | 98.4% | 95.2% | | confirmed |
| PD1TIM3-0476 | 271 | 100 | 97.8 | 230 | 98.9% | 100% | | confirmed |
| PD1TIM3-0477 | 211 | 94.3 | 85.3 | 159 | 97.4% | 94.7% | | confirmed |

Example 11C

Purification and Characterization of Multispecific Antibodies which Bind to PD1 and TIM3

The multispecific antibodies expressed above were purified from the supernatant by a combination of Protein A affinity chromatography and size exclusion chromatography. All multispecific antibodies can be produced in good yields and are stable. The obtained products were characterized for identity by mass spectrometry and analytical properties such as purity by SDS-PAGE, monomer content and stability Mass Spectrometry The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 μg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Health- Example 12

Characterization of Anti-PD1-TIM3 Multispecific Antibodies

Binding ELISA

ELISA for hu PD1

Nunc maxisorp streptavidin coated plates (MicroCoat #11974998001) were coated with 25 μl/well biotinylated PD1-ECD-AviHis at a concentration of 500 ng/ml and incubated at 4° C. over night. After washing (3×90 μl/well with PBST-buffer) 25 μl anti PD1 antibody samples were added in increasing concentrations and incubated 1 h at RT. After washing (3×90 μl/well with PBST-buffer) 25 μl/well goat-anti-human H+L-POD (JIR, JIR109-036-098) was added in 1:5000 dilution and incubated at RT for 1 h on a shaker. After washing (3×90 μl/well with PBST-buffer) 25 μl/well of TMB substrate (Roche, 11835033001) was added and incubated until OD 2-3. Measurement took place at 370/492 nm.

ELISA for hu TIM3

Nunc maxisorp streptavidin coated plates (MicroCoat #11974998001) were coated with 25 μl/well biotinylated TIM3-ECD-AviHis at a concentration of 60 ng/ml and incubated at 4° C. overnight. After washing (3×90 μl/well with PBST-buffer) 25 μl anti PD1 antibody samples were added in increasing concentrations and incubated 1 h at RT. After washing (3×90 μl/well with PBST-buffer) 25 μl/well goat-anti-human H+L-POD (JIR, JIR109-036-098) was added in 1:5000 dilution and incubated at RT for 1 h on a shaker. After washing (3×90 μl/well with PBST-buffer) 25 μl/well of TMB substrate (Roche, 11835033001) was added and incubated until OD 2-3. Measurement took place at 370/492 nm.

ELISA results are listed as $EC_{50}$ values [nM] in Table 16.

TABLE 16

Biochemial- and Cell-binding of anti-PD1-TIM3 bispecific antibodies (ELISA)

| Antibody | Sample | huPD1 $EC_{50}$ [nM] | huTIM3 $EC_{50}$ [nM] |
|---|---|---|---|
| PD1 IgG (bivalent) | Chimeric PD1-0103 | 0.12 | no binding |
| TIM3 IgG (bivalent) | Chimeric TIM3-0018 | no binding | 0.15 |
| 1 + 1 (bivalent) | 1 + 1 PD1TIM3-0168 | 0.11 | 0.41 |
| 2 + 2 (tetravalent) | 2 + 2 PD1TIM3-0359 | 0.09 | 0.11 |
| TIM3 IgG (bivalent) | Chimeric TIM3-0028 | no binding | 0.29 upper plateau at 66% |
| 1 + 1 (bivalent) | 1 + 1 PD1TIM3_0389 | 0.13 | no binding |
| 2 + 2 (tetravalent) | 2 + 2 PD1TIM3-0358 | 0.08 | 0.19 upper plateau at 65% |

Avid binding (i.e. binding with both arms) can be detected for antibodies that are bivalent for Tim3 (Chimeric TIM3-0018, 2+2 PD1TIM3-0359, Chimeric TIM3-0028, 2+2 PD1TIM3-0358). The higher EC50 values for the 1+1 CrossMabs result from monovalent (towards Tim3), non-avid binding to the coated antigen. Avidity effects were not detected for PD1-binding. EC50 values are comparable for bivalent and tetravalent formats.

Binding Biacore
Antigen Binding Properties of Multispecific Antibodies which Bind to PD1 and TIM3

Binding of the multispecific antibodies to their respective target antigens, i.e. PD1 and TIM3, was assessed by Biacore®.

PD1 Binding was Assessed According to the Following Procedure:

Anti-human Fc IgG was immobilized by amine coupling to the surface of a (Biacore) CM5 sensor chip. The samples were then captured and hu PD1-ECD was bound to them. The sensor chip surface was regenerated after each analysis cycle. The equilibrium constant and kinetic rate constants were finally gained by fitting the data to a 1:1 Langmuir interaction model.

About 10,000 response units (RU) of 20 μg/ml anti-human IgG (GE Healthcare #BR-1008-39) were coupled onto all flow cells of a CM5 sensor chip in a Biacore T200 using an amine coupling kit supplied by GE Healthcare. The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

Different samples were injected for 15 seconds with a concentration of 10 nM and consecutively bound to the flow cells 2, 3 and 4. Then a complete set of human PD1-ECD concentrations (300 nM, 100 nM, 2×33.3 nM, 11.1 nM, 3.7 nM, 1.2 nM and 2×0 nM) was injected over each sample for 300 s followed by a dissociation time of 10/600 s and two 30 s regeneration steps with 3 M $MgCl_2$, of which the last one contained an "extra wash after injection" with running buffer. Finally the double referenced data was fitted to a 1:1 Langmuir interaction model with the Biacore T200 Evaluation Software. Resulting $K_D$, $k_a$ and $k_d$ values are shown in Table 17.

TIM3 Binding was Assessed According to the Following Procedure:

Anti-human Fab IgG was immobilized by amine coupling to the surface of a (Biacore) CM5 sensor chip. The samples were then captured and hu Tim3-ECD was bound to them. The sensor chip surface was regenerated after each analysis cycle. The equilibrium constant and kinetic rate constants were finally gained by fitting the data to a 1:1 Langmuir interaction model.

About 10,000 response units (RU) of 20 μg/ml anti-human Fab IgG (GE Healthcare #28-9583-25) were coupled onto all flow cells of a CM5 sensor chip in a Biacore T200 using an amine coupling kit supplied by GE Healthcare. The sample and running buffer was HBS-EP+ (0.01 M HEPES, 0.15 M NaCl, 3 mM EDTA, 0.05% v/v Surfactant P20, pH 7.4). Flow cell temperature was set to 25° C. and sample compartment temperature to 12° C. The system was primed with running buffer.

Different samples were injected for 30 seconds with a concentration of 10 nM and bound consecutively to the flow cells 2, 3 and 4. Then a complete set of human Tim3-ECD concentrations (600 nM, 200 nM, 2×66.7 nM, 22.2 nM, 7.4 nM and 2×0 nM) was injected over each sample for 200 s followed by a dissociation time of 10/600 s and two 30 s regeneration steps with Glycine HCl pH 2.1, of which the last one contained an "extra wash after injection" with running buffer. Finally the double referenced data was fitted to a 1:1 langmuir interaction model with the Biacore T200 Evaluation Software. Resulting $K_D$, $k_a$ and $k_d$ values are shown in Table 17.

Results are indicated in Table 17.

TABLE 17

Affinity for PD1-Tim3 Bispecific Antibodies

| Sample | PD1-arm KD [nM] | Tim3-arm KD [nM] |
|---|---|---|
| PD1TIM3-0389 (0357) | 1.3 | 245 |
| PD1TIM3-0358 (2 + 2) | 0.3 | 240 |
| PD1TIM3-0168 | 1.2 | 10.3 |
| PD1TIM3-0359 (2 + 2) | 1.8 | 2.3 |
| PD1TIM3-0476 | 0.1 | 332 |
| PD1TIM3-0477 | <0.1 | 12 |

All tested antibodies specifically bind to both targets, PD1 and TIM3, and exhibit an antigen affinity in the nanomolar range.

Example 13: FRET Assay for Simultaneous Binding of Anti-PD1/TIM3 Bispecific Antibodies to Recombinant Cells This example describes the development of a cell-based TR-FRET assay to determine the simultaneous binding of bispecific antibody formats to two different receptors present on one cell. The chosen Tag-lite technology is a combination of a classical TR-FRET (time-resolved fluorescence resonance energy transfer) and SNAP-tag technology (e.g. New England Biolabs, CISBIO), which allows antigens present on the cell surface to be labeled with a fluorescent donor or acceptor dye.

Aim of this Technology Evaluation

Figure 6:
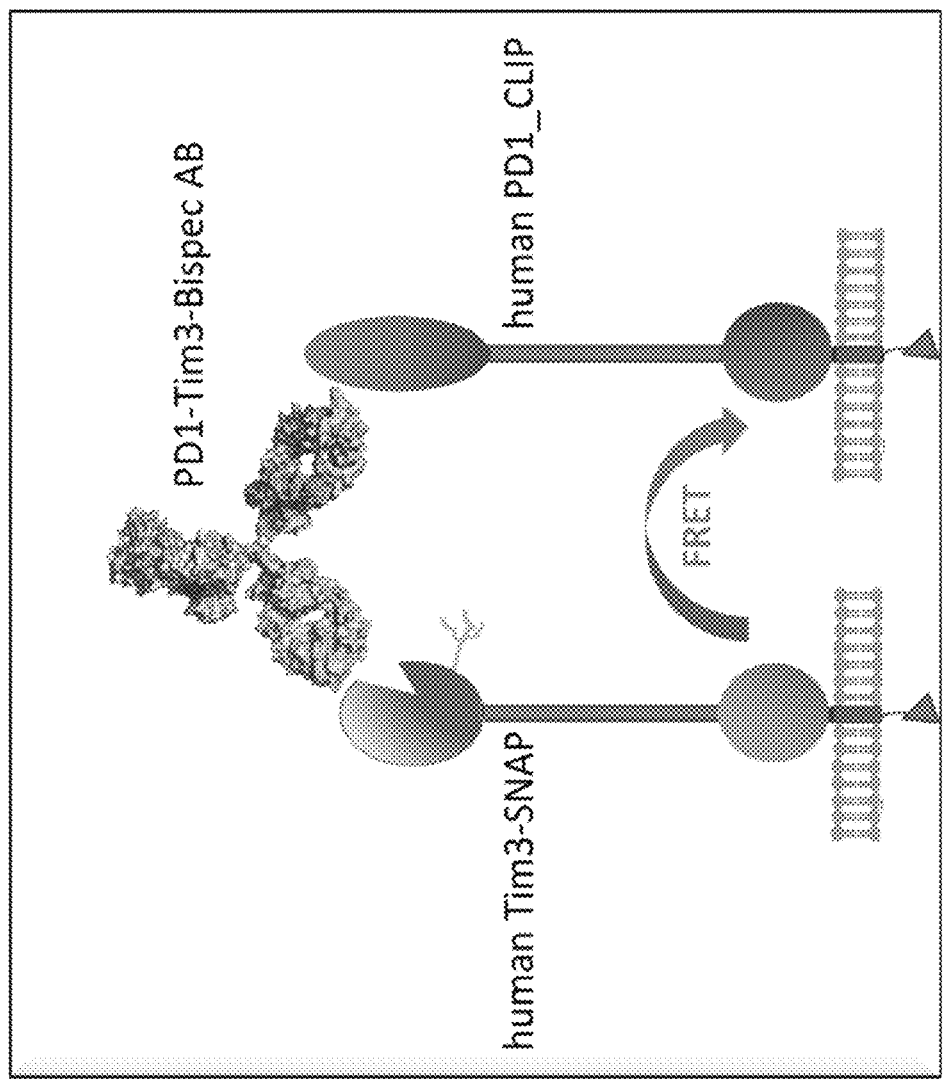
FIG. 6: Scheme of FRET assay for simultaneous binding of anti-PD1/Tim3 bispecific antibodies to recombinant cells

This assay is intended to demonstrate the simultaneous binding of anti-PD1/Tim3 bispecific antibodies to cells expressing both PD1 and Tim3 receptors as recombinant fusion proteins consisting of the extracellular domains (ECD) of the given receptor and a tag, to which a fluorescence dye can bind. In the presence of a PD1-Tim3 bispecific antibody, which can bind both labeled receptors, the proteins will come into close proximity to allow energy transfer between the two FRET dyes (see FIG. 6).

Generation of Recombinant PD1$^+$TIM3$^+$ HEK Cells

Standard methods were used to generation DNA as described in Sambrook et al., Molecular cloning: A laboratory manual; Cold Spring Harbor Laboratory Press, Cold Spring Harbor, N.Y., 1989. For Cloning of PD1 and TIM3 variants SNAP or CLIP was inserted proximal to TM-region of the receptor and cytoplasmatic domain was removed except for 7 aa and replaced by Flag-tag.

Transient Transfection

HEK293 cells were co-transfected with transfection reagent 293 free (Novagen) and Opti-MEM® I Reduced Serum Media (Life Technologies) in 30 ml culture volume using two plasmids at a time with 15 µg total amount of DNA. Briefly, HEK293 cells were transiently transfected with the following plasmids encoding for a fusion protein consisting of PD1 or Tim3 ECDs and a SNAP or CLIP tag as described elsewhere:

Plasmid ID's and reference e.g. PD1-SNAP, Tim3-CLIP (the combination PD1-CLIP and Tim3-SNAP was also constructed and expressed, but did result in only low FRET signals).

Plasmids:

a) PD1-SNAP (in 5' to 3' direction):
nucleic acid encoding human PD1-extracellular domain including the signal peptide (residue 1-170 of SEQ ID NO: 89 (30),
nucleic acid encoding GGGGS spacer (SEQ ID NO: 90),
nucleic acid encoding SNAP from pSNAP-tag(T7)2 (without N-terminal methionine residue) which is a mutant form of the human gene for O6-alkylguanine-DNA-alkyltransferase (hAGT). (Compared to wild type hAGT, the SNAP-tag protein contains the mutations C26A, K125A, A127T, R128A, G131K, G132T, M134L, R135S, C150S, N157G, S159E, and is truncated after G182) (SEQ ID NO: 91),
nucleic acid encoding GGGGS spacer (SEQ ID NO: 90),
nucleic acid encoding human PD1-transmembrane and cytoplasmic domain (residue 171-191 of SEQ ID NO: 89),
nucleic acid encoding GGGGS spacer (SEQ ID NO: 90),
nucleic acid encoding the Flag-tag (DYKDDDDK; SEQ ID NO: 92).

b) Tim3-CLIP (in 5' to 3' direction):
nucleic acid encoding human Tim3-extracellular domain including the signal peptide (residue 1-202 of SEQ ID NO: 93)
nucleic acid encoding GGGGS spacer (SEQ ID NO: 90),
nucleic acid encoding CLIP from pCLIPf (without N-terminal methionine residue), which is a mutant form of the human gene for O6-alkylguanine-DNA-alkyltransferase (hAGT) (SEQ ID NO: 94),
nucleic acid encoding GGGGS spacer (SEQ ID NO: 90),
nucleic acid encoding human Tim3 transmembrane and cytoplasmic domain (residue 203-230 of SEQ ID NO: 93)
nucleic acid encoding GGGGS spacer (SEQ ID NO: 90),
nucleic acid encoding the Flag-tag (DYKDDDDK; SEQ ID NO: 92).

Upon transfection, cells were incubated in shaker flasks until final usage for FACS (24-48 hrs after transfection) or FRET experiments (after 48 hrs).

Confirmation of PD1 and Tim3 Expression on Transiently Transfected HEK293 Cells (FACS)

24-48 hrs after transient transfection of Hek293 cells, cells were analyzed for PD1 and Tim3 expression: Usually, 1-3×10$^5$ single or double transfected cells were stained 30 min on ice at 10 µg/ml, washed two times with PBS/2% FCS and analyzed on a FacsCanto II using
PD1-FITC Biolegend 329904, clone EH12.2H7) or PD1-PE (R&D #FAB1086P) and/or
Tim3-PE (R&D FAB2365P clone 344823) and/or Description Cell Labeling and FRET Assay with Anti-PD1/TIM3 Bispecific Antibodies Description cell labeling and FRET assay with anti-PD1/TIM3 bispecific antibodies:

Transfected cells were sedimented and resuspended at a density of 1×10$^6$ cells/ml in Tag-lite buffer (Cisbio). Then, cells were stained with 100 nM SNAP-Lumi4-Tb (Cisbio) and 100 nM Clip-Red (Cisbio) for 1 h at 37° C. in Tag-Lite buffer (Cisbio). After washing and resuspension in PBS/2% FCS, about 50.000 cells (in 50 µl volume) were seeded into 96-well flat-bottom white plates (Costar) bevor control (e.g. single specificity, isotype reference) or bispecific antibodies were added to the cells at a final concentration of 0.001-10 nM. In some experiments, parental monoclonal antibodies were cross-linked via goat anti human Fc (20 nM final concentration, data not shown). After an incubation of 1 h at 4° C. or room temperature, time-resolved fluorescence was measured as ratio of 665/620 nm with an BMG Pherastar reader or Tecan Infinite M1000 Pro using standard settings provided by vendor. Optionally, SNAP-Lumi4-Tb and 100 nM Clip-Red labeled cells were stored at −80° C. or in liquid nitrogen and freshly thawed for FRET experiments.

Results:

Characterization of Different Bispecific Antibodies and Antibody Formats for Simultaneous Receptor Binding and Cross-Linking as Demonstrated by FRET Induction.

PD1 and TIM3 expressing HEK cells were treated as described above to measure FRET signal upon simultaneous receptor binding via incubation with titrated amounts of different bispecific antibodies (0.12-10 nM).

Figure 7A:
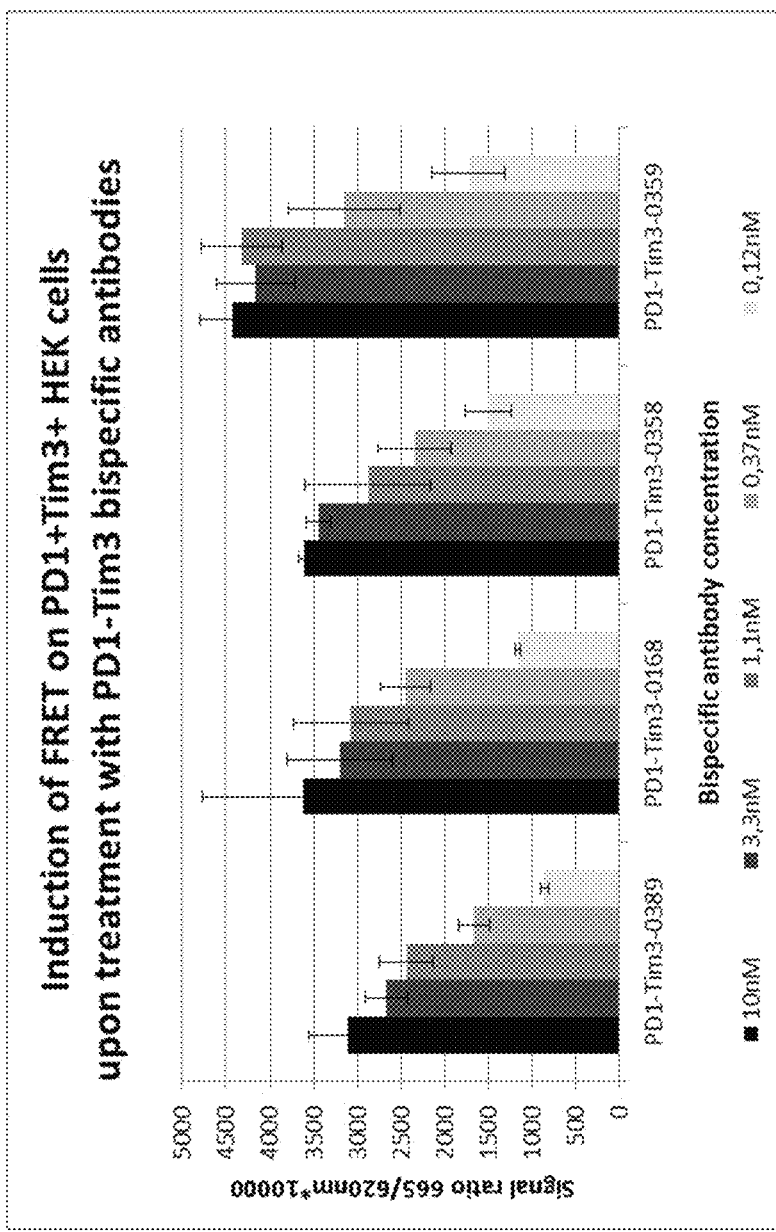
FIGS. 7A and 7B: Induction of FRET upon treatment/binding of different bispecific PD1TIM3 antibodies on PD1 and TIM3 expressing cells: HEK293 cells, double transfected with PD1 SNAP Tim3 CLIP, were stained with 100 nM SNAP-Lumi4-Tb (Cisbio) and 100 nM Clip-Red (Cisbio) for 1 h at 37° in Tag-Lite buffer (Cisbio). After washing, labelled cells were incubated with indicated bispecific anti-PD1/Tim3 antibodies [0-10 nM] for 1 h at 4° C. before time-resolved fluorescence was measured at 665/620 nm with an BMG Pherastar reader (depicted is the mean+/−SD of the FRET signal [ratio 665/620 nm*10,000], n=3).

All bispecific antibodies induced a FRET signal in PD-1-TIM3-expressing cells in a dose-dependent manner. There was no dramatic difference between 1+1 formats (antibodies #389 and 168) compared to 2+2 constructs (358+359) as can be seen in FIG. 7A.

Figure 7B:
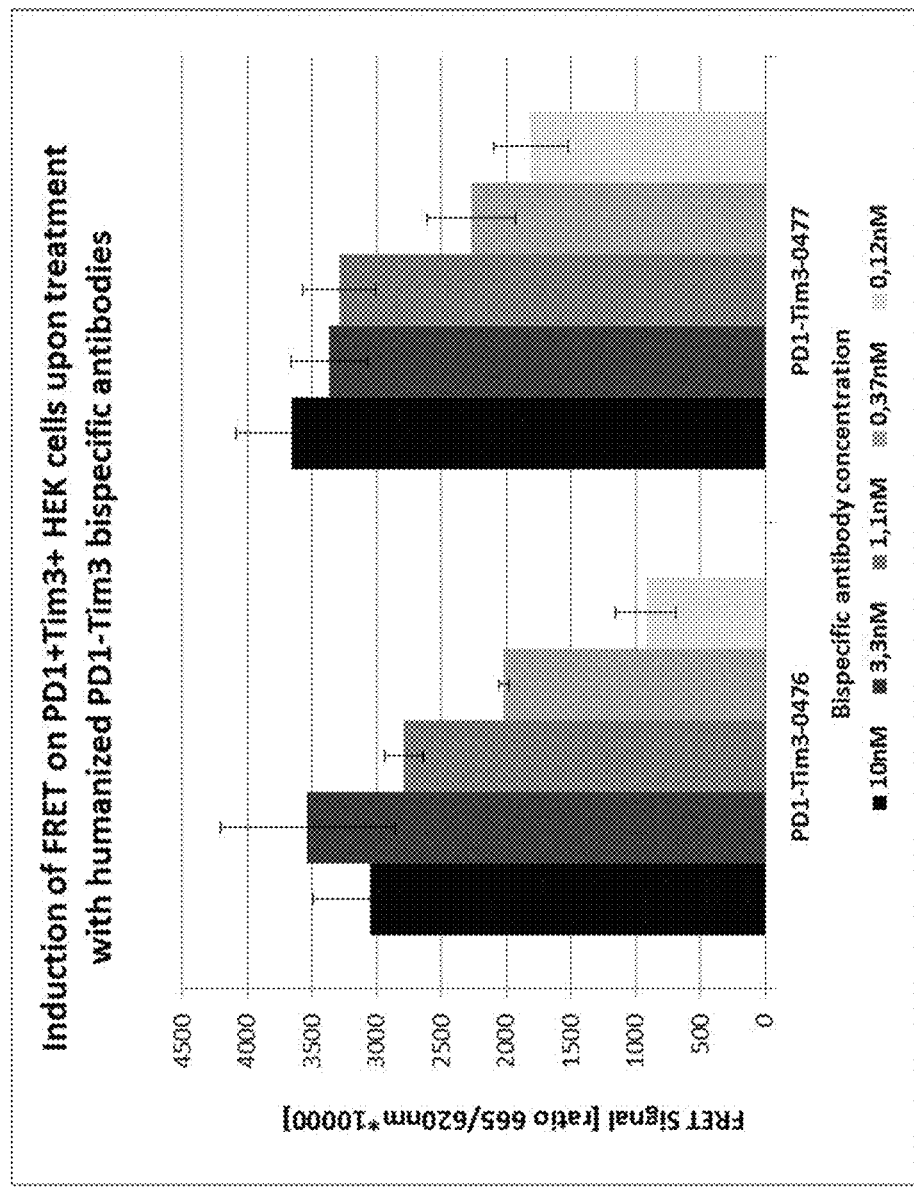

In addition, two bispecific formats based on humanised PD1 TIM3 antibodies (#476 and 477) were also evaluated for their ability to induce FRET in cells upon treatment. As demonstrated in FIG. 7B, both constructs induced significant FRET signal in PD1+TIM3+ HEK cells underlining the simultaneous binding in a functional manner.

To Show the Specificity of the FRET Signal Induced by Simultaneous Binding of the Bispecific Antibody, Monoclonal IgGs of Only One Specificity Were Added for Competition.

Figure 8A:
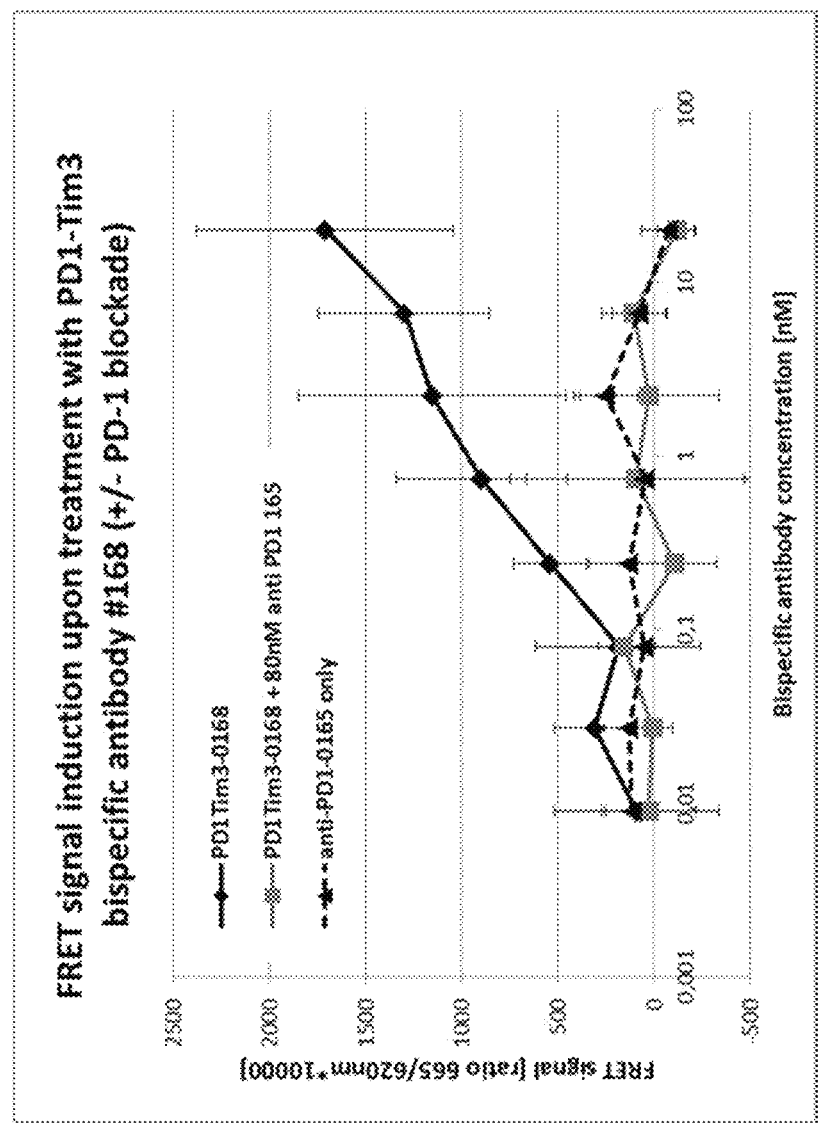
FIGS. 8A and 8B: FRET assay for simultaneous binding of anti-PD1/TIM3 bispecific antibody 1+1 PD1TIM3-0168: SNAP-tagged PD1 and CLIP-tagged TIM3 cells (as described before) were labelled with 100 nM SNAP-Lumi4-Tb and 100 nM Clip-Red. After washing, labelled cells were incubated with the bispecific anti-PD1/TIM3 antibody #0168 [at indicated concentrations] for 1 h at 4° C. before time-resolved fluorescence was measured at 665/620 nm with an BMG Pherastar reader (black lines). To underline the specificity of the bispecifc antibody induced FRET signal, either an anti-PD1 monoclonal antibody (#0165.

SNAP-tagged PD1 and CLIP-tagged TIM3 cells (as described before) were labelled with 100 nM SNAP-Lumi4-Tb and 100 nM Clip-Red. After washing, labelled cells were incubated with the bispecific anti-PD1/TIM3 antibody #0168 [at indicated concentrations] for 1 h at 4° C. before time-resolved fluorescence was measured at 665/620 nm with an BMG Pherastar reader (black lines). To underline the specificity of FRET signal after bispecific antibody treatment, an anti-PD1 monoclonal antibody (#0165, FIG. 8A, grey curve) or an anti Tim-3 monoclonal antibody (#0018, FIG. 8B, grey curve) was added for competition resulting in an almost complete prevention of the FRET signal. The parental (monospecific) anti-PD-1 antibody alone did not induce FRET (dotted lines).

Figure 8B:
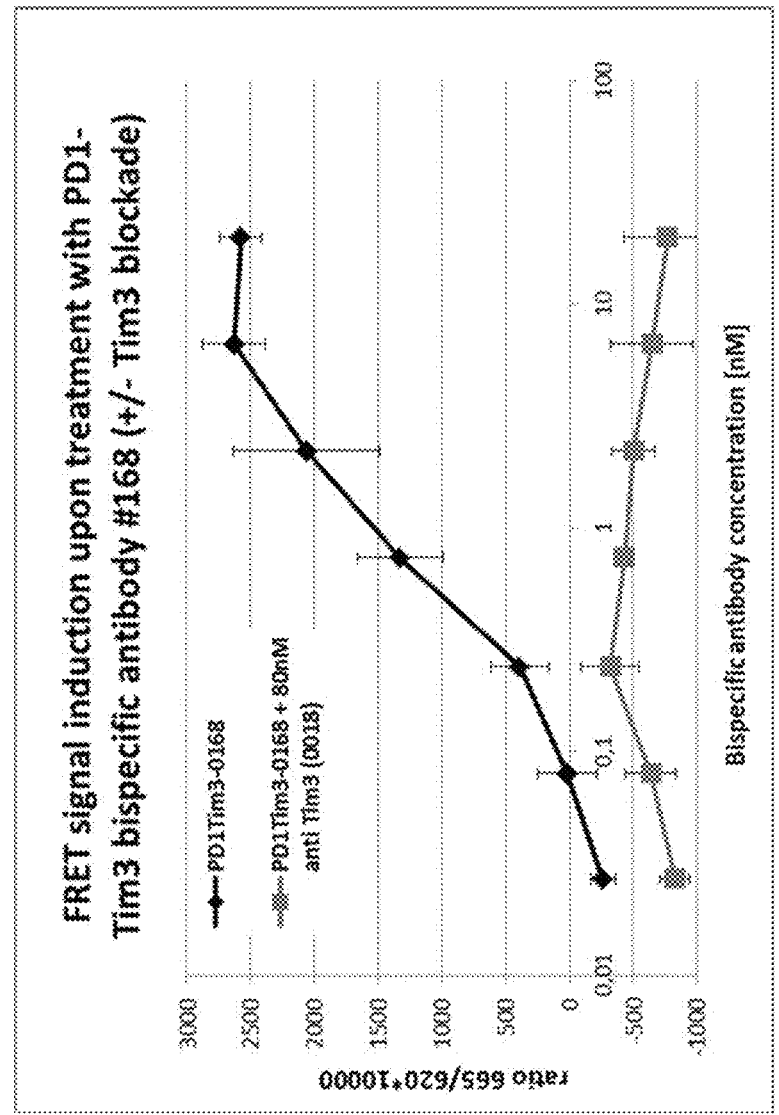
Figure 9A:
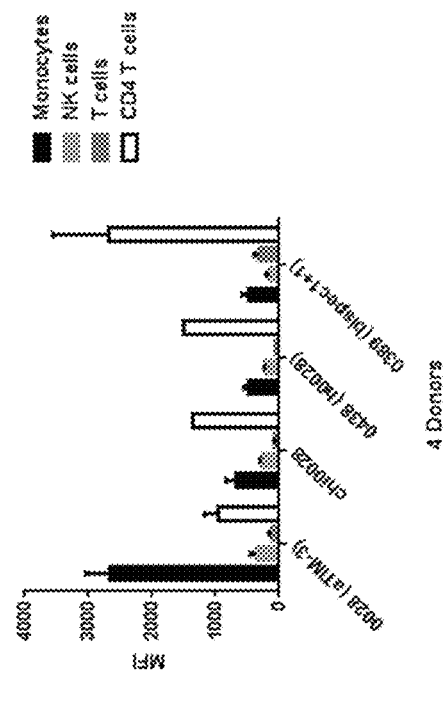
FIG. 9A: Bispecific 1+1 PD1TIM3-0389 shows the same binding ratio to positive CD4+ T-cells (PD1+, TIM3+) than chimeric TIM3_0028 (chi0028) and humanized TIM3-0438 (0438), but less binding to Monocytes, NK cells and CD3+ T-cells.
Figure 9B:
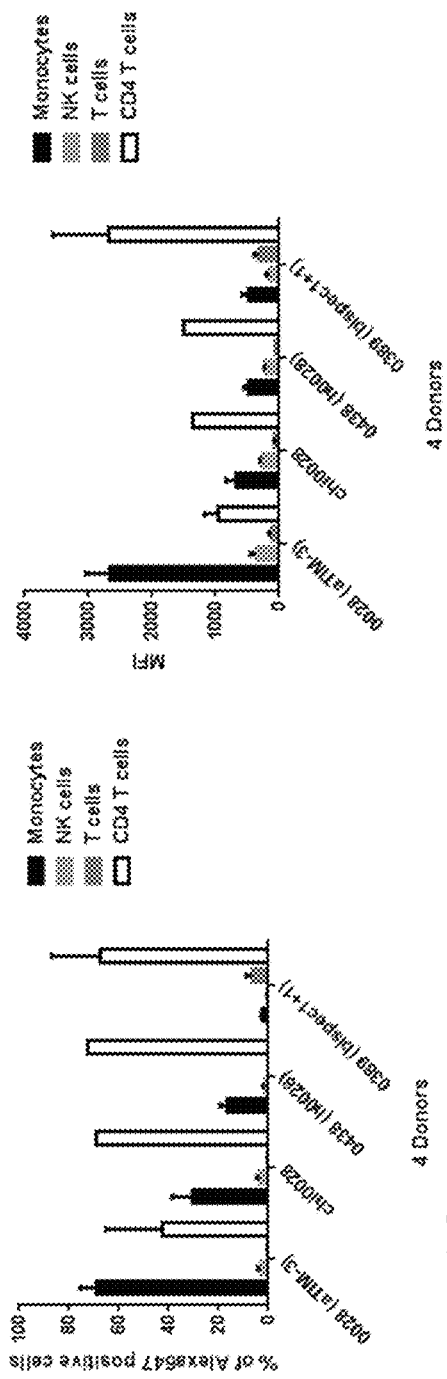
FIG. 9B: Bispecific 1+1 PD1TIM3-0389 show significantly increased MFI for binding to positive CD4+ T-cells (PD1+, TIM3+) than chimeric TIM3_0028 (chi0028) and humanized Tim3-0438 (0438).
Figure 9C:
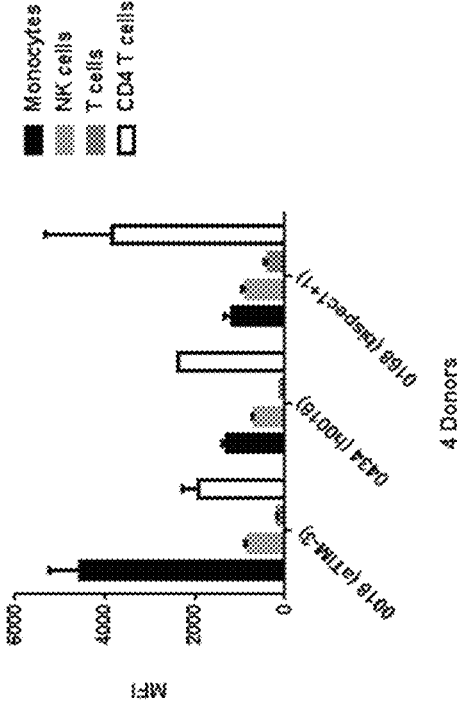
FIG. 9C: Bispecific 1+1 PD1TIM3-0168: no differences concerning binding to positive CD4+ T-cells (PD1+, TIM3+) than chimeric TIM3_0018 (Tim-chi0018) and humanized TIM3-0434 (0434).
Figure 9D:
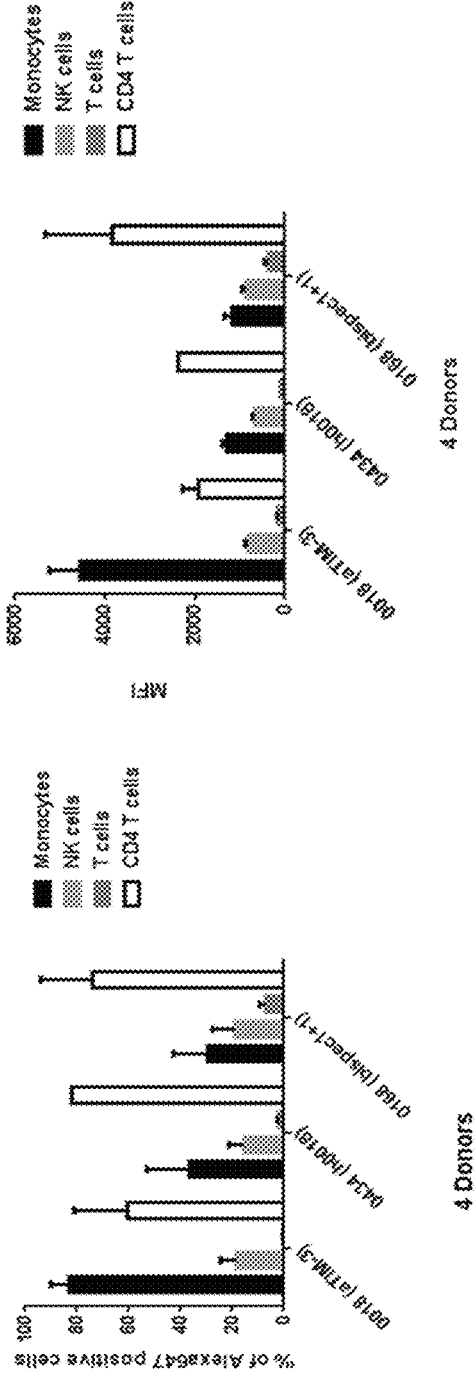
FIG. 9D: Bispecific 1+1 PD1TIM3-0168 show only slight increased MFI for binding to positive CD4+ T-cells (PD1+, Tim3+).
Figure 9F:
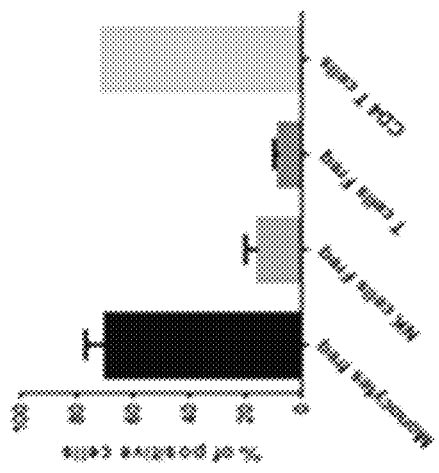
FIGS. 9E and 9F: anti-TIM3 antibody TIM3-0038 shows binding to both monocytes and CD4+ T-cells.
Figure 9H:
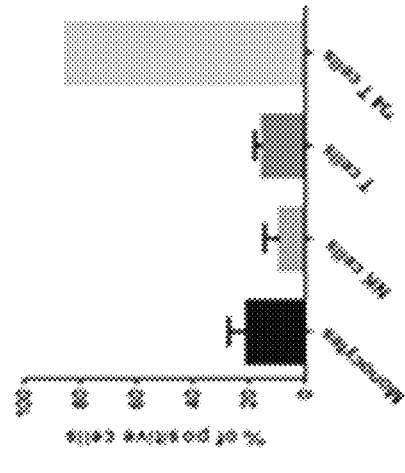
FIGS. 9G and 9H: Bispecific 1+1 PD1TIM3-0166 (based on chimeric PD1-0103//Tim3-0038) shows strongly reduced binding to monocytes (compared to parent anti-TIM3 antibody TIM3_0038 see FIGS. 4E and 4F) while retaining strong binding to CD4+ T cells.
Figure 9E:
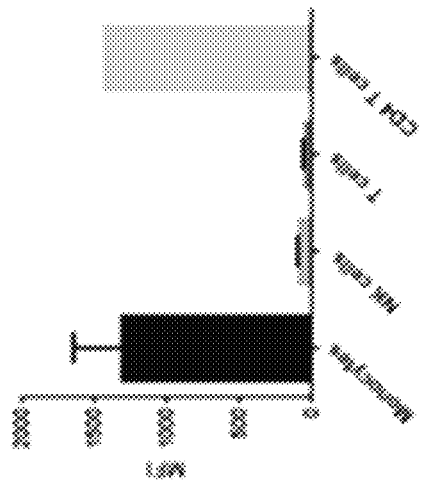
Figure 9G:
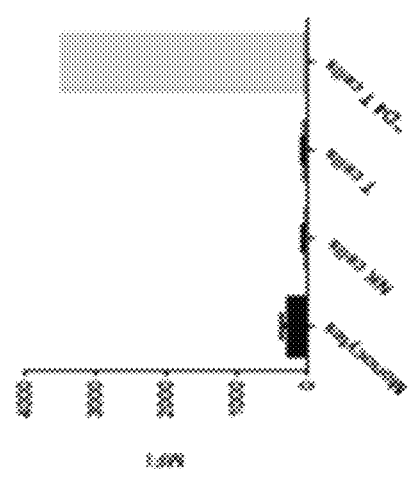
Figure 10A:
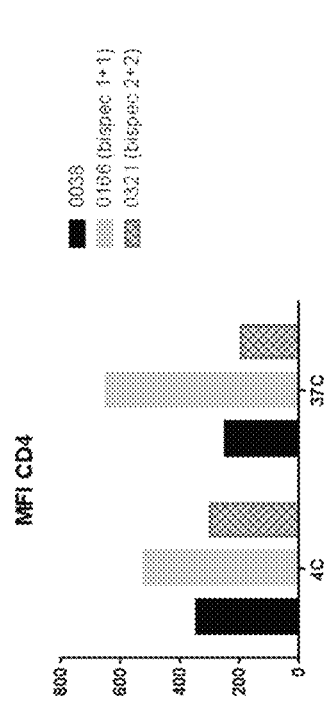
FIGS. 10A, 10B, 10C and 10D: Bispecific 1+1 PD1TIM3-0166 (based on chimeric PD1-0103//TIM3-0038) showed reduced internalization compared to Bispecific 2+2 PD1TIM3-0321 (also based on chimeric PD1-0103//TIM3-0038, but having two antigen binding sites for PD and two for TIM3) and compared to parent TIM3-0038 antibody on activated CD4+ T-Cells and on activated NK cells.
Figure 10B:
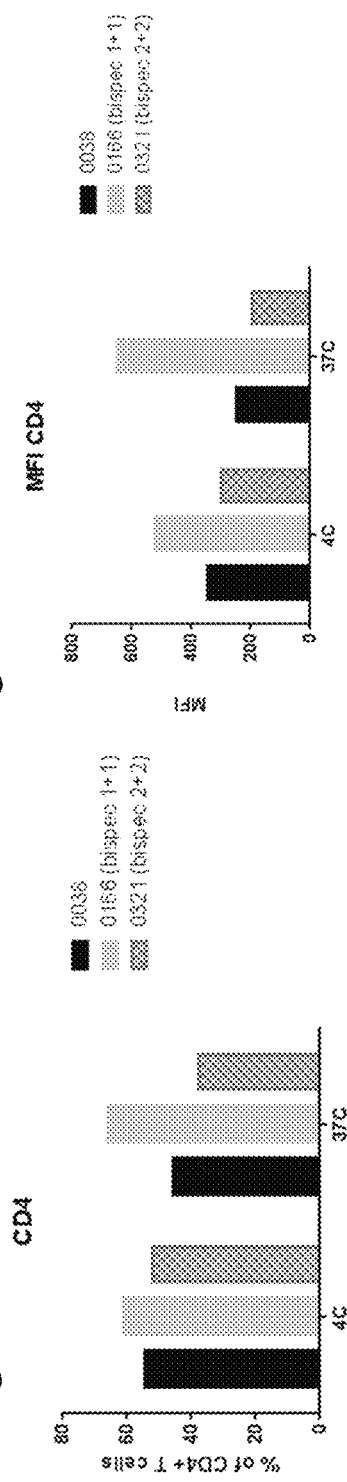
Figure 10C:
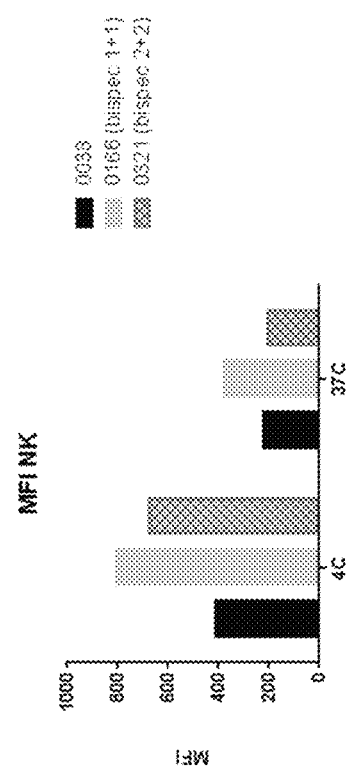
Figure 10D:
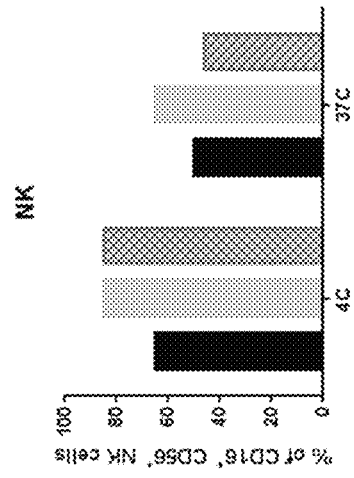

The induction of the FRET signal was also prevented in presence of a TIM3 parental antibody (0018; grey curves) added in parallel to the bispecific antibody (FIG. 8B).

Example 14: Binding of Antibodies to Different Peripheral Blood Mononuclear Cells (PBMC) Binding Assay Freshly isolated PBMCs or 3 days polyclonally activated (plate bound anti-CD3 and soluble anti-CD28 antibodies, 1 ug/ml each, both from BD Pharmingen) CD4 T cells were stained either with Alexa 647-directly conjugated anti-TIM-3 or anti-TIM-3/anti-PD-1 bispecific antibodies for 1 hour at 4 C degrees. The cells were then washed to eliminate unbound antibody and stained for surface markers for 30 minutes at 4 C degrees to discriminate monocytes (CD14$^+$ (BD Pharmingen)), NK cells (CD16$^+$ (eBioscience), CD56$^+$ (BioLegend) and CD3$^-$) and T cells (CD3$^+$ (eBioscience)) before being fixed with BD Cell Fix. The cells were acquired at LSRFortessa, BD Biosciences. Results for the bispecific antibodies in comparison to anti-Tim3 antibodies are shown in FIGS. 9A to 9H.

Example 15: Internalization

Example 15A) Three days polyclonally activated CD4 T cells, previously cultured with 1 mg/ml of plate bound anti-CD3 and 1 mg/ml of soluble anti-CD28 antibodies, were incubated in presence of either anti-TIM-3 or anti-TIM-3/anti-PD-1 bispecific antibodies (in duplicates) for 30 minutes at 4° C. degrees. The cells were then washed, divided in two groups, one of which incubated for 3 additional hours at 37° C. degrees and the other immediately stained with a labelled secondary antibody (eBioscience) before being fixed with BD Cell Fix. After the 3 hours incubations also the second group of the cells were stained with the labelled secondary antibody before fixation.

The cells were acquired at LSRFortessa (BD Biosciences) and the expression levels of detectable antibody on the cell surface were compared among the two groups. Results are shown in FIGS. 10A to 10D. Bispecific 1+1 PD1TIM3-0166 (based on chimeric PD1-0103/TIM3-0038) showed reduced internalization compared to bispecific 2+2 PD1TIM3-0321 (also based on chimeric PD1-0103/TIM3-0038, but having two antigen binding sites for PD and two for TIM3) and compared to parent TIM3-0038 antibody on activated CD4+ T-Cells and on activated NK cells.

Example 15B) Visualization of Antibody Localization and Internalization by Fluorescence Confocal Microscopy Activated CD4-positive cells were stained with CMFDA (Molecular Probes, Life technologies), except when stained with a-PD1 antibody, and plated on round coverslips treated with Poly-L-Lysine (Sigma). Cells were allowed 30 minutes to adhere at 37° C. before fluorescently-tagged antibodies (1 ug/mL: a-TIM3 (chi18-A647=cimeric Tim3_0018 labeled with AlexaA647), a-TIM3 (chi28-A647=cimeric Tim3_0028 labeled with AlexaA647), Bispec (0168-A647=1+1 PD1TIM3_0168 (based on chimeric PD1-0103/Tim3-0018) labeled with AlexaA647) and Bispec (0389-A647=1+1 PD1TIM3_0389 (based on chimeric PD1-0103/Tim3-0028) labeled with Alexa 647) and a-PD1 (0165-A488=chimeric PD1-0103 labeled with Alexa488) were added directly into growth media for different durations (15 min, 1 hr, 2 hr, 3 hr). Cold PBS (Lonza) was used to quench the reaction and to wash off unbounded antibodies. Cells were then fixed (BD Cytofix) for 20 minutes and washed twice with wash buffer (BD stain buffer). After transferring the coverslips to a dry surface, they were then mounted on glass slides with mounting medium (Fluoromount G, eBioscience) and kept in the dark at 4° C. before imaging. The intensity of the fluorescent signal from the membrane ROI, of highly targeted cells, was divided by the intensity of the fluorescent signal from the cytoplasm ROI of the same cells, resulting in a ratio displayed in the Box Charts. In order to compare samples, One Way ANOVA analysis was used (*=$p<0.05$; **=$p<0.001$). Fluorescence confocal microscopy was performed with an inverted LSM 700 from Zeiss with a 60× oil objective. Images were collected using Zen software (Zeiss) coupled to the microscope. The analysis of the images were performed with Imaris Software (Bitplane; Oxford Instrument) and the statistical analysis were performed by GraphPad Prism (Graphpad Software). The analysis over time showing higher membrane localization in both bispecific and PD1 antibodies when compared to intracellular clustering of TIM3 antibodies is shown in FIGS. 11A and 11B. The anti-PD1 and the Bispec 0389 show only very slow internalization, even after 3 h, whereas the internalization for the other Bispec 0168 is stronger. Stronger internalization is shown by aTim3 Ab 0028, the most internalization is shown by aTim3-0018.

Example 16: T Cell Activation Via Mixed Lymphocyte Reaction (MLR) Assay

The Mixed Lymphocyte Reaction (MLR) is an immune cell assay which measures the activation of lymphocytes from one individual (donor X) to lymphocytes from another individual (donor Y). A mixed lymphocyte reaction was used to demonstrate the effect of blocking the PD1 pathway to lymphocyte effector cells. T cells in the assay were tested for activation and their IFN-gamma secretion in the presence or absence of an anti-PD1/TIM3 bispecific mAbs.

To perform an allogeneic MLR, peripheral blood mononuclear cells (PBMCs) from at least four healthy donors of unknown HLA type were isolated by density gradient centrifugation using Leukosep (Greiner Bio One, 227 288). Briefly, heparinized blood samples were diluted with the three fold volume of PBS and 25 ml aliquots of the diluted blood were layered in 50 ml Leukosep tubes. After centrifugation at 800×g for 15 min at room temperature (w/o break) the lymphocyte containing fractions were harvested, washed in PBS and used directly in functional assay or resuspended in freezing medium (10% DMSO, 90% FCS) at 1.0E+07 cells/ml and stored in liquid nitrogen. Individual 2-way MLR reactions were set up by mixing PBMCs from two different donors at a 1:1 stimulator/responder cell ratio and co-cultures were done at least in duplicate in flat-bottomed 96-well plates for 6 days at 37° C., 5% $CO_2$, in the presence or w/o of a different concentration range of purified bispecific PD1-TIM3 antibodies or their parental monospecific antibodies (either alone or in combination). Either no antibody or an isotype control antibody was used as a negative control and rec hu IL-2 (20 EU/ml) was used as positive control. After day 6 100 µl of medium was taken from each culture for cytokine measurement. The levels of IFN-gamma were measured using OptEIA ELISA kit (BD Biosciences).

The results are shown in Table 18A to 18D (IFN-γ secretion/release). The bispecific PD1TIM3 antibodies promoted T cell activation and IFN-gamma secretion in concentration dependent manner. The value of % increase of IFNγ secretion was calculated in relation to IFNγ production of MLR w/o adding of any blocking mAbs (basal allogeneic stimulation induced IFNγ value as E-c) and MLR with adding of 20 EU/ml rec hu IL-2 (positive control=100% IFNγ value as E+c) and was calculated according to formula: Rel. Stimulation [%]=((Example-E-c)/(E+c-E-c)*100.

Four separate experiments were performed:

In Experiment 1 the potency of PD1-TIM3 Bispecific Antibody 1+1 PD1TIM3_0168 (based on chimeric PD1-0103/TIM3-0018 (=AB 0168) in comparison with chimeric PD1-0103 (=PD1-0165) and chimeric TIM3_0018 (=Tim3-chi18) and combinations thereof was evaluated. Results are shown in FIG. 12A and Table 18A.

TABLE 18A

| Antibody | $EC_{50}$ [nM] D2 + D6 |
| --- | --- |
| aPD1-0165 (=chimeric PD1-0103) | 7.7 |
| aTIM3-chi18 (=cimeric TIM3__0018) | >274 |
| Combo aPD1-0165 + aTIM3-chi18 | 1.7 |
| Bispec AB 0168 (=1 + 1 PD1TIM3__0168 (based on chimeric PD1-0103/Tim3-0018) | 4.3 |

In Experiment 2 the potency of PD1-TIM3 Bispecific Antibody 1+1 PD1TIM3_0389 (based on chimeric PD1-0103/TIM3-0028 (=Bispec AB 0389) in comparison with chimeric PD1-0103 (=PD1-0165) and chimeric TIM3_0028 (=TIM3-chi28) and combinations thereof was evaluated. Results are shown in FIG. 12B and Table 18B.

TABLE 18B

| Antibody | $EC_{50}$ [nM] D2 + D6 |
| --- | --- |
| aPD1-0165 (=chimeric PD1-0103) | 6.5 |
| aTIM3-chi28 (=cimeric TIM3__0028) | >274 |
| Combo aPD1-0165 + aTIM3-chi18 | 1.5 |
| Bispec AB 0389 (=1 + 1 PD1TIM3__0389 (based on chimeric PD1-0103/TIM3-0028) | 2.8 |

In Experiment 3 the potency of PD1-TIM3 Bispecific Antibody 1+1 PD1-0103/Ky8213 (based on chimeric PD1-0103/and anti-TIM3 Ky8213 from US 2012/0189617 (see antibody 8213 e.g. Example 33) which was produced analogously as described in Example 1 as a 1+1 CrossMab) in comparison with chimeric chimeric PD1-0103 (=PD1-0165) and anti-TIM3-Ky8213 (from US 2012/0189617 (see antibody 8213) e.g. Example 33) and combinations thereof was evaluated. Results are shown in FIG. 12C and Table 18C.

TABLE 18C

| Antibody | $EC_{50}$ [nM] D2 + D6 |
| --- | --- |
| aPD1-0165 (=chimeric PD1-0103) | 6.0 |
| aTIM3-Ky8213 | 111 |
| Combo aPD1-0165 + aTIM3-Ky8213 | 0.9 |
| Bispec AB 1 + 1 PD1-0103/TIM3-Ky8213 | 4.6 |

In Experiment 4 the potency of PD1-TIM3 Bispecific Antibody 1+1 PD1TIM3_0389 (based on chimeric PD1-0103/TIM3-0028 (=Bispec AB 0389 (1+1))) in comparison with PD1-TIM3 Bispecific Antibody 2+2 PD1TIM3_0358 based on chimeric PD1-0103/TIM3-0028 (=Bispec AB 0358 (2+2)), and chimeric PD1-0103 (=PD1-0165) and chimeric TIM3_0028 (=TIM3-chi28) and combinations thereof was evaluated. Results are shown in FIG. 12D and Table 18D.

TABLE 18D

| Antibody | $EC_{50}$ [nM] D2 + D4 | $EC_{50}$ [nM] D1 + D3 |
| --- | --- | --- |
| aPD1-0165 (=chimeric PD1-0103) | 5.7 | 5.7 |
| aTIM3-chi28(=cimeric Tim3__0028) | >264 | >264 |
| Combo aPD1-0165 + aTim3-chi28 | 0.6 | 0.8 |
| Bispec AB 0389 (1 + 1) (=1 + 1 PD1TIM3__0389 (based on chimeric PD1-0103/Tim3-0028) | 1.9 | 2.0 |
| Bispec AB 0358 (2 + 2) (=2 + 2 PD1TIM3__0358 (based on chimeric PD1-0103/Tim3-0028) | 5.7 | 6.8 |

TABLE 19

Summary of observed properties/results:

| | Binding | | | | Internalization | MLR IFN-γ |
| --- | --- | --- | --- | --- | --- | --- |
| Antibody | Monocytes | NK cells | T cells | CD4 T cells | CD4 T cells | ELISA |
| Monospecific TIM3-0018 | ++ | +/- | − | ++ | ++ | +/- |
| Bispecific 1 + 1 PD1TIM3_0168 | ++ | + | +/- | +++ | − | +++ |
| Bispecific 2 + 2 PD1TIM3_0359 | ++++ | +/- | -/+ | +++ | − | |
| Monospecific TIM3-0038 | ++ | +/- | -/+ | ++ | + | + |
| Bispecific 1 + 1 PD1TIM3_0166 | + | +/- | +/- | ++ | − | ++ |
| Bispecific 2 + 2 PD1TIM3_0321 | +++ | +/- | -/+ | +++ | ++ | +++ |

TABLE 19-continued

Summary of observed properties/results:

| | Binding | | | | Internalization | MLR IFN-γ |
|---|---|---|---|---|---|---|
| Antibody | Monocytes | NK cells | T cells | CD4 T cells | CD4 T cells | ELISA |
| Monospecific TIM3-0028 | + | +/− | −/+ | + | ++ | +/− |
| Bispecific 1 + 1 PD1TIM3_0389 | − | − | +/− | +++ | − | +++ |
| Bispecific 2 + 2 PD1TIM3_0358 | | | | | | ++ |

Assay ( − = no effect, +/− = very weak effect, + = weak effect, ++ = medium effect, +++ = strong effect, ++++ = very strong effect)

Example 17: Co-Culture of Antigen-Specific CD4 T Cells with B Cell-Lymphoblastoid Cell Line ARH77

To investigate the effect of anti-PD-1 blockade on CD4 T cells in presence of a MHCII-expressing tumor cell line we developed an assay in which freshly purified CD4 T cells are cocultured for 5 days in presence of an EBV-immortalized B cell lymphoblast cell line (ARH77). On the day of the minimal mixed lymphocyte reaction (mMLR), CD4 T cells were enriched via a microbead kit (Miltenyi Biotec) from $10^8$ PBMCs obtained from a healthy donor. Prior culture, CD4 T cells were labeled with 5 mM of carboxy-fluorescein-succinimidyl ester (CFSE). $10^5$ CD4 T cells were then plated in a 96 well plate together with the B cell line (5:1) in presence or absence of blocking anti-PD1 antibodies (either humanized PD-1 0376, nivolumab or pembrolizumab), anti-TIM3 antibodies (either humanized anti-TIM3 0438 or Kyowa-8213) or anti-PD-1/TIM3 bispecific antibody (humanized 0476) at the concentration of 10 μg/ml. Five days later we collected the cell-culture supernatants used to measure the IFN-γ levels by ELISA (R&D systems).

As shown in FIG. 13, we interestingly observed that anti-PD-1 treatment significantly increased the ability of CD4 T cells to produce IFN-γ when compared to untreated CD4 T cells (dashed line). In this assay the anti-PD-1 antibody 0376 has been equally able as the bench mark antibodies in inducing the secretion of IFN-γ by CD4 T cells, while anti-TIM3 antibody 0438 alone has only a marginal effect even if stronger than the benchmark antibody Kyowa-8213.

Surprisingly, the bispecific antibody 0476 was better than the combination of parental antibodies, anti-PD1 antibody 0376 alone and the benchmark antibodies in driving IFN-γ secretion by CD4 T cells (P<0.01, one way ANOVA).

Example 18: Enhanced Efficacy of the PD1-TIM3 Bispecific Antibody In Vivo

Immune supressed female mice (NOG), aged 6-8 weeks at start of the experiments, were challenged subcutaneously with $10^6$ MKN45 cells (human gastric carcinoma cell line, expressing high level of CEA) at day 0 in presence of matrigel at 1:1 ratio. At day 7, PBMC from healthy human donor were isolated: human heparinized blood was diluted ~2:1 in phosphate buffer saline (PBS) (Gibco) and transferred into prepared 50 ml Leucosep tubes, each containing 15 ml Histopaque-1077 (Sigma Aldrich). After centrifugation (30 minutes, 450×g, RT, no brake), the PBMC bands were collected with a 5 ml pipette. Cells were transferred into 50 ml tubes and washed with PBS (centrifugation at 350×g, 10 min). The washing step was repeated (centrifugation at 300×g, 10 min). After centrifugation (10 min, 350×g), cells were re-suspended in RPMI medium. $10^7$ PBMC were injected intravenously in the NOG mice creating a mouse-human chimeric model. At day 10, a weekly scheduled therapy (vehicle or treatment with a compound selected from anti-PD1 (0376), Nivolumab, anti-TIM3 (0438) or anti PD1-TIM3 (0476)) started and was given by intra-peritoneal injection. The treatment with the PD1-Tim3 bispecific antibody (either 3 or 10 mg/kg; open triangle) was compared with equimolar (1.5 or 5 mg/Kg) concentration of the single agent PD1 antibody (0376), of Nivolumab and of the Tim3 antibody (0438). Tumour size was measured by Caliper in mm over a period of 30 days every 2-3 days. In FIGS. 14A and 14B, the measurements of tumour volume are shown as mean volume within the group of mice.

All the treatments showed the capability to control tumor growth when compared the vehicle treated group. The inhibition of only PD1 (by PD1 antibody (0376) or the benchmark Nivolumab) and of only TIM3 antibody (0438), lead to a similar efficacy in controlling the tumor growth. This shows that by blocking either PD1 or TIM3 it is possible to enhance the anti-tumoral response. However, an increase of tumor growth inhibition can be observed when both PD1 and TIM3 are bound by the PD1-TIM3 bispecific antibody. Whereas at low concentration a difference in tumor growth between bi-specific antibody and the other treatment cannot be observed, at higher doses the inhibition of both PD1 and TIM3 by the treatment with the PD1-TIM3 bispecific antibody results in a strong inhibition of tumour growth.

What is claimed is:

1. A method of treating a disease in an individual, the method comprising administering a therapeutically effective amount of a bispecific antibody comprising a first antigen-binding site that specifically binds to PD1 and a second antigen-binding site that specifically binds to TIM3, wherein said first antigen-binding site specifically binding to PD1 comprises
   a VH domain comprising
   (i) HVR-H1 comprising the amino acid sequence of SEQ ID NO:37,
   (ii) HVR-H2 comprising the amino acid sequence of SEQ ID NO:38, and
   (iii) HVR-H3 comprising an amino acid sequence of SEQ ID NO:39; and
   a VL domain comprising
   (i) HVR-L1 comprising the amino acid sequence of SEQ ID NO:40;
   (ii) HVR-L2 comprising the amino acid sequence of SEQ ID NO:41, and
   (iii) HVR-L3 comprising the amino acid sequence of SEQ ID NO:42; and
said second antigen-binding site specifically binding to TIM3 comprises
   (a) a VH domain comprising
      (i) HVR-H1 comprising the amino acid sequence of SEQ ID NO:1,
      (ii) HVR-H2 comprising the amino acid sequence of SEQ ID NO:2, and
      (iii) HVR-H3 comprising an amino acid sequence of SEQ ID NO:3; and
      a VL domain comprising
      (i) HVR-L1 comprising the amino acid sequence of SEQ ID NO:4 or SEQ ID NO:11 or SEQ ID NO:12,
      (ii) HVR-L2 comprising the amino acid sequence of SEQ ID NO:5, and
      (iii) HVR-L3 comprising the amino acid sequence of SEQ ID NO:6; or
   (b) a VH domain comprising
      (i) HVR-H1 comprising the amino acid sequence of SEQ ID NO:17,
      (ii) HVR-H2 comprising the amino acid sequence of SEQ ID NO:18, and
      (iii) HVR-H3 comprising an amino acid sequence of SEQ ID NO:19; and
      a VL domain comprising
      (i) HVR-L1 comprising the amino acid sequence of SEQ ID NO:20,
      (ii) HVR-L2 comprising the amino acid sequence of SEQ ID NO:21, and
      (iii) HVR-L3 comprising the amino acid sequence of SEQ ID NO:22; or
   (c) a VH domain comprising
      (i) HVR-H1 comprising the amino acid sequence of SEQ ID NO:29,
      (ii) HVR-H2 comprising the amino acid sequence of SEQ ID NO:30, and
      (iii) HVR-H3 comprising an amino acid sequence of SEQ ID NO:31; and
      a VL domain comprising
      (i) HVR-L1 comprising the amino acid sequence of SEQ ID NO:32,
      (ii) HVR-L2 comprising the amino acid sequence of SEQ ID NO:33, and
      (iii) HVR-L3 comprising the amino acid sequence of SEQ ID NO:34.

2. The method of claim 1, wherein the bispecific antibody binds to TIM3 with an at least 50-fold lower binding affinity when compared to the binding to PD1.

3. The method according to claim 1, wherein
said first antigen-binding site specifically binding to PD1 comprises
   (a) a VH domain comprising the amino acid sequence of SEQ ID NO: 43 and a VL domain comprising the amino acid sequence of SEQ ID NO: 44, or
   (b) a VH domain comprising the amino acid sequence of SEQ ID NO: 45 and a VL domain comprising the amino acid sequence of SEQ ID NO: 46, or
   (c) a VH domain comprising the amino acid sequence of SEQ ID NO: 45 and a VL domain comprising the amino acid sequence of SEQ ID NO: 47, or
   (d) a VH domain comprising the amino acid sequence of SEQ ID NO: 45 and a VL domain comprising the amino acid sequence of SEQ ID NO: 48, or
   (e) a VH domain comprising the amino acid sequence of SEQ ID NO: 45 and a VL domain comprising the amino acid sequence of SEQ ID NO: 49,
and said second antigen-binding site specifically binding to TIM3 comprises
   (a) a VH domain comprising the amino acid sequence of SEQ ID NO: 7 and a VL domain comprising the amino acid sequence of SEQ ID NO: 8, or
   (b) a VH domain comprising the amino acid sequence of SEQ ID NO: 9 and a VL domain comprising the amino acid sequence of SEQ ID NO: 10, or
   (c) a VH domain comprising the amino acid sequence of SEQ ID NO: 13 and a VL domain comprising the amino acid sequence of SEQ ID NO: 14, or
   (d) a VH domain comprising the amino acid sequence of SEQ ID NO: 15 and a VL domain comprising the amino acid sequence of SEQ ID NO: 16, or
   (e) a VH domain comprising the amino acid sequence of SEQ ID NO: 23 and a VL domain comprising the amino acid sequence of SEQ ID NO: 24, or
   (f) a VH domain comprising the amino acid sequence of SEQ ID NO: 25 and a VL domain comprising the amino acid sequence of SEQ ID NO: 26, or
   (g) a VH domain comprising the amino acid sequence of SEQ ID NO: 27 and a VL domain comprising the amino acid sequence of SEQ ID NO: 28, or
   (h) a VH domain comprising the amino acid sequence of SEQ ID NO: 35 and a VL domain comprising the amino acid sequence of SEQ ID NO: 36.

4. The method according to claim 1, wherein
said first antigen-binding site specifically binding to PD1 comprises a VH domain comprising the amino acid sequence of SEQ ID NO: 45 and a VL domain comprising the amino acid sequence of SEQ ID NO: 46, and said second antigen-binding site specifically binding to TIM3 comprises a VH domain comprising the amino acid sequence of SEQ ID NO: 15 and a VL domain comprising the amino acid sequence of SEQ ID NO: 16 or a VH domain comprising the amino acid sequence of SEQ ID NO: 25 and a VL domain comprising the amino acid sequence of SEQ ID NO: 26.

5. The method according to claim 1, wherein
said first antigen-binding site specifically binding to PD1 comprises a VH domain comprising the amino acid sequence of SEQ ID NO: 45 and a VL domain comprising the amino acid sequence of SEQ ID NO: 46, and
said second antigen-binding site specifically binding to TIM3 comprises a VH domain comprising the amino acid sequence of SEQ ID NO: 25 and a VL domain comprising the amino acid sequence of SEQ ID NO: 26.

6. The method according to claim 1, wherein the bispecific antibody is a human, humanized or chimeric antibody.

7. The method of claim 1, wherein the bispecific antibody comprises an Fc domain, a first Fab fragment comprising the antigen-binding site that specifically binds to PD1 and a second Fab fragment comprising the antigen-binding site that specifically binds to TIM3.

8. The method of claim 7, wherein the Fc domain is an IgG1 Fc domain or an IgG4 Fc domain.

9. The method of claim 7, wherein the Fc domain comprises one or more amino acid substitution that reduces binding to an Fc receptor, in particular towards Fcγ receptor.

10. The method of claim 7, wherein the Fc domain is of human IgG1 subclass with the amino acid mutations L234A, L235A and P329G (numbering according to Kabat EU index).

11. The method of claim 7, wherein the Fc domain comprises a modification promoting the association of the first and second subunit of the Fc domain.

12. The method of claim 7, wherein a first subunit of the Fc domain comprises knobs and a second subunit of the Fc domain comprises holes according to the knobs into holes method.

13. The method of claim 7, wherein the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

14. The method of claim 7, wherein in one of the Fab fragments the variable domains VL and VH are replaced by each other so that the VH domain is part of the light chain and the VL domain is part of the heavy chain.

15. The method of claim 14, wherein in the first Fab fragment comprising the antigen-binding site that specifically binds to PD1 the variable domains VL and VH are replaced by each other.

16. The method of claim 7, wherein in one of the Fab fragments in the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

17. The method of claim 16, wherein in the second Fab fragment comprising the antigen-binding site that specifically binds to TIM3 the constant domain CL the amino acid at position 124 is substituted independently by lysine (K), arginine (R) or histidine (H) (numbering according to Kabat EU Index), and in the constant domain CH1 the amino acids at positions 147 and 213 are substituted independently by glutamic acid (E) or aspartic acid (D) (numbering according to Kabat EU index).

18. The method of claim 1, wherein the bispecific antibody comprises
(a) a first heavy chain comprising an amino acid sequence with at least 95% sequence identity to the sequence of SEQ ID NO: 50, a first light chain comprising an amino acid sequence with at least 95% sequence identity to the sequence of SEQ ID NO: 52,
a second heavy chain comprising an amino acid sequence with at least 95% sequence identity to the sequence of SEQ ID NO: 51, and a second light chain comprising an amino acid sequence with at least 95% sequence identity to the sequence of SEQ ID NO:53, or
(b) a first heavy chain comprising an amino acid sequence with at least 95% sequence identity to the sequence of SEQ ID NO: 54, a first light chain comprising an amino acid sequence with at least 95% sequence identity to the sequence of SEQ ID NO: 56,
a second heavy chain comprising an amino acid sequence with at least 95% sequence identity to the sequence of SEQ ID NO: 55, and a second light chain comprising an amino acid sequence with at least 95% sequence identity to the sequence of SEQ ID NO:57, or
(c) a first heavy chain comprising an amino acid sequence with at least 95% sequence identity to the sequence of SEQ ID NO: 58, a first light chain comprising an amino acid sequence with at least 95% sequence identity to the sequence of SEQ ID NO: 60,
a second heavy chain comprising an amino acid sequence with at least 95% sequence identity to the sequence of SEQ ID NO: 59, and a second light chain comprising an amino acid sequence with at least 95% sequence identity to the sequence of SEQ ID NO:61, or
(d) a first heavy chain comprising an amino acid sequence with at least 95% sequence identity to the sequence of SEQ ID NO: 62, a first light chain comprising an amino acid sequence with at least 95% sequence identity to the sequence of SEQ ID NO: 64,
a second heavy chain comprising an amino acid sequence with at least 95% sequence identity to the sequence of SEQ ID NO: 63, and a second light chain comprising an amino acid sequence with at least 95% sequence identity to the sequence of SEQ ID NO:65, or
(e) a first heavy chain comprising an amino acid sequence with at least 95% sequence identity to the sequence of SEQ ID NO: 66, a first light chain comprising an amino acid sequence with at least 95% sequence identity to the sequence of SEQ ID NO: 68,
a second heavy chain comprising an amino acid sequence with at least 95% sequence identity to the sequence of SEQ ID NO: 67, and a second light chain comprising an amino acid sequence with at least 95% sequence identity to the sequence of SEQ ID NO:69.

19. The method of claim 1, wherein the bispecific antibody claim comprises
   (a) a first heavy chain comprising the amino acid sequence of SEQ ID NO: 50, a first light chain comprising the amino acid sequence of SEQ ID NO: 52, a second heavy chain comprising the amino acid sequence of SEQ ID NO: 51, and a second light chain comprising the amino acid sequence of SEQ ID NO:53, or
   (b) a first heavy chain comprising the amino acid sequence of SEQ ID NO: 54, a first light chain comprising the amino acid sequence of SEQ ID NO: 56, a second heavy chain comprising the amino acid sequence of SEQ ID NO: 55, and a second light chain comprising the amino acid sequence of SEQ ID NO:57, or
   (c) a first heavy chain comprising the amino acid sequence of SEQ ID NO: 58, a first light chain comprising the amino acid sequence of SEQ ID NO: 60, a second heavy chain comprising the amino acid sequence of SEQ ID NO: 59, and a second light chain comprising the amino acid sequence of SEQ ID NO:61, or
   (d) a first heavy chain comprising the amino acid sequence of SEQ ID NO: 62, a first light chain comprising the amino acid sequence of SEQ ID NO: 64, a second heavy chain comprising the amino acid sequence of SEQ ID NO: 63, and a second light chain comprising the amino acid sequence of SEQ ID NO:65, or
   (e) a first heavy chain comprising the amino acid sequence of SEQ ID NO: 66, a first light chain comprising the amino acid sequence of SEQ ID NO: 68, a second heavy chain comprising the amino acid sequence of SEQ ID NO: 67, and a second light chain comprising the amino acid sequence of SEQ ID NO:69.

20. A method of treating a disease in an individual, the method comprising administering a therapeutically effective amount of a bispecific antibody comprising a first antigen-binding site that specifically binds to PD1 and a second antigen-binding site that specifically binds to TIM3, wherein said bispecific antibody comprises
   (a) a first heavy chain comprising the amino acid sequence of SEQ ID NO: 62, and a first light chain comprising the amino acid sequence of SEQ ID NO: 64; and
   (b) a second heavy chain comprising the amino acid sequence of SEQ ID NO: 63, and a second light chain comprising the amino acid sequence of SEQ ID NO:65.

21. The method of claim 1, wherein the method of treating the disease comprises modulating or stimulating an immune response or function.

22. The method of claim 1, wherein the disease is an infection.

23. The method of claim 22, wherein the infection is a viral infection.

24. The method of claim 1, wherein the disease is cancer.

25. The method of claim 1, wherein the disease is cancer and the method of treating comprises delaying progression of cancer in the individual.

26. The method of claim 1, wherein the disease is cancer and the method of treating comprises prolonging the survival of the individual.

27. The method of claim 1, wherein the method further comprises administering a chemotherapeutic agent, radiation, and/or a cancer immunotherapy agent.

28. The method of claim 1, wherein the individual has a tumor and the antibody is administered in an amount effective to inhibit the growth of the tumor.

29. The method of claim 20, wherein the method of treating the disease comprises modulating or stimulating an immune response or function.

30. The method of claim 20, wherein the disease is an infection.

31. The method of claim 30, wherein the infection is a viral infection.

32. The method of claim 20, wherein the disease is cancer.

33. The method of claim 20, wherein the disease is cancer and the method of treating comprises delaying progression of cancer in the individual.

34. The method of claim 20, wherein the disease is cancer and the method of treating comprises prolonging the survival of the individual.

35. The method of claim 20, wherein the method further comprises administering a chemotherapeutic agent, radiation, and/or a cancer immunotherapy agent.

36. The method of claim 20, wherein the individual has a tumor and the antibody is administered in an amount effective to inhibit the growth of the tumor.

* * * * *